(12) United States Patent
Suttie et al.

(10) Patent No.: US 7,351,877 B2
(45) Date of Patent: *Apr. 1, 2008

(54) LAMBDA INTEGRASE MEDIATED RECOMBINATION IN PLANTS

(75) Inventors: Janet Louise Suttie, Research Triangle Park, NC (US); Mary-Dell Chilton, Research Triangle Park, NC (US); Qiudeng Que, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 547 days.

This patent is subject to a terminal disclaimer.

(21) Appl. No.: 10/403,232

(22) Filed: Mar. 28, 2003

(65) Prior Publication Data

US 2003/0226164 A1 Dec. 4, 2003

Related U.S. Application Data

(60) Provisional application No. 60/369,041, filed on Mar. 29, 2002, provisional application No. 60/425,512, filed on Nov. 12, 2002.

(51) Int. Cl.
| | | |
|---|---|---|
| *C12N 15/82* | (2006.01) | |
| *C12N 15/83* | (2006.01) | |
| *C12N 15/84* | (2006.01) | |
| *C12N 15/87* | (2006.01) | |
| *C12N 5/04* | (2006.01) | |
| *A01H 5/00* | (2006.01) | |
| *C12N 15/33* | (2006.01) | |

(52) U.S. Cl. ............... 800/278; 800/287; 435/412; 435/456; 435/462; 435/468; 435/469; 435/470; 536/23.72

(58) Field of Classification Search ............ 435/462, 435/419, 468, 235.1, 320.1, 469; 800/278, 800/287, 288, 294
See application file for complete search history.

(56) References Cited

U.S. PATENT DOCUMENTS

| | | | |
|---|---|---|---|
| 5,227,288 A | 7/1993 | Blattner | 435/6 |
| 5,888,732 A | 3/1999 | Hartley et al. | 435/6 |
| 6,121,014 A | 9/2000 | Koziel et al. | 435/69.1 |
| 6,143,557 A | 11/2000 | Hartley | 435/320.1 |
| 6,171,861 B1 | 1/2001 | Hartley | 435/455 |
| 6,187,994 B1 | 2/2001 | Baszczynski | 800/278 |
| 6,262,341 B1 | 7/2001 | Baszczynski | 800/278 |
| 6,270,969 B1 | 8/2001 | Hartley | 435/6 |
| 6,300,545 B1 | 10/2001 | Baszczynski | 800/294 |
| 6,331,661 B1 | 12/2001 | Baszczynski | 800/278 |
| 6,410,329 B1 | 6/2002 | Hansen | 435/468 |
| 6,455,315 B1 | 9/2002 | Baszczynski | 800/278 |
| 6,458,594 B1 | 10/2002 | Baszczynski | 435/468 |
| 6,541,231 B1 | 4/2003 | Baszczynski | 435/183 |
| 6,632,672 B2 | 10/2003 | Calos | 435/462 |
| 6,800,791 B1 * | 10/2004 | Bailey et al. | 800/278 |
| 6,933,146 B2 * | 8/2005 | Helliwell et al. | 435/320.1 |
| 2003/0027337 A1 | 2/2003 | Droge et al. | |
| 2003/0054552 A1 | 3/2003 | Hartley et al. | |
| 2003/0064515 A1 | 4/2003 | Hartley et al. | |
| 2003/0110532 A1 | 6/2003 | Armostrong et al. | |
| 2003/0140376 A1 | 7/2003 | Depicker et al. | |

FOREIGN PATENT DOCUMENTS

| | | |
|---|---|---|
| EP | 160571 | 11/1985 |
| EP | 632054 | 1/1995 |
| EP | 1 308 516 A1 | 5/2003 |
| WO | WO 94/17176 | 8/1994 |
| WO | WO 95/00555 | 1/1995 |
| WO | WO 99/21977 | 5/1999 |
| WO | WO 99/25821 | 5/1999 |
| WO | WO 99/25841 | 5/1999 |
| WO | WO 99/25854 | 5/1999 |
| WO | WO 99/25855 | 5/1999 |
| WO | WO 99/60842 | 12/1999 |
| WO | WO 01/07572 | 2/2001 |
| WO | WO 01/11058 A1 | 2/2001 |
| WO | WO 01/16345 | 3/2001 |
| WO | WO 01/18222 | 3/2001 |
| WO | WO 02/00875 | 1/2002 |
| WO | WO 02/08409 A2 | 1/2002 |
| WO | WO 02/16609 * | 2/2002 |
| WO | WO 02/079409 | 10/2002 |
| WO | WO 02/083867 | 10/2002 |

(Continued)

OTHER PUBLICATIONS

Groth et al. Journal of Molecular Biology 335(3): 667-678 (Jan. 2004).*

(Continued)

*Primary Examiner*—David T. Fox
(74) *Attorney, Agent, or Firm*—Michael E. Yates

(57) ABSTRACT

The present disclosure provides methods for obtaining the targeted integration of a DNA molecule into the genome of a host cell using a recombinase. The methods disclosed herein can be used with a variety of host cells, including, for example, dicotyledonous and monocotyledonous plant cells. The present disclosure provides a method for effecting site-specific recombination of DNA within a plant cell, comprising: introducing into the plant cell a target nucleotide sequence comprising a first Int recognition site; introducing into the plant cell a donor nucleotide sequence comprising a second Int recognition site; and introducing into the plant cell an integrase or integrase complex.

119 Claims, 15 Drawing Sheets

FOREIGN PATENT DOCUMENTS

| | | |
|---|---|---|
| WO | WO 02/083910 | 10/2002 |
| WO | WO 02/085104 | 10/2002 |
| WO | WO 02/086144 | 10/2002 |

OTHER PUBLICATIONS

Christ et al. Journal of Molecular Biology 319(2): 305-314 (May 2002).*

Christ et al. Journal of Molecular Biology 288(5): 825-836 (1998).*

Miller et al. Cell 20: 721-729 (Jul. 1980).*

Azaro, M.A. and Landy, A., "λ Integrase and the λ Int Family", Mobile DNA II, Edited by N.I. Craig et al (2002 ASM Press, Washington, D.C.), pp. 118-148.

Christ and Dröge, Genetic Manipulation of Mouse Embryonic Stem Cells by Mutant λ Integrase Genesis, vol. 32 (2002) pp. 203-208.

Dorgai et al, Identifying Determinants of Recombination Specificity: Construction and Characterization of Mutant Bacteriophage Integrases Journal of Molecular Biology, vol. 252 (1995), pp. 178-188.

Hoess et al, The role of the loxP spacer region in P1 site-specific recombination Nucleic Acids Research, vol. 14, No. 5, 1986.

Kolot et al, Site-specific recombination in mammalian cells expressing the Int recombinase of bacteriophage HK022 Molecular Biology Reports, vol. 26 (1999), pp. 207-213.

Landy, A., Mechanistic and structural complexity in the site-specific recombination pathways of Int and FLP Current Opinion in Genetics and Development, vol. 3 (1993) pp. 699-707.

Lorbach et al, Site-specific Recombination in Human Cells Catalyzed by Phage λ Integrase Mutants Journal of Molecular Biology, vol. 296 (2000), pp. 1175-1181.

Stanley et al, The nucleotide sequence of an infectious clone of the geminivirus beet curly top virus The European Molecular Biology Organization, vol. 5, No. 8 (1986) pp. 1761-1767.

Patrick Argos et al., "The integrase family of site-specific recombinases: regional similarities and global diversity," The EMBO Journal, vol. 5, No. 2, 433-440, 1986.

Dominic Esposito et al., "The integrase family of tyrosine recombinases: evolution of a conserved active site domain," Nucleic Acids Research, vol. 25, No. 18, 3605-3614, 1997.

Simone E. Nunes-Duby et al., "Similarities and differences among 105 members of the int family of site-specific recombinases," Nucleic Acids Research, vol. 26, No. 2, 391-406, 1998.

Margaret C.M. Smith et al., "Diversity in the serine recombinases," Molecular Microbiology, vol. 44, No. 2, 299-307, 2002.

* cited by examiner

SEQUENCE LISTING

```
<160> NUMBER OF SEQ ID NOS: 185

<210> SEQ ID NO 1
<211> LENGTH: 85
<212> TYPE: DNA
<213> ORGANISM: Artificial
<220> FEATURE:
<223> OTHER INFORMATION: Oligo 1A of SynInt

<400> SEQUENCE: 1
ggatccgcca ccatgggccg ccgccgcagc cacgagcgcc gcgacctgcc ccccaacctg      60
tacatccgca acaacggcta ctact                                            85
```

```
<210> SEQ ID NO 2
<211> LENGTH: 75
<212> TYPE: DNA
<213> ORGANISM: Artificial
<220> FEATURE:
<223> OTHER INFORMATION: Oligo 1B of SynInt

<400> SEQUENCE: 2
atgcggcggt cgcggcccag gccgaactcc ttgccggtgc gggggtcgcg gtagcagtag    60
tagccgttgt tgcgg                                                    75

<210> SEQ ID NO 3
<211> LENGTH: 75
<212> TYPE: DNA
<213> ORGANISM: Artificial
<220> FEATURE:
<223> OTHER INFORMATION: Oligo 1C of SynInt

<400> SEQUENCE: 3
ctgggccgcg accgccgcat cgccatcacc gaggccatcc aggccaacat cgagctgttc    60
agcggccaca agcac                                                    75

<210> SEQ ID NO 4
<211> LENGTH: 83
<212> TYPE: DNA
<213> ORGANISM: Artificial
<220> FEATURE:
<223> OTHER INFORMATION: Oligo 1D of SynInt

<400> SEQUENCE: 4
ccggtccagc cagctgtgca gggtcacgct gttgtcgctg ttgatgcggg cggtcagggg    60
cttgtgcttg tggccgctga aca                                           83

<210> SEQ ID NO 5
<211> LENGTH: 70
<212> TYPE: DNA
<213> ORGANISM: Artificial
<220> FEATURE:
<223> OTHER INFORMATION: Oligo 2E of SynInt

<400> SEQUENCE: 5
ccggaccgct acgagaagat cctggccagc cgcggcatca agcagaagac cctgatcaac    60
tacatgagca                                                          70

<210> SEQ ID NO 6
<211> LENGTH: 70
<212> TYPE: DNA
<213> ORGANISM: Artificial
<220> FEATURE:
<223> OTHER INFORMATION: Oligo 2F of SynInt

<400> SEQUENCE: 6
gatgtcctcc aggggggcgt cgggcaggcc gcggcggatg gccttgatct tgctcatgta    60
gttgatcagg                                                          70

<210> SEQ ID NO 7
<211> LENGTH: 70
<212> TYPE: DNA
<213> ORGANISM: Artificial
<220> FEATURE:
<223> OTHER INFORMATION: Oligo 2G of SynInt

<400> SEQUENCE: 7
```

```
acgccccct ggaggacatc accaccaagg agatcgccgc catgctgaac ggctacatcg    60
acgagggcaa                                                         70

<210> SEQ ID NO 8
<211> LENGTH: 70
<212> TYPE: DNA
<213> ORGANISM: Artificial
<220> FEATURE:
<223> OTHER INFORMATION: Oligo 2H of SynInt

<400> SEQUENCE: 8
cgcggaaggc gtcgctcagg gtgctgcgga tcagcttggc gctggcggcc ttgccctcgt   60
cgatgtagcc                                                         70

<210> SEQ ID NO 9
<211> LENGTH: 70
<212> TYPE: DNA
<213> ORGANISM: Artificial
<220> FEATURE:
<223> OTHER INFORMATION: Oligo 2I of SynInt

<400> SEQUENCE: 9
cctgagcgac gccttccgcg aggccatcgc cgagggccac atcaccacca accacgtggc   60
cgccacccgc                                                         70

<210> SEQ ID NO 10
<211> LENGTH: 80
<212> TYPE: DNA
<213> ORGANISM: Artificial
<220> FEATURE:
<223> OTHER INFORMATION: Oligo 2J of SynInt

<400> SEQUENCE: 10
ggagatcttc aggtactcgt cggcggtcag gcggctgcgg cgcacctcgc tcttggcggc   60
gcgggtggcg gccacgtggt                                              80

<210> SEQ ID NO 11
<211> LENGTH: 70
<212> TYPE: DNA
<213> ORGANISM: Artificial
<220> FEATURE:
<223> OTHER INFORMATION: Oligo 3K of SynInt

<400> SEQUENCE: 11
ccagatctac caggccgccg agagcagccc ctgctggctg cgcctggcca tggagctggc   60
cgtggtgacc                                                         70

<210> SEQ ID NO 12
<211> LENGTH: 70
<212> TYPE: DNA
<213> ORGANISM: Artificial
<220> FEATURE:
<223> OTHER INFORMATION: Oligo 3L of SynInt

<400> SEQUENCE: 12
tccacgatgt cgctccactt catctcgcac aggtcgccca cgcgctggcc ggtcaccacg   60
gccagctcca                                                         70

<210> SEQ ID NO 13
<211> LENGTH: 70
<212> TYPE: DNA
<213> ORGANISM: Artificial
```

-continued

```
<220> FEATURE:
<223> OTHER INFORMATION: Oligo 3M of SynInt

<400> SEQUENCE: 13
aagtggagcg acatcgtgga cggctacctg tacgtggagc agagcaagac cggcgtgaag    60
atcgccatcc                                                          70

<210> SEQ ID NO 14
<211> LENGTH: 70
<212> TYPE: DNA
<213> ORGANISM: Artificial
<220> FEATURE:
<223> OTHER INFORMATION: Oligo 3N of SynInt

<400> SEQUENCE: 14
cagggtctcc ttcatgctga tgcccagggc gtcgatgtgc agggcggtgg ggatggcgat    60
cttcacgccg                                                          70

<210> SEQ ID NO 15
<211> LENGTH: 70
<212> TYPE: DNA
<213> ORGANISM: Artificial
<220> FEATURE:
<223> OTHER INFORMATION: Oligo 3O of SynInt

<400> SEQUENCE: 15
tcagcatgaa ggagaccctg gacaagtgca aggagatcct gggcggcgag accatcatcg    60
ccagcacccg                                                          70

<210> SEQ ID NO 16
<211> LENGTH: 70
<212> TYPE: DNA
<213> ORGANISM: Artificial
<220> FEATURE:
<223> OTHER INFORMATION: Oligo 3P of SynInt

<400> SEQUENCE: 16
gggcgcgcat gaagtagcgg ctcacggtgc cgctgctcag gggctcgcgg cgggtgctgg    60
cgatgatggt                                                          70

<210> SEQ ID NO 17
<211> LENGTH: 65
<212> TYPE: DNA
<213> ORGANISM: Artificial
<220> FEATURE:
<223> OTHER INFORMATION: Oligo 4Q of SynInt

<400> SEQUENCE: 17
ccgcgcgccc gcaaggccag cggcctgagc ttcagggcg acccccccac cttccacgag     60
ctgcg                                                               65

<210> SEQ ID NO 18
<211> LENGTH: 65
<212> TYPE: DNA
<213> ORGANISM: Artificial
<220> FEATURE:
<223> OTHER INFORMATION: Oligo 4R of SynInt

<400> SEQUENCE: 18
aacttgtcgc tgatctgctt ctcgtacagg cgggcgctca ggctgcgcag ctcgtggaag    60
gtggg                                                               65
```

<210> SEQ ID NO 19
<211> LENGTH: 65
<212> TYPE: DNA
<213> ORGANISM: Artificial
<220> FEATURE:
<223> OTHER INFORMATION: Oligo 4S of SynInt

<400> SEQUENCE: 19
aagcagatca gcgacaagtt cgcccagcac ctgctgggcc acaagagcga caccatggcc    60
agcca                                                                65

<210> SEQ ID NO 20
<211> LENGTH: 76
<212> TYPE: DNA
<213> ORGANISM: Artificial
<220> FEATURE:
<223> OTHER INFORMATION: Oligo 4T of SynInt

<400> SEQUENCE: 20
ggagctctta cttgatctcg atcttgtccc actcgcggcc gcggtcgtcg cggtactggc    60
tggccatggt gtcgct                                                    76

<210> SEQ ID NO 21
<211> LENGTH: 1071
<212> TYPE: DNA
<213> ORGANISM: Artificial
<220> FEATURE:
<223> OTHER INFORMATION: Maize-optimized SynInt

<400> SEQUENCE: 21
atgggccgcc gccgcagcca cgagcgccgc gacctgcccc caacctgta catccgcaac      60 aacggctact actgctaccg cgaccccgc accggcaagg agttcggcct gggccgcgac     120
cgccgcatcg ccatcaccga ggccatccag gccaacatcg agctgttcag cggccacaag    180
cacaagcccc tgaccgcccg catcaacagc gacaacagcg tgaccctgca cagctggctg    240
gaccgctacg agaagatcct ggccagccgc ggcatcaagc agaagaccct gatcaactac    300
atgagcaaga tcaaggccat ccgccgcggc ctgcccgacg cccccctgga ggacatcacc    360
accaaggaga tcgccgccat gctgaacggc tacatcgacg agggcaaggc cgccagcgcc    420
aagctgatcc gcagcaccct gagcgacgcc ttccgcgagg ccatcgccga gggccacatc    480
accaccaacc acgtggccgc cacccgcgcc gccaagagcg aggtgcgccg cagccgcctg    540
accgccgacg agtacctgaa gatctaccag gccgccgaga gcagcccctg ctggctgcgc    600
ctggccatgg agctggccgt ggtgaccggc cagcgcgtgg gcgacctgtg cgagatgaag    660
tggagcgaca tcgtggacgg ctacctgtac gtggagcaga gcaagaccgg cgtgaagatc    720
gccatcccca ccgccctgca catcgacgcc ctgggcatca gcatgaagga ccctggac    780 aagtgcaagg agatcctggg cggcgagacc atcatcgcca gcaccgccg cgagcccctg    840 agcagcggca ccgtgagccg ctacttcatg cgcgcccgca aggccagcgg cctgagcttc    900
gagggcgacc cccccacctt ccacgagctg cgcagcctga gcgcccgcct gtacgagaag    960
cagatcagcg acaagttcgc ccagcacctg ctgggccaca gagcgacac catggccagc   1020 cagtaccgcg acgaccgcgg ccgcgagtgg gacaagatcg agatcaagta a            1071

<210> SEQ ID NO 22
<211> LENGTH: 356
<212> TYPE: PRT
<213> ORGANISM: Artificial

```
<220> FEATURE:
<223> OTHER INFORMATION: Amino acid sequence for SynInt

<400> SEQUENCE: 22

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
                20                  25                  30

Lys Glu Phe Gly Leu Gly Arg Asp Arg Arg Ile Ala Ile Thr Glu Ala
            35                  40                  45

Ile Gln Ala Asn Ile Glu Leu Phe Ser Gly His Lys His Lys Pro Leu
50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Glu Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355

<210> SEQ ID NO 23
<211> LENGTH: 70
<212> TYPE: DNA
<213> ORGANISM: Artificial
```

```
<220> FEATURE:
<223> OTHER INFORMATION: Oligo A' for SynHFa

<400> SEQUENCE: 23 gggatccat ggccctgacc aaggccgaga tgagcgagta cctgttcgac aagctgggcc      60
tgagcaagcg                                                            70

<210> SEQ ID NO 24
<211> LENGTH: 70
<212> TYPE: DNA
<213> ORGANISM: Artificial
<220> FEATURE:
<223> OTHER INFORMATION: Oligo B' for SynHFa

<400> SEQUENCE: 24
gggcgcggcg gatctcctcg aagaacagct ccaccagctc cttggcgtcg cgcttgctca     60
ggcccagctt                                                            70

<210> SEQ ID NO 25
<211> LENGTH: 70
<212> TYPE: DNA
<213> ORGANISM: Artificial
<220> FEATURE:
<223> OTHER INFORMATION: Oligo C' for SynHFa

<400> SEQUENCE: 25
cgaggagatc cgccgcgccc tggagaacgg cgagcaggtg aagctgagcg gcttcggcaa     60
cttcgacctg                                                            70

<210> SEQ ID NO 26
<211> LENGTH: 70
<212> TYPE: DNA
<213> ORGANISM: Artificial
<220> FEATURE:
<223> OTHER INFORMATION: Oligo D' for SynHFa

<400> SEQUENCE: 26
atgtcctcgc cggtcttggg gttgcggccg gggcgctggt tcttgtcgcg caggtcgaag     60
ttgccgaagc                                                            70

<210> SEQ ID NO 27
<211> LENGTH: 70
<212> TYPE: DNA
<213> ORGANISM: Artificial
<220> FEATURE:
<223> OTHER INFORMATION: Oligo E' for SynHFa

<400> SEQUENCE: 27
cccaagaccg gcgaggacat ccccatcacc gcccgccgcg tggtgacctt ccgccccggc     60
cagaagctga                                                            70

<210> SEQ ID NO 28
<211> LENGTH: 67
<212> TYPE: DNA
<213> ORGANISM: Artificial
<220> FEATURE:
<223> OTHER INFORMATION: Oligo F' for SynHFa

<400> SEQUENCE: 28
cccagatctc tactcgtcct tggggctggc gttctccacg cggctcttca gcttctggcc    60
ggggcgg                                                              67
```

<210> SEQ ID NO 29
<211> LENGTH: 300
<212> TYPE: DNA
<213> ORGANISM: Artificial
<220> FEATURE:
<223> OTHER INFORMATION: Maize-optimized SynHFa

<400> SEQUENCE: 29

```
atggccctga ccaaggccga gatgagcgag tacctgttcg acaagctggg cctgagcaag      60
cgcgacgcca aggagctggt ggagctgttc ttcgaggaga tccgccgcgc cctggagaac     120
ggcgagcagg tgaagctgag cggcttcggc aacttcgacc tgcgcgacaa gaaccagcgc     180
cccggccgca accccaagac cggcgaggac atccccatca ccgcccgccg cgtggtgacc     240
ttccgccccg gccagaagct gaagagccgc gtggagaacg ccagccccaa ggacgagtag     300
```

<210> SEQ ID NO 30
<211> LENGTH: 99
<212> TYPE: PRT
<213> ORGANISM: Artificial
<220> FEATURE:
<223> OTHER INFORMATION: Amino acid sequence for SynHFa

<400> SEQUENCE: 30

```
Met Ala Leu Thr Lys Ala Glu Met Ser Glu Tyr Leu Phe Asp Lys Leu
 1               5                  10                  15

Gly Leu Ser Lys Arg Asp Ala Lys Glu Leu Val Glu Leu Phe Phe Glu
             20                  25                  30

Glu Ile Arg Arg Ala Leu Glu Asn Gly Glu Gln Val Lys Leu Ser Gly
         35                  40                  45

Phe Gly Asn Phe Asp Leu Arg Asp Lys Asn Gln Arg Pro Gly Arg Asn
     50                  55                  60

Pro Lys Thr Gly Glu Asp Ile Pro Ile Thr Ala Arg Arg Val Val Thr
 65                  70                  75                  80

Phe Arg Pro Gly Gln Lys Leu Lys Ser Arg Val Glu Asn Ala Ser Pro
                 85                  90                  95

Lys Asp Glu
```

<210> SEQ ID NO 31
<211> LENGTH: 70
<212> TYPE: DNA
<213> ORGANISM: Artificial
<220> FEATURE:
<223> OTHER INFORMATION: Oligo a for SynHFb

<400> SEQUENCE: 31

```
ggggatccat gaccaagagc gagctgatcg agcgcctggc cacccagcag agccacatcc      60
ccgccaagac                                                            70
```

<210> SEQ ID NO 32
<211> LENGTH: 70
<212> TYPE: DNA
<213> ORGANISM: Artificial
<220> FEATURE:
<223> OTHER INFORMATION: Oligo b for SynHFb

<400> SEQUENCE: 32

```
ccagggtgct ggccatgtgc tccagcatct ccttcacggc gtcctccacg gtcttggcgg      60
ggatgtggct                                                            70
```

```
<210> SEQ ID NO 33
<211> LENGTH: 70
<212> TYPE: DNA
<213> ORGANISM: Artificial
<220> FEATURE:
<223> OTHER INFORMATION: Oligo c for SynHFb

<400> SEQUENCE: 33
gcacatggcc agcaccctgg cccagggcga gcgcatcgag atccgcggct tcggcagctt      60
cagcctgcac                                                            70

<210> SEQ ID NO 34
<211> LENGTH: 70
<212> TYPE: DNA
<213> ORGANISM: Artificial
<220> FEATURE:
<223> OTHER INFORMATION: Oligo d for SynHFb

<400> SEQUENCE: 34
tccaccttgt cgccggtctt ggggttgcgg ccggtgcggg gggcgcggta gtgcaggctg      60
aagctgccga                                                            70

<210> SEQ ID NO 35
<211> LENGTH: 60
<212> TYPE: DNA
<213> ORGANISM: Artificial
<220> FEATURE:
<223> OTHER INFORMATION: Oligo e for SynHFb

<400> SEQUENCE: 35
aagaccggcg acaaggtgga gctggagggc aagtacgtgc ccacttcaa gcccggcaag       60

<210> SEQ ID NO 36
<211> LENGTH: 62
<212> TYPE: DNA
<213> ORGANISM: Artificial
<220> FEATURE:
<223> OTHER INFORMATION: Oligo f of SynHFb

<400> SEQUENCE: 36
cccagatctc tagccgtaga tgttggcgcg gtcgcgcagc tccttgccgg gcttgaagtg      60
gg                                                                    62

<210> SEQ ID NO 37
<211> LENGTH: 285
<212> TYPE: DNA
<213> ORGANISM: Artificial
<220> FEATURE:
<223> OTHER INFORMATION: Maize-optimized SynHFb

<400> SEQUENCE: 37
atgaccaaga gcgagctgat cgagcgcctg gccacccagc agagccacat ccccgccaag      60
accgtggagg acgccgtgaa ggagatgctg agcacatgg ccagcaccct ggcccagggc     120
gagcgcatcg agatccgcgg cttcggcagc ttcagcctgc actaccgcgc ccccgcacc     180 ggccgcaacc ccaagaccgg cgacaaggtg gagctggagg caagtacgt gccccacttc     240 aagcccggca ggagctgcg cgaccgcgcc aacatctacg gctag                     285

<210> SEQ ID NO 38
<211> LENGTH: 94
<212> TYPE: PRT
<213> ORGANISM: Artificial
```

```
<220> FEATURE:
<223> OTHER INFORMATION: Amino acid sequence for SynHFb

<400> SEQUENCE: 38

Met Thr Lys Ser Glu Leu Ile Glu Arg Leu Ala Thr Gln Gln Ser His
1               5                   10                  15

Ile Pro Ala Lys Thr Val Glu Asp Ala Val Lys Glu Met Leu Glu His
            20                  25                  30

Met Ala Ser Thr Leu Ala Gln Gly Glu Arg Ile Glu Ile Arg Gly Phe
        35                  40                  45

Gly Ser Phe Ser Leu His Tyr Arg Ala Pro Arg Thr Gly Arg Asn Pro
    50                  55                  60

Lys Thr Gly Asp Lys Val Glu Leu Glu Gly Lys Tyr Val Pro His Phe
65                  70                  75                  80

Lys Pro Gly Lys Glu Leu Arg Asp Arg Ala Asn Ile Tyr Gly
                85                  90

<210> SEQ ID NO 39
<211> LENGTH: 75
<212> TYPE: DNA
<213> ORGANISM: Artificial
<220> FEATURE:
<223> OTHER INFORMATION: Oligo I for SynXis

<400> SEQUENCE: 39
ggatccgcca ccatgtacct gaccctgcag gagtggaacg cccgccagcg ccgccccgc       60 agcctggaga ccgtg                                                      75

<210> SEQ ID NO 40
<211> LENGTH: 75
<212> TYPE: DNA
<213> ORGANISM: Artificial
<220> FEATURE:
<223> OTHER INFORMATION: Oligo II for SynXis

<400> SEQUENCE: 40
cgcggccgtc cttcacgggc ggcgggaaga tgcggcactc gcgcacccag cggcgcacgg      60
tctccaggct gcggg                                                      75

<210> SEQ ID NO 41
<211> LENGTH: 75
<212> TYPE: DNA
<213> ORGANISM: Artificial
<220> FEATURE:
<223> OTHER INFORMATION: Oligo III for SynXis

<400> SEQUENCE: 41
gcccgtgaag gacggccgcg agtacctgtt ccacgagagc gccgtgaagg tggacctgaa      60 ccgcccccgtg accgg                                                     75

<210> SEQ ID NO 42
<211> LENGTH: 73
<212> TYPE: DNA
<213> ORGANISM: Artificial
<220> FEATURE:
<223> OTHER INFORMATION: Oligo IV for SynXis

<400> SEQUENCE: 42
ggagctctca gctcttggcc ttcttgccgt tgcggatgcg cttcagcagg ccgccggtca      60
cggggcggtt cag                                                        73
```

<210> SEQ ID NO 43
<211> LENGTH: 219
<212> TYPE: DNA
<213> ORGANISM: Artificial
<220> FEATURE:
<223> OTHER INFORMATION: Maize-optimized SynXis

<400> SEQUENCE: 43

```
atgtacctga ccctgcagga gtggaacgcc cgccagcgcc gccccgcag cctggagacc      60
gtgcgccgct gggtgcgcga gtgccgcatc ttcccgccgc ccgtgaagga cggccgcgag    120
tacctgttcc acgagagcgc cgtgaaggtg gacctgaacc gccccgtgac cggcggcctg    180
ctgaagcgca tccgcaacgg caagaaggcc aagagctga                           219
```

<210> SEQ ID NO 44
<211> LENGTH: 72
<212> TYPE: PRT
<213> ORGANISM: Artificial
<220> FEATURE:
<223> OTHER INFORMATION: Amino acid sequence for SynXis

<400> SEQUENCE: 44

Met Tyr Leu Thr Leu Gln Glu Trp Asn Ala Arg Gln Arg Arg Pro Arg
1               5                   10                  15

Ser Leu Glu Thr Val Arg Arg Trp Val Arg Glu Cys Arg Ile Phe Pro
            20                  25                  30

Pro Pro Val Lys Asp Gly Arg Glu Tyr Leu Phe His Glu Ser Ala Val
        35                  40                  45

Lys Val Asp Leu Asn Arg Pro Val Thr Gly Gly Leu Leu Lys Arg Ile
    50                  55                  60

Arg Asn Gly Lys Lys Ala Lys Ser
65                  70

<210> SEQ ID NO 45
<211> LENGTH: 35
<212> TYPE: DNA
<213> ORGANISM: Artificial
<220> FEATURE:
<223> OTHER INFORMATION: Oligonucleotide

<400> SEQUENCE: 45

```
cccgcgccgc caagagcaag gtgcgccgca gccgc                                35
```

<210> SEQ ID NO 46
<211> LENGTH: 35
<212> TYPE: DNA
<213> ORGANISM: Artificial
<220> FEATURE:
<223> OTHER INFORMATION: Oligonucleotide

<400> SEQUENCE: 46

```
gcggctgcgg cgcaccttgc tcttggcggc gcggg                                35
```

<210> SEQ ID NO 47
<211> LENGTH: 10
<212> TYPE: DNA
<213> ORGANISM: Artificial
<220> FEATURE:
<223> OTHER INFORMATION: Oligonucleotide

<400> SEQUENCE: 47

```
gatcactagt                                                            10
```

<210> SEQ ID NO 48
<211> LENGTH: 35
<212> TYPE: DNA
<213> ORGANISM: Artificial
<220> FEATURE:
<223> OTHER INFORMATION: Oligonucleotide

<400> SEQUENCE: 48
gcgtgggcga cctgtgcaag atgaagtgga gcgac                                35

<210> SEQ ID NO 49
<211> LENGTH: 35
<212> TYPE: DNA
<213> ORGANISM: Artificial
<220> FEATURE:
<223> OTHER INFORMATION: Oligonucleotide

<400> SEQUENCE: 49
gtcgctccac ttcatcttgc acaggtcgcc cacgc                                35

<210> SEQ ID NO 50
<211> LENGTH: 29
<212> TYPE: DNA
<213> ORGANISM: Artificial
<220> FEATURE:
<223> OTHER INFORMATION: Forward primer

<400> SEQUENCE: 50
gggtacgtaa gtttctgctt ctacctttg                                       29

<210> SEQ ID NO 51
<211> LENGTH: 29
<212> TYPE: DNA
<213> ORGANISM: Artificial
<220> FEATURE:
<223> OTHER INFORMATION: Reverse primer

<400> SEQUENCE: 51
ccccagctgc acatcaacaa attttggtc                                       29

<210> SEQ ID NO 52
<211> LENGTH: 14
<212> TYPE: DNA
<213> ORGANISM: Artificial
<220> FEATURE:
<223> OTHER INFORMATION: Oligonucleotide

<400> SEQUENCE: 52
catgagctcg ccac                                                       14

<210> SEQ ID NO 53
<211> LENGTH: 14
<212> TYPE: DNA
<213> ORGANISM: Artificial
<220> FEATURE:
<223> OTHER INFORMATION: Oligonucleotide

<400> SEQUENCE: 53
catggtggcg agct                                                       14

<210> SEQ ID NO 54
<211> LENGTH: 35
<212> TYPE: DNA
<213> ORGANISM: Artificial
<220> FEATURE:
<223> OTHER INFORMATION: Oligonucleotide

```
<400> SEQUENCE: 54
tcgatgaagc ctgcttttt atactaactt gagcg                           35

<210> SEQ ID NO 55
<211> LENGTH: 35
<212> TYPE: DNA
<213> ORGANISM: Artificial
<220> FEATURE:
<223> OTHER INFORMATION: Oligonucleotide

<400> SEQUENCE: 55
gtaccgctca agttagtata aaaaagcagg cttca                          35

<210> SEQ ID NO 56
<211> LENGTH: 28
<212> TYPE: DNA
<213> ORGANISM: Artificial
<220> FEATURE:
<223> OTHER INFORMATION: Forward primer

<400> SEQUENCE: 56
ggaagcttct gttacaggtc actaatac                                  28

<210> SEQ ID NO 57
<211> LENGTH: 27
<212> TYPE: DNA
<213> ORGANISM: Artificial
<220> FEATURE:
<223> OTHER INFORMATION: Reverse primer

<400> SEQUENCE: 57
cctcgagaaa tcaaataatg attttat                                   27

<210> SEQ ID NO 58
<211> LENGTH: 40
<212> TYPE: DNA
<213> ORGANISM: Artificial
<220> FEATURE:
<223> OTHER INFORMATION: Forward primer

<400> SEQUENCE: 58
cctcgagtga agcctgcttt tttatactaa gttggcatta                     40

<210> SEQ ID NO 59
<211> LENGTH: 39
<212> TYPE: DNA
<213> ORGANISM: Artificial
<220> FEATURE:
<223> OTHER INFORMATION: Oligonucleotide

<400> SEQUENCE: 59
tcgacggtac cagatctact agttgcggcc gcgctagcg                      39

<210> SEQ ID NO 60
<211> LENGTH: 39
<212> TYPE: DNA
<213> ORGANISM: Artificial
<220> FEATURE:
<223> OTHER INFORMATION: Oligonucleotide

<400> SEQUENCE: 60
gatccgctag cgcggccgca actagtagat ctggtaccg                      39

<210> SEQ ID NO 61
```

-continued

```
<211> LENGTH: 12
<212> TYPE: DNA
<213> ORGANISM: Artificial
<220> FEATURE:
<223> OTHER INFORMATION: Oligonucleotide

<400> SEQUENCE: 61
agctgcggcc gc                                                           12

<210> SEQ ID NO 62
<211> LENGTH: 10
<212> TYPE: DNA
<213> ORGANISM: Artificial
<220> FEATURE:
<223> OTHER INFORMATION: Oligonucleotide

<400> SEQUENCE: 62
agctagatct                                                              10

<210> SEQ ID NO 63
<211> LENGTH: 10
<212> TYPE: DNA
<213> ORGANISM: Artificial
<220> FEATURE:
<223> OTHER INFORMATION: Oligonucleotide

<400> SEQUENCE: 63
agctactagt                                                              10

<210> SEQ ID NO 64
<211> LENGTH: 3452
<212> TYPE: DNA
<213> ORGANISM: Artificial
<220> FEATURE:
<223> OTHER INFORMATION: PMI with introns

<400> SEQUENCE: 64
atgcaaaaac tcattaactc agtgcaaaac tatgcctggg gcagcaaaac ggcgttgact        60
gaactttatg gtatggaaaa tccgtccagc cagccgatgg ccgagctgtg gatgggcgca      120
catccgaaaa gcagttcacg agtgcagaat gccgccggag atatcgtttc actgcgtgat      180
gtgattgaga gtgataaatc gactctgctc ggagaggccg ttgccaaacg ctttggcgaa      240
ctgcctttcc tgttcaaagt attatgcgca gcacagccac tctccattca ggttcatcca      300
aacaaacaca attctgaaat cggttttgcc aaagaaaatg ccgcaggtac caagctgcga      360
atcttcgttt ttttaaggaa ttctcgatct ttatggtgta taggctctgg gttttctgtt      420
ttttgtatct cttaggattt tgtaaattcc gatccgcggt tgatgaaaga ataacgtatt      480
ctttcatcaa gatctgaagt tcctattctc tagaaagtat aggaacttcg gatctttcta      540
tggccactta gtagtatatt tcaaaaattc tccaatcgag ttcttcattc gcattttcag      600
tcattttctc ttcgacgttg tttttaagcc tgggtattac tcctatttag ttgaactctg      660
cagcaatctt agaaaattag ggttttgagg tttcgatttc tctaggtaac cgatctattg      720
cattcatctg aatttctgca tatatgtctt agatttctga taagcttacg atacgttagg      780
tgtaattgaa gtttatttt caagagtgtt atttttgtt tctgaatttt tcaggtatcc        840
cgatggatgc cgccgagcgt aactataaag atcctaacca aagccggag ctggtttttg       900 cgctgacgcc tttccttgcg atgaacgcgt tcgtgaatt tccgagatt gtctccctac        960 tccagccggt cgcaggtatt agtactattc ttttgtttct ctaatcagaa acaattaaac     1020
ttttaaaatg ttagtatatt cttaggtaga atacgtggcc gttattagtt ggatgcagta     1080
```

```
tacatatgga aataggaaaa aatgtacgga gttagtttgt ttaatatttt tcctttctag   1140
atttttttct ctaattgtga ttttttcttt atcatccaat taattgaatt tttcaaaatt   1200
attattcaaa aacgatggta aaaaaaaaca atgaatttta aagttattaa aatcacggaa   1260
aacaattcta taaaagttat gacgttgcat gggaaatata cgggttcggg tcaatttaag   1320
tggatcgggt catattttct tgagtaatta aaagttaatg atttaattta atgaaaaaat   1380
taataactaa tcaacacgaa atttgaatgt ttttgttcgt tacaggtgca catccggcga   1440
ttgctcactt tttacaacag cctgatgccg aacgtttaag cgaactgttc gccagcctgt   1500
tgaatatgca gggtgaagaa aaatcccgcg cgctggcgat tttaaaatcg gccctcgata   1560
gccagcaggg tgaaccgtgg caaacgattc gtttaatttc tgaattttac ccggaagaca   1620
gcggtctgtt ctccccgcta ttgctgaatg tggtgaaatt gaaccctggc gaagcgatgt   1680
tcctgttcgc tgaaacaccg cacgcttacc tgcaaggtat atatatgaat cgatttctcc   1740
cttttgattt atgaatctgc tggtgctttg atcatattat ctgattgatt tgtgaatcaa   1800
aactgcaatt atccgatggt ttcgatcatt taaatctcgt ctcgtgagtg ttaatgtagt   1860
tgcatattta gtaaccgatg atttcgattt cagtttgatt tttgatcatc ttcgcattgc   1920
actagtgaat ctctcacata tcgtgttttg atatttgatt aacgtttctc ttcattgatc   1980
tcttcatggt catggttcca attacagttt atgaattaca tgaacatgat ccgtcgatgt   2040
tcttgtgttt gatttgcgtt tttatggtgt ttctctcctg ttgattactg tttaagagtg   2100
agctgttaac acttaatgat tggctaggat ttagattttg tctattcttt atagtaaaaa   2160
gttaacatca ttgaaactaa ggacaatatc ctaatttggc ggtagtgtat tagtgtcccc   2220
taatgttttg ttccagattt gtgactgtgg atcaacaata tcacgtgaaa ccttaaaacc   2280
atatcgaatt ttataataag aactttaggg aatactcttg tgttgacact ttcgaggtga   2340
aacatatcac tttgtgggga tataattgaa taagcaagtg ggtcatgatt ggtttcagca   2400
attgttaaat aacatctcaa tacttttttgg atctggttta ggtataaggg acttctttag   2460
ttttgtagta cattgtttca cacttgttct taacatttct gtattacagg tgtggcgctg   2520
gaagtgatgg caaactccga taacgtgctg cgtgcgggtc tgacgcctaa atacattgat   2580
attccggaac tggttgccaa tgtgaaattc gaagccaaac cggctaacca gttgttgacc   2640
cagccggtga aacaaggtta ttaacgtttt ccacctctct tgtttttta tagtattctt   2700 cttagcctta ctagattgat ccaccttcag gggttaccga acattgccat tttaaactga   2760
aaacatatgt tccttcgttt tgttttacgg taactagcaa aacattggac attcttaagt   2820
atgtatgtct gagttttgag ttttgtacta gagagtctaa caaagctaag acaaaattta   2880
ataacgtaat tgtgtgagct ttaatgcaat tttattcggt tgttgtaaat tgtgtcatgt   2940
gttttcgtgg taataccggg tacttcatat ctagataact attcatgtat aagctaacaa   3000
gtagggtatc aatgtccaaa tgattgcttg ccattgtaac aaagaactct gtcttcttta   3060
tttgctttgc tcaaaatggc tctgtttcat ccattgctta tgacgagaaa cggcatattt   3120
aaccatgact ggttcatatg gtattgaaat attttttcat tgatgcaggt gcagaactgg   3180
acttcccgat tccagtggat gattttgcct tctcgctgca tgaccttagt gataaagaaa   3240
ccaccattag ccagcagagt gccgccattt tgttctgcgt cgaaggcgat gcaacgttgt   3300
ggaaaggttc tcagcagtta cagcttaaac cgggtgaatc agcgtttatt gccgccaacg   3360
aatcaccggt gactgtcaaa ggccacggcc gtttagcgcg tgtttacaac aagctgtaag   3420
```

-continued agcttactga aaaaattaac atctcttgct aa　　　　　　　　　　　　　　　　3452

<210> SEQ ID NO 65
<211> LENGTH: 47
<212> TYPE: DNA
<213> ORGANISM: Artificial
<220> FEATURE:
<223> OTHER INFORMATION: Oligonucleotide

<400> SEQUENCE: 65
aattggtacc tgaagcctgc tttttatac taacttgagc gcctagg　　　　　　　　47

<210> SEQ ID NO 66
<211> LENGTH: 47
<212> TYPE: DNA
<213> ORGANISM: Artificial
<220> FEATURE:
<223> OTHER INFORMATION: Oligonucleotide

<400> SEQUENCE: 66
aattcctagg cgctcaagtt agtataaaaa agcaggcttc aggtacc　　　　　　　　47

<210> SEQ ID NO 67
<211> LENGTH: 32
<212> TYPE: DNA
<213> ORGANISM: Artificial
<220> FEATURE:
<223> OTHER INFORMATION: Forward primer

<400> SEQUENCE: 67
ttgactggca ggtaccaagc tgcgaatctt cg　　　　　　　　　　　　　　　32

<210> SEQ ID NO 68
<211> LENGTH: 32
<212> TYPE: DNA
<213> ORGANISM: Artificial
<220> FEATURE:
<223> OTHER INFORMATION: Reverse primer

<400> SEQUENCE: 68
attggccacc acctgaaaaa ttcagaaaca aa　　　　　　　　　　　　　　　32

<210> SEQ ID NO 69
<211> LENGTH: 29
<212> TYPE: DNA
<213> ORGANISM: Artificial
<220> FEATURE:
<223> OTHER INFORMATION: Forward primer

<400> SEQUENCE: 69
ggatccaacc atgttacgtc ctgtagaaa　　　　　　　　　　　　　　　　29

<210> SEQ ID NO 70
<211> LENGTH: 32
<212> TYPE: DNA
<213> ORGANISM: Artificial
<220> FEATURE:
<223> OTHER INFORMATION: Reverse primer

<400> SEQUENCE: 70
cagcttggta cctgccagtc aacagacgcg ac　　　　　　　　　　　　　　　32

<210> SEQ ID NO 71
<211> LENGTH: 32
<212> TYPE: DNA
<213> ORGANISM: Artificial

```
<220> FEATURE:
<223> OTHER INFORMATION: Forward primer

<400> SEQUENCE: 71
ttgactggca ggtaccaagc tgcgaatctt cg                                      32

<210> SEQ ID NO 72
<211> LENGTH: 30
<212> TYPE: DNA
<213> ORGANISM: Artificial
<220> FEATURE:
<223> OTHER INFORMATION: Reverse primer

<400> SEQUENCE: 72
gtcgactcat tgtttgcctc cctgctgcgg                                         30

<210> SEQ ID NO 73
<211> LENGTH: 42
<212> TYPE: DNA
<213> ORGANISM: Artificial
<220> FEATURE:
<223> OTHER INFORMATION: Oligonucleotide

<400> SEQUENCE: 73
gatctcgctc aagttagtat aaaaaagcag gcttcagcta gc                           42

<210> SEQ ID NO 74
<211> LENGTH: 42
<212> TYPE: DNA
<213> ORGANISM: Artificial
<220> FEATURE:
<223> OTHER INFORMATION: Oligonucleotide

<400> SEQUENCE: 74
gatcgctagc tgaagcctgc tttttatac taacttgagc ga                            42

<210> SEQ ID NO 75
<211> LENGTH: 410
<212> TYPE: DNA
<213> ORGANISM: Artificial
<220> FEATURE:
<223> OTHER INFORMATION: CMPS promoter fragment

<400> SEQUENCE: 75
ggatcctggc agacaaagtg gcagacatac tgtcccacaa atgaagatgg aatctgtaaa        60
agaaaacgcg tgaataatg cgtctgacaa aggttaggtc ggctgccttt aatcaatacc        120
aaagtggtcc ctaccacgat ggaaaaactg tgcagtcggt ttggcttttt ctgacgaaca       180
aataagattc gtggccgaca ggtggggtc caccatgtga aggcatcttc agactccaat        240
aatggagcaa tgacgtaagg gcttacgaaa taagtaaggg tagtttggga aatgtccact       300
cacccgtcag tctataaata cttagcccct ccctcattgt taagggagca aaatctcaga      360
gagatagtcc tagagagaga aagagagcaa gtagcctaga agtaggatcc                 410

<210> SEQ ID NO 76
<211> LENGTH: 10
<212> TYPE: DNA
<213> ORGANISM: Artificial
<220> FEATURE:
<223> OTHER INFORMATION: Oligonucleotide

<400> SEQUENCE: 76
actagtggcc                                                              10
```

<210> SEQ ID NO 77
<211> LENGTH: 21
<212> TYPE: DNA
<213> ORGANISM: Artificial
<220> FEATURE:
<223> OTHER INFORMATION: Forward primer

<400> SEQUENCE: 77
ggaagcttct gttacaggtc a                                              21

<210> SEQ ID NO 78
<211> LENGTH: 27
<212> TYPE: DNA
<213> ORGANISM: Artificial
<220> FEATURE:
<223> OTHER INFORMATION: Reverse primer

<400> SEQUENCE: 78
cctcgagaaa tcaaataatg attttat                                        27

<210> SEQ ID NO 79
<211> LENGTH: 22
<212> TYPE: DNA
<213> ORGANISM: Artificial
<220> FEATURE:
<223> OTHER INFORMATION: Oligonucleotide

<400> SEQUENCE: 79
agctggtacc caattgggta cc                                             22

<210> SEQ ID NO 80
<211> LENGTH: 22
<212> TYPE: DNA
<213> ORGANISM: Artificial
<220> FEATURE:
<223> OTHER INFORMATION: Oligonucleotide

<400> SEQUENCE: 80
tcgacctagg caattgccta gg                                             22

<210> SEQ ID NO 81
<211> LENGTH: 22
<212> TYPE: DNA
<213> ORGANISM: Artificial
<220> FEATURE:
<223> OTHER INFORMATION: Oligonucleotide

<400> SEQUENCE: 81
agctgctagc ggatccgcta gc                                             22

<210> SEQ ID NO 82
<211> LENGTH: 22
<212> TYPE: DNA
<213> ORGANISM: Artificial
<220> FEATURE:
<223> OTHER INFORMATION: Oligonucleotide

<400> SEQUENCE: 82
tcgaagatct cggccgagat ct                                             22

<210> SEQ ID NO 83
<211> LENGTH: 10
<212> TYPE: DNA
<213> ORGANISM: Artificial
<220> FEATURE:
<223> OTHER INFORMATION: Oligonucleotide

```
<400> SEQUENCE: 83
actagtggcc                                                               10

<210> SEQ ID NO 84
<211> LENGTH: 36
<212> TYPE: DNA
<213> ORGANISM: Artificial
<220> FEATURE:
<223> OTHER INFORMATION: Forward primer

<400> SEQUENCE: 84
gggcaattgg gtacctacag gtcactaata ccatct                                  36

<210> SEQ ID NO 85
<211> LENGTH: 36
<212> TYPE: DNA
<213> ORGANISM: Artificial
<220> FEATURE:
<223> OTHER INFORMATION: Reverse primer

<400> SEQUENCE: 85
gggcaattgc ctaggcaaat aatgatttta ttttga                                  36

<210> SEQ ID NO 86
<211> LENGTH: 33
<212> TYPE: DNA
<213> ORGANISM: Artificial
<220> FEATURE:
<223> OTHER INFORMATION: Forward primer

<400> SEQUENCE: 86
ggatccgcta gctacaggtc actaatacca tct                                     33

<210> SEQ ID NO 87
<211> LENGTH: 30
<212> TYPE: DNA
<213> ORGANISM: Artificial
<220> FEATURE:
<223> OTHER INFORMATION: Reverse primer

<400> SEQUENCE: 87
gggagatctc aaataatgat tttattttga                                         30

<210> SEQ ID NO 88
<211> LENGTH: 10
<212> TYPE: DNA
<213> ORGANISM: Artificial
<220> FEATURE:
<223> OTHER INFORMATION: Oligonucleotide

<400> SEQUENCE: 88
cgcgactagt                                                               10

<210> SEQ ID NO 89
<211> LENGTH: 14
<212> TYPE: DNA
<213> ORGANISM: Artificial
<220> FEATURE:
<223> OTHER INFORMATION: Oligonucleotide

<400> SEQUENCE: 89
gtacggctcg agcc                                                          14

<210> SEQ ID NO 90
```

```
<211> LENGTH: 12
<212> TYPE: DNA
<213> ORGANISM: Artificial
<220> FEATURE:
<223> OTHER INFORMATION: Oligonucleotide

<400> SEQUENCE: 90
ctaggagatc tc                                                         12

<210> SEQ ID NO 91
<211> LENGTH: 10
<212> TYPE: DNA
<213> ORGANISM: Artificial
<220> FEATURE:
<223> OTHER INFORMATION: Oligonucleotide

<400> SEQUENCE: 91
agctactagt                                                            10

<210> SEQ ID NO 92
<211> LENGTH: 14
<212> TYPE: DNA
<213> ORGANISM: Artificial
<220> FEATURE:
<223> OTHER INFORMATION: Oligonucleotide

<400> SEQUENCE: 92
ccagatctgg tgca                                                       14

<210> SEQ ID NO 93
<211> LENGTH: 14
<212> TYPE: DNA
<213> ORGANISM: Artificial
<220> FEATURE:
<223> OTHER INFORMATION: Oligonucleotide

<400> SEQUENCE: 93
gtacggacta gtcc                                                       14

<210> SEQ ID NO 94
<211> LENGTH: 10
<212> TYPE: DNA
<213> ORGANISM: Artificial
<220> FEATURE:
<223> OTHER INFORMATION: Oligonucleotide

<400> SEQUENCE: 94
agctctcgag                                                            10

<210> SEQ ID NO 95
<211> LENGTH: 14
<212> TYPE: DNA
<213> ORGANISM: Artificial
<220> FEATURE:
<223> OTHER INFORMATION: Oligonucleotide

<400> SEQUENCE: 95
ccggatccgg catg                                                       14

<210> SEQ ID NO 96
<211> LENGTH: 31
<212> TYPE: DNA
<213> ORGANISM: Artificial
<220> FEATURE:
<223> OTHER INFORMATION: Forward primer

<400> SEQUENCE: 96
```

```
ctaaggatcc aagatcaaag gcttaaaaag c                              31
```

<210> SEQ ID NO 97
<211> LENGTH: 30
<212> TYPE: DNA
<213> ORGANISM: Artificial
<220> FEATURE:
<223> OTHER INFORMATION: Reverse primer

<400> SEQUENCE: 97

```
ggaatctaga tgtataaacc aaatgagcag                                30
```

<210> SEQ ID NO 98
<211> LENGTH: 43
<212> TYPE: DNA
<213> ORGANISM: Artificial
<220> FEATURE:
<223> OTHER INFORMATION: Oligonucleotide

<400> SEQUENCE: 98

```
gatctgggga caagtttgta caaaaaagca ggcttcagct agc                 43
```

<210> SEQ ID NO 99
<211> LENGTH: 43
<212> TYPE: DNA
<213> ORGANISM: Artificial
<220> FEATURE:
<223> OTHER INFORMATION: Oligonucleotide

<400> SEQUENCE: 99

```
gatcgctagc tgaagcctgc tttttgtac aaacttgtcc cca                  43
```

<210> SEQ ID NO 100
<211> LENGTH: 46
<212> TYPE: DNA
<213> ORGANISM: Artificial
<220> FEATURE:
<223> OTHER INFORMATION: Oligonucleotide

<400> SEQUENCE: 100

```
aattggtacc tgaacccagc tttcttgtac aaagtggtcc cctagg              46
```

<210> SEQ ID NO 101
<211> LENGTH: 46
<212> TYPE: DNA
<213> ORGANISM: Artificial
<220> FEATURE:
<223> OTHER INFORMATION: Oligonucleotide

<400> SEQUENCE: 101

```
aattcctagg ggaccacttt gtacaagaaa gctgggttca ggtacc              46
```

<210> SEQ ID NO 102
<211> LENGTH: 12
<212> TYPE: DNA
<213> ORGANISM: Artificial
<220> FEATURE:
<223> OTHER INFORMATION: Oligonucleotide

<400> SEQUENCE: 102

```
tcgaagcatg ct                                                   12
```

<210> SEQ ID NO 103
<211> LENGTH: 10
<212> TYPE: DNA

```
<213> ORGANISM: Artificial
<220> FEATURE:
<223> OTHER INFORMATION: Oligonucleotide

<400> SEQUENCE: 103
gatcacgcgt                                                              10

<210> SEQ ID NO 104
<211> LENGTH: 12
<212> TYPE: DNA
<213> ORGANISM: Artificial
<220> FEATURE:
<223> OTHER INFORMATION: Oligonucleotide

<400> SEQUENCE: 104
ccggatccgg gc                                                           12

<210> SEQ ID NO 105
<211> LENGTH: 38
<212> TYPE: DNA
<213> ORGANISM: Artificial
<220> FEATURE:
<223> OTHER INFORMATION: Oligonucleotide

<400> SEQUENCE: 105
gatccgctca agttagtata aaaaagcagg cttcatga                               38

<210> SEQ ID NO 106
<211> LENGTH: 38
<212> TYPE: DNA
<213> ORGANISM: Artificial
<220> FEATURE:
<223> OTHER INFORMATION: Oligonucleotide

<400> SEQUENCE: 106
gatctcatga agcctgcttt tttatactaa cttgagcg                               38

<210> SEQ ID NO 107
<211> LENGTH: 35
<212> TYPE: DNA
<213> ORGANISM: Artificial
<220> FEATURE:
<223> OTHER INFORMATION: Forward primer

<400> SEQUENCE: 107
gggccctctg ttacaggtca ctaataccat ctaag                                  35

<210> SEQ ID NO 108
<211> LENGTH: 31
<212> TYPE: DNA
<213> ORGANISM: Artificial
<220> FEATURE:
<223> OTHER INFORMATION: Reverse primer

<400> SEQUENCE: 108
actagtgaaa tcaaataatg attttatttt g                                      31

<210> SEQ ID NO 109
<211> LENGTH: 37
<212> TYPE: DNA
<213> ORGANISM: Artificial
<220> FEATURE:
<223> OTHER INFORMATION: Forward primer

<400> SEQUENCE: 109
agggcccagc ctgcttttttt atactaagtt ggcatta                               37
```

<210> SEQ ID NO 110
<211> LENGTH: 35
<212> TYPE: DNA
<213> ORGANISM: Artificial
<220> FEATURE:
<223> OTHER INFORMATION: Reverse primer

<400> SEQUENCE: 110
tactagtcaa ataatgattt tattttgact gatag                      35

<210> SEQ ID NO 111
<211> LENGTH: 37
<212> TYPE: DNA
<213> ORGANISM: Artificial
<220> FEATURE:
<223> OTHER INFORMATION: Oligonucleotide

<400> SEQUENCE: 111
cttgatgaaa gaataacgta ttctttcatc aagggcc                    37

<210> SEQ ID NO 112
<211> LENGTH: 37
<212> TYPE: DNA
<213> ORGANISM: Artificial
<220> FEATURE:
<223> OTHER INFORMATION: Oligonucleotide

<400> SEQUENCE: 112
cttgatgaaa gaatacgtta ttctttcatc aaggtac                    37

<210> SEQ ID NO 113
<211> LENGTH: 34
<212> TYPE: DNA
<213> ORGANISM: Artificial
<220> FEATURE:
<223> OTHER INFORMATION: Forward primer

<400> SEQUENCE: 113
tagatctgtt acaggtcact aataccatct aagt                       34

<210> SEQ ID NO 114
<211> LENGTH: 35
<212> TYPE: DNA
<213> ORGANISM: Artificial
<220> FEATURE:
<223> OTHER INFORMATION: Reverse primer

<400> SEQUENCE: 114
atggccacgc tcaagttagt ataaaaaagc tgaac                      35

<210> SEQ ID NO 115
<211> LENGTH: 29
<212> TYPE: DNA
<213> ORGANISM: Artificial
<220> FEATURE:
<223> OTHER INFORMATION: Oligonucleotide

<400> SEQUENCE: 115
ggagatcttg aagcctgctt ttttatact                             29

<210> SEQ ID NO 116
<211> LENGTH: 32
<212> TYPE: DNA
<213> ORGANISM: Artificial
<220> FEATURE:

-continued

```
<223> OTHER INFORMATION: Oligonucleotide

<400> SEQUENCE: 116
cccctaggaa atcaaataat gattttattt tg                              32

<210> SEQ ID NO 117
<211> LENGTH: 27
<212> TYPE: DNA
<213> ORGANISM: Artificial
<220> FEATURE:
<223> OTHER INFORMATION: Oligonucleotide

<400> SEQUENCE: 117
ggtaccaagc tgcgaatctt cgttttt                                    27

<210> SEQ ID NO 118
<211> LENGTH: 27
<212> TYPE: DNA
<213> ORGANISM: Artificial
<220> FEATURE:
<223> OTHER INFORMATION: Oligonucleotide

<400> SEQUENCE: 118
ggccatagaa agatctggaa tttacaa                                    27

<210> SEQ ID NO 119
<211> LENGTH: 24
<212> TYPE: DNA
<213> ORGANISM: Artificial
<220> FEATURE:
<223> OTHER INFORMATION: Oligonucleotide

<400> SEQUENCE: 119
agatctgtta caggtcacta atac                                       24

<210> SEQ ID NO 120
<211> LENGTH: 35
<212> TYPE: DNA
<213> ORGANISM: Artificial
<220> FEATURE:
<223> OTHER INFORMATION: Oligonucleotide

<400> SEQUENCE: 120
cctaggcgct caagttagta taaaaaagct gaacg                           35

<210> SEQ ID NO 121
<211> LENGTH: 28
<212> TYPE: DNA
<213> ORGANISM: Artificial
<220> FEATURE:
<223> OTHER INFORMATION: Oligonucleotide

<400> SEQUENCE: 121
ccgctagctg aagcctgctt ttttatac                                   28

<210> SEQ ID NO 122
<211> LENGTH: 30
<212> TYPE: DNA
<213> ORGANISM: Artificial
<220> FEATURE:
<223> OTHER INFORMATION: Oligonucleotide

<400> SEQUENCE: 122
ggagatctga aatcaaataa tgattttatt                                 30
```

<210> SEQ ID NO 123
<211> LENGTH: 29
<212> TYPE: DNA
<213> ORGANISM: Artificial
<220> FEATURE:
<223> OTHER INFORMATION: Oligonucleotide

<400> SEQUENCE: 123
ggtctagatg aagcctgctt ttttatact                                29

<210> SEQ ID NO 124
<211> LENGTH: 27
<212> TYPE: DNA
<213> ORGANISM: Artificial
<220> FEATURE:
<223> OTHER INFORMATION: Oligonucleotide

<400> SEQUENCE: 124
gctagctctg ttacaggtca ctaatac                                  27

<210> SEQ ID NO 125
<211> LENGTH: 35
<212> TYPE: DNA
<213> ORGANISM: Artificial
<220> FEATURE:
<223> OTHER INFORMATION: Oligonucleotide

<400> SEQUENCE: 125
agatctcgct caagttagta taaaaaagct gaacg                         35

<210> SEQ ID NO 126
<211> LENGTH: 27
<212> TYPE: DNA
<213> ORGANISM: Artificial
<220> FEATURE:
<223> OTHER INFORMATION: Oligonucleotide

<400> SEQUENCE: 126
tctagatctg ttacaggtca ctaatac                                  27

<210> SEQ ID NO 127
<211> LENGTH: 30
<212> TYPE: DNA
<213> ORGANISM: Artificial
<220> FEATURE:
<223> OTHER INFORMATION: Oligonucleotide

<400> SEQUENCE: 127
cgagctcagc tgatgaaaaa gcctgaactc                               30

<210> SEQ ID NO 128
<211> LENGTH: 30
<212> TYPE: DNA
<213> ORGANISM: Artificial
<220> FEATURE:
<223> OTHER INFORMATION: Oligonucleotide

<400> SEQUENCE: 128
tgcagcaagc ttcactggat tttggtttta                               30

<210> SEQ ID NO 129
<211> LENGTH: 30
<212> TYPE: DNA
<213> ORGANISM: Artificial
<220> FEATURE:
<223> OTHER INFORMATION: Oligonucleotide

<400> SEQUENCE: 129
tgcagctcta gacactggat tttggtttta					30

<210> SEQ ID NO 130
<211> LENGTH: 30
<212> TYPE: DNA
<213> ORGANISM: Artificial
<220> FEATURE:
<223> OTHER INFORMATION: Oligonucleotide

<400> SEQUENCE: 130
ggctgaggta cctgaagcct gcttttttat					30

<210> SEQ ID NO 131
<211> LENGTH: 30
<212> TYPE: DNA
<213> ORGANISM: Artificial
<220> FEATURE:
<223> OTHER INFORMATION: Oligonucleotide

<400> SEQUENCE: 131
cgtagcccta gggaaatcaa ataatgattt					30

<210> SEQ ID NO 132
<211> LENGTH: 30
<212> TYPE: DNA
<213> ORGANISM: Artificial
<220> FEATURE:
<223> OTHER INFORMATION: Oligonucleotide

<400> SEQUENCE: 132
ggctgaggta cctctgttac aggtcactaa					30

<210> SEQ ID NO 133
<211> LENGTH: 30
<212> TYPE: DNA
<213> ORGANISM: Artificial
<220> FEATURE:
<223> OTHER INFORMATION: Oligonucleotide

<400> SEQUENCE: 133
cgtagcccta ggcgctcaag ttagtataaa					30

<210> SEQ ID NO 134
<211> LENGTH: 30
<212> TYPE: DNA
<213> ORGANISM: Artificial
<220> FEATURE:
<223> OTHER INFORMATION: Oligonucleotide

<400> SEQUENCE: 134
ggctgaggta cctgaagcct gcttttttat					30

<210> SEQ ID NO 135
<211> LENGTH: 30
<212> TYPE: DNA
<213> ORGANISM: Artificial
<220> FEATURE:
<223> OTHER INFORMATION: Oligonucleotide

<400> SEQUENCE: 135
cgtagcgagc tcgaaatcaa ataatgattt					30

<210> SEQ ID NO 136
<211> LENGTH: 30

```
<212> TYPE: DNA
<213> ORGANISM: Artificial
<220> FEATURE:
<223> OTHER INFORMATION: Oligonucleotide

<400> SEQUENCE: 136
ggctgaggta cctctgttac aggtcactaa                                30

<210> SEQ ID NO 137
<211> LENGTH: 30
<212> TYPE: DNA
<213> ORGANISM: Artificial
<220> FEATURE:
<223> OTHER INFORMATION: Oligonucleotide

<400> SEQUENCE: 137
cgtagcgagc tccgctcaag ttagtataaa                                30

<210> SEQ ID NO 138
<211> LENGTH: 12
<212> TYPE: DNA
<213> ORGANISM: Artificial
<220> FEATURE:
<223> OTHER INFORMATION: Oligonucleotide

<400> SEQUENCE: 138
ctaggagatc tc                                                   12

<210> SEQ ID NO 139
<211> LENGTH: 10
<212> TYPE: DNA
<213> ORGANISM: Artificial
<220> FEATURE:
<223> OTHER INFORMATION: Oligonucleotide

<400> SEQUENCE: 139
gtacgaattc                                                      10

<210> SEQ ID NO 140
<211> LENGTH: 12
<212> TYPE: DNA
<213> ORGANISM: Artificial
<220> FEATURE:
<223> OTHER INFORMATION: Oligonucleotide

<400> SEQUENCE: 140
aattgtctag ac                                                   12

<210> SEQ ID NO 141
<211> LENGTH: 26
<212> TYPE: DNA
<213> ORGANISM: Artificial
<220> FEATURE:
<223> OTHER INFORMATION: Oligonucleotide

<400> SEQUENCE: 141
gctagcctcc gtccgacgac tcaatc                                    26

<210> SEQ ID NO 142
<211> LENGTH: 34
<212> TYPE: DNA
<213> ORGANISM: Artificial
<220> FEATURE:
<223> OTHER INFORMATION: Oligonucleotide

<400> SEQUENCE: 142
```
ggtaccggcg cgccgcaaca tgagatggca ccgt                                     34

<210> SEQ ID NO 143
<211> LENGTH: 10
<212> TYPE: DNA
<213> ORGANISM: Artificial
<220> FEATURE:
<223> OTHER INFORMATION: Oligonucleotide

<400> SEQUENCE: 143
ctaggcgcgc                                                                10

<210> SEQ ID NO 144
<211> LENGTH: 12
<212> TYPE: DNA
<213> ORGANISM: Artificial
<220> FEATURE:
<223> OTHER INFORMATION: Oligonucleotide

<400> SEQUENCE: 144
gtacggcgcg cc                                                             12

<210> SEQ ID NO 145
<211> LENGTH: 28
<212> TYPE: DNA
<213> ORGANISM: Artificial
<220> FEATURE:
<223> OTHER INFORMATION: Forward primer

<400> SEQUENCE: 145
gggctagctc tgttacaggt cactaata                                            28

<210> SEQ ID NO 146
<211> LENGTH: 30
<212> TYPE: DNA
<213> ORGANISM: Artificial
<220> FEATURE:
<223> OTHER INFORMATION: Reverse primer

<400> SEQUENCE: 146
ccctcgagcg ctcaagttag tataaaaaag                                          30

<210> SEQ ID NO 147
<211> LENGTH: 30
<212> TYPE: DNA
<213> ORGANISM: Artificial
<220> FEATURE:
<223> OTHER INFORMATION: Forward primer

<400> SEQUENCE: 147
ggggcgcgcc tctgttacag gtcactaata                                          30

<210> SEQ ID NO 148
<211> LENGTH: 30
<212> TYPE: DNA
<213> ORGANISM: Artificial
<220> FEATURE:
<223> OTHER INFORMATION: Reverse primer

<400> SEQUENCE: 148
cccctaggcg ctcaagttag tataaaaaag                                          30

<210> SEQ ID NO 149
<211> LENGTH: 14
<212> TYPE: DNA
<213> ORGANISM: Artificial

```
<220> FEATURE:
<223> OTHER INFORMATION: Oligonucleotide

<400> SEQUENCE: 149
gtacggcaat tgcc                                                           14

<210> SEQ ID NO 150
<211> LENGTH: 34
<212> TYPE: DNA
<213> ORGANISM: Artificial
<220> FEATURE:
<223> OTHER INFORMATION: Oligonucleotide

<400> SEQUENCE: 150
tcgagagcct gcttttttgt acaaacttgt cccc                                     34

<210> SEQ ID NO 151
<211> LENGTH: 34
<212> TYPE: DNA
<213> ORGANISM: Artificial
<220> FEATURE:
<223> OTHER INFORMATION: Oligonucleotide

<400> SEQUENCE: 151
aattggggac aagtttgtac aaaaaagcag gctc                                     34

<210> SEQ ID NO 152
<211> LENGTH: 38
<212> TYPE: DNA
<213> ORGANISM: Artificial
<220> FEATURE:
<223> OTHER INFORMATION: Oligonucleotide

<400> SEQUENCE: 152
aattgaccca gcttcttgt acaaagtggt ccccctgca                                 38

<210> SEQ ID NO 153
<211> LENGTH: 30
<212> TYPE: DNA
<213> ORGANISM: Artificial
<220> FEATURE:
<223> OTHER INFORMATION: Oligonucleotide

<400> SEQUENCE: 153
ggggaccact ttgtacaaga aagctgggtc                                          30

<210> SEQ ID NO 154
<211> LENGTH: 28
<212> TYPE: DNA
<213> ORGANISM: Artificial
<220> FEATURE:
<223> OTHER INFORMATION: Forward primer

<400> SEQUENCE: 154
gtaattaagc ttttccacct ctcttgtt                                            28

<210> SEQ ID NO 155
<211> LENGTH: 32
<212> TYPE: DNA
<213> ORGANISM: Artificial
<220> FEATURE:
<223> OTHER INFORMATION: Reverse primer

<400> SEQUENCE: 155
gatcctgcag caatggaaaa atatttcaat ac                                       32
```

```
<210> SEQ ID NO 156
<211> LENGTH: 20
<212> TYPE: DNA
<213> ORGANISM: Artificial
<220> FEATURE:
<223> OTHER INFORMATION: Forward primer

<400> SEQUENCE: 156
ggcggtagtg tattagtgtc                                              20

<210> SEQ ID NO 157
<211> LENGTH: 20
<212> TYPE: DNA
<213> ORGANISM: Artificial
<220> FEATURE:
<223> OTHER INFORMATION: Reverse primer

<400> SEQUENCE: 157
gatgctcttc gtccagatca                                              20

<210> SEQ ID NO 158
<211> LENGTH: 20
<212> TYPE: DNA
<213> ORGANISM: Artificial
<220> FEATURE:
<223> OTHER INFORMATION: Forward primer

<400> SEQUENCE: 158
ggaagcgacc aacgccttga                                              20

<210> SEQ ID NO 159
<211> LENGTH: 20
<212> TYPE: DNA
<213> ORGANISM: Artificial
<220> FEATURE:
<223> OTHER INFORMATION: Reverse primer

<400> SEQUENCE: 159
tgcgacacct gcgtcgaaga                                              20

<210> SEQ ID NO 160
<211> LENGTH: 30
<212> TYPE: DNA
<213> ORGANISM: Artificial
<220> FEATURE:
<223> OTHER INFORMATION: Forward primer

<400> SEQUENCE: 160
gggctagctg aagcctgctt ttttatacta                                   30

<210> SEQ ID NO 161
<211> LENGTH: 32
<212> TYPE: DNA
<213> ORGANISM: Artificial
<220> FEATURE:
<223> OTHER INFORMATION: Reverse primer

<400> SEQUENCE: 161
ccctcgagaa atcaaataat gattttattt tg                                32

<210> SEQ ID NO 162
<211> LENGTH: 32
<212> TYPE: DNA
<213> ORGANISM: Artificial
<220> FEATURE:
<223> OTHER INFORMATION: Forward primer
```

```
<400> SEQUENCE: 162
ggggcgcgcc tgaagcctgc tttttttatac ta                              32

<210> SEQ ID NO 163
<211> LENGTH: 32
<212> TYPE: DNA
<213> ORGANISM: Artificial
<220> FEATURE:
<223> OTHER INFORMATION: Reverse primer

<400> SEQUENCE: 163
cccctaggaa atcaaataat gattttattt tg                              32

<210> SEQ ID NO 164
<211> LENGTH: 20
<212> TYPE: DNA
<213> ORGANISM: Artificial
<220> FEATURE:
<223> OTHER INFORMATION: Forward primer

<400> SEQUENCE: 164
gaagcgaagg ttgtggatct                                            20

<210> SEQ ID NO 165
<211> LENGTH: 34
<212> TYPE: DNA
<213> ORGANISM: Beet curly top virus

<400> SEQUENCE: 165
ggggccatcc ggtaatatta atgcggatgg cccc                            34

<210> SEQ ID NO 166
<211> LENGTH: 37
<212> TYPE: DNA
<213> ORGANISM: Artificial
<220> FEATURE:
<223> OTHER INFORMATION: Forward primer

<400> SEQUENCE: 166
ggcctcgagg atatcttggc aattgtagat gctattt                         37

<210> SEQ ID NO 167
<211> LENGTH: 34
<212> TYPE: DNA
<213> ORGANISM: Artificial
<220> FEATURE:
<223> OTHER INFORMATION: Reverse primer

<400> SEQUENCE: 167
ggcctcgaga tatcacaacg aacacttcct atga                            34

<210> SEQ ID NO 168
<211> LENGTH: 28
<212> TYPE: DNA
<213> ORGANISM: Artificial
<220> FEATURE:
<223> OTHER INFORMATION: Forward primer

<400> SEQUENCE: 168
ggcgcgcctc acatcaacat ctttagct                                   28

<210> SEQ ID NO 169
<211> LENGTH: 28
<212> TYPE: DNA
```

```
<213> ORGANISM: Artificial
<220> FEATURE:
<223> OTHER INFORMATION: Reverse primer

<400> SEQUENCE: 169
ggacgcgtat tgaatcgggc tctcttca                                          28

<210> SEQ ID NO 170
<211> LENGTH: 14
<212> TYPE: DNA
<213> ORGANISM: Artificial
<220> FEATURE:
<223> OTHER INFORMATION: Oligonucleotide

<400> SEQUENCE: 170
gatcggtacg tacc                                                         14

<210> SEQ ID NO 171
<211> LENGTH: 12
<212> TYPE: DNA
<213> ORGANISM: Artificial
<220> FEATURE:
<223> OTHER INFORMATION: Oligonucleotide

<400> SEQUENCE: 171
aattggcgcg cc                                                           12

<210> SEQ ID NO 172
<211> LENGTH: 31
<212> TYPE: DNA
<213> ORGANISM: Bacteriophage lambda

<400> SEQUENCE: 172
tgaagcctgc tttttatac taacttgagc g                                       31

<210> SEQ ID NO 173
<211> LENGTH: 243
<212> TYPE: DNA
<213> ORGANISM: Bacteriophage lambda

<400> SEQUENCE: 173
tctgttacag gtcactaata ccatctaagt agttgattca tagtgactgc atatgttgtg       60
ttttacagta ttatgtagtc tgttttttat gcaaaatcta atttaatata ttgatattta      120
tatcatttta cgtttctcgt tcagcttttt tatactaagt tggcattata aaaaagcatt      180
gcttatcaat ttgttgcaac gaacaggtca ctatcagtca aaataaaatc attatttgat      240
ttc                                                                    243

<210> SEQ ID NO 174
<211> LENGTH: 108
<212> TYPE: DNA
<213> ORGANISM: Bacteriophage lambda

<400> SEQUENCE: 174
tgaagcctgc tttttatac taagttggca ttataaaaaa gcattgctta tcaatttgtt       60
gcaacgaaca ggtcactatc agtcaaaata aaatcattat tgatttc                   108

<210> SEQ ID NO 175
<211> LENGTH: 166
<212> TYPE: DNA
<213> ORGANISM: Bacteriophage lambda

<400> SEQUENCE: 175
```

```
tctgttacag gtcactaata ccatctaagt agttgattca tagtgactgc atatgttgtg    60
ttttacagta ttatgtagtc tgtttttat gcaaaatcta atttaatata ttgatattta    120
tatcatttta cgtttctcgt tcagctttt tatactaact tgagcg                    166
```

```
<210> SEQ ID NO 176
<211> LENGTH: 25
<212> TYPE: DNA
<213> ORGANISM: Artificial
<220> FEATURE:
<223> OTHER INFORMATION: AttB1

<400> SEQUENCE: 176
agcctgcttt tttgtacaaa cttgt                                          25
```

```
<210> SEQ ID NO 177
<211> LENGTH: 233
<212> TYPE: DNA
<213> ORGANISM: Artificial
<220> FEATURE:
<223> OTHER INFORMATION: AttP1

<400> SEQUENCE: 177
caaataatga ttttattttg actgatagtg acctgttcgt tgcaacaaat tgatgagcaa    60 tgcttttta taatgccaac tttgtacaaa aaagctgaac gagaaacgta aaatgatata    120
aatatcaata tattaaatta gattttgcat aaaaaacaga ctacataata ctgtaaaaca    180
caacatatcc agtcactatg aatcaactac ttagatggta ttagtgacct gta          233
```

```
<210> SEQ ID NO 178
<211> LENGTH: 25
<212> TYPE: DNA
<213> ORGANISM: Artificial
<220> FEATURE:
<223> OTHER INFORMATION: AttB2

<400> SEQUENCE: 178
acccagcttt cttgtacaaa gtggt                                          25
```

```
<210> SEQ ID NO 179
<211> LENGTH: 233
<212> TYPE: DNA
<213> ORGANISM: Artificial
<220> FEATURE:
<223> OTHER INFORMATION: AttP2

<400> SEQUENCE: 179
tacaggtcac taataccatc taagtagttg attcatagtg actggatatg ttgtgtttta    60
cagtattatg tagtctgttt tttatgcaaa atctaattta atatattgat atttatatca    120
ttttacgttt ctcgttcagc tttcttgtac aaagttggca ttataagaaa gcattgctta    180
tcaatttgtt gcaacgaaca ggtcactatc agtcaaaata aatcattat ttg           233
```

```
<210> SEQ ID NO 180
<211> LENGTH: 100
<212> TYPE: DNA
<213> ORGANISM: Artificial
<220> FEATURE:
<223> OTHER INFORMATION: AttL1

<400> SEQUENCE: 180
agcctgcttt tttgtacaaa gttggcatta taaaaaagca ttgctcatca atttgttgca    60
```

```
acgaacaggt cactatcagt caaaataaaa tcattatttg                      100
```

<210> SEQ ID NO 181
<211> LENGTH: 158
<212> TYPE: DNA
<213> ORGANISM: Artificial
<220> FEATURE:
<223> OTHER INFORMATION: AttR1

<400> SEQUENCE: 181

```
tacaggtcac taataccatc taagtagttg attcatagtg actggatatg ttgtgtttta   60
cagtattatg tagtctgttt tttatgcaaa atctaattta atatattgat atttatatca   120
ttttacgttt ctcgttcagc ttttttgtac aaacttgt                            158
```

<210> SEQ ID NO 182
<211> LENGTH: 100
<212> TYPE: DNA
<213> ORGANISM: Artificial
<220> FEATURE:
<223> OTHER INFORMATION: AttL2

<400> SEQUENCE: 182

```
acccagcttt cttgtacaaa gttggcatta taagaaagca ttgcttatca atttgttgca   60
acgaacaggt cactatcagt caaaataaaa tcattatttg                          100
```

<210> SEQ ID NO 183
<211> LENGTH: 158
<212> TYPE: DNA
<213> ORGANISM: Artificial
<220> FEATURE:
<223> OTHER INFORMATION: AttR2

<400> SEQUENCE: 183

```
tacaggtcac taataccatc taagtagttg attcatagtg actggatatg ttgtgtttta   60
cagtattatg tagtctgttt tttatgcaaa atctaattta atatattgat atttatatca   120
ttttacgttt ctcgttcagc tttcttgtac aaagtggt                            158
```

<210> SEQ ID NO 184
<211> LENGTH: 30
<212> TYPE: DNA
<213> ORGANISM: Artificial
<220> FEATURE:
<223> OTHER INFORMATION: Forward primer

<400> SEQUENCE: 184

```
caggtatata tatgaatcga tttctccctt                                    30
```

<210> SEQ ID NO 185
<211> LENGTH: 32
<212> TYPE: DNA
<213> ORGANISM: Artificial
<220> FEATURE:
<223> OTHER INFORMATION: Reverse primer

<400> SEQUENCE: 185

```
tcgtccagat catcctgtaa tacagaaatg tt                                 32
```

LAMBDA INTEGRASE MEDIATED RECOMBINATION IN PLANTS

CROSS REFERENCE TO RELATED APPLICATIONS

This application claims the benefit of U.S. Provisional Application Ser. No. 60/369,041, filed Mar. 29, 2002, and U.S. Provisional Application Ser. No. 60/425,512, filed Nov. 12, 2002, both of which are hereby incorporated by reference in their entireties.

FIELD OF THE INVENTION

The invention relates generally to methods for plant transformation using an integrase and, more particularly, to methods for integrating foreign DNA at a pre-selected site in the genome of a plant. The invention also relates to the excision or inversion of a DNA sequence within a plant cell using an integrase. The invention also relates to transgenic plants obtained by such methods.

BACKGROUND

In recent years, the development of genetic engineering techniques has had dramatic implications for the field of crop improvement. Using these techniques, beneficial traits can be introduced into almost any crop, and improved crops can be rapidly obtained. The use of genetic engineering obviates the need for lengthy processes that introduce the desired trait through conventional breeding methods.

Present plant transformation methods generally lead to the random integration of transgenes into a host genome. This random integration is problematic for a variety of reasons, including, for example, potentially variable transgene expression resulting from different integration loci, so-called "position effect," and the risk of mutating the host genome during integration of the transgene. As a result of these potential problems, a large number of transformation events must be screened and tested in order to obtain a transgenic plant exhibiting the desired level of transgene expression without concomitant abnormalities resulting from an inadvertent sequence interruption at an important locus in the plant's genome. Moreover, if a transgenic plant is to be modified by the subsequent addition of one or more transgenes, random integration of the additional transgene(s) renders the implementation of breeding programs for plants containing these multiple transgenes cumbersome and difficult, especially for elite plant lines.

One approach to targeted transgene integration employs site-specific recombinases. Site-specific recombination systems have been identified in several prokaryotic and lower eukaryotic organisms. Such systems typically comprise one or more proteins that recognize two copies of a specific nucleotide sequence, cleave and ligate those nucleotide sequences, and thereby provide a precise, site-specific exchange of genetic information. Several site-specific recombinases are known in the art. These include, but are not limited to, e.g., the bacteriophage P1 Cre/lox system (Austin et al. (1981) Cell 25: 729-736), the R/RS recombinase system from the pSR1 plasmid of the yeast *Zygosaccharomyces rouxii* (Araki et al. (1985) J. Mol. Biol. 182: 191-203), the Gin/gix system of phage Mu (Maeser and Kahlmann (1991) Mol. Gen.Genet. 230: 170-176), the FLP/FRT recombinase system from the 2 μm plasmid of the yeast *Saccharomyces cerevisiae* (Broach et al. (1982) Cell 29: 227-234), and the Int recombinase from bacteriophage Lambda (Landy (1989) Annu. Rev. Biochem. 58: 912-949; Landy (1993) Curr. Opin. Genet. Dev. 3: 699-707; Lorbach et al. (2000) J. Mol. Biol. 296: 1175-1181; and WO 01/16345).

DESCRIPTION OF THE DRAWINGS

The drawings form a part of the present specification and are included to further demonstrate certain aspects of the methods disclosed herein.

SUMMARY

Figure 1:
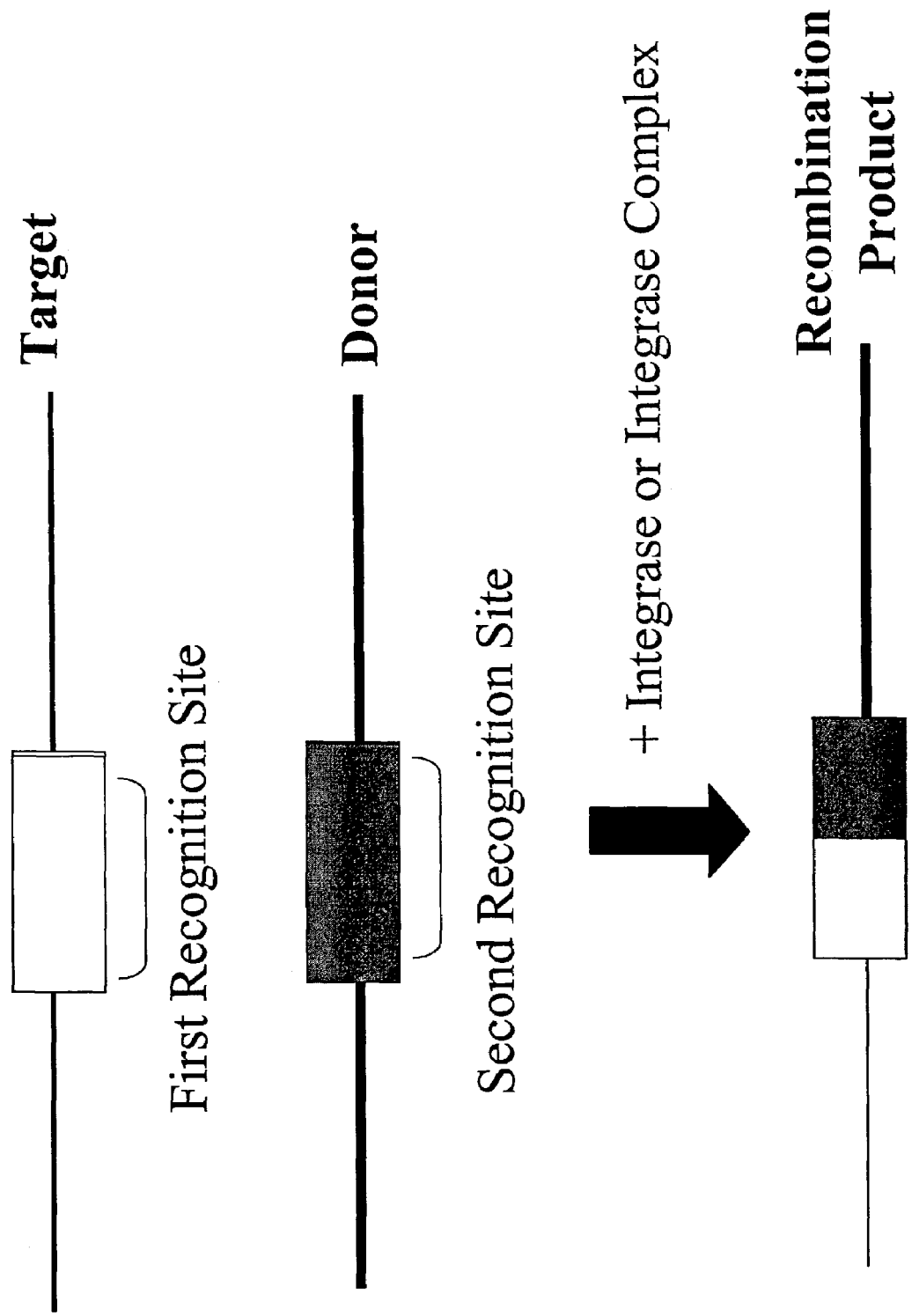
FIG. 1 represents a single crossover recombination event. A first Int recognition site is present on the target molecule, and a second Int recognition site is present on the donor molecule. Nucleotide sequences flanking the recognitions sites of the target and donor molecules are represented by thin and thick lines, respectively. The donor molecule can be a circular DNA molecule or a linear DNA molecule. An integrase or integrase complex is introduced to the target and donor molecules, and an Int-mediated recombination product is formed. The recombination process is termed a "single crossover" because one Int recognition site on each of the target and donor molecules participates in the integrase-mediated recombination.

The present disclosure provides methods for effecting the targeted integration of a DNA molecule into the genome of a host cell using a recombinase. The methods disclosed herein can be used with a variety of host cells, including, for example, dicotyledonous and monocotyledonous plant cells. The present disclosure provides a method for effecting site-specific recombination of DNA within a plant cell, comprising: introducing into the plant cell a target nucleotide sequence comprising a first Int recognition site; introducing into the plant cell a donor nucleotide sequence comprising a second Int recognition site; and introducing into the plant cell an integrase or integrase complex.

DETAILED DESCRIPTION

Definitions

An "attB/attP reaction" or a "B/P reaction" is a recombination reaction between an attB recognition site and an attP recognition site mediated by an Int.

An "attL/attR reaction" or an "L/R reaction" is a recombination reaction between an attL recognition site and an attR recognition site mediated by an Int.

An "att site" is an attachment site on a DNA molecule for an integrase or integrase complex. As used herein, "att site" is generally used interchangeably with "recognition site," described in greater detail below. Generally, "att site" is used to refer to a particular type of recognition site, such as, for example, an attB, an attP, an attL, or an attR site.

"Chromosomally-integrated" or "integrated" refers to the integration of a foreign gene or nucleotide sequence into a host genome by covalent bonds that are formed with the host DNA.

"Deletion reaction" and "excision reaction" are used interchangeably and refer to a recombination reaction between two recognition sites that are on the same DNA molecule and are in direct orientation with respect to one another. This reaction results in the removal of a nucleotide sequence that is positioned between the two recognition sites.

"Direct orientation" refers to an orientation of two or more recognition sites such that 15 base pair core regions of the recognition sites are oriented in the same 5' to 3' direction. "Direct repeat," as used herein, refers to two or more recognition sites that are in direct orientation with respect to each other.

"Donor," "donor molecule," "donor sequence," and "donor DNA" are used interchangeably to refer to a nucleotide sequence that has been selected to undergo recombination with the target DNA sequence using site-directed recombination. The donor nucleotide sequence can be any nucleotide sequence, such as, for example, a gene, an expression cassette, a promoter, a molecular marker, a selectable marker, a visible marker, a portion of any of these, or the like. The donor DNA sequence comprises at least one recombinase recognition site.

"Endogenous" as used herein means "of the same origin," i.e., derived from a host cell.

"Expression cassette" as used herein includes a nucleotide sequence that is capable of directing or driving the expression of another nucleotide sequence in an appropriate host cell. An expression cassette typically comprises a promoter operably linked to a nucleotide sequence, such as a nucleotide sequence of interest, for example, which is operably linked to a termination signal. The expression cassette also typically comprises sequences needed for proper translation of the nucleotide sequence. The nucleotide sequence of interest usually codes for a protein of interest but can also code for a functional RNA of interest, for example antisense RNA or a non-translated RNA that, in the sense or antisense direction, inhibits expression of a particular gene, e.g., antisense RNA. The expression cassette comprising the nucleotide sequence can be chimeric, meaning that at least one of its components is heterologous with respect to at least one of its other components. The expression cassette can include endogenous DNA that has been obtained in a recombinant form and is useful for heterologous expression. Typically, however, the expression cassette is heterologous with respect to the host; that is, the particular DNA sequence of the expression cassette does not occur naturally in the host cell and must be introduced into the host cell or an ancestor of the host cell through a transformation event. The expression of the nucleotide sequence in the expression cassette can be under the control of any suitable promoter, such as for example, either a constitutive promoter or an inducible promoter that initiates transcription only when the host cell is exposed to some particular external stimulus. In the case of a multicellular organism, such as a plant, the promoter can also be specific to a particular tissue or organ or stage of development.

A "foreign" gene or DNA refers to a gene or a nucleotide sequence that is not normally found in the host organism but can be introduced by gene transfer. Foreign genes and DNA that are not integrated into the genome of the host cell are referred to as "extrachromosomal."

The term "gene" is used broadly to include any segment of a nucleotide sequence associated with a biological function. Thus, a gene can include a coding sequence either with or without the regulatory sequences required for its expression. Further, a gene can include both exon and intron sequences or can include only exon sequences. A gene can also include non-expressed DNA segments that, for example, form recognition sequences for other proteins. A "portion of a gene" or "an incomplete gene" as used herein means a part of a gene that is non-functional because it does not contain all of the sequence needed for functionality. The portion can be the 5' portion of a gene (i.e., the sequence at the 3' end of the gene is not present), or the portion can be the 3' portion of a gene (i.e., the sequence at the 5' end of the gene is not present). The 5' and 3' portions can be non-functional on their own, but when the 5' and 3' portions are operably linked, the gene is "functional" or "complete."

"Gene of interest," "sequence of interest," and "DNA of interest" are used interchangeably and include any nucleotide sequence which, when transferred to a plant, confers upon the plant a desired characteristic, such as virus resistance, insect resistance, abiotic stress resistance, disease resistance, resistance to other pests, herbicide tolerance, improved nutritional value, improved performance in an industrial process, or altered reproductive capability, for example. The sequence of interest can also be one that is transferred to plants for the production of commercially valuable enzymes or metabolites in the plant.

"Genome" refers to the complete genetic material of an organism.

"Heterologous" as used herein means "of different natural origin," i.e., representing a non-natural state. For example, if a host cell is transformed with a gene derived from another organism, particularly from another species, that gene is heterologous with respect to both the host cell and descendants of the host cell that carry the gene. Similarly, "heterologous" refers to a nucleotide sequence which is derived from a natural or original cell type and is inserted into that same natural or original cell type, but which is present in a non-natural state, such as, for example, in a different copy number, under the control of different regulatory elements, or the like.

To "identify" a recombination product means that the recombination product is detected and distinguished from both the target and donor sequences. There are many means for identifying a recombination product. For example, a selectable marker gene can be used, whereby site-specific integration results in the selectable marker gene becoming operatively linked with a promoter only in a recombinant product. Alternatively, a visible marker gene can be used, whereby a gain or loss of marker gene expression identifies a recombination product. Alternatively, a negative selectable marker gene can be used, whereby a loss or lack of expression of the marker gene identifies a recombination product. Additionally, molecular markers that are characteristic of the target sequence and/or donor sequence can be used, such that the molecular marker pattern is unique for the recombination product.

"Integrase" as used herein refers to a bacteriophage λ-derived integrase, including wild-type integrase and any of a variety of mutant or modified integrases. "Integrase complex" as used herein refers to a complex comprising integrase and integration host factor (IHF). "Integrase complex" as used herein may also refer to a complex comprising integrase, integration host factor, and a bacteriophage λ-derived excisionase (Xis). Further, as used herein, "Int" refers to both "integrase" and "integrase complex."

An "integrase-mediated recombination product" is a recombination product formed between target and donor sequences in the presence of an integrase or integrase complex. The integrase-mediated recombination results in strand exchange between at least one recombinase recognition site on the target and at least one recombinase recognition site on the donor, whereby a recombination product is formed. Consistent with the usage defined above, "Int-mediated recombination" or "Int-mediated recombination product" means a recombination or recombination product that is mediated by either an integrase or an integrase complex.

"Intramolecular recombination" refers to recombination between recognition sites on a single nucleic acid molecule. Recombination between recognition sites on different molecules is termed "intermolecular recombination."

"Intrachromosomal recombination" refers to recombination between recognition sites on a single chromosome. Recombination between recognition sites on different chromosomes is termed "interchromosomal recombination."

An "inversion reaction" refers to an intramolecular recombination reaction between two att sites that are in inverted orientation with respect to each other. For example, an inversion reaction can be effected by an intramolecular reaction between either an attB site and an attP site in inverted orientation or an attL site and an attR site in inverted orientation.

"Inverted orientation" refers to an orientation of two recognition sites such that 15 base pair core regions of the recognition sites are oriented in the opposite 5' to 3' direction.

"Operably linked" or "operatively linked" refers to the relationship between two or more nucleotide sequences that interact physically or functionally. For example, a promoter or regulatory nucleotide sequence is said to be operably linked to a nucleotide sequence that codes for an RNA or a protein if the two sequences are situated such that the regulatory nucleotide sequence will affect the expression level of the coding or structural nucleotide sequence. A 5' portion of a gene is operatively or operably linked with a 3' portion of a gene if the two portions are situated to form a functional gene.

The term "plant," as used herein, refers to, without limitation, whole plants, plant organs (e.g., leaves, stems, roots, fruit, etc.), seeds, plant cells and progeny of plant cells, plant tissue, plant cell or tissue cultures, protoplasts, callus, and any groups of plant cells organized into structural and/or functional units. A plant "regenerated" from a plant cell means that all cells of the plant are derived from that plant cell. The class of plants that can be used with the disclosed methods is generally as broad as the class of higher plants amenable to transformation techniques, including both monocotyledonous and dicotyledonous plants. Preferred plants include, without limitation, Acacia, alfalfa, aneth, apple, apricot, artichoke, Arabidopsis, arugula, asparagus, avocado, banana, barley, bean, beet, blackberry, blueberry, broccoli, Brussels sprouts, cabbage, canola, cantaloupe, carrot, cassava, cauliflower, celery, cherry, chicory, clover, cilantro, citrus, clementines, coffee, corn, cotton, cucumber, eggplant, endive, escarole, eucalyptus, fennel, figs, garlic, gourd, grape, grapefruit, hemp, honey dew, jicama, kiwifruit, lettuce, leeks, lemon, lime, mango, maize, melon, mushroom, nectarine, nut, oat, okra, onion, orange, an ornamental plant, papaya, parsley, pea, peach, peanut, pear, pepper, persimmon, pineapple, plantain, plum, pomegranate, potato, pumpkin, quince, radicchio, radish, raspberry, rice, rye, safflower, sorghum, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, zucchini, and woody plants such as coniferous and deciduous trees. Once a sequence of interest has been transformed into a particular plant species, the sequence of interest can be propagated in that species or can be moved into other varieties of the same species, including commercial varieties, using traditional breeding techniques.

"Plant cell" refers to a structural and physiological unit of a plant, comprising a protoplast and a cell wall, and includes, without limitation, seed suspension cultures, embryos, meristematic regions, callus tissue, leaves, roots, shoots, gametophytes, sporophytes, pollen, and microspores. The plant cell can be in the form of an isolated single cell, a cultured cell, or a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes, and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant, such as a root, stem, leaf, flower bud, or embryo.

"Plant tissue" as used herein means a group of plant cells, including any tissue of a plant either in planta or in culture, organized into a structural and functional unit. The term includes, but is not limited to, whole plants, plant organs, plant seeds, tissue culture, and any groups of plant cells organized into structural and/or functional units. The use of this term in conjunction with, or in the absence of, any specific type of plant tissue, as listed above or otherwise embraced by this definition, is not intended to be exclusive of any other type of plant tissue.

"Recognition site" or "recombination site" refers to a nucleotide sequence that can be recognized by a recombinase protein. The recognition site is the nucleotide sequence at which binding, cleavage, and strand exchange is performed by the recombinase and any associated accessory proteins. Integrase or integrase complex recognizes recognition sites comprising an attB, attL, attR, attP, and/or suitable mutations of such sites. The attB site can be approximately 25-30 bps and includes two 9 bp core sequences and a 7 bp overlap (or spacer) region, whereas the attP site can be approximately 240 bps and comprises binding sites for an integrase and one or more accessory proteins. The attB and attP sites can be recombined together by Int or, alternatively, the attL and attR sites can be recombined together by Int.

"Recombinase" refers to an enzyme that is capable of performing site-specific recombination of DNA. Recombinase enzymes possess endonuclease and ligase activities. A recombinase can function either as a single protein or as a part of a complex of proteins. As used herein integrase and integrase complex are recombinases.

Generally, if a recombinase-mediated recombination occurs between two recombinase recognition sites that are on the same molecule, the recombination reaction results in either the deletion or inversion of a sequence flanked by the two recognition sites. If a recombinase-mediated recombination occurs between two recombinase recognition sites that are on different molecules (e.g., between a recombinase recognition site on a target sequence and a recombinase recognition site on a donor sequence), the recombination reaction results in the insertion of a sequence from one of the molecules into the other molecule (e.g., the insertion of a donor sequence into a target molecule). When particular recognition sites that are capable of recombining are present on both the target and the donor (e.g., an attB site on the target and an attP site on the donor or an attL site on the target and an attR site on the donor), the recombination product represents an exchange of nucleotide sequence between the two sites, resulting in two new sites. Each of these new sites contains a part of the original recognition sites from both the donor and target molecules. For example, when recombination occurs between an attB site on the target and an attP site on the donor, attL and attR sites are created in the recombination products. Additionally, the newly formed attL and attR sites are flanked on one side by sequence obtained from the donor molecule and on the other side by sequence obtained from the target molecule.

Figure 2:
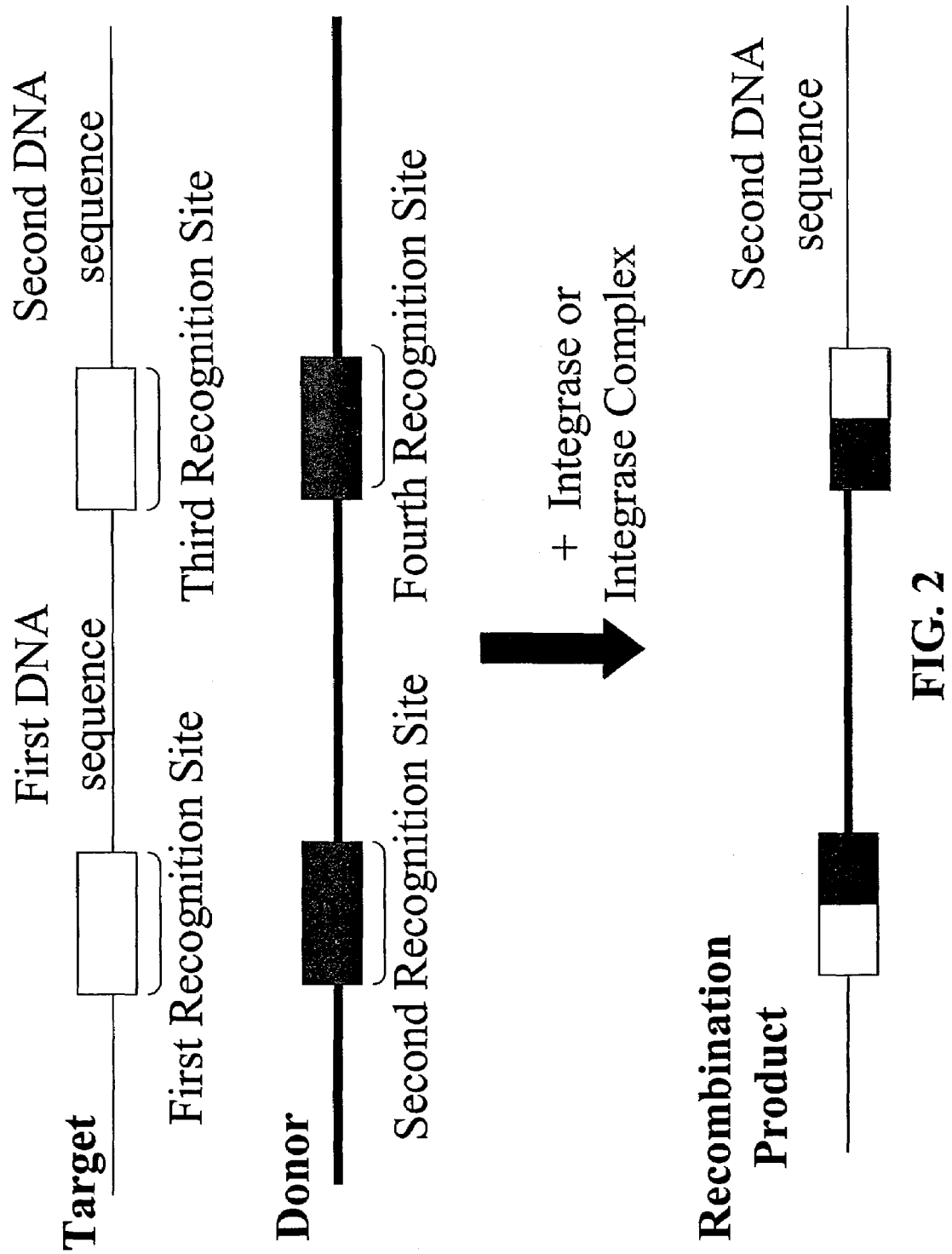
FIG. 2 represents a double crossover recombination event. First and third Int recognition sites are present on the target molecule, and second and fourth Int recognition sites are present on the donor molecule. An integrase or integrase complex is introduced to the target and donor molecules, and an Int-mediated recombination product is formed. The recombination process is termed a "double crossover" because two Int recognition sites on each of the target and donor molecules participate in the integrase-mediated recombination.

A recombination product can be obtained using one recognition site on the donor molecule and one on the target molecule, thereby generating a "single-crossover" recombination product (FIG. 1). Alternatively, two recognition sites on the target molecule and two on the donor molecule can be used. Recombination between two sites on the donor and two sites on the target generates a "double crossover" recombination product. If the recombination sites on the donor molecule flank the sequence of interest that is to be exchanged with the target molecule, a double crossover recombination with the target molecule results in a recombination product wherein the sequence of interest replaces the nucleotide sequence that was originally between the recognition sites within the target molecule. The exchange of nucleotide sequences between the target and donor molecules through recombination is termed "sequence exchange," "sequence replacement," or "cassette exchange" (FIG. 2).

"Regulatory element" includes a nucleotide sequence that is involved in conferring upon a host cell the expression of another nucleotide sequence, such as, for example, a sequence of interest. A regulatory element can comprise a promoter that is operably linked to the nucleotide sequence of interest and to a termination signal. Regulatory elements also typically encompass sequences useful for proper translation of the nucleotide sequence of interest.

"Selectable marker" or "selectable marker gene" refers to a nucleotide sequence whose expression in a plant cell gives the cell a selective advantage under particular conditions. The selective advantage possessed by the cell transformed with the selectable marker gene can be an improved ability to grow in the presence of a negative selective agent, such as an antibiotic or an herbicide, for example, as compared to the ability of non-transformed cells. Alternatively, the selective advantage possessed by the transformed cells can be an enhanced capacity, relative to non-transformed cells, to utilize a particular compound as a nutrient, growth factor, or energy source. Alternatively, the selective advantage possessed by the transformed cell can be the loss of a previously possessed trait or characteristic, effecting what is termed "negative selection." In this last case, the host cell is exposed to or contacted by a compound that is toxic only to cells that have not lost the ability to express a specific trait or characteristic (such as a negative selectable marker gene, for example) that was present in the parent cell, which is typically a transgenic parent cell.

"Site-directed recombination" as used herein refers to recombination between two nucleotide sequences that each comprises at least one recognition site.

"Site-specific" means at a particular nucleotide sequence, which can be in a specific location in the genome of a host cell. The nucleotide sequence can be endogenous to the host cell, either in its natural location in the host genome or at some other location in the genome, or it can be a heterologous nucleotide sequence, which has been previously inserted into the genome of the host cell by any of a variety of known methods.

"Stably transformed" refers to a host cell that contains a nucleotide sequence of interest that has been stably integrated into the genome of the host cell.

"Target," "target molecule," "target sequence," and "target DNA" are used interchangeably to refer to a nucleotide sequence containing at least one recombinase recognition site. The target nucleotide sequence can be a gene, an expression cassette, a promoter, a molecular marker, a portion of any of these, or the like. The target sequence can be stably transformed into a plant cell to create a "target line" comprising the target sequence integrated into a chromosomal location in the plant genome.

A "targeted integration event" or "target event" refers to a recombination product formed between target and donor sequences in the presence of an integrase or integrase complex. In particular, it refers to the integration of a donor sequence into a target sequence as a consequence of an Int-mediated recombination when the target sequence is stably transformed into a plant cell.

"Transient expression" of a gene or nucleotide sequence or "transiently expressed" refers to the expression of a gene or nucleotide sequence that is not integrated into the host chromosome but which can function either independently (e.g., by being a part of an autonomously replicating plasmid or an expression cassette) or as a part of another biological system, such as a virus, for example.

"Transiently transformed" or "transient transformation" of a host cell refers to the introduction of foreign DNA or a nucleotide sequence of interest into the host cell (for example, by such methods as *Agrobacterium*-mediated transformation or biolistic bombardment) without integration of the foreign DNA or nucleotide sequence of interest into a host cell chromosome, thereby precluding stable maintenance of the foreign DNA or nucleotide sequence of interest in the progeny of the host cell.

A "viral replicon" or "viral vector" refers to a DNA or RNA virus vector or portion thereof that is capable of undergoing replication in a plant cell. The replicon or vector comprises a cis-acting viral sequence, such as a replication origin, for example, that is necessary for replication. The replicon or vector may or may not comprise a trans-acting viral sequence, such as, for example, a viral replication gene (e.g., the AC1 and AL1 genes in ACMV and TGMV geminiviruses, respectively). The replicon or vector may or may not comprise a target sequence for expression in the host plant cell. The introduction of donor DNA on a viral replicons can increase the frequency of targeting by increasing the number of copies of donor DNA in a plant cell.

A "visible marker gene" refers to a gene or nucleotide sequence whose expression in a transformed cell may not confer an advantage to that cell but can be detected or made visible. Examples of visible markers include, but are not limited to, β-glucuronidase (GUS), luciferase (LUC), and fluorescent proteins (such as green fluorescent protein (GFP) or cyan fluorescent protein (CFP), for example).

In one aspect, the present disclosure provides novel nucleotide sequences that are modified for enhanced expression in a plant. The nucleotide sequences encode an Int that provides functional integrase activity in a plant.

In another aspect, the expression of an integrase or integrase complex in a plant cell comprising a target sequence with flanking recognition sites directs efficient excision and/or inversion of the target sequence. Accordingly, methods are provided for removing an unwanted sequence from a plant genome and/or for inversion of a desired target sequence within a plant genome. Inversion can be used, for example, as an on-off switch for a sequence of interest.

In another aspect, the disclosure provides a method for effecting site-directed recombination in plants.

The methods disclosed herein employ an integrase, either with or without an additional accessory factor(s), to carry out recombination. Recombination can result from the pairing and interaction of two integrase recognition sites, such as, for example, the attB recognition site (SEQ ID NO:172), which comprises a short ~25-30 bp recognition site, and the attP recognition site (SEQ ID NO:173), which is substantially larger, ~240-250 bp, and comprises not only the binding site for integrase but also binding sites for accessory factors (Landy (1989) Annu. Rev. Biochem. 58: 913-949). The reaction between the attB (SEQ ID NO:172) and attP (SEQ ID NO:173) sites exchanges sequences in the crossover to create two new sites in the recombination product, attL (SEQ ID NO:174) and attR (SEQ ID NO:175). Recombination can also result from the pairing and interaction of attL and attR recognition sites. The L/R reaction can be used to reverse the B/P reaction, since the recombination products of the L/R reaction recreate the attB (SEQ ID NO:172) and attP (SEQ ID NO:173) recognition sites.

In one embodiment, a host cell comprises a target sequence comprising a single recognition site (a "first Int recognition site") for an integrase or integrase complex. The recognition site can be any recognition site for Int, including for example, attB (SEQ ID NO:172), attP (SEQ ID NO:173), attL (SEQ ID NO:174), attR (SEQ ID NO:175), or any mutant recognition site described herein or otherwise known in the art that is functional in an Int-mediated B/P or L/R reaction.

A corresponding donor sequence is constructed with a second recognition site that is capable of recombining with the first recognition site of the target. For example, when attB (SEQ ID NO:172) is chosen as the first recognition site for the target sequence, attP (SEQ ID NO:173) is chosen as the second recognition site for the donor sequence. Similarly, when attR (SEQ ID NO:175) is chosen as the first recognition site for the target sequence, attL (SEQ ID NO:174) is chosen for the second recognition site of the donor sequence.

Further specificity and flexibility can be imparted to the recombination methods disclosed herein by using mutant or modified Int recognition sites. A recognition site can be mutated or modified to alter the site's binding affinity for one or more accessory proteins, such as integration host factor or an excisionase, for example. Furthermore, the mutations or modifications may increase the efficiency of forming the recombination product; they may increase the specificity of the recombination reaction; or they may increase the directionality of the recombination reaction, such as, for example, by favoring an L/R reaction rather than a B/P reaction. A large number of these recognition sites have been described in U.S. Pat. No. 5,888,732. In a similar manner to the above descriptions, corresponding recognition sites are paired such that a mutant attL site in the target sequence is paired with a mutant attR site in the donor sequence, a mutant attB site in the target sequence is paired with a mutant attP site in the donor sequence, a mutant attR site in the target sequence is paired with a mutant attL site in the donor sequence, or a mutant attP site in the target sequence is paired with a mutant attB site in the donor sequence. For example, the following pairs of recognition sites can be used in the target and donor sequences: attB1 (SEQ ID NO:176) and attP1 (SEQ ID NO:177), attB2 (SEQ ID NO:178) and attP2, P3 (referred to herein as attP2) (SEQ ID NO:179), attL1 (SEQ ID NO:180) and attR1 (SEQ ID NO:182), attL2 (SEQ ID NO:181) and attR2 (SEQ ID NO:183), attB3 and attP2, P3 (SEQ ID NO:179), and attL3 and attR3. (See U.S. Pat. No. 5,888,732).

In another embodiment, the target sequence comprises an additional Int recognition site, hereafter referred to as the third recognition site. The first and third recognition sites can be either identical or non-identical. In one embodiment, the first and third recognition sites are identical, and the two sites are in inverted orientation with respect to each other. In another embodiment, the first and third recognition sites are non-identical, and the two sites can be in either inverted or direct orientation with respect to each other. In one embodiment, the first and third recognition sites are chosen such that they are incapable of recombining with each other. For example, the target can comprise two attB sites, two attL sites, two attP sites, or two attR sites. In one embodiment, the recognition sites of the target can be positioned adjacent to each other. In another embodiment, the recognition sites of the target can be positioned proximate to each other. In another embodiment, the first and third recognition sites can be positioned within the target sequence such that a pre-selected nucleotide sequence (also referred to herein as a "first nucleotide sequence") is located between the first and third recognition sites. The pre-selected nucleotide sequence can comprise a molecular marker, a sequence of interest, a selectable marker, a visible marker, a promoter, an expression cassette, a portion of any of these, or the like.

The pre-selected nucleotide sequence can comprise one or more expression cassettes. In one embodiment, the pre-selected nucleotide sequence comprises an expression cassette comprising a selectable marker gene, such as any of the selectable marker genes described herein or otherwise known in the art. The selectable marker permits selection of host cells comprising a target sequence, including selection of host cells comprising a target sequence that has been integrated into the genome of the host cell. In an exemplary embodiment, the selectable marker gene is a protoporphyrinogen oxygenase (PPO) gene, which confers resistance to a protox inhibitory herbicide (U.S. Pat. No. 6,084,155). In another embodiment, the selectable marker gene is a phosphomannose isomerase gene (PMI), which confers upon a plant the ability to utilize mannose as a nutritive carbon source.

In another embodiment, the pre-selected nucleotide sequence comprises an expression cassette comprising a sequence of interest and, optionally, a visible marker gene, such as, e.g., a GUS gene, a luciferase gene, a fluorescent protein gene (such as GFP, for example), or any other selectable marker gene described herein or otherwise known in the art.

In a further embodiment, the pre-selected nucleotide sequence comprises an expression cassette comprising a negative selectable marker gene, such as, for example, a cytosine deaminase gene (Perera et al. (1993) PMB 23: 793-799), a Herpes Simplex Virus Thymidine Kinase gene (Czako and Marton (1994) Plant Physiol. 104: 1067-1071), a T-DNA gene 2 (Depicker et al. (1988) Plant Cell Reports 7: 63-66), or any other negative selectable marker gene described herein or otherwise known in the art.

In another embodiment, the donor sequence also comprises two Int recognition sites: a second recognition site as described above, and an additional site, hereafter referred to as the fourth recognition site. The second and fourth recognition sites can be either identical or non-identical. In one embodiment, the second and fourth recognition sites are identical, and the two sites are in inverted orientation with respect to each other. In another embodiment, the second and fourth recognition sites are non-identical, and the two sites can be in either inverted or direct orientation with respect to each other.

In one embodiment, the sequence of the fourth recognition site is chosen such that the fourth recognition site cannot recombine with the second recognition site. Additionally, the two recognition sites of the donor (the second and fourth recognition sites) are chosen such that they can recombine with the two recognition sites of the target (the first and third recognition sites, respectively). For example, if the target sequence comprises two attB sites (or, alternatively, two attL sites), the donor sequence is constructed to comprise two attP sites (or, alternatively, two attR sites).

In another embodiment, the donor sequence comprises one or more pre-selected nucleotide sequences between the second and fourth recognition sites. The pre-selected nucleotide sequences can include any of a promoter, a nucleotide sequence of interest, a molecular marker, a selectable marker, a visible marker, an expression cassette, a portion of any of these, or the like.

In another embodiment, the donor sequence comprises at least one nucleotide sequence of interest. The nucleotide sequence of interest can be comprised in an expression cassette, and expression of the sequence of interest can be controlled by any one of the promoters described herein or by any other plant expressible promoter known in the art. As used herein, "plant expressible" means that the promoter is operable within a plant cell and is therefore capable of driving expression of a nucleotide sequence to which the promoter is operably linked within a plant cell. The promoter that controls or drives expression of the nucleotide sequence of interest can be comprised by the expression cassette comprising the nucleotides sequence of interest or can be otherwise operably linked to the nucleotide sequence of interest. Exemplary nucleotide sequences of interest include, but are not limited to, sequences encoding traits related to any of the following desirable characteristics: waxy starch; herbicide tolerance; resistance to bacterial, fungal, or viral disease; insect resistance; abiotic stress resistance; enhanced nutritional quality; improved performance in an industrial process; altered reproductive capability, such as male sterility or male fertility; yield stability; yield enhancement; and the production of commercially valuable enzymes or metabolites in plants.

In another embodiment, the donor sequence comprises a selectable or visible marker gene. Such a selectable or visible marker gene can be any selectable or visible marker gene described herein or otherwise known in the art but is typically different from a selectable or visible marker gene comprised by the target line or target DNA. In one embodiment, a termination signal is fused to the 3' end of the coding region of the selectable or visible marker gene.

In accordance with the methods of the disclosure, target and donor nucleotide sequences are introduced into a plant cell. In one embodiment, the target DNA is stably integrated into the plant genome. A plant or plant cell transformed with the target sequence is obtained by a transformation method as described herein or by methods otherwise known in the art to form a target line. Such a target line can comprise a single copy of the target DNA integrated into its genome. Once such a target line has been obtained and identified, it is further characterized. For example, the location of the transgene insertion is precisely determined by genetic methods well known in the art or by using molecular markers, such as restriction fragment length polymorphism (RFLP), amplified fragment length polymorphism (AFLP), simple sequence repeat (SSR), and the like. Additionally, the host plant DNA flanking the site of insertion is sequenced to ensure that no essential gene has been mutated or otherwise disrupted by the insertion of the transgene. Once a well-characterized target line is obtained, it can be used as a recipient of one or more subsequently introduced nucleotide sequences or transgenes. Such additional sequences or transgenes can be comprised in a donor sequence and can be introduced into the target line by any suitable transformation method, including, but not limited to, *Agrobacterium*-mediated transformation, biolistic bombardment, electroporation, PEG-mediated transformation, and friction with whisker or glass beads, as described herein or otherwise known in the art.

In another embodiment, the donor sequence is stably integrated into the plant genome. A plant or plant cell transformed with the donor DNA is obtained by a transformation method as described herein or by methods otherwise known in the art to form a donor line. Such a donor line can comprise a single copy of the target DNA integrated into its genome. Once such a donor line has been obtained and identified, it is further characterized, as described in the preceding paragraph.

In one embodiment, a target line is crossed with a donor line by methods of sexual reproduction known in the art, such as, for example, by pollinating the target line with pollen of the donor line and obtaining seed comprising both the target and donor sequences. Upon introducing an integrase or integrase complex, as described herein, into a plant cell derived from a plant produced by crossing the target line with the donor line, an Int-mediated recombination product can be formed. The Int-mediated recombination product results from an exchange of nucleotide sequences between the target sequence locus and the donor sequence locus. When there is a single recognition site within each of the target and donor sequences, recombination between the target and donor produces a chromosomal rearrangement within the plant cell genome. When there are two recognition sites within each of the target and donor sequences, recombination between the target and donor does not produce a chromosomal rearrangement within the plant cell genome.

In another embodiment, the donor sequence can be introduced into a plant cell through a viral replicon. Introduction of the donor sequence on a viral replicon allows the donor sequence to be amplified by the replication of the viral replicon within the plant cell. In one embodiment, the donor sequence is introduced into the host plant cell on a viral replicon that is capable of autonomous replication within the plant cell. Exemplary viral replicons include, but are not limited to, replicons derived from a plant virus (e.g., a virus, such as the maize streak virus (Shen and Hohn (1995) J Gen Virol 76:965-969); the wheat dwarf virus (U.S. Pat. No. 6,051,409 and Matzeit et al. (1991) Plant Cell 3:247-258); a tobacco geminivirus, such as, e.g., the tobacco golden mosaic virus or the tobacco yellow dwarf virus; beet curly top virus; African casava mosaic virus; tomato golden mosaic virus; abutilon mosaic virus; bean dwarf mosaic virus; bean golden mosaic virus; chloris striate mosaic virus; digitaria streak virus; miscanthus streak virus; panicum streak virus; potato yellow mosaic virus; squash leaf curl virus; sugarcane streak virus; tomato leaf curl virus; tomato mottle virus; tomato yellow leaf curl; or other known viruses (Timmermans et al. (1994) Annu. Rev. Plant Physiol. Plant Mol. Biol. 45: 79-112)). A viral replicon comprising the donor sequence can be introduced into a host plant cell by any of a variety of known transformation methods. Exemplary transformation methods include *Agrobacterium*-mediated transformation (Grimsley et al. (1989) Mol Gen Genet 217:309-316), microprojectile bombardment (i.e., "biolistics" or "particle bombardment"), PEG-mediated transformation, electroporation, microinjection, and the like, as described herein or otherwise known in the art.

As provided herein, the recombination of target and donor sequences is mediated by an integrase or integrase complex. Int recognizes integrase recognition sites, such as, for example, attB, attP, attL, attR, and mutant recognition sites, as described herein, and mediates recombination between these recognition sites. In one embodiment, this reaction is mediated by an integrase, which can be accompanied by an accessory protein referred to as integration host factor (IHF). IHF comprises two bacterial protein subunits, $\alpha$ and $\beta$. IHF can play a role in DNA bending, thereby facilitating the recombination reaction performed by the integrase. In one embodiment, integrase and IHF are used to mediate recombination between the target and donor sequences. In another embodiment, the recombination reaction is mediated by an integrase, IHF, and an excisionase (Xis). The Xis protein can be derived from bacteriophage Lambda. An integrase, a combination of an integrase and IHF, or a combination of an integrase, IHF, and Xis can be used to mediate recombination between a target and a donor sequence. Further, the components of the selected Int (i.e., whether the Int comprises an integrase, an integrase with IHF, or an integrase with IHF and Xis) are determined by the nature of the particular integrase selected to mediate the recombination reaction. If wild-type Lambda integrase is used, then it is accompanied by IHF and, in the case of an L/R reaction, Xis. If a mutant integrase is used (e.g., Int-h or Int-h/218), then accompaniment by IHF and/or Xis can be optional.

In another embodiment, the Int comprises a mutant integrase. Mutations in the phage Lambda integrase coding sequence are known which effect particular amino acid changes and allow the integrase to facilitate recombination in the absence of accessory proteins such as IHF (Lorbach et al. (2000) J. Mol. Biol. 296: 1175-1181). Any suitably mutated integrases can be used with the methods provided herein and include, for example, Int-h and Int-h/218. The integrase mutant Int-h comprises a glutamic acid to lysine change at amino acid 174 in the integrase polypeptide. Int-h is capable of mediating recombination in mammalian cells in the absence of IHF and/or Xis. The integrase mutant Int-h/218 comprises a glutamic acid to lysine change at amino acid 174 and a glutamic acid to lysine change at amino acid 218. Int-h/218 is capable of mediating recombination in mammalian cells in the absence of IHF (Lorbach et al. (2000) J. Mol. Biol. 296: 1175-1181).

In another embodiment, the Int is introduced into the host cell as one or more nucleic acid molecules (DNA and/or RNA) that comprise the coding sequence for each constituent protein of the Int. The Int can be introduced as one or more expression cassettes comprising a coding region for each protein of the Int, wherein each coding region is operatively linked to a promoter capable of expression in plant cells. Promoters for each expression cassette can be selected such that expression of the Int can be spatially or temporally regulated in any desired manner. For example, a promoter can be selected such that expression of the Int is constitutive, developmentally regulated, tissue specific, tissue preferred, cell specific, specific to a particular cellular compartment (i.e., organellar-specific), or the like. Additionally, promoters can be chosen so that expression of the Int can be chemically induced in a plant, resulting in expression of the Int only in response to treatment of the plant cell or tissue with a chemical ligand. By combining promoter elements that confer specific expression with those conferring chemically induced expression, the Int can be expressed or activated within specific cells or tissues of the plant in response to a chemical application. Any of a variety of plant expressible promoters can be used to drive expression of the Int. Several of such promoters are described herein, and other such promoters are known in the art.

In another embodiment, the integrase or integrase complex is introduced into the plant cell by being stably transformed into the genome of the plant cell. For example, the Int can be comprised in one or more expression cassettes comprising the coding sequences of the Int, whereby the coding sequence for each protein component of the Int is operatively linked to a promoter capable of expression in plant tissues and cells. Suitable methods for stably transforming plant cells are known in the art and are described herein. In one embodiment, a plant cell that is stably transformed with the Int is also stably transformed with a donor sequence.

As will be appreciated by one of skill in the art, a whole plant can be regenerated from a plant cell or a group of plant cells that has been stably transformed with a selected nucleotide sequence. This regenerated whole plant is then also referred to as being transformed with the selected nucleotide sequence. Thus, in accordance with the methods disclosed herein, a first plant can be stably transformed with one or more expression cassettes comprising Int and a donor sequence, and this first plant then can be crossed with a second plant that is stably transformed with a target sequence. Accordingly, expression of the Int in an F1 plant or seed can mediate recombination between the target and donor sequences such that the Int-mediated recombination product is formed in the F1 plant or seed. The nucleotide sequence(s) encoding the Int and the unrecombined portion(s) of the donor sequence can then be segregated from a nucleotide sequence comprising the recombination product sequence(s) through breeding.

In another embodiment, the Int can be introduced into a plant cell such that the plant cell transiently expresses the Int. For example, one or more nucleotide sequences comprising Int, IHF, and Xis can be introduced into a plant cell through *Agrobacterium* or microprojectile bombardment, for example. Much of the introduced nucleotide sequences are not integrated into the genome but can be transcribed into mRNA. In another exemplary embodiment, the Int can be introduced into a plant cell and expressed using a viral expression system. A viral expression system can be constructed from an RNA or DNA virus capable of infecting a plant. In one embodiment, the coding sequences of the protein(s) of the Int are comprised in a viral replicon that is capable of autonomous replication in plant cells. Exemplary viral replicons are described herein.

In another embodiment, the coding sequences of the Int are supplied to the host cell in the form of messenger RNAs (mRNA). In this manner, the Int is provided to the host cell only transiently. The coding sequence for each of the proteins of the Int can be inserted into a vector for in-vitro transcription of the RNA using methods described in Lebel et al. (1995) Theor. Appl. Genet. 91:899-906 and U.S. Pat. No. 6,051,409. The RNA then can be transformed into a host cell, such as a cell from a donor line or a target line, for example. In one embodiment, the RNA is co-transformed into a host cell with a donor sequence. In an exemplary embodiment, the RNA is transferred to a host cell using microprojectile bombardment, as described in U.S. Pat. No. 6,051,409. In another embodiment, the RNA is introduced into protoplasts of a host cell by PEG-mediated transformation, as described in, e.g., Lebel et al. (1995) Theor. Appl. Genet. 91:899-906, or by electroporation. In another embodiment, other transformation techniques, such as microinjection of the RNA, are used to introduce the RNA into the host cell.

In a further embodiment, an active Int is introduced into a host cell as one or more proteins, such as one or more purified proteins, for example. The Int protein can be introduced into the cell by any suitable method known in the art, such as, for example, microinjection or electroporation. In another embodiment, the Int is introduced into the host cell by microinjection together with a donor DNA sequence (see, e.g., Neuhaus et al. (1993) Cell 73:937-952). In another embodiment, the Int protein is introduced into the host cell through infection with *Agrobacterium* comprising a VirE2 or VirF fusion protein (see, e.g., Vergunst et al. (2000) Science 290:979-82).

In one embodiment, the coding sequences of the Int protein(s) are optimized for expression in a particular plant host. It is known in the art that the expression of heterologous proteins in plants can be enhanced by optimizing the coding sequences of the proteins according to the codon preference of the host plant. The preferred codon usage in plants differs from the preferred codon usage in certain microorganisms. A comparison of the codon usage within a cloned microbial ORF (open reading frame) to the codon usage in plant genes (and, in particular, genes from the selected host plant) enables an identification of the codons within the ORF that can be changed in an effort to optimize the coding sequence for expression in the host plant.

The skilled artisan will recognize that Int-mediated recombination products generated by the methods disclosed herein can vary according to the target and donor sequences selected and the positioning of these sequences relative to the recombinase recognition sites.

In one embodiment, the target contains an incomplete nucleotide sequence, such as, for example, an incomplete sequence of interest, an incomplete gene, an incomplete selectable marker, an incomplete visible marker, an incomplete negative selectable marker, an incomplete promoter sequence, an incomplete expression cassette, or the like, and the donor is constructed to contain a completion sequence, such that recombination between the target and donor produces the complete nucleotide sequence. In this manner, only a host cell comprising the recombination product comprises the appropriate expression product (i.e., as derived from the complete nucleotide sequence). For example, in one embodiment, the target comprises two recognition sites, a sequence of interest, such as a selectable marker or visible marker gene, for example, and termination signals fused at the 3' end of the sequence of interest. The sequence of interest is positioned within the target sequence such that it does not lie between the two recognition sites, but the 5' end of the sequence of interest is adjacent to one of the recognition sites. The donor sequence comprises a promoter and two recognition sites. The promoter is positioned within the donor sequence such that it is adjacent to one of the recognition sites and is also located between the two recognition sites; further, the directionality of the promoter is such that the promoter is capable of driving transcription across the adjacent recognition site and away from the remainder of the sequence that lies between the two recognition sites. When the target and donor sequences are introduced into a host plant cell and are exposed to or contacted with an Int within the host cell, the resulting recombination product comprises the promoter of the donor operatively linked to the sequence of interest and the 3' termination signal of the target. Thus, the sequence of interest is then capable of being expressed within the host cell.

In another embodiment, the target sequence can comprise at least one recognition site inserted 5' to a portion of a gene, such as the 3' portion of a gene. The donor sequence is then constructed to comprise the corresponding 5' portion of that gene, preferably containing the portion of the coding region of the gene that is not present in the target sequence. In this embodiment, the donor sequence comprises at least one recognition site inserted 3' to the portion of the gene contained within the donor sequence. Upon Int-mediated recombination of the target and donor sequences, the recombination product comprises the 5' and 3' portions of the gene operably linked to each other, thereby forming a complete gene. In this embodiment, the promoter for the gene, operably linked with the 5' portion of the gene, can be comprised within the donor sequence. Thus, upon recombination of the target and donor sequences, the Int-mediated recombination product comprises the promoter operably linked to the complete gene that is formed from the operable linkage of the 5' and 3' portions of the gene.

In a further embodiment, the target sequence can comprise at least one recognition site inserted 3' to a portion of a gene, such as the 5' portion of a gene. The donor sequence is then constructed comprising the corresponding 3' portion of that gene, preferably containing the portion of the coding region of the gene that is not present in the target sequence. In this embodiment, the donor sequence comprises at least one recognition site inserted 5' to the portion of the gene contained within the donor sequence. Upon Int-mediated recombination of the target and donor sequences, the recombination product comprises the 5' and 3' portions of the gene operably linked to each other, thereby forming a complete gene. In this embodiment, the promoter for the gene can be contained in the target sequence, such that it is operably linked with the 5' portion of the gene. Thus, upon recombination of the target and donor sequences, the Int-mediated recombination product comprises the promoter operably linked to the complete gene formed from the operable linkage of the 5' and 3' portions of the gene.

Figure 3:
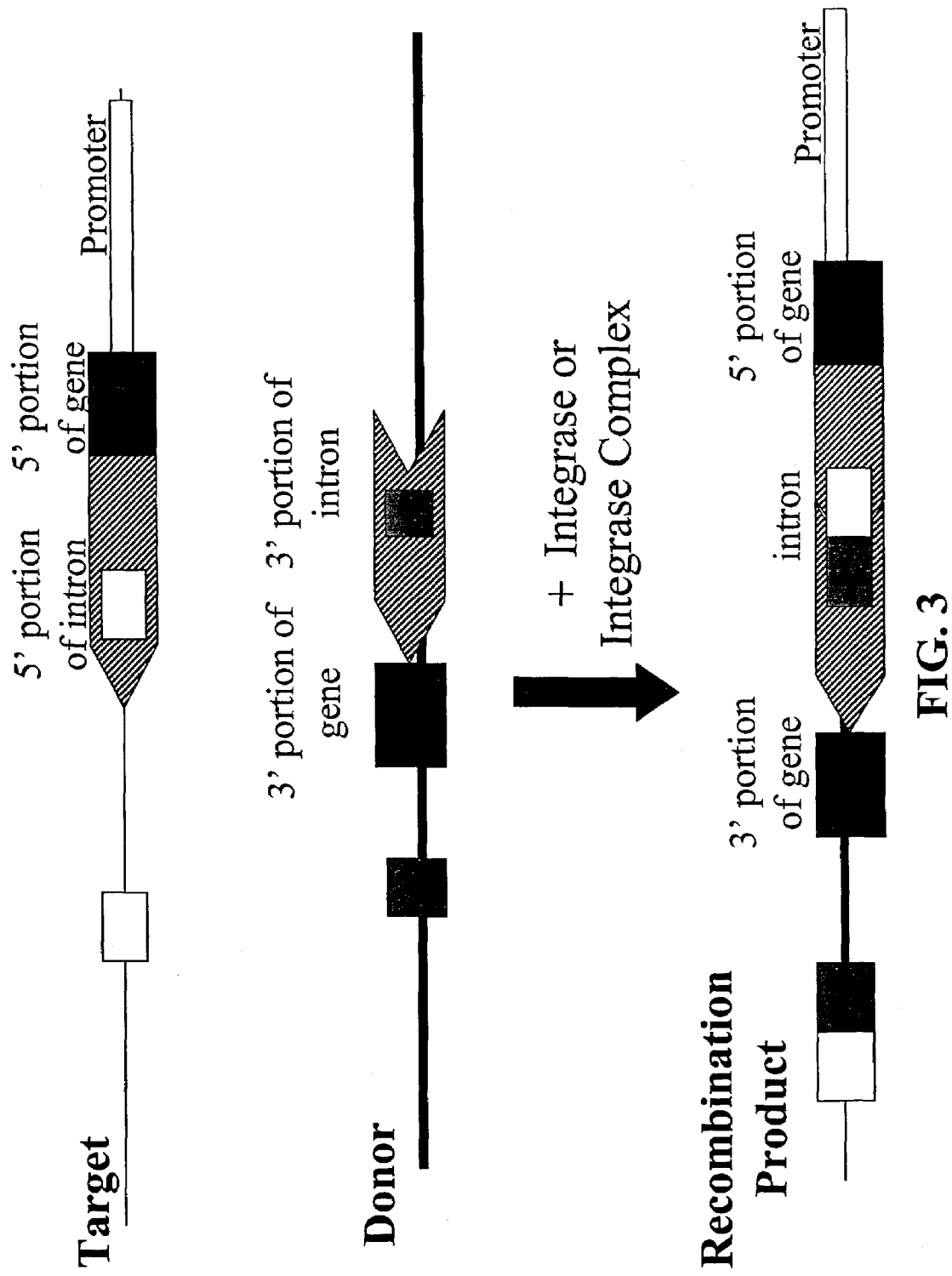
FIG. 3 represents a double crossover recombination event where one of the Int recognition sites on each of the target and donor molecules is present within a portion of an intron that is embedded within a portion of a coding sequence. An integrase or integrase complex is introduced to the target and donor molecules, and an Int-mediated recombination product is formed. The recombination product contains a complete intron that is formed by a crossover between the Int recognition sites present in both the 5' portion of the intron in the target molecule and the 3' portion of the intron in the donor molecule. The complete intron is located within a complete nucleotide sequence that is also formed by the crossover between the Int recognition sites present in both the target and donor molecules.

In one embodiment, an intron or a portion thereof can be operably linked to the 3' end of a sequence of interest (e.g., a gene, a selectable or visible marker gene, or the like), or a portion thereof, contained within the target sequence. In this embodiment, a recognition site is positioned either adjacent to or within the 5' end of the intron sequence. The donor sequence is then constructed such that a promoter is operably linked to the 5' end of the sequence of interest. In another embodiment, the intron or portion thereof can be operably linked to the 3' end of a portion of a sequence of interest comprised by the donor. Additionally, the donor can be constructed such that the promoter is operably linked to a 5' portion of a sequence of interest and an intron, and a recognition site can be placed adjacent to or within the 3' end of the intron sequence. Upon Int-mediated recombination of the target and donor sequences, the recombination product then contains the promoter from the donor construct operatively linked to the sequence of interest of the target construct as well as a complete intron. The recombination product would also contain a functional sequence of interest, which is formed from the operable linkage of the 5' portion of the sequence of interest (from the donor) with the 3' portion of the sequence of interest (from the target) (FIG. 3).

In another embodiment, additional recognition sites are used to facilitate integration of multiple nucleotide sequences of interest at one locus in the genome. The availability of a number of mutant attB, attP, attL, and attR recognition sites (as described herein) increases the number of recognition sites which can be used, since each recognition site can only recombine with its corresponding recognition site. A donor sequence can contribute additional recognition sites to a recombination product that are not used for recombination with the initial target sequence but are used in subsequent rounds of recombination to recombine a second, different donor sequence with a first recombination product. In one embodiment, the donor sequence comprises one or more additional recognition sites, which are different from the second and fourth recognition sites. One of the additional recognition sites can be adjacent to the 5' end of a sequence of interest, such as a selectable marker gene, for example. In the case where the sequence of interest is a selectable marker gene, any selectable marker gene described herein or otherwise known in the art can be used, but such selectable marker is preferably different from any selectable marker gene that can be comprised in the target line or target sequence. In another embodiment, termination signals are fused to the 3' end of the sequence of interest. The additional recognition site and the sequence of interest are located between the two recognition sites of the donor (i.e., between the second and fourth recognition sites described above). In one embodiment, the additional recognition site is flanked by two expression cassettes. After a first round of Int-mediated recombination, the third recognition site enables subsequent rounds of Int-mediated recombination, resulting in the integration of additional transgenes or sequences of interest using the additional recognition site and either one of the first two recognition sites.

In another embodiment, an Int is utilized to create a specific deletion in a target sequence. The target sequence comprises a first recognition site and a second recognition site in direct orientation with respect to one another. Additionally, the target sequence comprises a first nucleotide sequence between the first and second recognition sites. The first nucleotide sequence can comprise a selectable marker, a negative selectable marker, a visible marker, a sequence of interest, or the like, as described herein or as otherwise known in the art. The first and second recognition sites are chosen such that they are able to recombine with one another. For example, when the first recognition site is attB or attL the second recognition site is attP or attR, respectively. Integrase or an integrase complex is introduced into a host cell containing the target sequence, and the integrase or integrase complex mediates recombination between the first and second recognition sites. The recombination of the first and second recombination sites in direct orientation deletes the first nucleotide sequence from the target DNA, thereby forming an altered target sequence.

In further embodiment, the target DNA is integrated into the genome of a plant. A plant or plant cell transformed with the target sequence is obtained by any suitable transformation method, as described herein or otherwise known in the art, to form a target line. In one embodiment, such a target line contains a single copy of the target DNA integrated into its genome. Once such a line has been identified, it is further characterized as described supra. The integrase or integrase complex is then introduced into the target line as either a nucleic acid molecule or a protein by methods described herein or otherwise known in the art. The Int-mediated recombination product can be identified by methodologies that are known in the art, including, but not limited to, expression or absence of expression of a visible marker, selectable marker, or sequence of interest; PCR (polymerase chain reaction) identification of the deletion; and absence of a negative selectable marker.

In another embodiment, the integrase or integrase complex mediates an inversion of a nucleotide sequence located between two recognition sites within the nucleotide sequence, forming an altered nucleotide sequence. Inversion can be used as an on-off switch for a selected nucleotide sequence, such as, for example, a sequence of interest, a visible or selectable marker gene, or the like, as described herein or as otherwise known in the art. In one embodiment, the target sequence comprises a first recognition site and a second recognition site in inverted orientation with respect to one another. Additionally, the target sequence comprises a first nucleotide sequence located between the first and second recognition sites. The first nucleotide sequence can contain any selected nucleotide sequence, such as, for example, a selectable marker, a negative selectable marker, a visible marker, a sequence of interest, a portion of any of these, or the like. The first and second recognition sites are in inverted orientation relative to each other. Further, the first and second recognition sites are chosen such that they are capable of recombining with one another. For example, when the first recognition site is attB or attL, the second recognition site is attP or attR, respectively. Integrase or an integrase complex is introduced into a host cell containing the target sequence, and the integrase or integrase complex mediates recombination between the first and second recognition sites. When the first and second recombination sites in inverted orientation recombine, the first nucleotide sequence is inverted relative to its original orientation between the first and second recognition sites, and thereby forms an altered target sequence.

In one embodiment, the target sequence is integrated into the genome of a plant. A target line is obtained and characterized as described supra. The integrase or integrase complex is introduced either as a nucleic acid or as a protein by methods described herein or otherwise known in the art. The Int-mediated recombination product is characterized by known methods, such as by the expression or absence of expression of a visible marker, sequence of interest, selectable marker, negative selectable marker, or the like comprised within the first nucleotide sequence, as described supra.

In another embodiment, the target sequence comprises a second nucleotide sequence that is not positioned between the first and second recognition sites. Upon recombination of the first and second recognition sites, an Int-mediated recombination product is generated such that the first nucleotide sequence of the target is inverted, and the second nucleotide sequence of the target remains in its original orientation. The second nucleotide sequence can be any suitable nucleotide sequence, such as, for example, a promoter, an expression cassette, a sequence of interest, a selectable marker, a visible marker, a negative selectable marker, a portion of any of these, or the like, as described herein or otherwise known in the art. In one embodiment, the second nucleotide sequence comprises a selectable marker gene, such as, for example, a nucleotide sequence encoding phosphomannose isomerase (PMI), a sequence encoding β-glucuronidase (GUS), a nucleotide sequence encoding protoporphyrinogen oxidase (PPO), a nucleotide sequence encoding a luciferase enzyme (LUC), or the like.

In another embodiment, the second nucleotide sequence comprises an incomplete nucleotide sequence, such as, for example, an incomplete gene, an incomplete sequence of interest, an incomplete promoter, an incomplete expression cassette, or the like, and the target sequence is constructed such that recombination between the first and second recognition sites of the target sequence produces the complete nucleotide sequence. In such constructs, the incomplete nucleotide sequence is not functional in the target sequence unless and until the sequence is completed. For example, transcription of a nucleotide sequence of interest is not possible because of the absence of a complete promoter directing expression of the sequence of interest in the target or because a complete sequence of interest is not present in the target.

In a further embodiment, a sequence of interest, such as a selectable or visible marker gene having termination signals fused to the 3' end of the marker gene, for example, can be placed within the second nucleotide sequence of the target. The target sequence comprises a promoter that is positioned within the target sequence such that it is adjacent to one of the recognition sites and is also located between the two recognition sites; further, the directionality of the promoter is such that the promoter is capable of driving transcription across the adjacent recognition site and away from the remainder of the sequence that lies between the two recognition sites. Within the target sequence, the first nucleotide sequence is oriented such that the promoter is not operatively linked to the second nucleotide sequence. Upon recombination of the first and second recognition sites and inversion of the first nucleotide sequence, the recombination product then comprises the promoter of the first nucleotide sequence operatively linked to the sequence of interest and the 3' termination signal of the second nucleotide sequence.

General Components and Methods

I. Expression Cassettes

Coding sequences intended for expression in transgenic plants are first assembled in expression cassettes 3' to a suitable promoter expressible in plants. The expression cassettes can also comprise any further sequences needed or selected for the expression of the transgene. Such sequences include, but are not restricted to, transcription terminators, extraneous sequences to enhance expression such as introns, viral sequences, and sequences intended for the targeting of the gene product to specific organelles and cell compartments. These expression cassettes can then be transferred to the plant transformation vectors described herein.

The following is a description of various components of typical expression cassettes.

A. Promoters

Selection of the promoter to be used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and selection should reflect the desired location of accumulation of the gene product. Alternatively, the selected promoter can drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that can be used in the expression cassettes employed in the present invention.

1. Constitutive Promoters a. Ubiquitin Promoters

Ubiquitin is a gene product known to accumulate in many cell types and its promoter has been cloned from several species for use in transgenic plants (e.g. sunflower—Binet et al. Plant Science 79: 87-94 (1991); maize—Christensen et al Plant Molec. Biol. 12: 619-632 (1989); and *Arabidopsis*—Norris et al., *Plant Mol. Biol.* 21:895-906 (1993)). The maize ubiquitin promoter has been developed in transgenic monocot systems and its sequence and vectors constructed for monocot transformation are disclosed in the patent publication EP 0 342 926 (to Lubrizol), which is herein incorporated by reference. Taylor et al. (Plant Cell Rep. 12: 491-495 (1993)) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is ideal for use with the nucleotide sequences of the present invention. The ubiquitin promoter is suitable for gene expression in transgenic plants, both monocotyledons and dicotyledons. Suitable vectors include derivatives of pAHC25 or any of the transformation vectors described in this application. The vectors can be modified by the introduction of appropriate ubiquitin promoter and/or intron sequences.

b. The CaMV 35S Promoter

Construction of the plasmid pCGN1761 is described in published patent application EP 0 392 225 (published Sep. 25, 1991; Ciba Geigy; Example 23), which is hereby incorporated by reference. The plasmid contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative, designated pCGN1761ENX, is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that can enhance translation. This is particularly useful when overexpression is desired. For example, pCGN1761ENX can be modified by optimization of the translational initiation site as described in Example 37 of U.S. Pat. No. 5,639,949 (issued Jun. 17, 1997 to Ciba Geigy), incorporated herein by reference.

c. The Actin Promoter

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163-171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150-160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150-160 (1991)) can be easily modified for gene expression and are particularly suitable for use in monocotyledonous hosts. For example, promoter-containing fragments can be removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506-509 (1993)).

2. Inducible Expression a. PR-1 Promoters

The double 35S promoter in pCGN1761ENX can be replaced with any other promoter of choice that will result in suitably high expression levels. By way of example, one of the chemically regulatable promoters described in U.S. Pat. No. 5,614,395 (issued Mar. 25, 1997 to Ciba Geigy), such as the tobacco PR-1a promoter, can replace the double 35S promoter. Alternatively, the *Arabidopsis* PR-1 promoter described in Lebel et al., *Plant J.* 16:223-233 (1998) can be used. The promoter of choice can be excised from its source by restriction enzymes; alternatively, it can be PCR-amplified using primers that carry appropriate terminal restriction sites. If PCR-amplification be undertaken, then the promoter can be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104 (published Mar. 20, 1991; Ciba Geigy), which is hereby incorporated by reference) and transferred to plasmid pCGN1761ENX (Uknes et al., *Plant Cell* 4: 645-656 (1992)). The plasmid pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators can be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

b. Ethanol-Inducible Promoters

A promoter inducible by certain alcohols or ketones, such as ethanol, can also be used to confer inducible expression of a coding sequence of the present invention. Such a promoter is, for example, the alcA gene promoter from *Aspergillus nidulans* (Caddick et al. (1998) *Nat. Biotechnol* 16:177-180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177-180) are replaced by a coding sequence of the present invention to form an expression cassette having the coding sequence under the control of the alcA gene promoter. This is carried out using methods well known in the art.

c. Glucocorticoid-Inducible Promoter

Induction of expression of a nucleic acid sequence of the present invention using systems based on steroid hormones is also contemplated. For example, a glucocorticoid-mediated induction system is used (Aoyama and Chua (1997) *The Plant Journal* 11: 605-612) and gene expression is induced by application of a glucocorticoid, such as a synthetic glucocorticoid (e.g., dexamethasone). In one embodiment, the glutocorticoid is present at a concentration ranging from about 0.1 mM to about 1 mM. In another embodiment, the glutocorticoid is present at a concentration ranging from about 10 mM to 100 mM. For the purposes of the present disclosure, the luciferase gene sequences can be replaced by a sequence of interest to form an expression cassette having a sequence of interest under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699-704) fused to the transactivating domain of the herpes viral protein VP16 (Triezenberg et al. (1988) *Genes Devel.* 2: 718-729) fused to the hormone-binding domain of the rat glucocorticoid receptor (Picard et al. (1988) *Cell* 54: 1073-1080). The expression of the fusion protein can be controlled by any promoter suitable for expression in plants, as known in the art or described here. This expression cassette can also comprise a sequence of interest fused to the 6×GAL4/minimal promoter. Thus, tissue- or organ-specificity of the fusion protein can be achieved, leading to inducible tissue- or organ-specificity of the expression cassette.

d. Wound-Inducible Promoters

Wound-inducible promoters can also be suitable for gene expression. Numerous such promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

3. Tissue-Specific or Tissue-Preferred Expression a. Root-Preferred Expression

Another pattern of gene expression is root expression. A suitable root promoter for the constructs and methods of the present invention is the promoter of the maize metallothionein-like (MTL) gene described by de Framond (FEBS 290: 103-106 (1991)) and also in U.S. Pat. No. 5,466,785 (issued Nov. 14, 1995 to Ciba Geigy), incorporated herein by reference. This "MTL" promoter is transferred to a suitable vector such as pCGN1761ENX for the insertion of a selected gene and subsequent transfer of the entire promoter-gene-terminator cassette to a transformation vector of interest.

b. Pith-Preferred Expression

Patent Application WO 93/07278 (published Apr. 15, 1993; Ciba Geigy), which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

c. Leaf-Specific Expression

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a leaf-specific manner in transgenic plants.

d. Pollen-Specific Expression

WO 93/07278 (published Apr. 15, 1993; Ciba Geigy) describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a sequence of interest in a pollen-specific manner.

B. Transcriptional Terminators

A variety of transcriptional terminators are available for use in the expression cassettes of the present invention. These are responsible for the termination of transcription beyond the transgene and correct mRNA polyadenylation. Suitable transcriptional terminators are those that are known to function in plants and include, but are not limited to, the CaMV 35S terminator, the tml terminator, the nopaline synthase terminator and the pea rbcS E9 terminator. These can be used in both monocotyledons and dicotyledons. In addition, a gene's native transcription terminator can be used.

C. Sequences for the Enhancement or Regulation of Expression

Numerous sequences have been found to enhance gene expression from within the transcriptional unit, and these sequences can be used in conjunction with various genes to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183-1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res*. 15: 8693-8711 (1987); Skuzeski et al. *Plant Molec. Biol*. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126-6130 (1989)); potyvirus leaders, for example, TEV leader (Tobacco Etch Virus) (Allison et al., 1986); MDMV leader (Maize Dwarf Mosaic Virus); *Virology* 154:9-20); human immunoglobulin heavy-chain binding protein (BiP) leader, (Macejak, D. G., and Sarnow, P., *Nature* 353: 90-94 (1991); untranslated leader from the coat protein mRNA of alfalfa mosaic virus (AMV RNA 4), (Jobling, S. A., and Gehrke, L., *Nature* 325:622-625 (1987); tobacco mosaic virus leader (TMV), (Gallie, D. R. et al., *Molecular Biology of RNA*, pages 237-256 (1989); and Maize Chlorotic Mottle Virus leader (MCMV) (Lommel, S. A. et al., *Virology* 81:382-385 (1991). See also, Della-Cioppa et al., *Plant Physiology* 84:965-968 (1987).

D. Synthetic Genes

In a preferred embodiment of the present invention the coding sequences of the proteins of the integrase complex are optimized for expression in a particular plant host. It is known in the art that the optimization of protein expression in plants can be enhanced by optimizing the coding regions of genes to the codon preference of the host. Accordingly, the preferred codon usage in plants differs from the preferred codon usage in certain microorganisms. Comparison of the usage of codons within a cloned microbial ORF to usage in plant genes (and in particular genes from the target plant) enables an identification of the codons within the ORF which can be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as introns and may identify flanking splice sites (see below).

Plants differ from microorganisms in that their messages do not possess a defined ribosome-binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be achieved by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (NAR 15: 6643-6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

Position Before the Initiating ATG in 14 Maize Genes:

|   | −10 | −9 | −8 | −7 | −6 | −5 | −4 | −3 | −2 | −1 |
|---|---|---|---|---|---|---|---|---|---|---|
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

Genes cloned from non-plant sources and not optimized for expression in plants may also contain motifs which may be recognized in plants as 5' or 3' splice sites, and be cleaved, thus generating truncated or deleted messages. These sites can be removed using techniques well known in the art.

Techniques for modifying of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (published in Sep. 5, 1990 to Monsanto), EP 0 359 472 (issued Dec. 27, 1995 to Lubrizol) and WO 93/07278 (published Apr. 15, 1993 to Ciba-Geigy), all of which are incorporated herein by reference. In most cases it is preferable to assay the expression of gene constructions using transient assay protocols (which are well known in the art) prior to transferring to transgenic plants.

II. Plant Transformation Vectors and Selectable Markers

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet 79: 625-631 (1990)), the hpt gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,835 and 5,188,642, issued Jul. 10, 1990 and Feb. 23, 1993, respectively both to Monsanto), and the mannose-6-phosphate isomerase gene (also referred to herein as the phosphomannose isomerase gene), which provides the ability to metabolize mannose (U.S. Pat. Nos. 5,767,378 and 5,994,629, issued Jun. 16, 1998 and Nov. 30, 1999, respectively both to Novartis).

A. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

1. pCIB200 and pCIB2001

The binary vectors pcIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446-455 (1985)) allowing excision of the tetracycline-resistance gene, followed by insertion of an AccI fragment from pUC4K carrying an NPTII (Messing & Vierra, Gene 19: 259-268 (1982): Bevan et al., Nature 304: 184-187 (1983): McBride et al., Plant Molecular Biology 14: 266-276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153-161 (1987)), and the XhoI-digested fragment are cloned into SalI-digested pTJS75kan to create pCIB200 (see also EP 0 332 104, example 19; published Mar. 20, 1991; Ciba Geigy). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

2. pCIB10 and Hygromycin Selection Derivatives thereof

The binary vector pCIB10 contains a gene encoding kanamycin resistance for selection in plants and T-DNA right and left border sequences. pCIB10 incorporates sequences from the wide host-range plasmid pRK252 allowing it to replicate in both *E. coli* and *Agrobacterium*. Its construction is described by Rothstein et al. (Gene 53: 153-161 (1987)). Various derivatives of pCIB10 are constructed which incorporate the gene for hygromycin B phosphotransferase described by Gritz et al. (Gene 25: 179-188 (1983)). These derivatives enable selection of transgenic plant cells on hygromycin only (pCIB743), or hygromycin and kanamycin (pCIB715, pCIB717).

B. Vectors Suitable for non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

1. pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278 (published Apr. 15, 1993; Ciba Geigy). The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 may be obtained from the John Innes Centre, Norwich and the 400 bp SmaI fragment containing the bar gene from *Streptomyces viridochromogenes* is excised and inserted into the HpaI site of pCIB3060 (Thompson et al. EMBO J 6: 2519-2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI HindIII, and BamHI. This vector is suitable for the cloning of plant expression cassettes containing their own regulatory signals.

2. pSOG19 and pSOG35

The plasmid pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

C. Vector Suitable for Chloroplast Transformation

For expression of a nucleotide sequence of the present invention in plant plastids, plastid transformation vector pPH143 (WO 97/32011, example 36, published Sep. 4, 1997; Novartis) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

III. Transformation Methods

The target and donor DNA sequences cassettes of the present invention can be introduced into the plant cell in a number of art-recognized ways. Methods for regenerating plants are also well known in the art. For example, Ti plasmid-derived vectors have been utilized for the delivery of foreign DNA, as well as direct DNA uptake, liposomes, electroporation, microinjection, and microprojectiles. In addition, bacteria from the genus *Agrobacterium* can be utilized to transform plant cells.

Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis thaliana*, and woody plants such as coniferous and deciduous trees, especially maize, wheat, or sugarbeet.

Once a desired DNA sequence has been transformed into a particular plant species, it may be propagated in that species or moved into other varieties of the same species, particularly including commercial varieties, using traditional breeding techniques.

Below are descriptions of representative techniques for transforming both dicotyledonous and monocotyledonous plants, as well as a representative plastid transformation technique.

A. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming a plant cell with a gene involves propelling inert or biologically active particles at plant tissues and cells. This technique is disclosed in U.S. Pat. Nos. 4,945,050, 5,036,006, and 5,100,792 all to Sanford et al (issued Jul. 31, 1990, Jul. 30, 1991, Mar. 31, 1992, respectively). Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

B. Transformation of Monocotyledons

Transformation of most monocotyledon species has now also become routine. Preferred techniques include direct gene transfer into protoplasts using PEG (polyethylene glycol) or electroporation techniques, and particle bombardment into callus tissue and transformation mediated by *Agrobacterium*. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded as desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435 (issued Jul. 26, 1995 to Ciba Geigy), EP 0 392 225 (published Sep. 25, 1991; Ciba Geigy), and WO 93/07278 (published Apr. 15, 1993; Ciba Geigy) describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 (published Apr. 15, 1993; Ciba Geigy) and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for *Japonica*-types and *Indica*-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 (published Nov. 28, 1993; Plant Genetic Systems) describes techniques for the transformation of rice via electroporation. Patent Application EP 0 332 581 (issued Dec. 11, 1996 to Ciba Geigy) describes techniques for the generation, transformation and regeneration of Pooideae protoplasts. These techniques allow the transformation of *Dactylis* and wheat.

Furthermore, wheat transformation has been described by Vasil et al. (Biotechnology 10: 667-674 (1992)) using particle bombardment into cells of type C long-term regenerable callus, and also by Vasil et al. (Biotechnology 11: 1553-1558 (1993)) and Weeks et al. (Plant Physiol. 102: 1077-1084 (1993)) using particle bombardment of immature embryos and immature embryo-derived callus.

A preferred technique for wheat transformation, however, involves the transformation of wheat by particle bombardment of immature embryos and includes either a high sucrose or a high maltose step prior to gene delivery. Prior to bombardment, any convenient number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 (published Jan. 20, 1994; Japan Tobacco) and U.S. Pat. No. 5,591,616, (issued Jan. 7, 1997 to Japan Tobacco) both of which are incorporated herein by reference.

C. Transformation of Plastids

Seeds of *Nicotiana tabacum* c.v. 'Xanthi nc' are germinated seven per plate in a 1 inch circular array on T agar medium and bombarded 12-14 days after sowing with 1 μm tungsten particles (M10, Biorad, Hercules, Calif.) coated with DNA from plasmids pPH143 and pPH145 essentially as described (Svab, Z. and Maliga, P. (1993) *PNAS* 90, 913-917). Bombarded seedlings are incubated on T medium for two days after which leaves are excised and placed abaxial side up in bright light (350-500 μmol photons/m$^2$/s) on plates of RMOP medium (Svab, Z., Hajdukiewicz, P. and Maliga, P. (1990) *PNAS* 87, 8526-8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al. (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346-349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301-7305) and transferred to the greenhouse.

The foregoing describes various embodiments of the invention and is not intended to limit the scope of the invention as defined in the appended claims. The following Examples are included merely to demonstrate the practice of selected embodiments and should be regarded in an illustrative, rather than a restrictive, manner.

EXAMPLES

I. Demonstration of Lambda Int Activity in Maize Cells

A. General Methods for Recombination Assays in Maize Cells

1. Intermolecular and Intramolecular Recombination Test Substrates

The plasmids described herein are designed to demonstrate functional expression of Int. Intermolecular test substrates are constructed so that a portion of a luciferase expression cassette is on one of the substrates and the remaining portion of the cassette is on the other. A single site recombination event between the plasmids reconstitutes a complete, functional luciferase expression cassette. An intramolecular test substrate is constructed so that both portions of the luciferase expression cassette are on a single plasmid, but the 3' portion of the cassette is in an inverted orientation relative to the 5' portion of the cassette. The inverted 3' portion is flanked by compatible att sites which are also in an inverted orientation. An intramolecular recombination event between the att sites leads to inversion of the 3' portion producing a functional luciferase expression cassette. Luciferase assays are performed to demonstrate inter- and intra-molecular recombination activity of the Int.

2. Cell Culture

BMS (maize genotype Black Mexican Sweet) cells are grown in liquid suspension medium including 4.3 g/l MS salts (Murashige and Skoog, Plant Physiol. 15:473-439, (1962)), 10 mg/l thiamine-HCl, 100 mg/l myo-inositol, 30 g/l sucrose, 1.16 g/l proline, 3 mg/l 2,4-dichlorophenoxyacetic acid (2,4-D), pH 5.8. Casein hydrolysate is added at 1 g/l after bringing the medium to pH 5.8 and before autoclaving. Cells are incubated at 28° C. in BMS liquid medium on a rotary platform shaker at approximately 100 rpm in the dark. Cells are subcultured every seven days for maintenance, by transferring 10 ml of suspension cells into 40 ml of fresh BMS medium.

3. DNA Particle Bombardment

Cells are resuspended in fresh BMS medium two days prior to bombardment and incubated as described above. On the day of bombardment, 2 ml of cells are pipetted onto a membrane filter (Millipore cat.#GVWP04700) on the platform of a sterilized magnetic filter funnel apparatus (VWR cat#28143-550) and the liquid medium is gently pulled off the cells using a vacuum. The membrane with cells is placed onto osmoticum, BMS semi-solid medium with 12% sucrose and 0.8% phytagar. The cells are incubated at 28° C. in the dark for 3-5 hours and then used as the target of bombardment.

For particle bombardment, plasmid DNA is precipitated onto <1 µm gold particles (Crescent Chem. Co., Inc., NY) using standard $CaCl_2$-sperimidine chemistry (Klein et al. Nature 327:70-73 (1987)). Each target is bombarded once using a DuPont Helium Gun and 1100 psi rupture discs (Biorad).

4. Luciferase Assays

After bombardment, all plates are incubated in the dark at 28° C. for two or five days and then crude extracts are prepared and assayed for luciferase activity. The cells are harvested and lysed by mechanical disruption. Cellular debris is removed by centrifugation at ~20,000 g at 4° C. for 10 minutes. Cell lysates are assayed for luciferase expression levels using the Promega Luciferase Kit (Promega Cat# E1500) and using a Turner Designs TD Monolight 2010 luminometer. Luciferase expression is a measure of Int-mediated recombination activity.

B. Constructs for Recombination Assays in Maize

Example 1

Construction of a Synthetic Lambda Integrase Gene (SynInt) with Maize-Preferred Codons The amino acid sequence of the bacteriophage Lambda integrase protein (Hoess et al. (1980) PNAS USA 77 (5): 2482-2486) is back-translated using maize-preferred codons (U.S. Pat. No. 6,121,014) into a nucleotide sequence for SynInt. The unique restriction endonuclease cut sites, AvaII at 240, BglII at 560, and BssHII at 870, are identified within this DNA sequence that allow its construction in 4 segments of 250-300 bp ligated together to form the gene. Each of the four subfragments is constructed from oligonucleotides ranging from 65 to 83 bases, representing alternating strands of the double helix and overlapping the following and/or preceding oligonucleotide by 20 bp. Segment 1 of SynInt consists of the first 240 bp up to the AvaII site and is constructed from oligonucleotides 1A (BamHI site+Kozak sequence+top strand bases 1-73) (SEQ ID NO:1); 1B (bottom strand bases 53-128) (SEQ ID NO:2); 1C (top strand bases 108-183) (SEQ ID NO:3); and 1D (bottom strand bases 163-244+5'GG) (SEQ ID NO:4).

Segment 1 is constructed in two steps, a Klenow fill-in reaction to form dimers followed by a PCR joining of dimers to form a tetramer.

Two solutions of 50 µl containing 1×DNA polymerase salts and 1 µl each of 20 µM solution of 1A and 1B or 1C and 1D is heated at 67° C. for 5 minutes and then allowed to cool slowly to 22° C. To each reaction is added 1 µl of a mix of four deoxynucleotide triphosphates (10 mM each), plus 2 µl (10 units) of Klenow fragment of DNA polymerase (New England Biolabs). The reaction is incubated at 22° C. for 15 minutes, producing AB and CD precursors of SynInt segment 1.

Segment AB is joined to overlapping CD by 5-20 cycles of PCR. A PCR reaction mix containing 13 µl water, 5 µl each of the AB and CD Klenow reactions and 1 µl each of the 20 µM solutions of oligo 1A and 1D as primers is added to a Ready-to-Go PCR bead (Amersham Pharmacia Biotech Inc). The PCR reaction is: 95° C. for 5'; (95° C. for 1 min., 56° C. for 30 sec., 72° C. for 1 min.) 5-20 cycles; 72° for 10 min. The PCR product of tetrameric size is excised from an agarose minigel (2% Seaplaque agarose), and the DNA is purified by the QIAquick Gel Extraction Kit (QIAgen). The DNA fragment is cloned using the TOPO-TA Cloning Kit (InVitrogen), sequenced to assure fidelity of amplification, and excised from the TOPO vector with HindIII and AvaII for further assembly.

Segment 2 is constructed in three steps: a Klenow fill-in reaction to form dimers EF, GH, and IJ; a PCR joining of dimers EF and GH to form the tetramer EFGH; and a second PCR joining of EFGH with IJ to form the hexamer EFGHIJ. The dimers, tetramer, and hexamer of segment 2 are constructed of oligonucleotides 2E (SEQ ID NO:5), 2F (SEQ ID NO:6), 2G (SEQ ID NO:7), 2H (SEQ ID NO:8), 2I (SEQ ID NO:9), and 2J (SEQ ID NO:10), following the steps described above for segment 1.

The DNA fragment EFGHIJ is cloned using the TOPO-TA Cloning Kit (InVitrogen), sequenced to assure fidelity of amplification, and excised from the TOPO vector with AvaII and BglII for further assembly.

Segments 3 and 4 are constructed in a similar fashion from the hexamer KLMNOP and the tetramer QRST, respectively, using the following oligonucleotides:

| | |
|---|---|
| 3K, | (SEQ ID NO:11) |
| 3L, | (SEQ ID NO:12) |
| 3M, | (SEQ ID NO:13) |
| 3N, | (SEQ ID NO:14) |
| 3O, | (SEQ ID NO:15) |
| 3P, | (SEQ ID NO:16) |
| 4Q, | (SEQ ID NO:17) |
| 4R, | (SEQ ID NO:18) |
| 4S, and | (SEQ ID NO:19) |
| 4T. | (SEQ ID NO:20) |

KLMNOP and QRST are excised from their TOPO vectors as SpeI/BssHII and BssHII/ApaI fragments, respectively, and joined by 3-way ligation into pBluescript KS+ (Stratagene) cut with SpeI/ApaI to form pBS-KLM-NOPQRST. By a second 3-way ligation, fragments HindIII-ABCD-AvaII and AvaII-EFGHIJ-BglII are joined to HindIII/BglII digested pBS-KLMNOPQRST to form the entire SynInt gene. The complete maize-optimized DNA sequence for SynInt is set forth in SEQ ID NO:21. The corresponding amino acid sequence is set forth in SEQ ID NO:22.

Example 2

Construction of a Monocot Expression Cassette with the SynInt Coding Region

An expression vector, pBH16, containing the maize ubiquitin promoter (Christensen et al. (1992) Plant Mol. Biol. 18:675-689) and nopaline synthase terminator (Bevan et. al. (1982) J. Mol. Applied Genetics 1: 561-573), is digested at the polylinker site between the promoter and the terminator with BamHI/SacI. The SynInt gene, constructed as described in Example 1, is excised from pBSSynInt as a BamHI/SacI fragment and ligated into these sites in the expression vector to form MUSynInt.

Example 3

Construction of a Synthetic E. coli Integration Host Factor, Alpha Subunit (SynHFα) Gene with Maize-Preferred Codons The amino acid sequence of E. coli IHF, alpha subunit (Blattner et al. (1997) Science 277 (5331): 1453-1474; GenBank accession No. AE000266) is back-translated using maize-preferred codons into a nucleotide sequence for SynHFα. The oligonucleotides used to construct SynHFα are designed as described above for SynInt in Example 1 and include A' (SEQ ID NO:23), B' (SEQ ID NO:24), C' (SEQ ID NO:25), D' (SEQ ID NO:26), E' (SEQ ID NO:27), and F' (SEQ ID NO:28).

The coding region is flanked on the 5' end by two G residues (to facilitate cloning) and a BamHI site and on the 3' end by a BglII site and two G residues.

Construction of hexamer, A'B'C'D'E'F' proceeds as described above in Example 1 for hexamer EFGHIJ of SynInt. The complete maize optimized DNA sequence for SynHFα is set forth in SEQ ID NO:29. The corresponding amino acid sequence is set forth in SEQ ID NO:30.

Example 4

Construction of a Monocot Expression Cassette with the SynHFα Coding Region

The SynHFα gene sequence (Example 3) is excised from its TOPO vector as a BamHI/BglII fragment and inserted into the BamHI, site of expression vector, pBH16, containing the maize ubiquitin promoter and the nopaline synthase terminator described in Example 2, forming plasmid MUSynHFα.

Example 5

Construction of a Synthetic E. coli Integration Host Factor, Beta Subunit (SynHFβ) Gene with Maize-Preferred Codons The amino acid sequence of E. coli IHF, beta subunit (Blattner et al. (1997) Science 277 (5331): 1453-1474; GenBank accession #AE000193) is back-translated using maize-preferred codons into a nucleotide sequence for SynHFβ. The oligonucleotides used to construct SynHFβ are designed as described above in Example 1 for SynInt and include α (SEQ ID NO:31), β (SEQ ID NO:32), γ (SEQ ID NO:33), δ (SEQ ID NO:34), ε (SEQ ID NO:35), and ζ (SEQ ID NO:36).

The coding region is flanked on the 5' end by two G residues (to facilitate cloning) and a BamHI site and on the 3' end by a BglII site and two G residues.

Construction of hexamer α β γ δ ε ζ proceeds as described in Example 1 for hexamer EFGHIJ of SynInt. The complete maize-optimized DNA sequence for SynHFβ is set forth in SEQ ID NO:37. The corresponding amino acid sequence is set forth in SEQ ID NO:38.

Example 6

Construction of a Monocot Expression Cassette with the SynHFβ Coding Region

The SynHFβ gene sequence (from Example 5) is excised from its TOPO vector as a BamHI/BglII fragment and inserted into the BamHI, site of the expression vector, pBH16, containing the maize ubiquitin promoter and the nopaline synthase terminator described in Example 2, forming plasmid MUSynHFβ.

Example 7

Construction of a Synthetic Lambda Excisionase Gene (SynXis) with Maize-Preferred Codons The amino acid sequence of the bacteriophage Lambda excisionase protein (Hoess et al., P.N.A.S. USA 77(5): 2482-2486 (1980)) is back-translated using maize-preferred codons into a nucleotide sequence for SynXis. The oligonucleotides used to construct SynXis are designed as described in Example 1 for SynInt and include I. (SEQ ID NO:39), II. (SEQ ID NO:40), III. (SEQ ID NO:41), and IV. (SEQ ID NO:42).

The coding region is flanked on the 5' end by a BamHI site and a Kozak sequence and on the 3' end by a SacI site and an additional C residue, to facilitate cloning.

Construction of the tetramer, I II III IV, proceeds as described in Example 1 for the tetramer ABCD of SynInt. The complete maize-optimized DNA sequence for SynXis is set forth in SEQ ID NO:43. The corresponding amino acid sequence is set forth in SEQ ID NO:44.

Example 8

Construction of a Monocot Expression Cassette with the SynXis Coding Region

The SynXis gene sequence (from Example 7) is excised from its TOPO vector as a BamHI/SacI fragment and inserted into the BamHI/SacI sites of the expression vector, CMSynHFβ, to form 2994SynXis. The 404bp fragment of CMSynHFβ containing the CMPS promoter is inserted into the BamHI site of 2994SynXis to form pAdF61. The 945 bp EcoRI fragment of pAdF61 is ligated into the 5763 bp binary vector portion of VSInt-h/218 digested with EcoRI forming pAdF62. Both orientations of this construct are obtained in this non-directional cloning. In pAdF62A, the 5' end of the CMPS-SynXis gene is located next to the binary vector right border, and in pAdF62B it is located next to the binary vector left border.

Example 9

Construction of a Monocot Expression Cassette with a Synthetic Lambda Integrase Gene Mutant (SynInt-h)

A single base pair mutation (Lange-Gustafson et al., J. Biol. Chem. 259(20):12724-12732 (1984)) is introduced into the SynInt gene coding region of pBSSynInt, mutating base pair 520 from "G" to "A." This mutation is introduced using a QuikChange site-directed mutagenesis kit (Stratagene) and the following oligonucleotides: 5'-CCC GCG CCG CCA AGA GCA AGG TGC GCC GCA GCC GC-3' (SEQ ID NO:45) and 5'-GCG GCT GCG GCG CAC CTT GCT CTT GGC GGC GCG GG-3' (SEQ ID NO:46). The "G" to "A" mutation changes amino acid 174 of pBSSynInt from Glu to Lys forming pBSSynIntE174K.

To clone the E174K mutant integrase gene into an expression cassette, the BamHI site of MUSynInt is first converted into a SpeI site using the site changing oligonucleotide 5'-GAT CAC TAG T-3' (SEQ ID NO:47). Then the SpeI/BglII fragment of pBSSynIntE174K, containing the E174K mutation, is cloned as part of a 3-way ligation with the BglII/SacI fragment of MUSynInt into the SpeI/SacI sites of the MUSynInt vector, forming MUSynInt-h.

Example 10

Construction of a Monocot Expression Cassette with a Synthetic Lambda Integrase Gene Double Mutant (SynInt-h/218)

A double base pair mutation (Christ, N. and Droge, P. J. Mol. Biol. 288:825-836 (1998)) is introduced into the SynInt gene coding region of pBSSynInt, mutating base pair 520 from "G" to "A" and base pair 652 from "G" to "A." The base pair mutation 520 is described above. The base pair mutation 652 is introduced using a QuikChange site-directed mutagenesis kit (Stratagene) and the following oligonucleotides: 5'-GCG TGG GCG ACC TGT GCA AGA TGA AGT GGA GCG AC-3' (SEQ ID NO:48) and 5'-GTC GCT CCA CTT CAT CTT GCA CAG GTC GCC CAC GC-3' (SEQ ID NO:49). The "G" to "A" mutation changes amino acid 218 of pBSSynInt from Glu to Lys forming pBSSynIntE218K.

To clone the E174K mutation and E218K mutation into an expression cassette, the BamHI site of MUSynInt is first converted into a SpeI site using the site changing oligonucleotide 5'-GATCACTAGT-3' (SEQ ID NO:47). Then the SpeI/BglII fragment of pBSSynIntE174K, containing the E174K mutation, is cloned as part of a 3-way ligation with the BglII/SacI fragment of pBSSynIntE218K, containing the E218K mutation, into the SpeI/SacI sites of the MUSynInt vector, forming the double mutant gene in vector MUSynInt-h/218.

Example 11

Construction of a pAttB and pAttP, a Pair of Monocot Intermolecular Recombination Substrates Two plasmids are constructed such that a single site, intermolecular recombination event between the plasmids reconstitutes a complete luciferase expression cassette from two incomplete portions of the expression cassette. The intermolecular attB test substrate contains the 5' portion of a luciferase expression cassette ( 5'Luc-5'Intron-attB) and the attP test substrates contain the 3' portion of the cassette (attP-3'Intron-3'Luc). Intermolecular recombination between the attB and attP sites, as mediated by the Int complex, results in the reconstitution of an intact luciferase expression cassette capable of producing luciferase enzyme activity. The recombinant product contains MzUbi-5'Luc-5'Intron-attL-3' Intron-3'Luc-Nos.

Example 11A

5' Portion of the Luciferase Expression Cassette Containing the attB Site, pAttB The 3' end of luciferase from SphI to XbaI site is subcloned from pGL3-Basic (Promega) into pUC18 in order to isolate its HincII site for the insertion of an intron. The intron is PCR amplified from pBISN1 (Narasimhulu, S. B., et al. Plant Cell 8:873-886 (1996)) using the oligonucleotide primer pair, 5'-GGG TAC GTA AGT TTC TGC TTC TAC CTT TG-3' (SEQ ID NO:50) and 5'-CCC CAG CTG CAC ATC AAC AAA TTT TGG TC-3' (SEQ ID NO:51) forming SnaB1 and PvuII sites at either end. The PCR product is cloned using the TOPO-TA Cloning Kit (Invitrogen), and a perfect copy is identified through sequencing. The intron is excised as a SnaB1/PvuII fragment and ligated into the HincII site in the 3'-Luc clone to form 3'Luc-Intron. Correct orientation of the intron is determined by mapping with an asymmetric ApoI site and confirmed by sequencing. A unique MunI site near the center of the intron is cleaved and an oligonucleotide is inserted that replaced MunI with an XhoI site to form 3'Luc-Int-X.

P-U5'LucIntronAttB (pAttB) is constructed by three-way ligation of expression vector pBH16 (described in Example 2), digested with SacI and Asp718 to remove the nos terminator, with two parts of the 5' end of the Luc coding region (BamHI to SphI [Insert A] and SphI to Asp718 including attB [Insert B]) to form P-ULucIntronAttB. Insert A is derived from the luciferase gene of pGL3basic (Promega) subcloned into pUC18 and modified upstream of the initiation codon by inserting into the NcoI site the following oligonucleotide pair that adds a SacI site and a five base Kozak sequence: 5'-CAT GAG CTC GC CAC-3' (SEQ ID NO:52) and 5'-CAT GGT GGC GAG CT-3' (SEQ ID NO:53).

From the resulting plasmid, pAT134S, the 5'-end of the Luc coding region is excised as a SacI to SphI fragment, forming Insert A. Insert B is derived from 3'LucIntronX modified by digestion with XhoI and Asp718 and insertion of the following oligonucleotide pair containing the attB site with appropriate 5' extensions: 5'-TCG ATG AAG CCT GCT TTT TTA TAC TAA CTT GAG CG-3' (SEQ ID NO:54) and 5'-GTA CCG CTC AAG TTA GTA TAA AAA AGC AGG CTT CA-3' (SEQ ID NO:55).

Example 11B

3' Portion of the Luciferase Expression Cassette Containing the AttP Site, pAttP P-AttPIntronLuc (pAttP) is formed by three-way ligation of expression vector pBH16, digested with HindIII and BamHI to remove the promoter, to an attP fragment [Insert C], and the 3' end of the LucIntron gene from XhoI to Asp718 [Insert D]. To produce Insert C, the attP sequence is PCR amplified from bacteriophage Lambda DNA (New England Biolabs) with the following primer pair: HattP (5'-GGA AGC TTC TGT TAC AGG TCA CTA ATA C-3')

(SEQ ID NO:56) and XattP (5'-CCT CGA GAA ATC AAA TAA TGA TTT TAT-3') (SEQ ID NO:57).

The product is purified by Seaplaque agarose gel electrophoresis, extracted from agarose by the QIAquick Gel Extraction Kit (QIAgen) and cloned using the TOPO-A Cloning Kit (Invitrogen), forming TOPOAttP. A clone of perfect sequence is identified and from it Insert C is excised by digestion with HindIII and XhoI. Insert D is excised from 3'LucIntronX by digestion with XhoI and BamHI. The pBH16 vector is ligated to Inserts C and D to form plasmid pAttPIntronLuc.

This pair of intermolecular recombination test substrates is designated with the prefix "p" to distinguish them from similar constructs described below on a viral replicon (prefix "v").

Example 12

Construction of pAttL, a Monocot Recombinant Product Plasmid p-ULucIntronAttL (pAttL) is constructed to test whether the predicted product of integrase recombination between the intermolecular recombination test substrates produces a functional luciferase gene. The excised attP DNA fragment described above is converted into an attL fragment by eight cycles of PCR amplification using the following primer pair: X5AttL (5'-CCT CGA GTG AAG CCT GCT TTT TTA TAC TAA GTT GGC ATT A-3') (SEQ ID NO:58) and XattP (5'-CCT CGA GAA ATC AAA TAA TGA TTT TAT-3' (SEQ ID NO:57). The PCR product is gel-purified and Topo-TA cloned, and a perfect attL clone, TOPOAttL, is identified through sequencing. The attL fragment is excised with XhoI and ligated into the XhoI site of 3'LucIntronX to form 3'LucIntronAttL. From this intermediate the insert is excised with SphI and BamHI. From plasmid p-U5'LucIntronAttB, the 5' end of Luc with part of the maize ubiquitin promoter is excised with SalI/SphI. Vector pBH16 is digested with SalI/BamHI (discarding the unneeded part of the maize ubiquitin promoter) and a three-way ligation of these fragments produces plasmid p-ULucIntronAttL.

Example 13

Construction of vAttB/P, a Monocot Intramolecular Recombination Test Substrate on a WDV Replicon The intramolecular attB/attP test substrate contains the 5' portion of a luciferase expression cassette (5'Luc-5'Intron-attB) and the 3' portion of a luciferase expression cassette (attP-3'Intron-3'Luc), where the 3' portion is inverted relative to the 5' portion and the attB and attP sites are in inverted orientation. Intramolecular recombination between the attB and attP sites, as mediated by the Int, leads to inversion of the 3' portion of the luciferase expression cassette, producing an intact cassette and luciferase enzyme activity.

A shuttle plasmid capable of replication in E.coli and monocot plant cells is employed for this and further substrates. Plasmid pWI-11 (Ugaki et al., Nucl. Acids Res. 19: 371 (1991)), with replication origins from wheat dwarf virus (WDV replicon) and plasmid p15A is modified by addition of unique cloning sites with the following pair of oligonucleotides introduced between SalI and BamHI sites (creating Asp718, BglII, SpeI, NotI, and NheI sites): 5'-TCG ACG GTA CCA GAT CTA CTA GTT GCG GCC GCG CTA GCG-3' (SEQ ID NO:59) and 5'-GAT CCG CTA GCG CGG CCG CAA CTA GTA GAT CTG GTA CCG-3' (SEQ ID NO:60).

The resulting vector, pWI-11M, is digested with NotI and BglII to form the backbone of vAttB/P. Insert E is derived from pAttB after changing its HindIII site to a NotI site with the oligonucleotide 5'-AGC TGC GGC CGC-3' (SEQ ID NO:61). The insert containing UbiLucIntronAttB is excised with NotI and Asp718. Insert F is derived from pAttP after changing its HindIII site to a BglII site with the oligonucleotide 5'-AGC TAG ATC T-3' (SEQ ID NO:62). The insert containing AttPIntron 3'LucNos is excised with BglII and Asp718. Three-way ligation of pWI-11M with inserts E and F produces a plasmid, in which the 3' end of the gene is reversed with respect to the 5' end and flanked by oppositely oriented attB and attP sites called vAttB/P.

Example 14

Construction of vAttB and vAttP, Monocot Intermolecular Recombination Test Substrates on WDV Replicons The NotI/Asp718 fragment containing UbiLucIntronAttB, prepared in Example 13, is ligated into pWI-11M digested with NotI and Asp718 to form vAttB. The BglII/Asp718 fragment containing AttPInt 3'LucNos, also prepared above in Example 13, is ligated into pWI-11M digested with BglII and Asp718 to form plasmid vAttP.

Example 15

Construction of vMUSynInt, a WDV Replicon Carrying MUSynInt

The HindIII site at the 5' end of MUSynInt is converted to a SpeI site with the oligonucleotide 5'-AGC TAC TAG T-3' (SEQ ID NO:63). The expression cassette is excised with SpeI and Asp718 and ligated into SpeI/Asp718-digested pWI-11M to form plasmid vMUSynInt.

C. Recombination Assays in Maize Cells

Example 16

Intramolecular and Intermolecular Recombination Mediated by SynInt and SynIHFα/β in Maize Cells The intermolecular recombination substrates, vAttB with vAttP, and the intramolecular recombination substrate, vAttB/P, are bombarded separately into BMS cells at a concentration of 0.25 µg/plasmid/shot to determine background levels of luciferase transient expression in the absence of SynInt, SynIHFα and SynIHFβ expression. The same substrates are then co-bombarded with either vMUSynInt (0.25 µg/shot) or MUSynInt (0.25 µg/shot), and MUSynIHFα (0.5 µg/shot) and MUSynIHFβ (0.5 µg/shot). Bombarded BMS cells are incubated in the dark at 28° C. for either ~2 days or ~5 days. After incubation, the cells are assayed for luciferase expression levels. Luciferase expression is a measure of Int mediated recombination activity. The results are presented in Table 1 below.

As demonstrated in Table 1, expression of MUSynInt on either a plasmid (pSynInt) or a wheat geminivirus replicon (vSynInt) mediates intramolecular and intermolecular recombination in BMS cells. pSynHFα,β represents the co-bombardment of two plasmids, MUSynIHFα and MUSynIHFβ.

TABLE 1

| Co-Bombarded Plasmids | ~2 days post-bomb | | ~5 days post-bomb | |
|---|---|---|---|---|
| | Luciferase | Fold Increase | Luciferase | Fold Increase |
| vAttB + vAttP | 7,773 | | 4,559 | |
| vAttB + vAttP pSynInt + pSynHFα,β | 34,285 | 4 | 12,108 | 3 |
| vAttB + vAttP vSynInt + pSynHFα,β | 100,188 | 13 | 28,317 | 6 |
| vAttB/P | 2,601 | | 373 | |
| vAttB/vAttP pSynInt + pSynHFα,β | 152,731 | 59 | 19564 ± 3,702 | 52 |
| vAttB/vAttP vSynInt + pSynHFα,β | 152,976 | 59 | 76,506 ± 16,553 | 205 |
| pAttL | 5,150,847 | | 544,311 | |

Example 17

Intermolecular Recombination Between attB and attP Sites on Plasmid and Viral Replicon Substrates in Maize Cells The intermolecular recombination plasmid and viral replicon pairs, pAttB+pAttP, pAttB+vAttP, vAttB+pAttP, and vAttB+vAttP, are co-bombarded separately into BMS cells at a concentration of 0.25 µg/plasmid/shot to determine background levels of luciferase transient expression. The same intermolecular recombination substrate pairs are then co-bombarded with MUSynInt (0.25 µg/shot), MUSynIHFα (0.5 µg/shot) and MUSynIHFβ (0.5 µg/shot). Bombarded BMS cells are incubated in the dark at 28° C. for ~48 hours. After incubation, the cells are assayed for luciferase expression levels. The results are presented in Table 2 below.

TABLE 2

| Co-Bombarded Plasmids | Luciferase (LU ± Std Dev) | Fold Increase |
|---|---|---|
| pAttB + pAttP | 359 | |
| pAttB + pAttP + pSynInt + pSynHFα,β | 395 ± 184 | 1 |
| vAttB + pAttP | 1,006 | |
| vAttB + pAttP + pSynInt + pSynHFα,β | 1019 ± 325 | 1 |
| pAttB + vAttP | 494 | |
| pAttB + vAttP + pSynInt + pSynHFα,β | 314 ± 11 | <1 |
| vAttB + vAttP | 2,448 | |
| vAttB + vAttP + pSynInt + pSynHFα,β | 6,617 ± 479 | 3 |

Co-expression of MUSynInt, MUSynHFα, and MUSynHFβ in BMS cells mediates intermolecular recombination between attB and attP sites on Wheat geminivirus replicon substrates.

Example 18

Intermolecular Recombination Mediated by Mutant SynInt-h and SynInt-h/218 with and without Co-Expression of MUSynHFα and MUSynHFβ in Maize Cells The intermolecular recombination plasmid pairs, pAttB+pAttP, pAttB+vAttP, vAttB+pAttP, and vAttB+vAttP are co-bombarded separately into BMS cells to determine background levels of luciferase transient expression. The same intermolecular recombination plasmid pairs are then co-bombarded simultaneously with the following combinations of expression vectors:

A) MUSynInt-h (0.25 µg/shot)
B) MUSynInt-h (0.25 µg/shot), MUSynHFα (0.5 µg/shot) and MUSynHFβ (0.5 µg/shot)
C) MUSynInt-h/218 (0.25 µg/shot)
D) MUSynInt-h/218 (0.25 µg/shot), MUSynHFα (0.5 µg/shot) and MUSynHFβ (0.5 µg/shot)

Bombarded BMS cells are incubated in the dark at 28° C. for about 48 hours. After incubation, the cells are assayed for luciferase expression levels. The results are presented in Table 3 below.

TABLE 3

| Co-Bombarded Plasmids | Luciferase (LU ± Std Dev) | Fold Increase |
|---|---|---|
| pAttB + pAttP | 269 ± 20 | |
| pAttB + pAttP + pSynInt-h | 1,970 ± 1,143 | 7 |
| pAttB + pAttP + pSynInt-h + pSynHFα,β | 5,453 ± 4,402 | 20 |
| pAttB + pAttP + pSynInt-h.218 | 3,708 ± 482 | 14 |
| pAttB + pAttP + pSynInt-h/218 + pSynHFα,β | 8,479 ± 5,677 | 32 |
| vAttB + pAttP | 349 ± 192 | |
| vAttB + pAttP + pSynInt-h | 2,650 ± 511 | 8 |
| vAttB + pAttP + pSynInt-h + pSynHFα,β | 10,246 ± 682 | 29 |
| vAttB + pAttP + pSynInt-h/218 | 1,846 ± 239 | 5 |
| vAttB + pAttP + pSynInt-h/218 + pSynHFα,β | 9,560 ± 845 | 27 |
| pAttB + vAttP | 1,217 ± 907 | |
| pAttB + vAttP + pSynInt-h | 1,137 ± 334 | <1 |
| pAttB + vAttP + pSynInt-h + pSynHFα,β | 7,721 ± 2,721 | 6 |
| pAttB + vAttP + pSynInt-h/218 | 1,867 ± 808 | 2 |
| pAttB + vAttP + pSynInt-h/218 + pSynHFα,β | 3,882 ± 389 | 3 |

Expression of a mutant λ integrase, MUSynInt-h (pSynInt-h), in BMS cells mediates recombination between plasmid and viral replicon pairs, pAttB+pAttP and vAttB+pAttP, without expression of the *E. coli* IHF (i.e, MUSynHFα and MUSynHFβ). Co-expression of MUSynInt-h with MUSynHFα and MUSynHFβ mediates recombination between plasmid and viral replicon pairs, pAttB+pAttP, vAttB+pAttP, and pAttB+vAttP in BMS cells. Expression of a mutant λ integrase MUSynInt-h/218 (pSynInt-h/218) in BMS cells mediates recombination between plasmid and viral replicon pairs, pAttB+pAttP, vAttB+pAttP, and pAttB+vAttP with and without co-expression of MUSynHFα and MUSynHFβ.

Example 19

Intramolecular Recombination Mediated by SynInt, SynInt-h and SynInt-h/218 with and without Co-Expression of SynIHFP in Maize Cells The intramolecular recombination plasmid, vAttB/P, is bombarded into BMS cells at a concentration of 0.25 µg/shot to determine background level of luciferase transient expression. The same intramolecular recombination plasmid is then co-bombarded simultaneously with the following combinations of expression vectors:

A) MUSynInt (0.25 µg/shot)
B) MUSynInt (0.25 µg/shot), MUSynHFα (0.5 µg/shot) and MUSynHFβ (0.5 µg/shot)
C) MUSynInt-h (0.25 µg/shot)
D) MUSynInt-h (0.25 µg/shot), MUSynHFα (0.5 µg/shot) and MUSynHFβ (0.5 µg/shot)
E) MUSynInt-h/218
F) MUSynInt-h/218 (0.25 µg/shot), MUSynHFα (0.5 µg/shot) and MUSynHFβ (0.5 µg/shot)

Bombarded BMS cells are incubated in the dark at 28° C. for 48 hours. After incubation, the cells are assayed for luciferase expression levels. The results are presented in Table 4 below.

TABLE 4

| Co-Bombarded Plasmids | Luciferase (LU ± Std Dev) | Fold Increase |
|---|---|---|
| vattB/P | 751 | |
| vattB/P + pSynInt | 996 ± 16 | 1.3 |
| vattB/P + pSynInt + pSynHFα,β | 121,532 ± 86,904 | 162 |
| vattB/P + pSynInt-h | 11,378 ± 5,420 | 15 |
| vattB/P + pSynInt-h + pSynHFα,β | 128,307 ± 49,322 | 171 |
| vattB/P + pSynInt-h/218 | 36,771 ± 6,032 | 49 |
| vattB/P + pSynInt-h/218 + pSynIHFα,β | 46,842 ± 10,980 | 62 |

The wild type (pSynInt), single mutant (pSynInt-h), and double mutant (pSynInt-h/218) λ integrases all mediate intramolecular recombination in maize cells between attB and attP sites. The wild type λ integrase generally needs co-expression of E. coli integration host factor protein to mediate intramolecular recombination, but the single and double mutant λ integrases mediate intramolecular recombination both with and without the co-expression of E. coli integration host factor protein.

II. Targeted Integration in Maize Using a B/P Reaction

A. Construction of Target Sequences

Generally, a target sequence construct is introduced into the plant genome to serve as a locus for an Int-catalyzed site-specific insertion of a corresponding donor sequence. Selectable and screenable markers are incorporated as partial expression cassettes, split between targets ("LP" constructs) and donors ("don" constructs), so that the two portions are reconstituted into a complete, functional cassette when a targeted insertion has occurred. Assaying for the screenable marker permits the identification of cells containing a targeted insertion event. Applying selective pressure provides a means to enrich for cells containing a targeted insertion event.

In the exemplary constructs described herein, the plasmids used to insert a target sequence into maize contain an expression cassette for the mutant protoporphyrinogen oxidase (PPO) gene coding region (U.S. Pat. No. 6,288,306) to aid in identifying plant clones containing the target sequence. In addition, target sequence plasmids contain partial expression cassettes, β-glucuronidase (GUS) (5'GUS-5'Intron) and phosphomannose isomerase (PMI) (3'Intron-3'PMI), truncated in an intron and punctuated by either a single att site or a pair of identical att sites (any of which can be either wild type or mutant). Thus, a single att site target sequence contains a split marker gene in the form: 5'GUS-5'Intron-AttSite-3'Intron-3'PMI. A double att site target sequence has the form: 5'GUS-5'Intron-AttSite-PPO-AttSite-3'intron-3'PMI. The 5' and 3' intron portions in a target sequence correspond to different introns.

Single att sites may be in either a 5'-3' or a 3'-5' orientation relative to the gene coding regions of the target sequence. Pairs of att sites can be divergently oriented (inverted orientation) or convergently oriented (also an inverted orientation). When the 3' ends of the pair of att sites are directed away from each other, the sites are said to be divergently oriented. When the 3' ends of the pair of att sites are directed toward each other, the sites are said to be convergently oriented. Whichever orientation is selected, the att site or paired att sites in corresponding target and donor sequences have matching orientations. In addition, the att sites in the target and donor are compatible for recombination; that is, an attB target is matched with an attP donor, etc., as described herein.

Example 20

Monocot Target Sequence with Inverted attB Sites

The construct pNOV2790 contains the phosphomannose isomerase (PMI) gene of pNOV117 (Negrotto et al. (2000) Plant Cell Reports 19:798-803) divided into 5 exons by the introduction of 4 introns into the coding region, as set forth in SEQ ID NO:64. The beta-1 tubulin intron "A" from Arabidopsis thaliana (Oppenheimer et al. (1988) Gene 63: 87-102) is introduced between exons 3 and 4 of the gene coding region using a series of overlapping primer pairs. The intron is introduced and named PMI intron 3. This portion of pNOV2790 is used for further cloning.

An oligonucleotide pair is constructed (5'-AAT TGG TAC CTG AAG CCT GCT TTT TTA TAC TAA CTT GAG CGC CTA GG-3' (SEQ ID NO:65) and 5'-AAT TCC TAG GCG CTC AAG TTA GTA TAA AAA AGC AGG CTT CAG GTA CC-3' (SEQ ID NO:66)), carrying an attB site flanked by a 5'Asp718I site with an MfeI cohesive end and a 3' AvrII site with an EcoRI cohesive end. This oligonucleotide pair is annealed and ligated into the MfeI site of PMI intron3 of pNOV2790, forming the vector pNOV2790AttB.

pNOV2117 is a binary vector with both the pVS1 and ColE1 origins of replication. This vector contains the constitutive VirG gene from pAD1289 (Hansen et al. (1994) PNAS USA 91: 7603-7607) and a spectinomycin resistance gene from Tn7. Cloned into the polylinker between the right and left borders are the maize ubiquitin promoter, PMI coding region and nopaline synthase terminator of pNOV117 (Negrotto et al. (2000) Plant Cell Reports 19:798-803).

A portion of the PMI coding region with the PMI intron3 containing the attB site is excised from pNOV2790AttB as a BstBI/PshAI fragment and is ligated into binary vector pNOV2117, from which the corresponding region is removed by digestion with BstBI/PshAI. This forms a complete PMI expression cassette, called MUPMIAttB, containing an attB site in the intron.

pNOV5013 is a Bluescript vector containing the rice actin 1 promoter (McElroy et al. (1991) Mol. Gen. Genet. 231(1): 150-60) with the BamHI site removed from the intron, the mutant protoporphyrinogen oxidase (PPO) gene coding region (U.S. patent application Ser. No. 09/015,683), and the CaMV 35S terminator. The PPO expression cassette of pNOV5013 is excised as an Asp718I fragment and ligated into the Asp718I site of MUPMIAttB, forming PPO.PMI-AttB.

pNOV5003 contains an Arabidopsis intron (GenBank accession No. AB007650), named AT BAF60, introduced into the β-glucuronidase (GUS) gene coding sequence from pBI121 (Clonetech) using a series of overlapping primer pairs.

To construct a GUS gene with an Arabidopsis intron from AtBAF60 gene, the AtBAF60 intron (420 bps) is amplified from the Arabidopsis genome using two primers, GUS-BAFFW1 (5'-TTG ACT GGC AGG TAC CAA GCT GCG AAT CTT CG-3') (SEQ ID NO: 67) and GUSBAFRV1 (5'-ATT GGC CAC CAC CTG AAA AAT TCA GAA ACA AA-3')(SEQ ID NO:68). AtBAF60 (CHC1) is a gene that shares homology with the mammalian nucleosome-remodeling factor BAF60 (http://www.chromdb.org/). GUS exon1

(645 bps) is amplified from pBI121 (Clonetech) using two primers, GUSBAMHI (5'-GGA TCC AAC CAT GTT ACG TCC TGT AGA AA-3') (SEQ ID NO:69) and BAFGUSRV1 (5'-CAG CTT GGT ACC TGC CAG TCA ACA GAC GCG AC-3') (SEQ ID NO:70). GUS exon2 (1200 bps) is amplified from pBI121 using two primers, BAFGUSFW1 (5'-TTG ACT GGC AGG TAC CAA GCT GCG AAT CTT CG-3') (SEQ ID NO:71) and GUSSALI (5'-GTC GAC TCA TTG TTT GCC TCC CTG CTG CGG-3') (SEQ ID NO:72). GUS exon1-AtBAF60 intron fragment (1049 bp) is formed by PCR using gel-purified GUS exon1 (645 bp) and AtBAF60 intron (420 bp) fragments as template and two primers, GUSBAMHI (5'-GGA TCC AAC CAT GTT ACG TCC TGT AGA AA-3') (SEQ ID NO:69) and GUSBAFRV1 (5'-ATT GGC CAC CAC CTG AAA AAT TCA GAA ACA AA-3') (SEQ ID NO:68). GUS exon1-AtBAF60 intron fragment (1049 bp) is cloned into pCR2.1-TOPO vector to form pNOV5001. AtBAF60 intron-GUS exon2 fragment (1620 bp) is formed by PCR using AtBAF60 intron (420 bp) and GUS exon2 (1200 bp) fragments as template and GUSBAFFW1 (5'-3') and GUSSALI (5'-3') as primers. AtBAF60 intron-GUS exon2 fragment (1620 bp) is cloned into pCR2.1-TOPO to form pNOV5002. pNOV5003 is formed in a tripartite ligation of XhoI/BamHI-digested pBluescript KS(+) with two insert fragments, pNOV5001 BamHI/HindIII fragment (961 bp) and pNOV5002 XhoI/HindIII fragment (1312 bps).

A synthetic attB site of the oligonucleotide pair, 5'-GAT CTC GCT CAA GTT AGT ATA AAA AAG CAG GCT TCA GCT AGC-3' (SEQ ID NO:73) and 5'-GAT CGC TAG CTG AAG CCT GCT TTT TTA TAC TAA CTT GAG CGA-3' (SEQ ID NO:74) is ligated into the BglII site of the AT BAF60 intron of pNOV5003 in the opposite orientation to the attB site of pNOV2790AttB, forming the vector GUS-IntAttBrev.

pNOV4211 contains a promoter which is PCR amplified from the Cestrum Mosaic Virus with primers that flank the PCR product with BamHI sites. The amplified CMPS promoter, set forth in SEQ ID NO:75, is cloned into pBluescript KS+ as a BamHI fragment in the orientation opposite to that of the LacZ gene. The promoter is described in WO 0173087A1, which is hereby incorporated by reference.

The Cestrum mosaic virus promoter is excised from pNOV4211 as a BamHI fragment and ligated into the BamHI site of GUSIntAttBrev, forming the vector CMPS-GUSAttBrev.

The ApaI site of PPO.PMIAttB is first converted into a SpeI site using the site-change oligo 5'-ACT AGT GGC C-3' (SEQ ID NO:76) forming PPO.PMIAttB.Spe, and then the 5' SpeI/NheI fragment of CMPSGUSAttBrev, including the attB site, is ligated into the SpeI site of PPO.PMIAttB.Spe forming a target sequence (referred to as LPdbAttB) containing two inverted attB sites.

Example 21

Monocot Target Sequence with Inverted attP Sites

The attP site is PCR cloned from bacteriophage Lambda genomic DNA (New England Biolabs) with the oligonucleotide primer pair 5'-GGA AGC TTC TGT TAC AGG TCA CTA ATA C-3' (SEQ ID NO:77) and 5'-CCT CGA GAA ATC AAA TAA TGA TTT TAT-3' (SEQ ID NO:78) using a TOPO TA Cloning Kit (Invitogen). The HindIII site on the 5' end of the attP site is converted to three new sites, Asp718I/MfeI/Asp718I, using the site changing oligonucleotide 5'-AGC TGG TAC CCA ATT GGG TAC C-3' (SEQ ID NO:79). The XhoI site on the 3' end of the attP site is converted to three new sites, AvrII/MfeI/AvrII, using the site changing oligonucleotide 5'-TCG ACC TAG GCA ATT GCC TAG G-3' (SEQ ID NO:80). The attP fragment is then excised from the TOPO vector as an MfeI fragment and ligated into the MfeI site of the PMI intron3 of pNOV2790 forming the vector pNOV2790AttP.

The PMI intron3 containing the attP site is excised from pNOV2790AttP as a BstBI, PshAI fragment and is ligated into the binary vector pNOV2117, cut with BstBI, PshAI, forming a PMI expression cassette containing the PMI intron3 with an attP site called MUPMIAttP.

The PPO expression cassette of pNOV5013 is excised as an Asp718I fragment and ligated into the Asp718I site of MUPMIAttP, forming PPO.PMIAttP.

The HindIII site on the 5' end of the attP site in the TOPO clone described above is converted to three new sites, NheI/BamHI/NheI, using the site changing oligonucleotide 5'-AGC TGC TAG CGG ATC CGC TAG C-3' (SEQ ID NO:81). The XhoI site on the 3' end of the attP site of this clone is then converted into three new sites, BglII/EagI/BglII using the site changing oligonucleotide 5'-TCG AAG ATC TCG GCC GAG ATC T-3' (SEQ ID NO:82). The attP site is then excised as a BamHI/BglII fragment and ligated into the BglII site of the AT BAF60 intron of pNOV5003 in the opposite orientation to the attP site of pNOV2790AttP, forming the vector GUSIntAttPrev.

The Cestrum mosaic virus promoter is excised from pNOV4211 as a BamHI fragment and ligated into the BamHI site of GUSIntAttPrev, forming the vector CMPS-GUSAttPrev.

The ApaI site of PPO.PMIAttP is first converted into a SpeI site using the site-change oligo 5'-ACT AGT GGC C-3' (SEQ ID NO:83) forming PPO.PMIAttP.Spe, and then the 5' SpeI, NheI fragment of CMPSGUSAttPrev, including the attP site, is ligated into the SpeI site of PPO.PMIAttP.Spe forming a target sequence (referred to as LPdbAttP) containing two inverted attP sites.

Example 22

Monocot Target Sequence with Inverted attP1 and attP2 Sites

The intervening SalI fragment between "AttP1" and "AttP2" sites of pDON 201 (Life Technologies) is removed by SalI digestion followed by ligation to form AttP1SalIAttP2.

The attP2 site is PCR cloned from the ApaI, SalI fragment of AttP1 SalIAttP2 with the oligonucleotide primer pair 5'-GGG CAA TTG GGT ACC TAC AGG TCA CTA ATA CCA TCT-3' (SEQ ID NO:84) and 5'-GGG CAA TTG CCT AGG CAA ATA ATG ATT TTA TTT TGA-3' (SEQ ID NO:85) using a TOPO TA Cloning Kit. The attP2a site is excised from the TOPO vector as an MfeI fragment and ligated into the MfeI site of the PMI intron3 of pNOV2790 forming the vector pNOV2790AttP2.

The PMI intron3 containing the attP2 site is excised from pNOV2790AttP2 as a BstBI, PshAI fragment and is ligated into the binary vector pNOV2117, cut with BstBI, PshAI, forming a PMI expression cassette containing the PMI intron3 with an attP2 site called MUPMIAttP2.

The PPO expression cassette of pNOV5013 is excised as an Asp718I fragment and ligated into the Asp718I site of MUPMIAttP2, forming PPO.PMIAttP2.

The attP1 site is PCR cloned from the PstI, SalI fragment of AttP1SalIAttP2 with the oligonucleotide primer pair 5'-GGA TCC GCT AGC TAC AGG TCA CTA ATA CCA TCT-3' (SEQ ID NO:86) and 5'-GGG AGA TCT CAA ATA ATG ATT TTA TTT TGA-3' (SEQ ID NO:87) using a TOPO TA Cloning Kit. The attP1 site is excised from the TOPO vector as a BamHI/BglII fragment and ligated into the BglII site of the AT BAF60 intron of pNOV5003 in the opposite orientation to the attP2 site of pNOV2790AttP2, forming the vector GUSIntronAttP1rev.

The Cestrum mosaic virus promoter is excised from pNOV4211 as a BamHI fragment and ligated into the BamHI site of GUSIntronAttP1rev, forming the vector CMPSGUSAttP1rev.

The ApaI site of PPO.PMIAttP2 is first converted into a SpeI site using the site-change oligo 5'-ACT AGT GGC C-3' (SEQ ID NO:83) forming PPO.PMIAttP2.Spe, and then the 5' SpeI, NheI fragment of CMPSGUSAttP1rev, including the attP1 site, is ligated into the SpeI site of PPO.PMIAttP2.Spe forming a target sequence (referred to as LPAttP1.P2) containing attP1 and attP2 sites in inverted orientation.

Example 23

Monocot Target Sequence with an attB Site pNOV2114 is a binary vector with both the pVS1 and ColE1 origins of replication. This vector contains the constitutive VirG gene from pAD1289 (Hansen et al. (1994) PNAS USA 91: 7603-7607), a spectinomycin resistance gene from Tn7, and a polylinker between the right and left borders.

The PMI expression cassette of MUPMIAttB, 3' of the attB site, is introduced into the Asp718I, HindIII polylinker sites of pNOV2114, as an Asp718I, SbfI fragment in a three-way ligation along with the PstI, HindIII PPO expression cassette fragment of pNOV5013, forming the binary vector AttBPMI.PPO.

The AscI site of AttBPMI.PPO is first converted into a SpeI site using the site-change oligo 5'-CGC GAC TAG T-3' (SEQ ID NO:88) forming AttBPMI.PPO.Spe. Then the 5' BglII (klenow fill-in), SpeI, fragment of CMPSGUSAttBrev, excluding the attB site, is ligated into the Asp718I (klenow fill-in), SpeI sites of AttBPMI.PPO.Spe, forming a target sequence (referred to as LPsgAttB) with a single attB site.

Example 24

Monocot Target Sequence with an attP Site

The 3' half of the PMI expression cassette of MUPMIAttP, including the attP site, is introduced into pNOV2114, cut with Asp718I, HindIII, as an Asp718I, SbfI fragment in a three way ligation along with the PstI, HindIII fragment of pNOV5013 containing the complete PPO expression cassette forming the binary vector AttPPMI.PPO.

Figure 4:
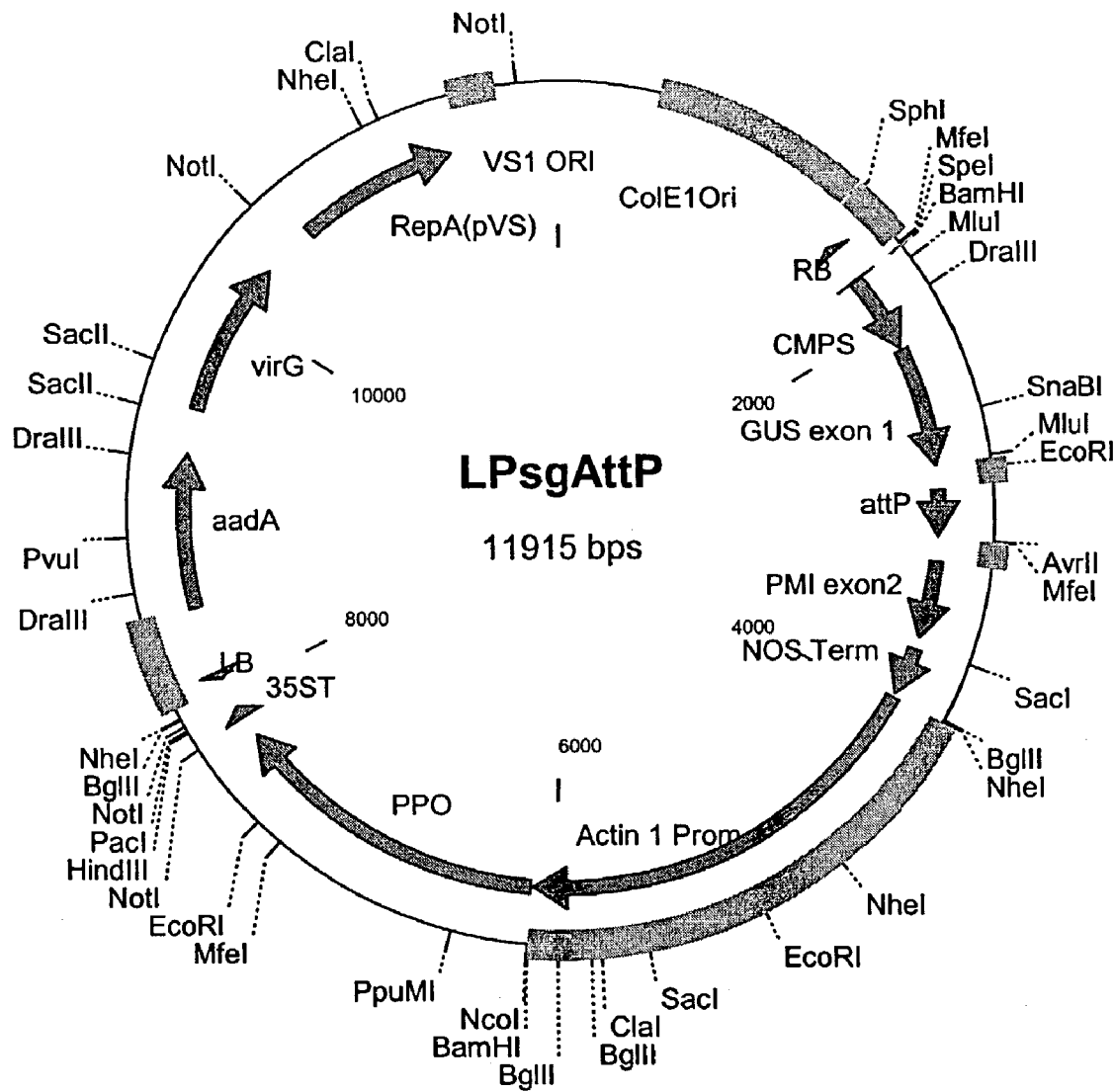
FIG. 4 represents the structure of LPsgAttP, an exemplary plasmid that contains a monocot target sequence with a single attP site.

The AscI site of AttPPMI.PPO is first converted into a SpeI site using the site-change oligo (SEQ ID NO:88) 5'-CGC GAC TAG T-3' forming AttPPMI.PPO.Spe. Then the 5' BglII (klenow fill-in), SpeI, fragment of CMPSGUSAttBrev, excluding the attB site, is ligated into the Asp718I (klenow fill-in), SpeI sites of AttPPMI.PPO.Spe, forming a target sequence (referred to as LPsgAttP) (FIG. 4) containing a single attP site.

B. Production of Maize Target Cell Lines

Example 25

Agrobacterium-Mediated Transformation of Maize to Introduce Target Sequence Constructs Transformation of immature maize embryos is performed essentially as described in Negrotto et al. (2000) Plant Cell Reports 19: 798-803.

Example 25A

Transformation Plasmids and Selectable Marker

The target sequences, LPdbAttB, LPdbAttP, LPAttP1.P2, LPsgAttB, and LPsgAttP (FIG. 4), are in a binary vector suitable for maize transformation and contain the mutant protoporphyrinogen oxidase (PPO) gene (U.S. Pat. No. 6,288,306) allowing for selection of maize transgenic cells with butafenacil supplemented media.

Example 25B

Preparation of Agrobacterium tumefaciens

Agrobacterium strain LBA4404 (pSB1) (Ishida et. al., (1996) Nature Biotechnology 14: 745-750) containing the target sequence binary vector is grown on YP (yeast extract (5 g/L), peptone (10 g/L), NaCl (5 g/L), 15 g/l agar, pH 6.8) solid medium for 2-4 days at 28° C. Approximately $0.8 \times 10^9$ Agrobacteria are suspended in LS-inf media supplemented with 100 μM AS (Negrotto et al. (2000) Plant Cell Rep 19: 798-803). Bacteria are pre-induced in this medium for 30-60 minutes.

Example 25C

Media Preparation

1. JMS Stocks

Major Salts 10×. To make 1 L: $NH_4NO_3$, 16.9 g; $KNO_3$, 18.2 g; $CaCl_2.2H_2O$, 2.1 g; $MgSO_4.7H_2O$, 4.0 g; $KH_2PO_4$, 3.5 g Minor Salts 100×. To make 1 L: KI, 0.1 g; $H_3BO_3$, 0.5 g; $MnSO_4.4H_2O$, 1.0 g; $ZnSO_4.7H_2O$, 0.1 g; $NaMoO_4.2H_2O$, 0.010 g; $CuSO_4.5H_2O$, 0.020 g; $CoCl_2.6H_2O$, 0.010 g G5 Additions 100×. To make 1 L: Casein hydrolysate, 10 g; Thiamine HCl, 0.5 g; Pyridoxine HCl, 0.05 g; Nicotinic acid, 0.5 g; Myo-inositol, 10 g; Proline, 10 g Filter Sterilize.

Dicamba. 1 mg/ml in 0.1M HCl

Ticarcillin. 100 mg/ml distilled water; filter sterilize

Silver Nitrate. $AgNO_3$ 10 mg/ml; filter sterilize

Mannose. 1 g/ml distilled water; heat to dissolve and filter sterilize

2. JMS Recipes

2JMSTi200Ag. To make 1 L: JMS major salts, 100 ml; SH minor salts, 10 ml; $FeSO_4 \cdot 7H_2O$, 27.8 mg; Dicamba, 5 ml; Sucrose, 20 g. pH adjusted to 5.8: Add 2.4 g/L Gelrite. Autoclave. Additions after autoclave: G5 additions, 10 ml; Ticarcillin, 2 ml; $AgNO_3$, 0.5 ml.

2JMSTi200. To make 1 L: JMS major salts, 100 ml; SH minor salts, 10 ml; $FeSO_4.7H_2O$, 27.8 mg; Dicamba, 5 ml; Sucrose, 20 g. pH adjusted to 5.8: Add 2.4 g/L Gelrite. Autoclave. Additions after autoclave: G5 additions, 10 ml; Ticarcillin, 2 ml.

2JMSAg. To make 1 L: JMS major salts, 100 ml; SH minor salts, 10 ml; FeSO$_4$.7H$_2$0, 27.8 mg; Dicamba, 5 ml; Sucrose, 20 g. pH adjusted to 5.8: Add 2.4 g/L Gelrite. Autoclave. Additions after autoclave: G5 additions, 10 ml; AgNO$_3$, 0.5 ml.

12JMS. To make 1 L: JMS major salts, 100 ml; SH minor salts, 10 ml; FeSO$_4$.7H$_2$0, 27.8 mg; Dicamba, 5 ml; Sucrose, 120 g. pH adjusted to 5.8: Add 2.4 g/L Gelrite. Autoclave. Additions after autoclave: G5 additions, 10 ml.

JMS 1M/0.5S. To make 1 L: JMS major salts, 100 ml; SH minor salts, 10 ml; FeSO$_4$.7H$_2$0, 27.8 mg; Dicamba, 5 ml; Sucrose, 5 g. pH adjusted to 5.8: Add 2.4 g/L Gelrite. Autoclave. Additions after autoclave: G5 additions, 10 ml; Ticarcillin, 2 ml; Mannose, 10 ml.

3. MS Recipes

MSAK3SPO$_4$200Ti. To make 1 L: MS salts, 4.3 g; MS vitamins (100×), 10 ml; ancimidol, 0.25 mg; kinitin, 0.5 mg; KH$_2$PO$_4$, 0.17 g; Sucrose, 30 g. pH adjusted to 5.8: Add 2.4 g/L Gelrite. Autoclave. Addition after autoclave: Ticarcillin, 2 ml.

MSAKPO$_4$200Ti2S/0.5M. To make 1 L: MS salts, 4.3 g; MS vitamins (100×), 10 ml; ancimidol, 0.25 mg; kinitin, 0.5 mg; KH$_2$PO$_4$, 0.17 g; Sucrose, 20 g. pH adjusted to 5.8: Add 2.4 g/L Gelrite. Autoclave. Additions after autoclave: Ticarcillin, 2 ml; Mannose, 10 ml.

MS200Ti2S/0.5M. To make 1 L: MS salts, 4.3 g; MS vitamins (100×), 10 ml; Sucrose, 20 g. pH adjusted to 5.8: Add 2.4 g/L Gelrite. Autoclave. Additions after autoclave: Ticarcillin, 2 ml; Mannose, 10 ml.

0.75MS3S10PPM. To make 1 L: MS salts, 4.3 g; MS vitamins (100×), 10 ml; Sucrose, 30 g. pH adjusted to 5.8: Add 2.4 g/L Gelrite. Autoclave. Additions after autoclave: Plant Preservative Mix (Plant Cell Technology), 10 ml/L.

Example 25D

Inoculation

Immature embryos from A188XHiII or other suitable genotypes are excised from 8-12 day old ears into liquid LS-inf+100 µM As (acetosyringone). Embryos are rinsed once with fresh infection medium and heat shock treated at 45° C. Agrobacterium solution is then added and embryos are vortexed for 30 seconds and allowed to settle with the bacteria for 5 minutes. The embryos are then transferred scutellum side up to LSAs medium containing 500 µM As (Negrotto et al. (2000) Plant Cell Rep 19: 798-803) and are cultured in the dark for two to three days. Subsequently, between 20 and 25 embryos per petri plate are transferred to 2JMSTi200Ag medium supplemented with 5 nM butafenacil and cultured in the dark at 28° C. for 9-14 days.

Example 25E

Selection of Transformed Maize Cells

Immature embryos producing embryogenic callus are transferred to 2JMSTi200 medium supplemented with 750 nM butafenacil. The cultures are selected on this medium for 2-3 weeks in the dark and then subcultured onto 2JMSTi200 medium supplemented with 750 nM butafenacil and subcultured for another 2-3 weeks in the dark.

Example 25F

Regeneration of Transformed Maize Plants

Calli surviving selection are transferred to MSAK3SPO$_4$200Ti medium for regeneration and are placed in the dark for 10-14 days. Surviving calli are transferred to MSAK3SPO$_4$200Ti medium and are placed in the light for 7-10 days. Regenerating shoots are transferred to Magenta GA-7 boxes (Magenta Corp, Chicago Ill.) containing 0.75MS3S10PPM medium and are grown in the light until root growth is sufficient for transfer to soil.

Example 25G

Analysis of Transformed Maize Plants

After 2-3 weeks in GA7 boxes, plants are tested for the presence of the PPO gene and other genes of interest by PCR. Positive plants from the PCR assay are tested by a Quantitative Real Time PCR Assay using TaqMan (Applied Biosystems), and single or low copy number insertion candidates are sent to the greenhouse. Southern analysis is conducted on candidates to further confirm that an intact insertion of the target sequence is present in the maize transformed plants.

C. Int Constructs for Expression in Plants

Example 26

Construction of Maize-Optimized Lambda Integrase, Int-h, Int-h/218, Excisionase, and E. coli Integration Host Factor Expression Vectors for Mediating Recombination in Monocots and Dicots Example 26A Construction of CMSynInt, a Dicot and Monocot Expression Vector MUSynInt is digested with PmlI in order to introduce an intron into the integrase coding region to guard against expression of the integrase in a bacterial host. A PvuII/SnaBI-excised intron fragment (whose cloning from pBISN1 is described above in Example 11A) is ligated into the unique PmlI site in the coding region of MUSynInt to form MUSynInt'.

An XhoI site is created at the 3' end of the MUSynInt' expression cassette by digesting with Asp718I and ligating in the following oligonucleotide: 5'-GTA CGG CTC GAG CC-3' (SEQ ID NO:89). The resulting plasmid, MUSynInt'X, is digested with HindIII/BamHI to excise the maize ubiquitin promoter.

pNOV4212 containing the CMPS promoter is digested with SpeI and the site converted to a BglII site by ligation with the oligonucleotide: 5'-CTA GGA GAT CTC-3' (SEQ ID NO:90) forming 4212Bg. The CMPS promoter fragment is excised from 4212Bg by digestion with HindIII and BglII, and ligated to the HindIII/BamHI-digested MUSynInt'X plasmid to form CMSynInt.

Example 26B

Construction of CMSynInt-h and CMSynInt-h/218, Both Dicot and Monocot Expression Vectors MUSynInt-h' and MUSynInt-h/218' are formed from MUSynInt-h and MUSynInt-h/218, respectively, as described in Example 26A. CMSynInt-h and CMSynInt-h/218 are made in exactly the same manner as CMSynInt, as described in Example 26A, using MUSynInt-h' and MUSynInt-h/218', respectively.

Example 26C

Construction of CMSynHFα, a Dicot and Monocot Expression Vector

MUSynHFα is digested with HindIII and the site converted to a SpeI site by ligation to the following oligonucleotide 5'-AGC TAC TAG T-3' (SEQ ID NO:91) The resulting plasmid, MUSynHFαSp, is digested with SpeI/BamHI to excise the ubiquitin promoter. pNOV4211 containing the CMPS promoter is digested with PstI and the site converted to a BglII site by ligating in the following oligonucleotide: 5'-CCAGATCTGGTGCA-3' (SEQ ID NO:92) forming 4211Bg. The CMPS promoter is excised from 4211Bg with SpeI and BglII, and ligated to SpeI/BamHI-digested MUSynHFαSp to form CMSynHFα.

Example 26D

Construction of CMSynIHFβ, a Dicot and Monocot Expression Vector

MUSynHFβ is digested with Asp718I and the site converted to a SpeI site by ligation to the following oligonucleotide: 5'-GTA CGG ACT AGT CC-3' (SEQ ID NO:93). The resulting plasmid, MUSynHFβSp, is digested with HindIII/BamHI to excise the ubiquitin promoter. 4212Bg is digested with HindIII/BglII and the resulting CMPS promoter fragment ligated into the MUSynHFβSp vector to form CMSynHFβ.

Example 26E

Combining CMSynInt, CMSynHFα, and CMSynHFβ into a Single Plasmid

1. Construction of pBSIntHF in pBluescript
CMSynInt is digested with HindIII and XhoI and the insert separated by preparative gel electrophoresis. CMSynHFα is digested with SpeI and Asp718I and its insert likewise purified. CMSynHFβ is digested with HindIII and the site converted to an XhoI site with the following oligonucleotide: 5'-AGC TCT CGA G-3' (SEQ ID NO:94). The resulting plasmid, CMSynHFβH, is digested with XhoI and SpeI and its insert purified in the same way. pBluescript plasmid is digested with HindIII/Asp718I and treated with alkaline phosphatase. After gel purification, this vector is joined with the three insert fragments in a four-way ligation to form pBSIntHF.
2. Construction of RKIntHF Binary Vector
Binary vector pNOV2122 is digested with HindIII/Asp718I and treated with alkaline phosphatase. After gel purification, this vector and the three insert fragments described above are joined by four-way ligation to form RKIntHF.

3. Construction of VSIntHF Binary Vector
RKIntHF is digested with HindIII and Asp718I and the fragment of 4099 bp is purified. pNOV2114 is digested with HindIII and Asp718I in the presence of alkaline phosphatase, and the vector purified. Ligation of the vector with the insert produces VSIntHF.

Example 26F

Combining CMSynInt-h, CMSynHFα, and CMSynHFβ into a Single Plasmid

1. Construction of pBSInt-hHF in pBluescript
The four-way ligation described above to form pBSIntHF is performed using the HindIII/XhoI-digested insert from CMSynInt-h in place of the HindIII/XhoI-digested insert from CMSynInt to form pBSInt-hHF.
2. Construction of RKInt-hHF Binary Vector
The four-way ligation described above to form RKIntHF is likewise performed using the HindIII/XhoI-digested insert from CMSynInt-h in place of the HindIII/XhoI-digested insert from CMSynInt to form RKInt-hHF.
3. Construction of VSInt-hHF Binary Vector
RKInt-hHF is digested with HindIII and Asp718I and the fragment of 4099 bp is purified. pNOV2114 is digested with HindIII and Asp718I in the presence of alkaline phosphatase, and the vector purified. Ligation of the vector with the insert produces VSInt-hHF.

Example 26G

Combining CMSynInt-h/218, CMSynHFα, and CMSynHFβ into a Single Plasmid

1. Construction of pBSInt-h/218HF in pBluescript
The four-way ligation described above to form pBSIntHF is performed using the HindIII/XhoI-digested insert from CMSynInt-h/218 in place of the HindIII/XhoI-digested insert from CMSynInt to form pBSInt-h/218HF.
2. Construction of RKInt-h/218HF Binary Vector
The four-way ligation described above to form RKIntHF is likewise performed using the HindIII/XhoI-digested insert from CMSynInt-h/218 in place of the HindIII/XhoI-digested insert from CMSynInt to form RKInt-h/218HF.
3. Construction of VSInt-h/218HF Binary Vector
RKInt-h/218HF is digested with HindIII and Asp718I and the fragment of 4099 bp is purified. pNOV2114 is digested with HindIII and Asp718I in the presence of alkaline phosphatase, and the vector purified. Ligation of the vector with the insert produces VSInt-h/218HF.

Example 26H

Construction of an RKInt Binary Vector

The expression cassette of CMSynInt is excised as an EcoRI fragment and ligated into the RK2 based binary vector, pNOV2122, digested with EcoRI and treated with alkaline phosphatase, to form plasmid RKInt.

Example 26I

Construction of RKInt-h Binary Vector

The expression cassette of CMSynInt-h is excised as an EcoRI fragment and ligated into the RK2 based binary vector, pNOV2122, digested with EcoRI and treated with alkaline phosphatase, to form plasmid RKInt-h.

Example 26J

Construction of an RKInt-h/218 Binary Vector

The expression cassette of CMSynInt-h/218 is excised as an EcoRI fragment and ligated into the RK2 based binary vector, pNOV2122, digested with EcoRI and treated with alkaline phosphatase to form plasmid RKInt-h/218.

Example 26K

Construction of a VSInt-h/218 Binary Vector

CMSynInt-h/218 is digested with EcoRI and the 2012 bp insert fragment is purified. pNOV2114 is digested with EcoRI in the presence of alkaline phosphatase and purified. This vector is ligated to the EcoRI fragment containing CMSynInt-h/218 and the two products formed are named VSInt-h/218A and VSInt-h/218B.

Example 26L

Construction of a Binary Vector Containing an Excisionase Expression Cassette

The SynXis gene sequence (from Example 7) is excised from its TOPO vector as a BamHI/SacI fragment and inserted into the BamHI/SacI sites of the expression vector, CMSynHFβ to form 2994SynXis. The 404 bp fragment of CMSynHFβ containing the CMPS promoter is inserted into the BamHI site of 2994SynXis to form CMSynXis. The 945 bp EcoRI fragment of CMSynXis is ligated into the binary vector portion of VSInt-h/218A digested with EcoRI forming VSXis.

Example 26M

Construction of vIntHF: a Wheat Geminivirus Replicon with CMSynInt, CMSynIHFα, and CMSynIHFβ pBSIntHF is digested with SpeI and XhoI, and a fragment of 2047 bp containing the CMPSInt gene is purified. Digestion of the same plasmid with XhoI and Asp718I affords a 2088 bp fragment containing the IHF genes. By three-way ligation, these two insert fragments are joined to purified viral vector pWI-11M, digested with SpeI and Asp718I. The product is named vIntHF.

Example 26N

Construction of a vInt-h/218HF: a Wheat Geminivirus Replicon with CMSynInt-h/218, CMSynHFα, and CMSynHFβ pBSInt-h/218HF is digested with SpeI and XhoI, and a fragment of 2047 bp containing the CMPSInt-h/218 gene is purified. The IHF gene fragment of 2088 bp from above is employed here again. By three-way ligation, these two insert fragments are joined to SpeI and Asp718I-digested viral vector pWI-11M. The product is named vInt-h/218HF.

Example 26O

Construction of a vInt-h/218: Wheat Geminivirus Replicon with CMSynInt-h218

The 2047-bp SpeI/XhoI fragment of pBSInt-h/218HF described above is ligated to pWI-11M digested with SpeI and SalI. The resulting plasmid is named vInt-h/218.

Example 26P

Introduction of CMPSIntHF, CMPSInt-h/218HF, and CMPSInt-h/218 into Binary Vector pNOV2114 Flanked by Direct Repeats of a Wheat Dwarf Gemini Viral DNA Replicon in *Agrobacterium* LBA4404 (pSB1)

A T-DNA vector with repeated copies of a viral replicon allows excision of the viral genome, together with the DNA inserted between repeats. Such excision events may either precede or follow T-DNA insertion into the plant genome. This approach allows the inserted DNA to be replicated to high copy number in appropriate host plant cells. The constructs are made in two steps. First, a binary vector with a part of the viral genome (excluding the NPTII gene and incompatible *E. coli* ori) between the T-DNA borders is constructed and transformed into an *Agrobacterium* helper strain such as LBA4404.

Next, this *Agrobacterium* strain is retransformed with the viral plasmid to be inserted into T-DNA, selecting for KmR. Since the viral vector cannot replicate in *Agrobacterium*, selection for KmR identifies clones in which the virus has co-integrated into T-DNA. Plasmid vCMLucB/P (Example 67A, below) is digested with SphI and an oligonucleotide (5'-CCG GAT CCG GCA TG-3' (SEQ ID NO:95)) is ligated into the resulting vector to convert the SphI site to BamHI.

From the resulting plasmid, vCMLucB/P-BamHI, digestion with BamHI provides a fragment of 3149 bp containing the viral vector (pWI-11M) minus the 637 bp p15Q ori region. Binary vector pNOV2114 is digested with BglII in the presence of alkaline phosphatase, and the purified vector fragment is ligated with the 3149 bp fragment of pWI-11M. A plasmid is identified which has the insert oriented such that the NPTII gene is near the RB of T-DNA and named 2114WI-11B. It is digested with XbaI and religated to remove most of the NPTII gene, and the product named 2114WI-ΔXB. This plasmid is transformed into *Agrobacterium* strain LBA4404 (pSB1), selecting for the spectinomycin resistance of pNOV2114. The resulting *Agrobacterium* strain is LBA4404 (pSB1) (2114WI-ΔXB). Electro-competent cells are prepared from this strain for introduction of viral constructs.

Example 26Q

Construction of VexCMIntHF in *Agrobacterium*

Plasmid vIntHF is transformed into LBA4404 (pSB1) (2114WI-ΔXB) and transformants are selected on YP agar with Km50, Spec100 and Tc5. Structure of the DNA with viral-flanked CMIntHF construct is confirmed by analysis of miniprep DNA isolated from *Agrobacterium*.

Example 26R

Construction of VexCMInt-h/218HF in *Agrobacterium*

Plasmid vInt-h/218HF is electro-transformed into LBA4404 (pSB1) (2114WI-ΔXB) and transformants are selected on YP agar with K-m50, Spec100 and Tc5. Structure of the T-DNA with viral-flanked CMInt-h/218HF construct is confirmed by analysis of miniprep DNA isolated from *Agrobacterium*.

Example 26S

Construction of VexCMInt-h/218 in *Agrobacterium*

Plasmid vInt-h/218 is transformed into LBA4404 (pSB1) (2114WI-ΔXB) and transformants are selected on YP agar with Km50, Spec100 and Tc5. Structure of the T-DNA with viral-flanked CMInt-h/218 construct is confirmed by analysis of miniprep DNA isolated from *Agrobacterium*.

D. Construction of Donor Sequences for Recombination with Target Sequences in Maize Generally, the exemplary donor sequences constructed herein contain the 5'-portion of the PMI expression cassette and the 3'-portion of the GUS expression cassette; that is, the portion of each that is missing from the target sequence. The division point of the intron within each gene is punctuated by an att site.

Donor constructs may contain a single att site, taking the form 5'PMI-5'Intron-AttSite-3'Intron-3'GUS. Alternatively, donor constructs may contain two att sites, taking the form AttSite-3'Intron-3'GUS-5'PMI-5Intron-AttSite. The 3' portion of an intron in the donor corresponds to the 5' portion of the same intron in the compatible target sequence. The 5' portion of an intron in the donor corresponds to the 3' portion of the same intron in the compatible target sequence. The att site(s) in the donor are capable of recombining with the att site(s) in the corresponding target sequence. In addition, the orientation of the att sites with respect to the truncated genes is the same in the donor and target sequences.

Example 27

Monocot Donors with Inverted attB Sites

The *Arabidopsis* Act2 3'-UTR (An, Y. Q. et. al., (1996) Plant J. 10: 107-121) is amplified from *Arabidopsis thaliana* ecotype Columbia with primers PAct2BH (5'-CTA AGG ATC CAA GAT CAA AGG CTT AAA AAG C-3') (SEQ ID NO:96) and PAct2XbaI (5'-GGA ATC TAG ATG TAT AAA CCA AAT GAG CAG-3') (SEQ ID NO:97). The PCR product is digested with BamHI and XbaI and ligated into pBluescript II KS(+) forming pNOV2713.

The *Arabidopsis thaliana* actin-2 3' untranslated region is excised as a BamHI (klenow), NotI terminator fragment from pNOV2713 and ligated into the AvaI (klenow), PspOMI sites at the 3' end of the GUS exon2 of CMPSGU-SAttBrev forming a complete GUS expression cassette named CMGUSAttBrTact.

The donor with inverted attB sites is formed by a 3-way ligation between (1) the 3' portion of the GUS expression cassette, including the attB site, excised as an XbaI (klenow)/BglII fragment from CMGUSAttBrTact; (2) the 5' portion of the PMI expression cassette, including the attB site, excised as an SphI (klenow)/AvrII fragment from MUPMIAttB; and (3) pNOV2114 digested with BamHI/XbaI. The 3-way ligation forms the donor named DONdbAttB.

The PPO expression cassette of pNOV5013 can be ligated into the unique SbfI site of DONdbAttB as a PstI fragment forming DONdbAttB.PPO, which can be used as described in Example 48.

Example 28

Monocot Donors with Inverted attP Sites

The *Arabidopsis thaliana* Actin-2 3' untranslated region is excised as a BamHI (klenow), NotI terminator fragment from pNOV2713 and ligated into the AvaI (klenow), PspOMI sites at the 3' end of the GUS exon2 of CMPSGU-SAttPrev forming a complete GUS expression cassette named CMGUSAttPrTact.

The donor with inverted attP sites is formed by a 3-way ligation between (1) the 3' portion of the GUS expression cassette, including the attP site, excised as an XbaI (klenow)/BglII fragment from CMGUSAttPrTact; (2) the 5' portion of the PMI expression cassette, including the attP site, excised as an SphI (klenow)/AvrII fragment from MUPMIAttP; and (3) pNOV2114 digested with BamHI/XbaI. The 3-way ligation forms the donor named DONdbAttP.

The PPO expression cassette of pNOV5013 can be ligated into the unique SbfI site of DONdbAttP as a PstI fragment forming DONdbAttP.PPO, which can be used as described in Example 48.

Example 29

Monocot Donors with Inverted attB1 and attB2 Sites

The attB1 site is introduced into the BglII site of the AT BAF60 intron in the GUS gene of pNOV5003 using the oligonucleotide pair 5'-GAT CTG GGG ACA AGT TTG TAC AAA AAA GCA GGC TTC AGC TAG C-3' (SEQ ID NO:98) and 5'-GAT CGC TAG CTG AAG CCT GCT TTT TTG TAC AAA CTT GTC CCC A-3' (SEQ ID NO:99). These oligonucleotides are phosphorylated using T4 polynucleotide kinase and then combined in a ligation reaction with pNOV5003 digested with BglII and treated with alkaline phosphatase. The resulting plasmid, GUSAttB1rev, is sequenced to determine that the attB1 site is in the 3' to 5' direction relative to the orientation of the GUS coding region.

The *Arabidopsis thaliana* Actin-2 3' untranslated region is excised (Tact) of pNOV2713 is added at the 3'end of GUSAttB1rev by 3-way ligation. The vector, pUC18 digested with EcoRI,XbaI, is ligated together with GUSAttB1rev digested with MfeI/XhoI and pNOV2713 digested with XhoI,XbaI to produce GUSAttB1revTact.

The attB2 site is introduced into the MfeI site of the PMI intron3 of pNOV2790 using the oligonucleotide pair 5'-AAT TGG TAC CTG AAC CCA GCT TTC TTG TAC AAA GTG GTC CCC TAG G-3' (SEQ ID NO:100) and 5'-AAT TCC TAG GGG ACC ACT TTG TAC AAG AAA GCT GGG TTC AGG TAC C-3' (SEQ ID NO:101). These oligonucleotides are phosphorylated using T4 polynucleotide kinase and then combined in a ligation reaction with pNOV2790 digested with MfeI and treated with alkaline phosphatase. The resulting plasmid, pNOV2790AttB2, is sequenced to determine that the attB2 site is in the 5' to 3' direction relative to the orientation of PMI intron3.

The PMI intron3 containing the attB2 site is excised from pNOV2790AttB2 as a BstBI,PshAI fragment and is ligated into the binary vector pNOV2117, cut with BstBI,PshAI, forming a PMI expression cassette, called MUPMIAttB2, which contains the PMI intron3 with an attB2 site.

The donor with inverted attB1 and attB2 sites is formed by a 3-way ligation between (1) the 3' portion of the GUS expression cassette, including the attB1 site, excised as a BglII,SphI fragment from GUSAttB1rTact; (2) the 5'portion of the PMI expression cassette, including the attB2 site, excised as an SphI,AvrII fragment from MUPMIAttB2; and (3) pNOV2114 digested with BamHI/XbaI. The 3-way ligation forms the donor named DONAttB1.B2.

The PPO expression cassette of pNOV5013 can be ligated into the unique SbfI site of DONAttB1.B2 as a PstI fragment forming DONAttB1.B2.PPO, which can be used as described in Example 48.

Example 30

Monocot Donor with a Single attB Site

Bluescript cloning vector pBS-SKminus is modified by conversion of the XhoI site in the polylinker to an SphI site by insertion of the oligonucleotide: 5'-TCG AAG CAT GCT-3' (SEQ ID NO:102) to form pBS.XSph. A three-way ligation is performed with the following fragments: pBS.X-SpH digested with HindIII and SphI; MUPMIAttB digested with HindIII and AvrII (excising 5'UbiPMI/AttB) and CMGusAttBrevTact digested with NheI and SphI (excising 3'Gus.Act2utr but not AttBrev) to form pBSDONsgAttB.

Example 31

Monocot Donor with a Single attP Site

A three-way ligation is performed with the following fragments: pBS.XSpH digested with HindIII and SphI; MUPMIAttP digested with HindIII and AvrII (excising 5'UbiPMI/AttP) and CMGusAttBrevTact digested with NheI and SphI (excising 3'Gus.Act2utr but not AttBrev) to form pBSDONsgAttP.

Example 32

T-DNA Monocot Donor with a Single attB Site pBSDONsgAttB is digested with AscI and SbfI, and the insert fragment of about 6 kb is ligated into binary vector pNOV2114 digested with AscI and SbfI to form DONsgAttB.

Example 33

T-DNA Monocot Donor with a Single attP Site pBSDONsgAttP is digested with AscI and SbfI, and the insert fragment of about 6 kb is ligated into binary vector pNOV2114 digested with AscI and SbfI to form DONsgAttP.

Example 34

Monocot Viral Replicon Donor with a Single attB Site

Figure 5:
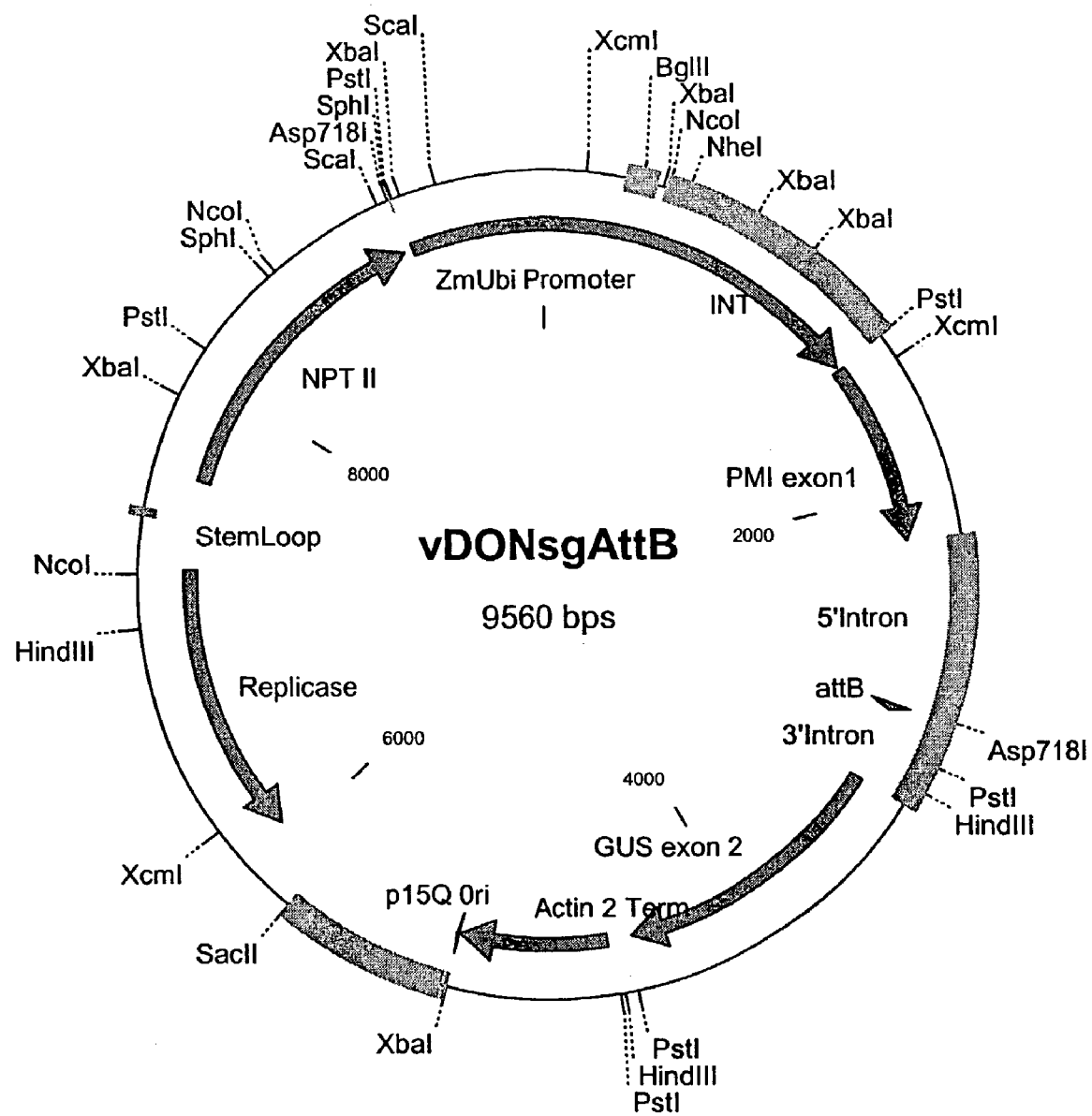
FIG. 5 represents the structure of vDONsgAttB, an exemplary plasmid that contains a monocot donor sequence with a single attB site.

The BamHI site of pWI-11M is converted into a MluI site using the following oligonucleotide 5'-GAT CAC GCG T-3' (SEQ ID NO:103) to form pWI-11M.Mlu. pBSDONsgAttB is digested with SbfI, made blunt by 3'-5' exonuclease, and AscI to form a fragment of about 6 kb. This fragment is ligated into pWI-11M.Mlu digested with Asp718I, made blunt by klenow, and MluI to form vDONsgAttB (FIG. 5).

Example 35

Monocot Viral Replicon Donor with a Single attP Site pBSDONsgAttP is digested with SbfI, made blunt by 3'-5' exonuclease, and AscI to form a fragment of about 6 kb. This fragment is ligated into pWI-11M.Mlu digested with Asp718I, made blunt by klenow, and MluI to form vDONsgAttP.

Example 36

Monocot Viral Replicon Donor with Inverted attB Sites

DONdbAttB is digested with AgeI, made blunt by klenow, and AscI to form a fragment of about 6 kb. This fragment is ligated into pWI-11M.Mlu digested with Asp718I, made blunt by klenow, and MluI to form vDONdbAttB.

Example 37

Monocot Viral Replicon Donor with Inverted attP Sites

DONdbAttP is digested with AgeI, made blunt by klenow, and AscI to form a fragment of about 6 kb. This fragment is ligated into pWI-11M.Mlu digested with Asp718I, made blunt by klenow, and MluI to form vDONdbAttP.

Example 38

Monocot Viral Replicon Donor with Inverted attB1 and attB2 Sites

DONAttB1.B2 is digested with AgeI, made blunt by klenow, and AscI to form a fragment of about 6 kb. This fragment is ligated into pWI-11M.Mlu digested with Asp718I, made blunt by klenow, and MluI to form vDONAttB1.B2.

Example 39

Construction of VexDONsgAttB: DONsgAttB Flanked by Monocot Viral Replicon in *Agrobacterium*

In this and several of the following examples, a series of binary viral excision (Vex) vectors is constructed whose T-DNA has nearly-complete copies of the wheat dwarf virus replicon flanking the gene(s) of interest. These viral excision vectors permit excision from T-DNA, after delivery to the plant cell, of a circular viral replicon that carries the gene(s) of interest and is capable of multiplying the gene(s) of interest to a high copy number. The general approach is to construct a receptor binary vector, 2114-pWI-ΔX, whose T-DNA contains one nearly-complete viral copy from pWI-11M but lacks its KmR gene. 2114-pWI-ΔX is electro-transformed into *Agrobacterium* LBA4404(pSB1) to produce LBA4404(pSB1)(2114-pWI-ΔX). Subsequently, any donor or other construct of interest is cloned into pWI-11M (with its intact KmR gene), a plasmid that cannot replicate in *Agrobacterium*. The latter plasmid is electro-transformed into LBA4404 (2114-pWI-ΔX), and the bacteria are plated on kanamycin-containing agar to select for clones in which the donor DNA has co-integrated with the receptor binary through viral DNA homology, yielding a T-DNA with viral copies flanking the gene(s) of interest.

For construction of 2114-pWI-ΔX, plasmid vCMLucB/P (Example 67A, below) is digested with SacII and the site is converted to BamHI (bold) with a site change oligonucleotide, 5'-CCG GAT CCG GGC-3' (SEQ ID NO:104), yielding CMPSVLucB/P.BamHI. This product is digested with BamHI, and a 3145 bp fragment containing the entire viral replicon but lacking most of the P15Q ori is gel purified. Binary vector pNOV2114 is digested with BglII and alkaline phosphatase and gel-purified. The two are ligated together to form 2114WI-11A and 2114WI-11B. The latter has the NPTII marker nearer the right border and is used in the next step. By digestion with XbaI and religation, it is converted to 2114WI-ΔXB, from which most of the NPTII gene is deleted. This plasmid is transformed into LBA4404 (pSB1) by selection for spectinomycin resistance, creating recipient strain LBA4404(pSB1)(2114WI-ΔXB), which is employed here and in Examples 40-43.

Plasmid vDONsgAttB (FIG. 5) is transformed into LBA4404(pSB1)(2114WI-ΔXB), and transformants are selected on YP agar with Km50, Spec100, and Tc5. The structure of the T-DNA with the viral-flanked DONsgAttB construct is confirmed by analysis of miniprep DNA isolated from *Agrobacterium*.

Example 40

Construction of VexDONsgAttP: DONsgAttP Flanked by Monocot Viral Replicon in *Agrobacterium*

Plasmid vDONsgAttP is transformed into LBA4404 (pSB1)(2114WI-ΔXB) and transformants are selected on YP agar with Km50, Spec100 and Tc5. Structure of theT-DNA with viral-flanked DONsgAttP construct is confirmed by analysis of miniprep DNA isolated from *Agrobacterium*.

Example 41

Construction of VexDONdbAttB: DONdbAttB Flanked by Monocot Viral Replicon in *Agrobacterium*

Plasmid vDONdbAttB is transformed into LBA4404 (pSB1)(2114WI-ΔXB) and transformants are selected on YP agar with Km50, Spec100 and Tc5. Structure of theT-DNA with viral-flanked DONdbAttB construct is confirmed by analysis of miniprep DNA isolated from *Agrobacterium*.

Example 42

Construction of VexDONdbAttP: DONdbAttP Flanked by Monocot Viral Replicon in *Agrobacterium*

Plasmid vDONdbAttP is transformed into LBA4404 (pSB1)(2114WI-ΔXB) and transformants are selected on YP agar with Km50, Spec100 and Tc5. Structure of the T-DNA with viral-flanked DONdbAttP construct is confirmed by analysis of miniprep DNA isolated from *Agrobacterium*.

Example 43

Construction of VexDONAttB1.B2: DONAttB1.B2 Flanked by Monocot Viral Replicon in *Agrobacterium*

Plasmid vDONAttB1.B2 is transformed into LBA4404 (pSB1)(2114WI-ΔXB) and transformants are selected on YP agar with Km50, Spec100 and Tc5. Structure of the T-DNA with viral-flanked DONAttB1.B2 construct is confirmed by analysis of miniprep DNA isolated from *Agrobacterium*.

E. Targeted Integration of a Donor Sequence into a Maize Target Line

Example 44

Targeted Integration of Donor Constructs into Transformed Maize Embryogenic Callus via Bombardment

Example 44A

Production of Maize Callus for Targeted Integration Experiments

Transformed maize plants containing a single copy insertion of a target sequence T-DNA are selfed or backcrossed in the greenhouse and produce seed. Immature embryos are excised from ears essentially as described in Negrotto et al. (2000) Plant Cell Reports 19: 798-803. Transformed embryogenic callus is initiated by placing the immature embryos onto 2JMSAg containing no butafenacil or 100 nM butafenacil for selection of positive segregants. Transformed, embryogenic callus is used for targeted integration either directly off the zygotic embryo at 9-12 days after callus initiation or from a propagated culture.

Example 44B

Co-Precipitation of Plasmid DNA onto Gold Beads for Bombardment

The combination of plasmids used for each treatment includes an appropriate donor DNA, compatible for recombination with the target sequence T-DNA, and an integrase expression cassette with or without co-expression of *E. coli* integration host factor protein. These plasmids are aliquoted as 1-10 μg per plasmid into a sterile, 50 μl volume of 50% glycerol with 3 mg of <1 μm gold particles (Crescent Chem. Co., Inc., NY). Plasmid DNA is precipitated onto the gold particles using standard CaCl$_2$-sperimidine chemistry (Klein et al. (1987) *Nature* 327:70-73).

Example 44C

Bombardment of Maize Callus for Targeted Integration

Transgenic maize callus is arranged in a 2 cm diameter ring placed on 12JMS medium containing 12% sucrose, which provides an osmotic pressure treatment to the callus for at least 3 hours prior to bombardment. Each target plate is bombarded 1-2 times using a DuPont Helium Gun with 650 psi rupture discs (Biorad) and is then placed into the dark.

Example 44D

Scoring GUS Positive Targeted Events

A Lambda integrase mediated insertion of the bombarded donor DNA into the target sequence T-DNA site creates an intact β-glucuronidase (GUS) expression cassette. Bombarded maize callus is incubated in the dark for 2-10 days. A subset of the targeted calli is assayed for targeted integration using a GUS histochemical assay (Jefferson et al. (1987) EMBO J. 6:3901-3907). A positive, blue stained cell (GUS spot) is scored as a stable, targeted insertion event.

Example 44E

Selection of Maize Targeted Events

An integrase-mediated insertion of the bombarded donor sequence into the target sequence T-DNA site also creates an intact phosphomannose isomerase (PMI) expression cassette (Negrotto et al. (2000) Plant Cell Reports 19: 798-803) and allows for selection of targeted events. The calli not sacrificed for GUS assays are placed onto selection medium, JMS 1M/0.5S, at 1-2 weeks after bombardment. The maize callus is incubated in the dark on selection medium until growth of microcalli on mannose is evident. Calli growing on mannose are subcultured onto fresh selection medium and bulked-up for regeneration.

Example 44F

PCR Analysis of Maize Targeted Events

Selected tissue is regenerated on MSAKPO$_4$200Ti2S/0.5M medium in the dark for 10-14 days (Negrotto et al. (2000) Plant Cell Reports 19: 798-803). Tissue is then transferred to fresh MSAKPO$_4$200Ti2S/0.5M medium and cultured in the light (16 hour light/8 hour dark regimen). After 1 week, green tissues are transferred to MS200Ti2S/0.5M medium and are grown in the light. Plantlets are transferred to Magenta GA-7 boxes containing 0.75MS3S10PPM medium and are grown in the light until root growth is sufficient for transfer to soil. Regenerated maize plants are analyzed using a PCR assay. One primer of the pair is homologous to the target DNA and the other is homologous to the donor DNA, so that a predictable size PCR product forms only if the donor DNA has undergone Lambda integrase mediated recombination with the attachment site(s) of the target DNA. Those plants confirmed by PCR to contain a targeted integration event are sent to the greenhouse. Southern analysis is conducted on PCR positive candidates to further confirm the molecular structure of the targeted integration events.

Example 44G

GUS Positive Targeted Events p Target sequence T-DNA's which are inserted into different locations in the maize genome are designated in Table 5 below as Lines 1, 2, etc.

TABLE 5

| Target sequence | Donor | Integrase and HF Protein | Average GUS Spots/Target |
|---|---|---|---|
| Exp. #1: | | | |
| LPsgAttP Line1 | vDONsgAttB | | 1 |
| LPsgAttP Line1 | vDONsgAttB | pBSInt-h/218HF | 200 |
| Exp. #2: | | | |
| LPsgAttP Line2 | vDONsgAttB | | 0.5 |
| LPsgAttP Line2 | vDONsgAttB | pBSInt-h/218HF | 35 |
| LPsgAttP Line2 | vDONsgAttB | pBSIntHF | 2.5 |
| LPsgAttP Line2 | pBSDONsgAttB | pBSInt-h/218HF | 2.0 |
| Exp. #3: | | | |
| LPsgAttP Line3 | vDONsgAttB | pBSInt-h/218HF | 160 |
| Exp. #4: | | | |
| LPsgAttP Line1 | vDONsgAttB | pBSInt-h/218HF | 116 |
| Exp. #5: | | | |
| LPdbAttP Line1 | vDONdbAttB | pBSInt-h/218HF | 12 |
| LPdbAttP Line1 | vDONdbAttB | vInt-h/218HF | 6 |
| LPdbAttP Line1 | DONdbAttB | vInt-h/218HF | 10 |
| Exp. #6 | | | |
| LPdbAttP Line2 | vDONdbAttB | pBSInt-h/218HF | 148 |
| LPdbAttP Line2 | vDONdbAttB | vInt-h/218HF | 20 |
| LPdbAttP Line2 | DONdbAttB | vInt-h/218HF | 8 |
| Exp. #7 | | | |
| LPAttP1.P2 Line1 | vDONAttB1.B2 | | 0 |
| LPAttP1.P2 Line1 | vDONAttB1.B2 | pBSInt-h/218HF | 7 |

These results show that expression of Lambda integrase genes, enhanced by the expression of the E. coli integration host factor protein, mediates intermolecular recombination between the donor recognition site(s) and the recognition site(s) in the maize target lines.

Example 45

Targeted Integration of Donor Constructs into Maize Target Sequence Embryos via Agrobacterium-Mediated Transformation

Example 45A

Binary Vectors for Transformation

The donor binary vectors, DonsgAttB, DonsgAttP, DondbAttB, DondbAttP, DonAttP1.P2, VexDonsgAttB, VexDonsgAttP, VexDondbAttB, VexDondbAttP and VexDonAttB1.B2 and the Lambda integrase binary vectors, VSIntHF, VSInt-h/218, VSInt-h/218HF, VexIntHFαβ, VexInt-h/218, and VexInt-h/218HFαβ are suitable for maize transformation.

Example 45B

Preparation of Agrobacterium tumefaciens

An Agrobacterium strain LBA4404 (pSB1) containing one of the donor binary vectors and a second Agrobacterium strain LBA4404 (pSB1) containing one of the Lambda integrase binary vectors are grown and pre-induced for transformation experiments as described in Example 25. Alternatively, an Agrobacterium strain LBA4404 containing one of the donor binary vectors and a compatible Lambda integrase binary vector is grown and pre-induced for transformation experiments as described in Example 25.

Example 45C

Inoculation and Co-Cultivation

An *Agrobacterium* strain containing a donor binary vector and a second *Agrobacterium* strain containing a Lambda integrase binary vector are mixed in a 1:1 ratio for inoculation. Alternatively, a single *Agrobacterium* strain containing both donor and Lambda integrase binary vectors is used for inoculation. The donor binary vector is compatible for recombination with the target sequence T-DNA insertion in the maize immature embryos used for the inoculation. Inoculation and co-cultivation are carried out as described in Example 25.

Example 45D

Pre-Selection and Selection of Maize Targeted Events

After co-cultivation, the callus is transferred to pre-selection medium, 2JMSTi200Ag, for 10-14 days in the dark. Embryogenic calli are transferred to JMS1M0.5S medium and are selected on this medium for 6-10 weeks with a subculture step at 2-3 week intervals. Surviving calli are transferred to MSAKPO$_4$200Ti2S/0.5M medium and kept in the dark for 10-14 days. Tissue is transferred to MSAKPO$_4$200Ti2S/0.5M medium and placed in the light (16 hour light/8 hour dark regiment). After 1 week, green tissues are then transferred to MS200Ti2S/0.5M medium and incubated for 1-2 weeks. Plantlets are transferred to Magenta GA-7 boxes (Magenta Corp., Chicago, Ill.) containing 0.75MS3S10PPM medium and grown in the light. After 2-3 weeks, plants are tested for a targeted insertion event (see below) and plants testing positive are transferred to soil in the greenhouse.

Example 45E

GUS and PCR Assays for Maize Targeted Events

A Lambda integrase mediated insertion of the Donor DNA into the target sequence T-DNA site creates an intact β-glucuronidase (GUS) expression cassette. Maize tissues are submerged in GUS histochemical mix (Jefferson, R. A. et. al., (1987) EMBO J. 6: 3901-3907) at 37° C. for about 24-72 hours. The appearance of blue colored regions is scored as a Lambda integrase targeted event. Maize tissues are assayed by PCR using primer pairs which lead to amplification of a DNA fragment across the newly formed attL, attR, attL1, and attL2 recombination sites. One primer of the pair is homologous to the target sequence DNA and the other is homologous to the donor DNA, so that a predictable size PCR product forms only if the donor DNA has undergone Lambda integrase mediated recombination with the attachment sites of the target sequence T-DNA. Amplification of the predictable size PCR product is scored as a Lambda integrase targeted event.

Example 46

Targeted Integration via a Cross between Maize Plants Transgenic for the Target Sequence and Maize Plants Transgenic for the Donor Sequence

Example 46A

*Agrobacterium*-Mediated Transformation of Maize to Introduce Target Sequence Constructs Transformation of immature maize embryos with *Agrobacterium* strain LBA4404 (pSB1) containing one of the target sequence binary vectors is performed as described in Example 25.

Example 46B

Selection and Regeneration of Maize Plants Transformed with Target Sequence T-DNA Butafenacil resistant maize calli are selected and regenerated as described in Example 25. Butafenacil resistant maize plants are screened for single or low copy number insertion of the target sequence using PCR and Southern analysis as described in Example 25.

Example 46C

Production of Maize Plants Transformed with Target Sequence T-DNA

Transformed maize plants containing a single or low copy number of the target sequence are selfed in the greenhouse and produce seed. Embryos are rescued from seed as described in Hill et al. (1995) Euphytica 85: 119-123, and are placed onto B5 medium with 2% sucrose and 50 nM butafenacil to select for transformants containing the target sequence T-DNA. Germinated seedlings are transferred to GA7 Magenta Boxes and rooted on rooting medium. Taqman PCR is done on these plants to distinguish between transformants that are homozygous and those that are heterozygous for the target sequence T-DNA. When roots have developed on the homozygous transformants, they are transferred to soil in the greenhouse. These plants are used as one parent in the cross.

Example 46D

*Agrobacterium*-Mediated Transformation of Maize to Introduce a Donor:PPO and a Lambda Integrase Expression Cassette Transformation of immature maize embryos with *Agrobacterium* strain LBA4404 containing one of the Donor: PPO binary vectors and one of the "RK" Lambda integrase expression cassette binary vectors is performed as described above for maize.

Example 46E

Selection and Regeneration of Maize Plants Transformed with a Donor:PPO and an Integrase Expression Cassette Butafenacil resistant maize calli are selected and regenerated as described above. Butafenacil resistant maize plants are screened for single or low copy number insertion of the Donor:PPO T-DNA and Lambda integrase expression cassette T-DNA using PCR and Southern analysis as described above.

Example 46F

Production of Maize Plants Transformed with Donor:PPO and Lambda Integrase Expression Cassette T-DNA Transformed maize plants containing a single or low copy number insertion of the Donor:PPO and Lambda integrase T-DNA are selfed in the greenhouse to produce seed. Embryos are rescued from the seed as described in Hill et al. (1995) Euphytica 85: 119-123 and are germinated on B5 medium with 2% sucrose and 50 nM butafenacil to select for positive segregants. Germinated seedlings are transferred to GA7 Magenta Boxes and rooted on rooting medium. Taqman PCR is done on these plants to distinguish between transformants that are either homozygous or heterozygous for the inserted T-DNA's. The plants are also assayed by Northern analysis and/or ELISA to determine the expression level of the integrase. The homozygous segregants with the best level of integrase expression are used as the other parent in the cross.

Example 46G

Targeted Integration via a Cross Between a Target Sequence Parent and a Donor:PPO/Lambda Integrase Expressing Parent Maize plants homozygous for the target sequence are crossed with maize plants homozygous for a compatible Donor:PPO and expressing Lambda integrase. Embryos are rescued from the seed, as described in Hill, M. et al., Euphytica 85: 119-123, 1995, and are germinated on B5 medium with mannose to select for transformants containing an intact PMI gene expression cassette and therefore a targeted insertion event.

Example 46H

Assays for Maize Targeted Events

Maize calli growing on mannose are regenerated into plants following the protocol described above for maize. Maize plants are assayed by GUS and PCR analysis to confirm that they contain a targeted integration event. Plants containing a targeted integration event are sent to the greenhouse. Southern analysis is conducted on PCR positive candidates to further confirm the molecular structure of the targeted integration events.

Example 46I

Segregation of Targeted Integrants from Donor and Lambda Integrase T-DNA

Maize plants containing a targeted insertion are backcrossed in the greenhouse and produce seed. Embryos are rescued from the ears as described above and are germinated onto B5 medium containing mannose. The germinated seedlings are screened for the absence of butafenacil resistance. The butafenacil sensitive plants are assayed by PCR for the presence of the targeted insertion structure and the absence of both the Donor:PPO and Lambda integrase T-DNA. This PCR assay is used to screen for segregants that contain the targeted insertion alone.

III. Intrachromosomal Excision of a Nucleotide Sequence in Maize

Example 47

Construction of a Monocot Vector Containing attB and attP Recombination Sites for Intrachromosomal Excision of a Nucleotide Sequence Binary vector pQD203A11 containing CMPS:GUSintron:Tact2 and ZmUbi:PMIintron:Tnos cassettes is constructed as described below. In pQD203A11, an attB site is inserted into the first intron of a PMIintron gene (i.e., a PMI gene that includes 4 introns inserted within the PMI coding sequence) and an attP site is inserted upstream of the ZmUbi promoter (see FIG. 6). AttB and attP sequences are in the same orientation. This vector allows the use of phage Lambda integrase to excise the intervening DNA sequence, thereby inactivating the selectable marker by removing the whole maize Ubi promoter (ZmUbi) and a portion of PMIintron upstream of the attB sequence. To do this, complementary oligonucleotides ATTB1 (5'-GAT CCG CTC AAG TTA GTA TAA AAA AGC AGG CTT CAT GA-3') (SEQ ID NO:105) and ATTB2 (5'-GAT CTC ATG AAG CCT GCT TTT TTA TAC TAA CTT GAG CG-3') (SEQ ID NO:106) are annealed and inserted into BglII digested- pNOV2790 to form pQD187A8. A binary vector (pNOV5099) containing a positive control PMIintron gene with the attB sequence in the first intron is constructed by inserting the 3551 bp BamHI fragment of pQD187A8 into BamHI-digested pNOV041. pNOV041 is a binary vector containing ZmUbi:PMIintron:Tnos expression cassette in its T-DNA region.

Figure 6:
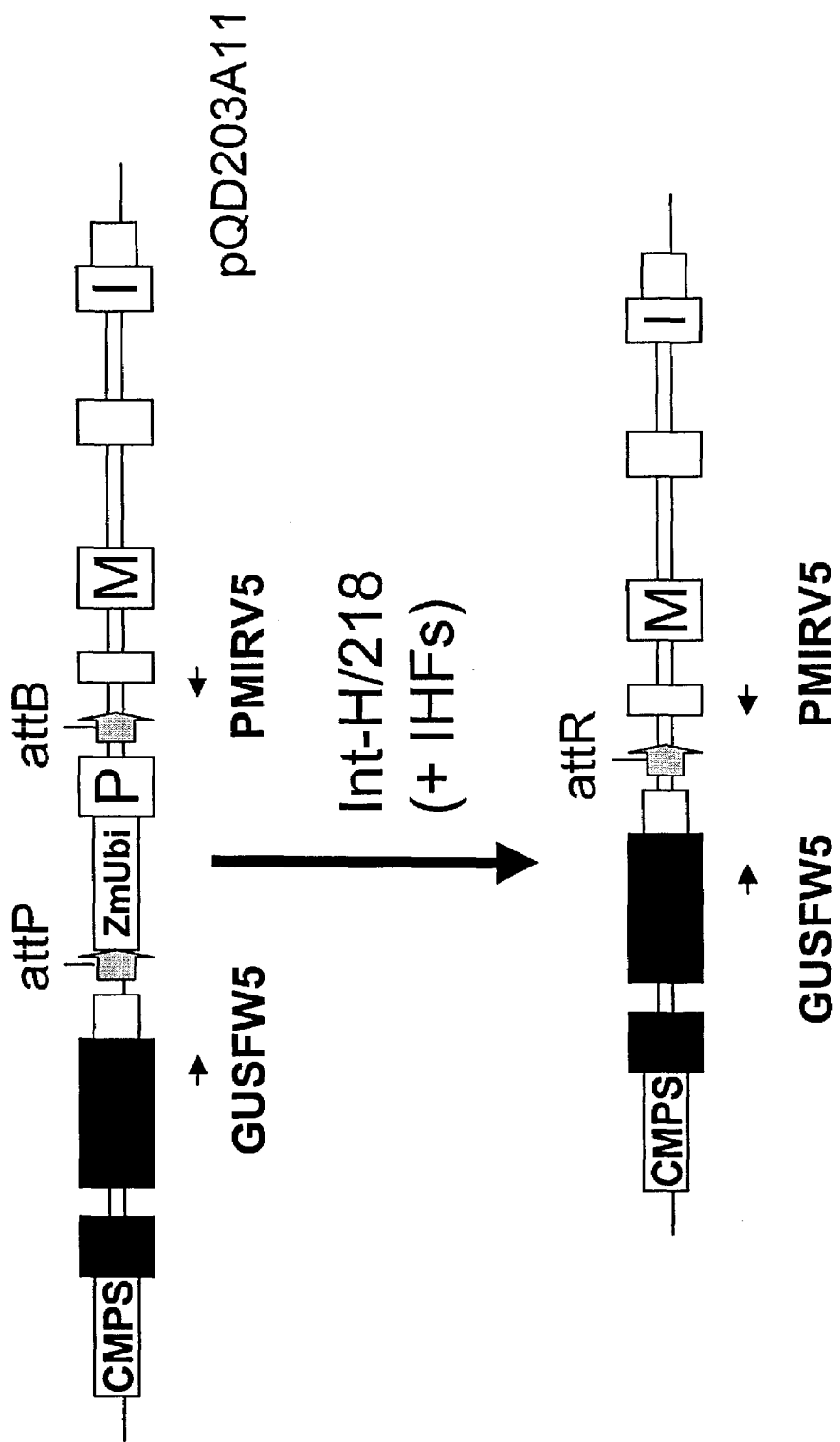
FIG. 6 represents a recombination event where a nucleotide sequence located between an attP recognition site and an attB recognition site on a target molecule is excised using an Int and IHF.

The attP sequence is amplified by PCR from the phage DNA with two primers, ATTPSPOMI (5'-GGG CCC TCT GTT ACA GGT CAC TAA TAC CAT CTA AG-3') (SEQ ID NO:107) and ATTPSPEI (5'-ACT AGT GAA ATC AAA TAA TGA TTT TAT TTT G-3') (SEQ ID NO:108), and the PCR product is cloned into the pCR2.1-TOPO vector to form pNOV5088. pQD189A12 is digested with XbaI, filled-in with Klenow, and then cut with NotI. pQD189A12 is a pBluescrpt KS (+) cloning vector containing CMPS:GUS:Tact2 expression cassette. The above XbaI/NotI fragment of pQD189A12 is then ligated with the ApaI/NotI fragment of pNOV5088 to form pQD194A1. pQD110A5 is a pBluescript KS(+) vector containing an RS sequence. The RS sequence is excised from pQD110A5 by NotI and SacI digestion and inserted into SacI/NotI-digested pQD194A1 (6370 bps) to form pQD198A1. The NcoI(blunt)/PspOMI fragment (3.6 kb) of pQD198A1 is inserted into a (PacI) blunt/PspOMI fragment (11535 bps) of pNOV5099 to form binary vector pQD203A11, which contains both attB and attP sites in the same orientation (FIG. 6).

Example 48

Figure 7:
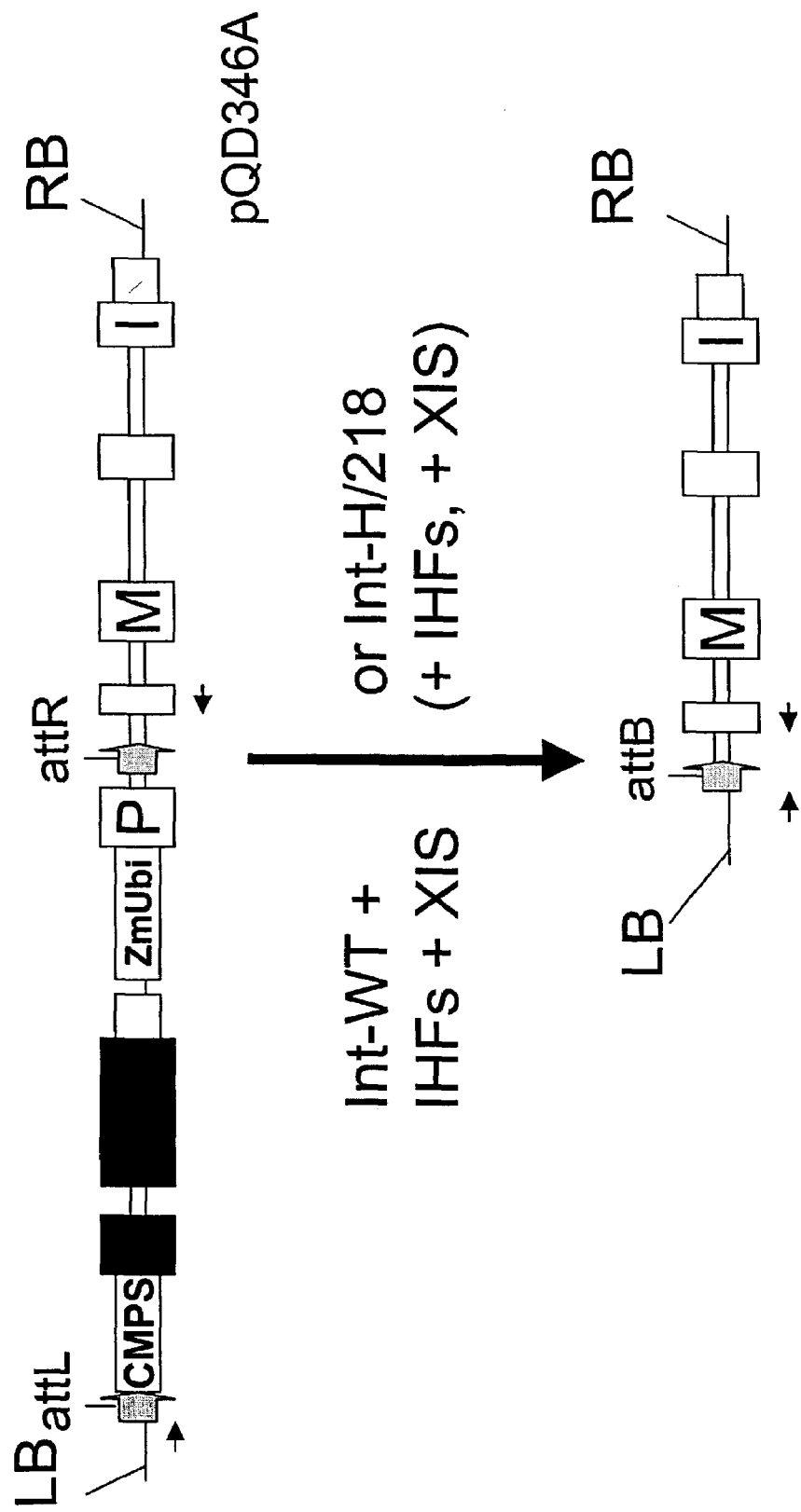
FIG. 7 represents a recombination event where a nucleotide sequence located between an attL recognition site and an attR recognition site on a target molecule is excised using an Int, IHF, and Xis.

Construction of a Monocot Vector Containing attL and attR Recombination Sites for Intrachromosomal Excision of a Nucleotide Sequence Binary vector pQD346A containing CMPS-GUSintron-Tact2 and ZmUbi-PMIintron-Tnos cassettes is constructed as described below. In pQD346A, an attR site is inserted into the first intron of PMIintron and an attL site is inserted upstream of the CMPS promoter (see FIG. 7). AttL and attR sequences are in the same orientation. This vector allows the use of phage Lambda integrase to excise the DNA sequence flanked by the attL and attR sites, removing the whole GUS expression cassette, maize Ubi promoter (ZmUbi), and a portion of PMIintron upstream of the attR sequence (FIG. 7). The phage Lambda attL sequence is amplified from phage DNA using two primers, attLApaI (5'-AGG GCC CAG CCT GCT TTT TTA TAC TAA GTT GGC ATT A-3') (SEQ ID NO:109) and attLSpeI (5'-TAC TAG TCA AAT AAT GAT TTT ATT TTG ACT GAT AG -3') (SEQ ID NO:110). The attL PCR product is digested with ApaI and SpeI and inserted into ApaI/SpeI-digested pQD189A12 to form pQD340B5. An RS sequence derived from annealing two oligonucleotides, RSKpnI (5'-CTT GAT GAA AGA ATA ACG TAT TCT TTC ATC AAG GGC C-3') (SEQ ID NO:111) and RSApaI (5'-CTT GAT GAA AGA ATA CGT TAT TCT TTC ATC AAG GTA C-3') (SEQ ID NO:112), is inserted upstream of the attL site of pQD340B5 to form pQD342B. The phage Lambda attR sequence is amplified from phage DNA using two primers, ATTRBGLII (5'-TAG ATC TGT TAC AGG TCA CTA ATA CCA TCT AAG T-3') (SEQ ID NO:113) and ATTRMSCI (5'-ATG GCC ACG CTC AAG TTA GTA TAA AAA AGC TGA AC-3') (SEQ ID NO:114). The attR PCR product is digested with BglII and MscI and inserted into BglII/MscI-digested pNOV2790 to form pQD341C7. The whole PMI gene is then excised from pQD341C7 by BamHI digestion and inserted into BamHI-digested pNOV041 to replace its PMI gene to form pQD344A1. pNOV041 is a binary vector containing a ZmUbi-PMIintron-Tnos expression cassette. pQD342B is digested with KpnI and NotI to release the fragment containing RS-AttL-CMPS promoter-GUSintron-Act2 terminator cassette. PQD344A is digested NotI and AscI to excise the fragment containing ZmUbi-PMIintron-NOS terminator cassette. The above two fragments are ligated with KpnI/AscI-digested base binary vector pNOV2114 to form pQD346A, which contains both attL and attR sites in the same orientation (FIG. 7).

Example 49

Generation of Transgenic Maize Lines from Binary Vectors Containing attB and attP or attL and attR Recombination Sites Binary vectors pQD203A11 and pQD346A are electroporated individually into *Agrobacterium* strain LAB4404 (pSB1). The individual cultures of the *Agrobacterium* strain are then used for co-cultivation with immature maize embryos using mannose selection (as described in Negrotto et al. (2000) Plant Cell Rep 19: 798-803). The transgenic maize plants are crossed directly to integrase expressing lines or are self-pollinated to produce seeds, which are used to generate additional plant material to cross with other plants.

Example 50

Construction of Binary Vectors for the Expression of Integrase, an Integrase Mutant, and an Integration Host Factor The (HindIII)blunt/AscI fragment (4122 bp) containing the Int and IHF expression cassettes are excised from VSIntHF (described in Example 26E.3) by HindIII digestion, filled-in with a Klenow treatment, re-cut with HindIII, and ligated with a (BamHI)blunt/AscI fragment (9541 bps) of pWC057 to form pQD208B12. pWC057 is a binary vector containing a ZmUbi promoter-AtPPO(dm)-T35S expression cassette (see U.S. Pat. No. 6,282,837 entitled "Methods of Controlling the Growth of Undesired Vegetation with Herbicide Tolerant Plants or Plant Seeds Having Altered Protoporphyrinogen Oxidase Activity"). pQD208B12 is a binary transformation vector containing the CMPS promoter-Int-Tnos, CMPS promoter-IHFα-Tnos, and CMPS promoter-IHFβ-Tnos expression cassettes, as well as the ZmUbi promoter-AtPPOdm-T35S selectable marker cassette. The (HindIII)blunt/AscI fragment (4122 bp) containing the Int-h/218 and IHF expression cassettes are removed from VSInt-h/218HF (described in Example 26G.3) by HindIII digestion, filled-in with a Klenow treatment, re-cut with HindIII, and ligated with a (BamHI)blunt/AscI fragment (9541 bps) of pWC057 to form pQD209B16. pQD209B16 is a binary transformation vector containing the CMPS promoter-IntH218-Tnos, CMPS promoter-IHFα-Tnos, CMPS promoter-IHFβ-Tnos expression cassettes, as well as the ZmUbi promoter-AtPPOdm-T35S selectable marker cassette.

Example 51

Construction of Binary Vectors for the Expression of Integrase, an Integrase Mutant, an Integration Host Factor (IHF), and an Excisionase (Xis)

Plasmid vector pAdF62A (described in Example 8) is cut with SpeI, filled-in with Klenow, and then re-cut with AscI to isolate the SpeI(blunt)/AscI fragment containing the CMPS-Xis-Tnos expression cassette. This fragment is inserted into either AscI/SwaI-digested pQD208B12 to form pQD350A or pQD209B16 to form pQD351A.

Example 52

Generation of Transgenic Maize Lines Expressing IntIHFs and IntH/218IHFs

Binary vectors pQD208B12, pQD209B16, pQD349A, and pQD350A are each transformed, individually, into *Agrobacterium* strain LAB4404(pSB1). The individual cultures of the *Agrobacterium* strain are then used for co-cultivation with immature maize embryos. The co-cultivated embryos are placed on a selection medium containing butafenacil (CGA 854,276) to generate transgenic plants. The transgenic plants are crossed directly to target plants or they are self-pollinated to produce seeds, which are used to generate additional plant material to cross with other plants. Transgenic lines containing T-DNA region from either pQD208B12 or pQD209B16 are morphologically normal and have good seed set.

Example 53

Intrachromosomal Excision of a Nucleotide Sequence Flanked by attB and attP or attL and attR Recombination between attB and attP or attL and attR sites can be used to excise the sequence flanked by these sites (FIGS. 6 and 7). Transgenic maize lines expressing synthetic Lambda integrase, or its mutant Int-h/218, along with integration host factor and excision factor (Xis) are obtained by *Agrobacterium*-mediated transformation. Integrase-expressing lines are crossed with desirable substrate lines to delete the sequence flanked by either the attB/attP or attL/attR sites. The progeny are screened by PCR for the deletion. Lines with the deletion are backcrossed with a non-transgenic parent line to produce seeds. These seeds are then germinated, and the seedlings are screened by PCR to recover lines with the desired deletion but without the integrase locus.

IV. Targeted Integration in Rice Using an L/R Reaction

A. Construction of Target Sequences

Example 54

Monocot Target Sequence with a Single attL Site and a Protoporphyrinogen Oxidase Expression Cassette A monocot target sequence containing a single attL site is constructed by converting the attP site of LPsgAttP (FIG. 4) to an attL site. LPsgAttP is digested with Asp718I and AvrII, which removes the attP site and a piece of the AT BAF60 intron to form the vector. An attL site is cloned by PCR using the oligonucleotide pair, 5'-GGA GAT CTT GAA GCC TGC TTT TTT ATA CT-3' (SEQ ID NO:115) and 5'-CCC CTA GGA AAT CAA ATA ATG ATT TTA TTT TG-3' (SEQ ID NO:116) with CMPSGUSAttPrev as the template and using a TOPO TA Cloning Kit. The resulting TOPO clone, named TOPOBAttLAv, contains the attL site and is digested with BglII and AvrII to form one of the fragments for a 3-way ligation. The piece of the AT BAF60 intron removed from the vector is cloned by PCR using the oligonucleotide pair, 5'-GGT ACC AAG CTG CGA ATC TTC GTT TTT-3' (SEQ ID NO:117) and 5'-GGC CAT AGA AAG ATC TGG AAT TTA CAA-3' (SEQ ID NO:118) and CMPSGUSAttPrev as the template. The resulting TOPO clone is digested with Asp718I and BglII to form the other fragment. Both fragments and vector are ligated together to form a target sequence with a single attL site (LPsgAttL).

Example 55

Monocot Target Sequence with a Single attR Site and a Protoporphyyrinogen Oxidase Expression Cassette A monocot target sequence containing a single attR site is constructed by converting the attP site of LPsgAttP to an attR site. LPsgAttP (FIG. 4) is digested with Asp718I and AvrII, which removes the attP site and a piece of the AT BAF60 intron to form the vector. An attR site is cloned by PCR using the oligonucleotide pair, 5'-AGA TCT GTT ACA GGT CAC TAA TAC-3' (SEQ ID NO:119) and 5'-CCT AGG CGC TCA AGT TAG TAT AAA AAA GCT GAA CG-3' (SEQ ID NO:120) with CMPSGUSAttPrev as the template and using a TOPO TA Cloning Kit. The resulting TOPO clone, named TOPOBAttRAv, contains the attR site and is digested with BglII and AvrII to form one of the fragments for a 3-way ligation. A piece of the AT BAF60 intron is cloned by PCR as described in Example 54, and the resulting TOPO clone is digested with Asp718I and BglII to form the other fragment. Both fragments and vector are ligated together to form a target sequence single attR (LPsgAttR).

Example 56

Monocot Target Sequence with Inverted attL Sites and a Protoporphyrinogen Oxidase Expression Cassette A monocot target sequence containing inverted attL sites is constructed by converting the attP sites of LPdbAttP to attL sites. The HindIII/SpeI fragment of CMPSGUSAttPrev is first subcloned into pBluescript KS+ and the attP site is removed by digestion with NheI and BglII. An attL site is cloned by PCR using the oligonucleotide pair, 5'-CCG CTA GCT GAA GCC TGC TTT TTT ATA C-3' (SEQ ID NO:121) and 5'-GGA GAT CTG AAA TCA AAT AAT GAT TTT ATT-3' (SEQ ID NO:122) with CMPSGUSAttPrev as the template. The resulting TOPO clone, called TOPONAttRBg, contains the attL site and is ligated as an NheI/BglII fragment, replacing the attP site of the subclone and forming 5'GUSAttLrev. The attP site of PPO.PMIAttP.Spe is removed by digestion with XbaI and AvrII. An attL site is cloned by PCR from CMPSGUSAttPrev using the oligonucleotide pair, 5'-GGT CTA GAT GAA GCC TGC TTT TTT ATA CT-3' (SEQ ID NO:123) and SEQ ID NO:116. The resulting TOPO clone, named TOPOXAttLAv, contains an attL site and is ligated as an XbaI/AvrII fragment, replacing the attP site of PPO.PMIAttP.Spe, forming PPOPMIAttLf-.Spe. 5'GUSAttLrev is digested with NheI/SpeI and the resulting fragment is ligated into the SpeI site of PPOPMI-AttLf.Spe forming a target sequence double attL (LPdbAttL).

Example 57

Monocot Target Sequence with Inverted attR Sites and a Protoporphyrinogen Oxidase Expression Cassette A monocot target sequence containing inverted attR sites is constructed by converting the attP sites of LPdbAttP into attR sites. The HindIII/SpeI fragment of CMPSGUSAttPrev is first subcloned into pBluescript KS+ and the attP site is removed by digestion with NheI and BglII. An attR site is cloned by PCR using the oligonucleotide pair, 5'-GCT AGC TCT GTT ACA GGT CAC TAA TAC-3' (SEQ ID NO:124) and 5'-AGA TCT CGC TCA AGT TAG TAT AAA AAA GCT GAA CG-3' (SEQ ID NO:125) with CMPSGUSAttPrev as the template. The resulting TOPO clone, called TOPONAttRBg, contains the attR site and is ligated as an NheI/BglII fragment, replacing the attP site of the subclone and forming 5'GUSAttRrev. The attP site of PPO.PMIAttP.Spe is removed by digestion with XbaI and AvrII. An attR site is cloned by PCR from CMPSGUSAttPrev using the oligonucleotide pair, 5'-TCT AGA TCT GTT ACA GGT CAC TAA TAC-3' (SEQ ID NO:126) and SEQ ID NO:120. The resulting TOPO clone, named TOPOXAttRAv, contains an attR site and is ligated as an XbaI/AvrII fragment, replacing the attP site of PPO.PMIAttP.Spe, forming PPOP-MIAttRfwd. 5'GUSAttRrev is digested with NheI/SpeI and the resulting fragment is ligated into the SpeI site of PPOP-MIAttRfwd forming a target sequence with two attR sites (LPdbAttR).

Example 58

Monocot Target Sequence with a Single attL Site and a Hygromycin Phosphotransferase Expression Cassette The monocot target sequence containing a single attL site and a hygromycin phosphotransferase expression cassette is constructed by replacing the protoporphyrinogen oxidase (PPO) gene and 35S terminator of LPsgAttL with the hygromycin phosphotransferase gene (HPT) and 35S terminator. LPsgAttL is digested with NcoI, followed by treatment with Mung Bean endonuclease, and is then further digested with HindIII to form the vector. pAdF55 contains the rice actin 1 promoter (as described in Example 20), the hygromycin phosphotransferase gene, and the 35S terminator (as described in Example 20). The hygromycin phosphotransferase gene and 35S terminator are cloned as a PCR fragment from pAdF55 using the oligonucleotide pair, 5'-CGA GCT CAG CTG ATG AAA AAG CCT GAA CTC-3' (SEQ ID NO:127) and 5'-TGC AGC AAG CTT CAC TGG ATT TTG GTT TTA-3' (SEQ ID NO:128). The PCR fragment is digested with PvuII/HindIII and ligated into the vector forming LPsgAttL.HYG.

Example 59

Monocot Target Sequence with a Single attR Site and a Hygromycin Phosphotransferase Expression Cassette The monocot target sequence containing a single attR site and a hygromycin phosphotransferase expression cassette is constructed by replacing the protoporphyrinogen oxidase (PPO) gene and 35S terminator of LPsgAttR with the hygromycin phosphotransferase gene and 35S terminator. LPsgAttR is digested with NcoI, followed by treatment with Mung Bean endonuclease, and is then further digested with HindIII to form the vector. The hygromycin phosphotransferase gene and 35S terminator are PCR cloned as described in Example 58. The PCR fragment is digested with PvuII/HindIII and ligated into the vector forming LPsgAttR.HYG.

Example 60

Monocot Target Sequence with Inverted attR Sites and a Hygromycin Phosphotransferase Expression Cassette The monocot target sequence containing inverted attR sites and a hygromycin phosphotransferase expression cassette is constructed by replacing the protoporphyrinogen oxidase (PPO) gene and 35S terminator of LPdbAttR with the hygromycin phosphotransferase gene and 35S terminator. LPdbAttR is digested with NcoI, followed by treatment with Mung Bean endonuclease, and is then further treated with alkaline phosphatase to form the vector. The hygromycin phosphotransferase gene and 35S terminator are cloned as a PCR fragment from pAdF55 using the oligonucleotide pair, SEQ ID NO:127) and 5'-TGC AGC TCT AGA CAC TGG ATT TTG GTT TTA-3' (SEQ ID NO:129). The PCR fragment is digested with PvuII/XbaI, then subjected to a Klenow fill-in reaction and finally ligated into the vector forming LPdbAttR.HYG.

Example 61

Figure 8:
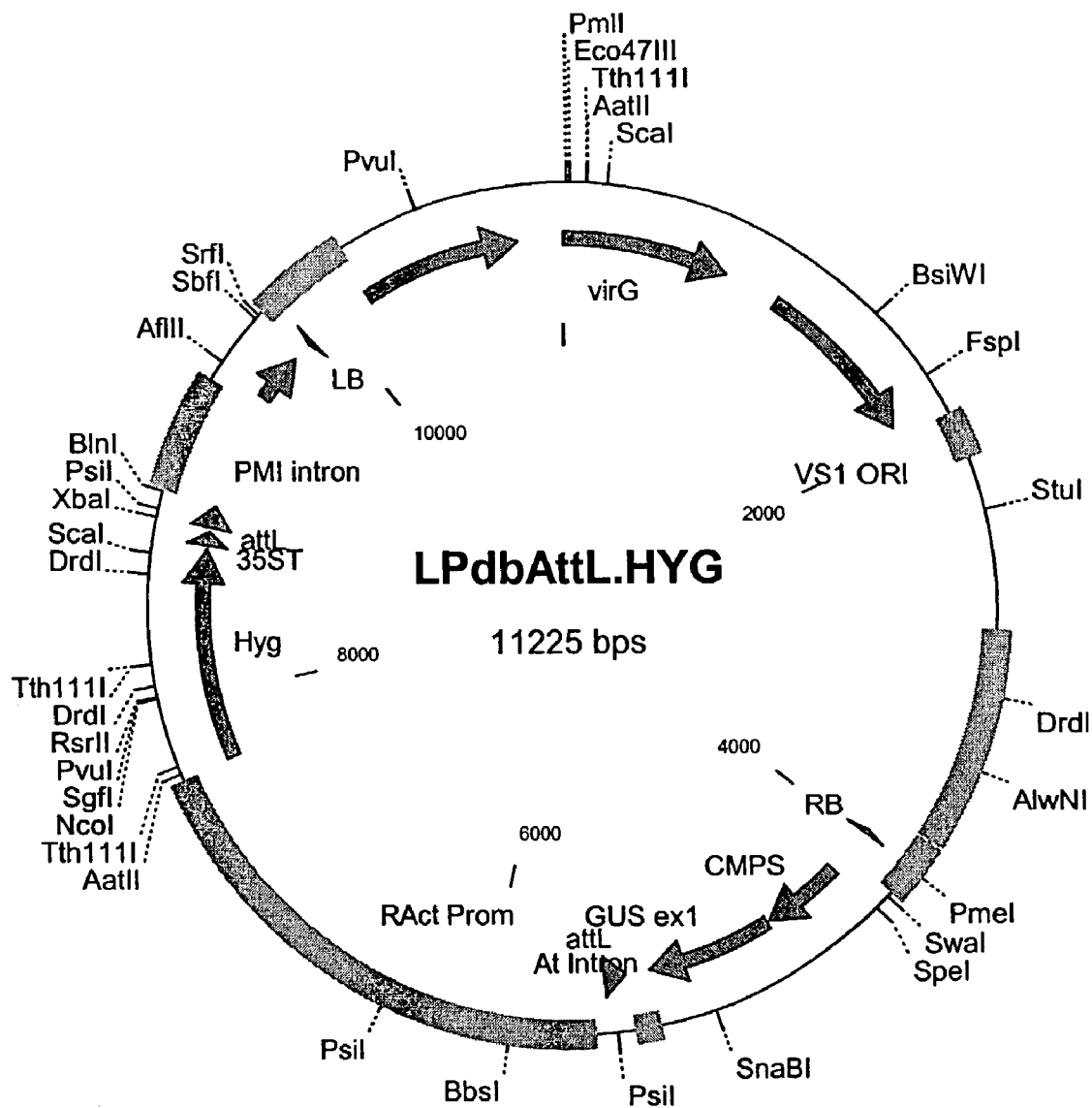
FIG. 8 represents the structure of LPdbAttL.HYG, an exemplary plasmid that contains a monocot target sequence with two attL sites in inverted orientation.

Construction of LPdbAttL.HYG, a Monocot Target Sequence with Inverted attL Sites and a Hygromycin Phosphotransferase Expression Cassette LPdbAttL.HYG (FIG. 8) is constructed by ligating the 2940 bp XbaI-BbsI fragment of LPdbAttR.HYG into the 8285 bp XbaI-BbsI vector fragment of construct LPdbAttL.

B. Production of a Rice Target Cell Line

Example 62

*Agrobacterium*-Mediated Transformation of Rice to Introduce Target Sequence Constructs Binary vectors LPsgAttL, LPsgAttR, LPdbAttL, LPdbAttR, LPsgAttL.HYG, LPsgAttR.HYG, LPdbAttL.HYG (FIG. 8), and LPdbAttR.HYG are each transformed, individually, into *Agrobacterium* strain LBA4404. The individual cultures of the *Agrobacterium* strain are then used for co-cultivation, as described below, to generate the respective target line. The rice (*Oryza sativa* var. *javonica*) cultivar "Kaybonnet" is used for generating the target lines. Other rice cultivars also can be used (Hiei et al. (1994) Plant Journal 6:271-282; Dong et al. (1996) Molecular Breeding 2:267-276; Hiei et al. (1997) Plant Molecular Biology35: 205-218). Also, various media constituents described below may be substituted.

Embryogenic cultures are established from mature embryos by culturing on MSB medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Established culture lines are inoculated and co-cultivated with *Agrobacterium* LBA4404 containing the desired target sequence construct. *Agrobacterium* is cultured in solid YP medium (100 mg/L spectinomycin) for 3 days at 28° C. *Agrobacterium* is re-suspended in liquid MSB medium. The *Agrobacterium* culture is diluted to an $OD_{600}$ of 0.2-0.3 and acetosyringone is added to a final concentration of 200 μM. *Agrobacterium* is induced with acetosyringone for at least 30 minutes before mixing the solution with the rice cultures. For inoculation, the cultures are immersed in the bacterial suspension for 30 minutes. The liquid suspension is removed with a vacuum aspirator, and the inoculated cultures are placed on a Whatman paper filter on co-cultivation medium MSB-As (MSB with 200 μM acetosyringone) and incubated at 22° C. for two days. The cultures are then transferred to MSB medium with timentin (400 mg/liter) to inhibit the growth of *Agrobacterium*.

Transformed cells containing LPsgAttL, LPsgAttR, LPdbAttL, or LPdbAttR are selected using a protox inhibitory herbicide (e.g., butafenacil) (U.S. Pat. No. 6,282,837). Cultures are transferred to selection medium containing butafenacil (i.e., MS induction medium with 1000 nM butafenacil, 200 mg/liter timentin) after 14 days, and cultured for 28 days in the dark. Resistant colonies are then transferred to regeneration induction medium (MS with no 2,4-D, 0.5 mg/liter IAA, 1 mg/liter zeatin, 200 mg/liter timentin and 3% Sorbitol) and moved to the light growth room. Regenerated shoots are transferred to rooting medium containing butafenacil (MS with no hormones and 2% Sorbitol) for 3 weeks and then sent to the greenhouse for planting in soil.

Transformed cells containing LPsgAttL.HYG, LPsgAttR.HYG, LPdbAttL.HYG (FIG. 8), or LPdbAttR.HYG undergo a similar selection process, except that hygromycin (50 mg/L) is used as the selection agent throughout the transformation process, and the cultures are transferred to selection medium immediately following co-cultivation.

Transgenic events carrying a single copy insertion of the target sequence are identified by Taqman and are transplanted into soil and grown in a greenhouse to maturity.

C. Construction of Donor Sequences

Example 63

Monocot Donor with a Single attL Site or a Single attR Site

The *Arabidopsis thaliana* Actin-2 3' untranslated region is added as a terminator to a 3' portion of the GUS gene of CMPSGUSAttPrev by 3-way ligation. The vector is formed by digestion of pUC18 with EcoRI and XbaI. CMPSGU-SAttPrev is digested with MfeI and XhoI to produce a partial GUS containing fragment and pNOV2713 is digested with XbaI and XhoI to produce a fragment containing the *Arabidopsis thaliana* Actin-2 3' untranslated region. The 3-way ligation between these components forms 3'GUSAttPrTact. The attP2 site of MUPMIAttP2 is replaced with an attL or attR site with 2 cloning steps.

In the first step, MUPMIAttP2 is digested with SbfI and PshAI generating a vector that is reserved for future use. The fragment produced by this digestion contains an attP2 site and is subcloned into the vector formed by digestion of 3'GUSAttPrTact with SbfI and PshAI creating PMIAttP2i. The attL or attR site used to replace the attP2 site of PMIAttP2i is formed as a PCR fragment using the oligonucleotide pair 5'-GGC TGA GGT ACC TGA AGC CTG CTT TTT TAT-3' (SEQ ID NO:130) with 5'-CGT AGC CCT AGG GAA ATC AAA TAA TGA TTT-3' (SEQ ID NO:131) to make attL using LPsgAttL as template and 5'-GGC TGA GGT ACC TCT GTT ACA GGT CAC TAA-3' (SEQ ID NO:132) with 5'-CGT AGC CCT AGG CGC TCA AGT TAG TAT AAA-3' (SEQ ID NO:133) to make attR using LPsgAttR as template.

In the second step, PMIAttP2i is digested with AvrII and Kpn. The excised attP2 site is replaced by either the attL or attR PCR fragment, digested with AvrII and KpnI, forming PMIAttLi and PMIAttRi, respectively. These 2 constructs are digested with SbfI and PshAI. The resulting fragments containing either attL or attR are ligated separately into the reserved vector described above forming MUPMIAttL and MUPMIAttR, respectively. The binary vector, pNOV2114, is digested with SphI and HindIII, and is then used in a 3-way ligation with a fragment formed by NheI/SphI digestion of 3'GUSAttPrTact and AvrII/HindIII digestion of MUPMIAttL or MUPMIAttR to form DONsgAttL or DONsgAttR, respectively.

Example 64

Monocot Donor with Inverted attL Sites or Inverted attR Sites

The monocot donor sequence, DONdbAttP, is digested with KpnI and SacI to remove the attP site. The attL or attR site used to replace the attP site is formed as a PCR fragment using the oligonucleotide pair 5'-GGC TGA GGT ACC TGA AGC CTG CTT TTT TAT-3' (SEQ ID NO:134) with 5'-CGT AGC GAG CTC GAA ATC AAA TAA TGA TTT-3' (SEQ ID NO:135) to make attL using LPsgAttL as template and 5'-GGC TGA GGT ACC TCT GTT ACA GGT CAC TAA-3' (SEQ ID NO:136) with 5'-CGT AGC GAG CTC CGC TCA AGT TAG TAT AAA-3' (SEQ ID NO:137) to make attR using LPsgAttR as template. The excised attP site of DONdbAttP is replaced with the attL or attR PCR fragments digested with KpnI and SacI, forming DONAttLi and DONAttRi, respectively.

A partial GUS gene containing the attP site of DONdbAttP is excised using BglII and SphI digestion. This GUSAttP fragment is subcloned into pNOV2790AttB and digested with BglII and SphI to remove its attP site, forming GUSAttPi. The attP site of GUSAttPi is removed by digestion with NheI and BglII and replaced with the attL site of TOPONAttLBg or the attR site of TOPONAttRBg, both digested with NheI and BglII, forming GUSAttLi and GUSAttRi, respectively. The binary vector, DONdbAttP, is digested with BglII/SacI and used in a 3-way ligation with a fragment formed by BglII/SphI digestion of GUSAttLi and SacI/SphI digestion of DONAttLi to form DONdbAttL.

Figure 9:
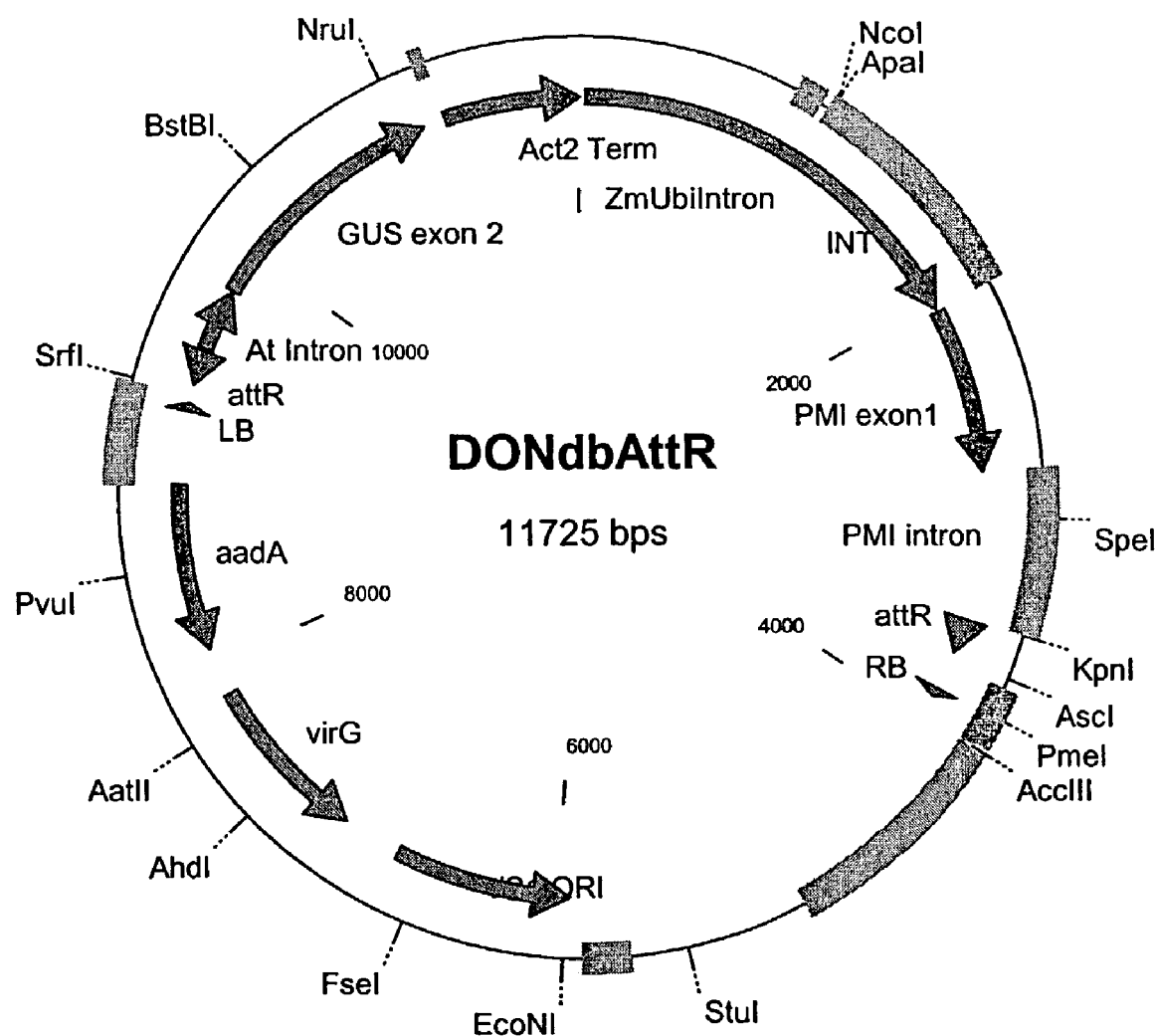
FIG. 9 represents the structure of DONdbAttR, an exemplary plasmid that contains a monocot donor sequence with two attR sites in inverted orientation.

Likewise, the binary vector, DONdbAttP, is digested with BglII and SacI and is then used in a 3-way ligation with a fragment formed by BglII/SphI digestion of GUSAttri and SacI/SphI digestion of DONAttRi to form DONdbAttR (FIG. 9).

D. Targeted Integration of a Donor Sequence into a Rice Target Cell Line

Example 65

Targeted Integration of a Donor Sequence into a Rice Target Line Using Biolistics Primary target lines are self-pollinated to obtain seeds. Seeds from selfed progeny of these lines are used to establish embryogenic cultures and suspension cultures for targeting experiments. Immature embryos from young seeds or mature embryos from dry seeds are used to establish embryogenic cultures (Hiei et al. (1994) Plant Journal 6:271-282; Dong et al. (1996) Molecular Breeding 2:267-276; Hiei et al. (1997) Plant Molecular Biology 35:205-218). These cultures or suspension cell cultures are used for targeting experiments using biolistics delivery, as described by Chen et al. (1998) Plant Cell Reports 18:25-31, using 2% mannose as a selection agent.

The combination of plasmids used for each treatment includes an appropriate donor DNA, compatible with the recognition site(s) within the target sequence, a Lambda integrase expression cassette with or without co-expression of the integration host factor, and excisionase.

A Lambda integrase-mediated recombination of the bombarded donor sequence with the target sequence creates an intact β-glucuronidase (GUS) expression cassette. A subset of the targeted calli are assayed for targeted integration using a GUS histochemical assay as described in Example 44D.

The integrase-mediated recombination of the bombarded donor sequence with the target sequence also creates an intact phosphomannose isomerase (PMI) expression cassette, which permits selection and recovery of the targeted event. The calli that are not used for GUS assays are placed onto mannose selection medium, and calli growing on mannose are subcultured onto fresh medium and bulked-up for regeneration.

These calli are then analyzed using a PCR assay. One primer of a primer pair is homologous to the target sequence and the other primer of the pair is homologous to the donor sequence, so that a predictable size PCR product forms only if the donor has undergone Lambda integrase-mediated recombination with the target sequence. Sequencing of the PCR products is carried out to show the presence of the expected att sites at the recombination site(s). Plants confirmed by PCR to contain a targeted integration event are sent to the greenhouse. Genomic Southern analysis is conducted on PCR positive candidates to further confirm the molecular structure of the targeted integration events.

Example 66

Targeted Integration of a Donor Sequence into a Rice Target Line Using *Agrobacterium*-Mediated Transformation Primary target lines are self-pollinated to obtain seeds. Seeds from selfed progeny of these lines are used for establishing embryogenic cultures and suspension cultures for targeting experiments. Immature embryos from young seeds or mature embryos from dry seeds are used to establish embryogenic cultures (Hiei et al. (1994) Plant Journal 6:271-282; Dong et al. (1996) Molecular Breeding 2:267-276; Hiei et al. (1997) Plant Molecular Biology 35:205-218). These cultures or suspension cell clusters are then used for *Agrobacterium*-mediated transformation.

The binary vectors carrying either the donor constructs or the Lambda integrase (wild-type or Int-h or Int-h/218) expression cassettes (with or without integration host factor) and the excisionase are transformed, individually, into *Agrobacterium* strain LBA4404.

For targeting, each rice target cell line is co-cultivated with three LBA4404 *Agrobacterium* strains, one containing the compatible donor sequence, one containing the integrase (with or without IHF), and one containing the excisionase. Alternatively, one *Agrobacterium* strain can be transformed with an expression cassette containing the integrase (with or without IHF) as well as an expression cassette containing the excisionase. When a single *Agrobacterium* strain is used, the two expression cassettes can be located either on two different T-DNAs or a single T-DNA. Co-cultivations are carried out as described in Example 62 and targeted events are selected using 2% mannose as a selection agent.

Molecular analysis (PCR and genomic Southern) of mannose resistant events is carried out as described in the preceding Example.

V. Demonstration of Lambda Integrase Activity in Tobacco Cells

A. Constructs for Recombination Assays in Tobacco Cells

Example 67

Intramolecular Recombination between attB and attP Mediated by Lambda Integrase, Int-h, and Int-h/218 on a T-DNA Test Substrate in Tobacco Cells

Example 67A

Construction of CMLucB/P, a Binary Vector Intramolecular Recombination Test Substrate vAttB/P is digested with BamHI and the 1783 bp fragment with the 5' part of the Luc gene is purified. pNOV4211 containing the CMPS promoter is digested with SpeI and the site converted to a BglII site by ligation with the oligonucleotide 5'-CTA GGA GAT CTC-3' (SEQ ID NO:138) to form 4211Bg. Plasmid 4211Bg is digested with BglII in the presence of alkaline phosphatase, and this vector is purified and ligated with the 1783 bp BamHI fragment above to form CM 5'LucIntAttB. This plasmid is digested with Asp718I and NotI, and the 1923 bp fragment is purified. vAttB/P is digested with BglII/Asp718I and the 1025 bp fragment containing AttPInt 3'LucNos is purified. Viral vector pWI-11M is digested with NotI/BamHI and ligated to the previous two fragments to produce vCMLucB/P.

CMLucB/P is introduced into a binary vector for delivery by *Agrobacterium* by digesting vCMLucB/P with NheI and BglII. The 2955 bp fragment is isolated and ligated to binary vector pNOV2122 digested with XbaI and BamHI to form RKLucB/P. This plasmid is transformed by electroporation into competent *Agrobacterium* strain LBA4404, selecting for kanamycin resistance. Presence of the RKLucB/P plasmid is confirmed by analysis of miniprep DNA from the transformant.

Example 67B

Construction of RKLucAttL, a Positive Control for the Intramolecular B/P Recombination Test Substrate pAttL positive control plasmid is digested with SphI and Asp718I, and the 3' end of LucIntAttL gene is purified as a 1641 bp fragment. This is ligated into pNOV2122 vector that has been digested with Asp718I and SphI. The resulting plasmid is next digested with SphI in the presence of alkaline phosphatase, and into this vector is ligated the 1298 bp SphI digest fragment of RK2LucB/P containing the CMPS promoter and 5'-end of the luciferase gene. The resulting plasmid is designated RKLucAttL. This plasmid is transformed by electroporation into competent *Agrobacterium* strain LBA4404, selecting for kanamycin resistance. Presence of the RKLucAttL plasmid is confirmed by analysis of miniprep DNA from the transformant.

Example 68

Construction of pBS.CMPSLucL/R, an Intramolecular L/R Recombination Test Substrate Plasmid pBS.CMPSLucL/R is built in a three-way ligation as described below. First the 2952 bp pBluescript II KS (−) vector is digested with BamHI and XbaI; second, the construct CMPSVLucInAttL is digested with XhoI, filled-in with Klenow, then cut with SpeI to release the 1987bp carrying the CMPS promoter spliced to the 5' end of the luciferase gene followed by an attL site in forward orientation (with respect to the luciferase open reading frame) inserted in an intron; third, construct AttR3'LucNos-A is digested with Asp718, filled-in with Klenow, then cut with BglII to release the 962 bp fragment carrying the 3' end of the luciferase gene preceded by an attR site located in an intron in a forward orientation with respect to the luciferase open reading frame, and followed by the 3' nos terminator. The three DNA fragments described above are ligated together to form an intramolecular L/R recombination test substrate, pBS.CMPSLucL/R, in which the CMPS promoter is spliced to the 5' end of the luciferase gene, followed by the 3' end of the luciferase gene in an inverted orientation and flanked by an attR site (on the 5' side) and an attL site (on the 3' side). The attR and attL sites are in an inverted orientation. Upon L/R recombination mediated by lambda integrase, the 3'end of the luciferase is inverted, and consequently the full-length luciferase open-reading frame is reconstituted. The amount of luciferase detected is a measure of the amount of L/R recombination mediated by Lambda integrase.

B. Recombination Assays in Tobacco Cells Using *Agrobacterium*

1. Intramolecular Recombination Test Substrate

The binary vector test substrate used in this study is designed to demonstrate functional expression of Int. The intramolecular attB/attP test substrate contains the 5' portion of a luciferase expression cassette (5'Luc-5'Intron-attB) and the 3' portion of a luciferase expression cassette (attP-3'Intron-3'Luc) where the 3' portion is inverted relative to the 5' portion and the attB and attP sites are in inverted orientation. Intramolecular recombination between the attB and attP sites, mediated by the Int complex, leads to inversion of the 3' portion of the luciferase expression cassette, producing an intact cassette and luciferase enzyme activity.

2. Co-Cultivation with *Agrobacterium*

BY2 Tobacco suspension cells are used 2-3 days after transfer to fresh BY2 medium (Narasimhulu et al., The Plant Cell, Vol. 8: 873-886 (1996)). *Agrobacterium* strains used in the experiments are grown overnight at 25° C. in YP medium (Example 25) with appropriate antibiotics. Bacteria are centrifuged and resuspended in BY2 medium, and their concentration adjusted to $OD_{660}$=0.5. For each co-cultivation, 3 ml fresh BY2 medium in a sterile 25×90 mm petri dish is inoculated with various volumes (usually between 15 and 60 microliters) of the indicated strains of *Agrobacterium* and mixed thoroughly. To the bacterial suspension, 3 ml of BY2 suspension is added, and the mixture swirled vigorously to mix bacteria and plant cells. Co-cultivations are incubated for 2 days at 25° C. in darkness, after which the suspensions are washed from the petri dish into sterile 125 ml erlenmeyer culture flasks with 3 ml of BY2 medium containing 800 mg/liter ticarcillin. Suspensions are cultivated in darkness at 25° C. on a rotary shaker for approximately one week.

3. Luciferase Assays

For luciferase assays, plant cells (1 ml) are removed at intervals of approximately two days, collected by centrifugation, ground with carborundum using a hand-held battery-powered homogenizer, centrifuged (10', 10,000 G) and the clear supernatant is assayed for luciferase activity by the Luciferase Assay System of Promega. Protein concentration is determined by the BioRad Protein Assay Reagent, and the results are used to calculate the specific activity of luciferase as recorded in Tables 6, 7, and 8 below.

4. Intramolecular Recombination Studies

In the following studies, an *Agrobacterium* host strain, LBA4404, containing the intramolecular test substrate, RKLucB/P (abbreviated as B/P in Table 6, 7, and 8 below), is co-cultivated with BY2 tobacco cells alone or in combination with an *Agrobacterium* LBA4404 host strain containing one of the integrase binary vectors, RKInt, RKInt-h, RKInt-h/218, RKIntHF, RKInt-hHF, or RKInt-h/218HF (as described in Example 26) (abbreviated as Int, Int-h, Int-h/218, IntHF, Int-hHF, and Int-h/218HF, respectively, in Tables 6, 7, and 8). Intramolecular recombination mediated by Lambda integrase, Int-h, or Int-h/218 results in luciferase expression. An *Agrobacterium* LBA4404 strain containing the binary vector, RKLucAttL (abbreviated as LucAttL in Tables 6, 7, and 8), is co-cultivated with BY2 cells as a positive control. The "#1" or "#2" following the strain abbreviations indicates which of two *Agrobacterium* transformant colonies is employed for that part of the experiment. Luciferase activity assays are performed on Day 2, Day 4, etc., after antibiotics are applied. Luciferase expression is a measure of Int-mediated recombination activity.

TABLE 6

Experiment 1

| Strains of Agrobacterium Added (abbreviations explained above) | Luciferase Activity (Light Units/mg Protein) | | | |
|---|---|---|---|---|
| | Day 2 | Day 4 | Day 6 | Day 8 |
| None | 0.78 | 0.96 | 11.1 | 5.9 |
| B/P#1 | 82.1 | 163 | 452 | 131 |
| B/P#2 | 75.2 | 7.8 | 143 | 35.5 |
| B/P#1 + [IntHF]#1 | 40.6 | 185 | 80.4 | 108 |
| B/P#1 + [IntHF]#2 | 6.8 | 52.3 | 193 | 298 |
| B/P#1 + [Int-hHF]#1 | 170 | 859 | 4891 | 766 |
| B/P#1 + [Int-hHF]#2 | 73.2 | 1898 | 3789 | 3501 |
| B/P#1 + [Int-h/218HF]#1 | 9.5 | 2188 | 5966 | 2404 |
| B/P#1 + [Int-h/218HF]#2 | 331 | 164 | 7594 | 668 |
| B/P#2 + [IntHF]#1 | 60.1 | 6.3 | 234 | 44 |
| B/P#2 + [Int-hHF]#1 | 61.1 | 140 | 1832 | 776 |
| B/P#2 + [Int-h/218HF]#1 | 424 | 192 | 7582 | 3722 |
| LucAttL#1 (120 λ) | 22670 | 52650 | 138600 | 223000 |
| LucAttL#2 (120 λ) | 85930 | 27560 | 1841 | 212100 |
| LucAttL#1 (240 λ) | 27500 | 163000 | 396800 | 145600 |
| LucAttL#2 (240 λ) | 464 | 5821 | 5244 | 73400 |

TABLE 7

Experiment 2

| Strains of Agrobacterium Added (abbreviations explained above) | Luciferase Activity (Light Units/mg Protein) | |
|---|---|---|
| | Day 2 | Day 5 |
| none | 2.6 | 4.2 |
| B/P#1 (60 λ) | 202 | 126 |
| B/P#1 (120 λ) | 51.2 | 421 |
| B/P#1 (60 λ) + [Int-h/218HF]#2 (60 λ) | 1154 | 10260 |
| B/P#1 (60 λ) ++ [Int-h/218HF]#2 (120 λ) | 8893 | 11610 |
| B/P#1 (60 λ) ++ [Int-h/218HF]#2 (240 λ) | 17360 | 14360 |
| B/P#1 (120 λ) ++ [Int-h/218HF]#2 (240 λ) | 796 | 9490 |
| B/P#1 (240 λ) ++ [Int-h/218HF]#2 (240 λ) | 1410 | 5670 |
| LucAttL#1 (60 λ) | 21280 | 498600 |
| LucAttL#1 (120 λ) | 10290 | 112100 |
| LucAttL#1 (240 λ) | 1190 | 136400 |
| LucAttL#1 (480 λ) | 1960 | 100000 |

TABLE 8

Experiment 3

| Strains of Agrobacterium Added | Luciferase Activity (Light Units/mg Protein) | | |
|---|---|---|---|
| | Day 2 | Day 4 | Day 7 |
| B/P#1 (60 λ) | 114 | 952 | 183 |
| B/P#1 (60 λ) ++ [IntHF]#2 (120 λ) | 67.7 | 1648 | 272 |
| B/P#1 (60 λ) ++ [Int-hHF]#2 (120 λ) | 120 | 7200 | 1100 |
| B/P#1 (60 λ) ++ [Int-h/218HF]#2 (120 λ) | 6640 | 17200 | 1950 |
| B/P#1 (60 λ) ++ [Int#1 (120 λ) | 84.4 | 526 | 163 |
| B/P#1 (60 λ) ++ [Int-h#1 (120 λ) | 94.4 | 1340 | 511 |
| B/P#1 (60 λ) ++ [Int-h/218#1 (120 λ) | 310 | 3630 | 634 |
| B/P#1 (60 λ) ++ [Int-h/218 #2 (120 λ) | 230 | 2320 | 850 |
| LucAttL#1 (30 λ) | 56800 | 33800 | 187000 |
| LucAttL#1 (60 λ) | 25900 | 429000 | 117000 |
| LucAttL#1 (90 λ) | 164000 | 475000 | 193000 |
| LucAttL#1 (120 λ) | 37700 | 234000 | 185000 |

The results presented in Tables 6, 7, and 8 above show that *Agrobacterium* delivery of the integrase gene and its mutants, enhanced by the IHF genes, produces active integrase that successfully mediates recombination between the attB and attP sites on the LucB/P substrate that is delivered into the cell by *Agrobacterium*.

C. Recombination Assays in Tobacco Cells Using Microprojectile Bombardment

Example 69

Testing of an Intramolecular L/R Recombination in Tobacco Cells Using Biolistics pBS.CMPSLucL/R test substrate is used to demonstrate functional expression of the three maize-optimized integrases (wild-type integrase, Int-h and Int-h/218 mutant), in combination with IHF and Xis. PBS.CMPSLucL/R contains the 5' portion of a luciferase expression cassette (5'Luc-5'Intron-attL) and the 3' portion of a luciferase expression cassette (attR-3'Intron-3'Luc) where the 3' portion is inverted relative to the 5' portion and the attL and attR sites are in inverted orientation. Intramolecular recombination between the attL and attR sites, mediated by the Int complex, leads to inversion of the 3' portion of the luciferase expression cassette, producing an intact cassette and luciferase enzyme activity.

Wild-type BY2 suspension cells are grown in BY2 liquid medium [Per liter: 4.31 g MS salts, 370 mg $KH_2PO_4$, 1 mg Thiamine, 0.2 mg 2,4-D, 30 g sucrose, pH 5.7] at 28° C. in the dark on a rotary shaker at 100-150 rpm. They are subcultured weekly using a 1:50 dilution in fresh BY2 medium. For transient expression assay, a 1:5 to 1:10 dilution of a one week-old culture is grown for 2 days. On the day of bombardment, 2 to 5 ml of cells are pipetted onto a membrane filter (Millipore cat.#GVWP04700) on the platform of a sterilized magnetic filter funnel apparatus (VWR cat#28143-550) and the liquid medium is gently pulled off the cells using vacuum. The membrane with cells is placed onto osmoticum BY2 medium with 12% sucrose and 0.8% phytagar. The cells are incubated in the dark for 3-5 hours prior to bombardment.

For particle bombardment, the plasmid DNAs are co-precipitated onto <1 μm gold particles (Crescent Chem. Co., Inc., NY) using standard $CaCl_2$-spermidine chemistry. Each target is bombarded twice using a DuPont Helium Gun and 1100 psi rupture discs (Biorad).

The intramolecular plasmid recombination test substrate, pBS.CMPSLucL/R is first bombed separately into BY2 cells at a concentration of 0.666 μg/shot to establish background levels of luciferase transient expression in the absence of integrases, IHF, or excisionase. The substrate is then co-bombarded with each integrase and IHF construct (0.166 μg/shot) and excisionase construct pAdF61 (0.166 μg/shot). Duplicate target plates are bombarded for each DNA mixture. After bombardment, the plates are incubated in the dark at 28° C. for 2 days and crude extracts are then prepared and assayed for luciferase activity as described above in Section I.A.4. Luciferase expression is a measure of Int mediated recombination activity. The average Relative Light Units (RLU) for duplicate plates is shown in Table 9 below.

TABLE 9

| Co-Bombarded Plasmids | Average RLU | Fold Increase |
| --- | --- | --- |
| pBS.CMPSLucL/R | 7,944 | |
| pBS.CMPSLucL/R<br>pBSIntHF<br>pAdF61 | 36,250 | 4.6 |

TABLE 9-continued

| Co-Bombarded Plasmids | Average RLU | Fold Increase |
| --- | --- | --- |
| pBS.CMPSLucL/R<br>pBSInt-hHF<br>pAdF61 | 24,249 | 3 |
| pBS.CMPSLucL/R<br>pBSInt-h/218HF<br>pAdF61 | 46,496 | 5.9 |

The data in Table 9 show that each of the three integrases, when combined with IHF and Xis, mediates intramolecular L/R recombination in tobacco BY2 cells.

D. Intrachromosomal Recombination in Tobacco Cells

Example 70

Int-Mediated Intramolecular Recombination Between attB and attP Sites Integrated into Tobacco Chromosomal DNA Example 70A Construction of VSUbq3IntHyg, a Dicot Selectable Marker pCIB7613, containing a hygromycin phosphotransferase gene attached to the maize ubiquitin promoter, is digested with BamHI and the HygR gene excised and purified as a fragment of 1032 bp. pPEH30, an expression vector containing the *Arabidopsis* ubiquitin-3 promoter/intron and nos terminator, is digested with BamHI and treated with alkaline phosphatase. This vector is ligated together with the HygR gene, and a clone whose insert is in the correct orientation is identified by digestion with SacII and XbaI. The product plasmid, Ubq3IntHyg, serves as a dicot expressible form of hygromycin resistance.

Ubq3IntHyg is inserted into a binary vector by digesting pNOV2114 with XbaI and treating it with alkaline phosphatase. Plasmid Ubq3IntHyg, whose Asp718I site has been converted to an EcoRI site with an oligonucleotide, 5'-GTA CGA ATT C-3' (SEQ ID NO:139), is digested with XbaI, and the 3089 bp Ubq3IntHyg expression cassette is separated and purified. Ligation of Ubq3IntHyg with pNOV2114 yields products with two orientations of the insert. The one with the 5'-end of the gene near the T-DNA right border is chosen for plant transformation experiments and named VSUbq3IntHyg.

Example 70B

Co-transformation of the Intramolecular B/P Recombination Test Substrate and the Dicot Selectable Marker into *Agrobacterium* LBA4404

A 1:1 mixture of VSUbq3IntHyg and RKLucB/P (about 50 ng of each) is transformed into 50 microliters of competent *Agrobacterium* LBA4404 by electroporation, and after a recovery period of three hours, the bacteria are plated on YP agar supplemented with 50 mg/l kanamycin and 100 mg/l spectinomycin to select for acquisition of both binary vectors. Transformants appear after 2-3 days and one is picked and purified by single colony isolation on selective agar. This strain is named LBA4404 (VSUbq3Int-Hyg) (RKLucB/P).

Example 70C

Stable Integration of the Test Substrate into Tobacco Chromosomal DNA

1. Co-Cultivation and Selection

Tobacco suspension cells of line BY2, two days after 10-fold dilution into fresh medium, are inoculated with *Agrobacterium* LBA4404(VSUbq3IntHyg)(RKLucB/P) by essentially the same protocol as described above in Section V.B.2. For each co-cultivation, 3 ml of fresh BY2 plant cell culture medium is pipetted into a deep petri dish, and 60 microliters of resuspended bacteria is added and mixed well. BY2 suspension cells (6 ml) are added and the dish is swirled to mix plant cells and bacteria thoroughly. A control of uninoculated BY2 cells is prepared similarly. After three days incubation at 25° C. in darkness, plant cells are rinsed into a sterile filtration apparatus fitted with a filter of 8 micron pore size (white SCWP, 47 mm) and washed three times with 15 ml of BY2 medium containing ticarcillin (200 mg/liter). Finally the plant cells are resuspended in 5 ml of BY2 medium plus ticarcillin (200 mg/liter) and the suspension is spread on 2-3 plates of BY2 medium supplemented with hygromycin (25 mg/liter) and ticarcillin (400 mg/liter). Plates are incubated at 28° in darkness for 3½ weeks, at which time small clones of rapidly growing hygromycin resistant cells are visible against a background of dead untransformed (hygromycin sensitive) cells.

2. Identification of Cell Lines Stably Transformed with the RKLucB/P T-DNA

Hygromycin resistant clones are picked from the selection plates at about 3½ weeks after plating. Each clone is numbered and divided into two portions, one of which is inoculated into 5 ml of liquid selection medium and the other of which is re-plated on selective agar, both media containing ticarcillin (400 mg/liter) and hygromycin (25 mg/l for agar, 50 mg/l for liquid medium). After one week of incubation on a rotary shaker (123 rpm) at 28° in darkness, a 3 ml aliquot of each suspension culture is diluted 10-fold into fresh selection medium and a sample of the cells is centrifuged and DNA isolated from it by protocol of the IsoQuick Nucleic Acid Isolation kit (Orca Research Inc.). The DNA of each clone is analyzed by PCR using primers that are specific for the virG gene (to test for *Agrobacterium* contamination), the HygR gene (positive control), and the inverted Luciferase gene. One of the cell lines that is free from *Agrobacterium* and is PCR positive for the inverted luciferase gene is named B/P-6 and is used as described below.

Example 70D

Assays to Test for Recombination Between attB and attP in Tobacco Chromatin

1. Co-Cultivation with *Agrobacterium*

Suspension cells of line B/P-6, two days past transfer, are washed onto a filter apparatus fitted with 6 micron filter and washed six times successively with 50 ml aliquots of sterile BY2 medium free from selection agents. Washed B/P-6 cells are rinsed off the filter into a sterile flask with 50 ml fresh BY2 medium, and are allowed to incubate at 28° on a rotary shaker in darkness for 6 hours before inoculation with *Agrobacterium*.

2. Study of Intrachromosomal Recombination Between attB and attP Sites

The *Agrobacterium* strains containing binary vectors for delivering wild type or mutant Int genes with or without the integration host factors are described above in Example 45. Intramolecular recombination between the chromosomal attB and attP sites mediated by Lambda integrase, Int-h or Int-h/218 results in luciferase expression. All strains are cultured in YPKan50 broth, centrifuged and resuspended in BY2 medium at $OD_{660}$=0.5. As described above, 60 µl of bacterial suspension is inoculated into 3 ml BY2 medium in a deep petri dish, and to this suspension is added a 6 ml aliquot of the washed B/P-6 tobacco suspension cells described above with vigorous mixing. The co-cultivations are incubated at 25° in darkness for three days, at which time the plant cells are transferred to flasks and 3 ml of fresh BY2 medium added with sufficient ticarcillin to give a final concentration of 400 mg/l. Cultures are incubated on a rotary shaker for two days, at which time 1.5 ml aliquots of each are removed for luciferase enzyme assay and protein determination as described in Example 34 above. Results of such an assay are presented below in Table 12.

TABLE 12

| Strain of Agrobacterium Added | Luciferase LU/mg protein |
| --- | --- |
| RKIntHF | 5.8 |
| RKInt-hHF | 34.4 |
| RKInt-h/218HF | 266.1 |
| RKInt | 1.3 |
| RKInt-h | 2.9 |
| RKInt-h/218 | 300.9 |
| RKLucIntAttL | 14,285 |
| Uninoculated Control | 19.2 |

The results presented in Table 12 show that *Agrobacterium* delivery of the Int-h and Int-h/218 genes, enhanced by the Integration Host Factor protein, produces active integrase that successfully mediates recombination between the attB and attP sites integrated stably into tobacco chromosomal DNA. *Agrobacterium* delivery of the Int-h/218 gene, not enhanced by the IHF protein, also produces integrase that can mediate recombination between attB and attP inserted into tobacco chromosomal DNA.

Example 71

Lambda Integrase-Mediated Intramolecular Recombination Between attL and attR Sites Integrated into Tobacco Chromosomal DNA

Example 71A

Construction of a Binary Vector for Transformation of the Intramolecular L/R Test Substrate into the Tobacco Genome Binary vector VSUbq3InHyg is digested with HindIII, filled-in with Klenow, then cut with ApaI, and ligated to the 3031 bp MslI-ApaI fragment from pBS.CMPSLucL/R to form construct pAdF66. Construct pAdF66 is then electroporated into *Agrobacterium* strain LBA4404, selecting for spectinomycin resistance.

Example 71B

Stable Integration of the Test Substrate into Tobacco Chromosomal DNA

BY2 suspension cells are co-cultivated with LBA4404 (pAdF66) as described in Example 45. After three days incubation at 25° C. in darkness, the plant cells are sedimented at 1000 rpm for 1 minute in a table-top IEC centrifuge and rinsed with fresh BY2 medium. They are then resuspended in fresh BY2 medium and plated onto BY2-agar supplemented with hygromycin (15 mg/liter or 25 mg/liter) and ticarcillin (400 mg/liter). The plates are incubated in the dark for 10 days, at which time hygromycin resistant calli are picked and transferred to fresh selection plates. The number of T-DNA inserts in each transformed callus is estimated using Taqman analysis and lines with a low number of T-DNA inserts are selected. Suspension cell cultures are then initiated by growing small clumps of transformed callus in liquid BY2 medium supplemented with hygromycin (15 mg/l) and ticarcillin (400 mg/l).

Example 71C

Assay to Test for Recombination Between attL and attR in Tobacco Chromatin

Three independent transgenic pAdF66 BY2 suspension cell lines carrying the intramolecular L/R substrate are used in this experiment and cells are prepared for bombardment as described in Example 69. The integrase with or without IHF (0.833 µg/shot) and with excisionase (0.166 µg/shot) are co-bombarded into the pAdF66 cells, and transient luciferase expression is measured on cell extracts two days after bombardment. Duplicate plates are bombarded with each DNA mixture, with each plate shot once at 1100 psi. One plate is also shot once with a control plasmid, 2122-CMPSLucInAttL, to indicate the ability of individual cell line to display transient expression. As seen in the table below, various cell lines show varied degrees of transient luciferase expression using the positive control plasmid. The average Relative Light Units (RLU) for duplicate plates is shown in Table 10 below. No luciferase activity above the standard background is detected from the cell lines carrying the intramolecular substrate, as shown in Table 10 in the row labeled "No Plasmids."

TABLE 10

| Co-Bombarded Plasmids | Average RLU | | |
| --- | --- | --- | --- |
| | Line #7 | Line #29 | Line #33 |
| No Plasmids | 105 | 137 | 186 |
| 2122-CMPSLucInAttL | 39,766 | 74,456 | 49,435 |
| PBSIntHF pAdF61 | 3,516 | 3,844 | 8,667 |
| pBSInt-hHF pAdF61 | 2,291 | 4,171 | 7,843 |
| CMSynInt-h/218 pAdF61 | 1,970 | 6,621 | 17,384 |
| pBSInt-h/218HF pAdF61 | 8,423 | 7,368 | 21,581 |

The data in Table 10 show that each of the three integrases, when delivered with IHF and an excisionase, mediates intramolecular L/R recombination in plant chromatin.

VI. Targeted Integration in Tobacco

A. Donor Sequence and Int Delivered Using *Agrobacterium*-Mediated Transformation 1. Construction of a Positive Control Binary Vector

Example 72

In Vitro Treatment of Plasmid CMPSVLucB/P with Integrase to Form CMPSVLucIntronAttL, a Positive Control Luciferase Construct Containing an Intron with an attL Site Using enzyme and buffer from the Gateway cloning kit (Invitrogen), about 300 ng of plasmid vCMLucB/P (2 µl) is mixed with 10 µl water, 4 µl BP buffer, and 4 µl of BP clonase enzyme and incubated at 25° C. for 1.5 hours. *E. coli* DH5α is transformed with half of the reaction mixture. The intramolecular reaction product CMPSVLucIntronAttL is identified by digestion of minipreps with Asp718I and BglII.

2. Construction of a Target Sequence

In the exemplary constructs described herein, the plasmids used for insertion of target sequences into tobacco contain an expression cassette for HPT (hygromycin resistance gene) to aid in identifying plant clones containing target sequences. In addition, target sequence plasmids contain partial luciferase (5'Luc-5'Intron-) and neomycin phosphotransferase (NPTII) (3'Intron-3'NPTII) expression cassettes, truncated in an intron and punctuated by either a single att site or a pair of identical att sites (any of which can be either wild type or mutant). Thus, a single att site target sequence contains a split marker gene in the form: 5'Luc-5'Intron-AttSite-3'Intron-3'NPTII. A double att site target sequence has the form: 5'Luc-5'Intron-AttSite-spacer-AttSite-3'Intron-3'NPTII. The 5' and 3' intron portions correspond to different introns. The spacer DNA included between the att sites may be an expression cassette, a gene or a gene fragment. The spacer DNA is removed and replaced by a donor sequence upon Int-mediated double recombination between the donor and the target sequences.

Single att sites may be in either a 5'-3' or a 3'-5' orientation relative to the gene coding regions of the target sequence. Pairs of att sites can be divergently oriented (inverted orientation) or convergently oriented (also an inverted orientation). When the 3' ends of the pair of att sites are directed away from each other, the sites are said to be divergently oriented. When the 3' ends of the pair of att sites are directed toward each other, the sites are said to be convergently oriented. Whichever orientation is selected, the att site or paired att sites in corresponding target and donor sequences have matching orientations. In addition, the att sites in the target and donor are compatible for recombination; that is, an attB target is matched with an attP donor, etc., as described herein.

Example 73

Construction of a Target Sequence with a Single attR Site

Plasmid VLucIntronAttL (Example 72) is digested to completion with BglII, then partially with SphI, and the partial digest fragment of 4860 bp is isolated to form Vector 1. Plasmid 3'LucIntron, an intermediate in Example 11A, is digested with MfeI and ligated with a site-change oligonucleotide: 5'-AAT TGT CTA GAC-3' (SEQ ID NO:140) to form 3'LucIntronXba. Plasmid 3'LucIntronXbaI is digested with SphI and XbaI to isolate Insert 1, a fragment of 762 bp containing the central part of Luc with a 5'-portion of the intron. Insert 2 is excised from TOPOBAttRAv (an intermediate in the construction of LPsgAttR and LPdbAttR in Examples 55 and 56) by digestion with BglII and AvrII and gel-purification of the attR fragment (169 bp). The plasmid V5'LucIntronAttRrev is formed by three-way ligation of Vector 1, Insert 1, and Insert 2.

The target sequence plasmid is constructed by four-way ligation of fragments that are prepared as follows: For Fragment 1, binary vector pNOV2114 is digested with PacI and XbaI with alkaline phosphatase and gel purified. For Fragment 2, plasmid V5'LucIntronAttRrev is digested with BglII (Klenow)/SpeI, and the 2047 bp fragment is gel-purified. For Fragment 3, pNOV2720 is digested with MfeI, the site filled in with Klenow polymerase, the plasmid is re-digested with SacI, and the 1291 bp fragment containing 3'-NPTII is gel-purified. Fragment 4 is excised from 2114Ubq3HygB by digestion with SacI and PacI and gel purification of the HygR cassette as a 3157 bp fragment. Four-way ligation of Fragments 1, 2, 3, and 4 produces LPAttRrev.BY2.

Example 74

Construction of LPAttP1P2.BY2

A dicot landing pad is constructed to contain a "stuffer" DNA sequence, flanked by inverted attP1 and attP2 sites, that separates a 5' portion of a luciferase expression cassette and a 3' portion of a neomycin phosphotransferase expression cassette. The CMPS promoter is linked to a 5' portion of the luciferase gene and intron of pAttL by digesting pAttL with NcoI (klenow), XhoI and ligating this fragment into the vector pNOV4211, digested with EcoRI (klenow), XhoI forming Cm5'LucInt. The attP1 site is introduced into the intron of CM5'LucInt by digesting TOPOAttP1 with BamHI (klenow), XhoI and ligating the fragment to the CM5'LucInt vector digested with PspOMI (klenow), XhoI forming CM5'LucP1. The DNA "stuffer" fragment is PCR cloned from the template, pNOV5013, using the oligonucleotide pair 5'-GCT AGC CTC CGT CCG ACG ACT CAA TC-3' (SEQ ID NO:141) and 5'-GGT ACC GGC GCG CCG CAA CAT GAG ATG GCA CCG T-5' (SEQ ID NO:142) and the TOPO TA Cloning Kit forming TOPO.fPPO. The "stuffer" DNA is added 3' of the attP1 site by ligating the NheI, Asp718I fragment of TOPO.fPPO into the CM5'LucP1 vector digested with NheI, Asp718I forming CMLucP1fPPO. The unique SpeI site of CMLucP1fPPO is converted to an AscI site using the oligonucleotide 5'-CTA GGC GCG C-3' (SEQ ID NO:143) forming CMLucP1fPPO.Asc.

The attP2 site is inserted into the 3' region of the tubulin-1-β intron of pNOV2720 using the following 3-way ligation. The 3' region of the NPTII expression cassette of pNOV2720 is excised using MfeI, SacI, the attP2 site is excised from TOPOAttP2 using KpnI, MfeI and the 2 fragments are ligated into Bluescript KS+ digested with KpnI, SacI to form pBSAttP2Kan. The unique Asp718I site of pBSAttP2Kan is converted to an AscI site using the oligonucleotide 5'-GTA CGG CGC GCC-3' (SEQ ID NO:144), forming pBSAttP2Kan.Asc. The 3'region of the NPTII expression cassette containing the attP2 site is excised from pBSAttP2Kan.Asc as an AscI, SacI fragment and ligated into the binary vector, VSUbq3IntHyg, digested with AscI, SacI to form VSP2KanHYG.

The 5' region of the luciferase expression cassette with the attP1 site and the DNA "stuffer" region are excised from CMLucP1fPPO.Asc as an AscI fragment and inserted into the unique AscI site of VSP2KanHYG forming a target sequence with inverted attP1 and attP2 sites, named LPAttP1P2.BY2.

Example 75

Construction of a Target Sequence with Inverted attR Sites

First, the attPI site of pAdF56 is replaced by an attR site as follows: a PCR fragment carrying an attR site flanked on its 5' end by an NheI site and on its 3' end by an XhoI site is amplified from construct TOPOBAttRAv using PCR primers NheAttRFOR (5'-GGG CTA GCT CTG TTA CAG GTC ACT AAT A-3' (SEQ ID NO:145)) and XhoAttRREV (5'-CCC TCG AGC GCT CAA GTT AGT ATA AAA AAG-3' (SEQ ID NO:146)). The attR PCR fragment is re-cut with NheI and XhoI and cloned into the vector construct pAdF56 digested with NheI and XhoI, to form pAdF58A.

Secondly, the attP2 site of pAdF58A is replaced by an attR site as follows: an attR site flanked on its 5' end by an AscI site and on its 3' end by an AvrII site is amplified from TOPOBAttRAv using PCR primers AscAttRFOR (5'-GGG GCG CGC CTC TGT TAC AGG TCA CTA ATA-3') (SEQ ID NO:147)) and AvrAttrREV (5'-CCC CTA GGC GCT CAA GTT AGT ATA AAA AAG-3') (SEQ ID NO:148)). The attR PCR product is re-cut with AscI and AvrII and cloned into vector construct pAdF58A digested with AscI and AvrII, to form pAdF58.

Figure 12:
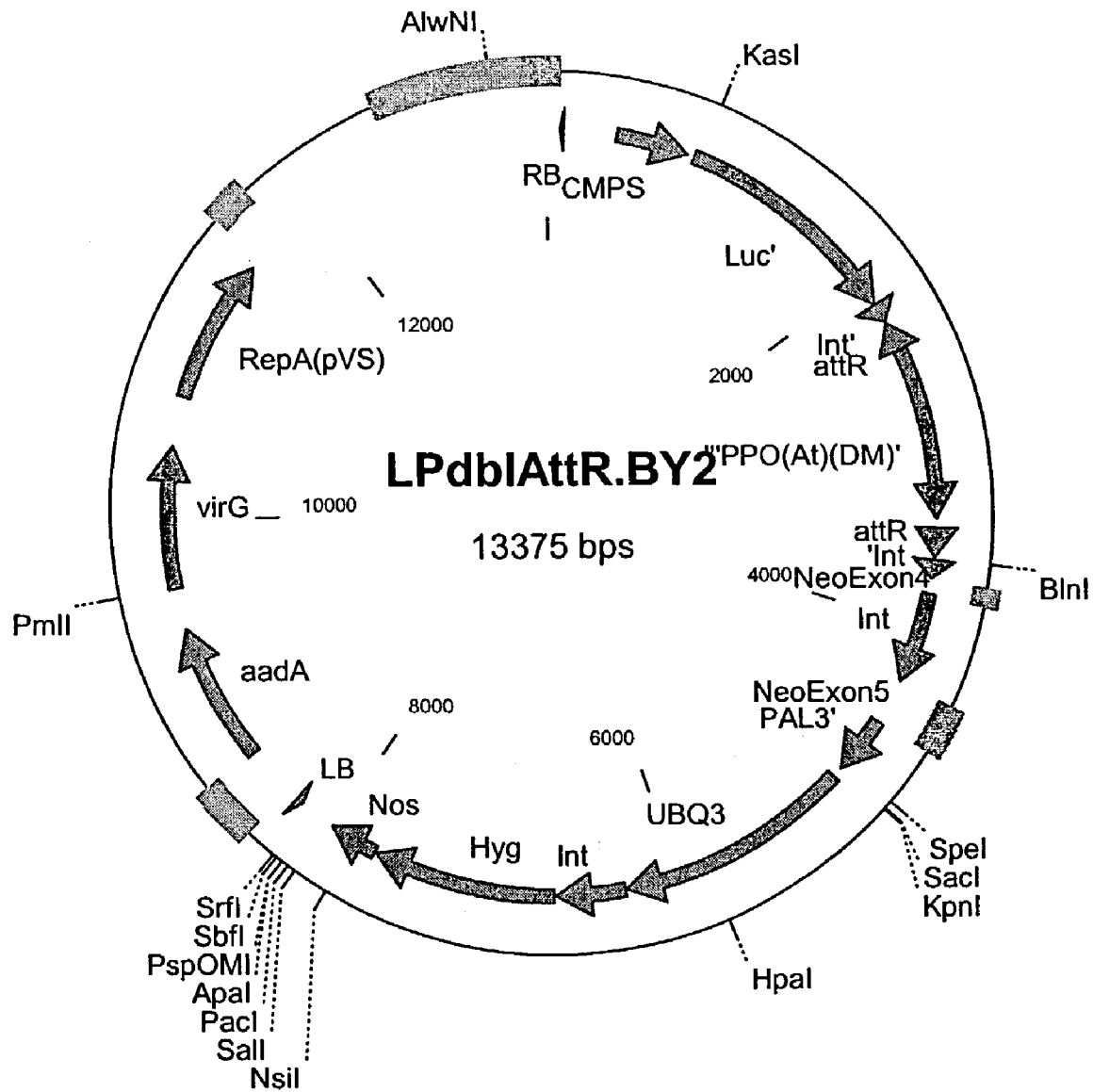
FIG. 12 represents the structure of LPdblAttR.BY2, an exemplary plasmid harbored in *Agrobacterium* that contains a dicot target sequence with two attR sites in inverted orientation.

Finally, the 4049 bp SfoI-Acc65I fragment of pAdF58 is ligated to the 9326 bp SfoI-Acc65I vector portion of construct LPAttP1P2.BY2, to form binary vector pAdF60 (i.e., LPdblAttR.BY2) (FIG. 12).

3. Construction of Donor Sequences

Generally, the exemplary donor sequences constructed herein contain the 5'-portion of the NPTII expression cassette and the 3'-portion of the Luc expression cassette; that is, the portion of each that is missing from the target sequence. The division point of the intron within each gene is punctuated by an att site.

Donor constructs may contain a single att site, taking the form 5'NPTII-5'Intron -AttSite-3'Intron-3'Luc. Alternatively, donor constructs may contain two att sites, taking the form AttSite-3'Intron-3'Luc-5'NPTII-5Intron-AttSite. The 3' portion of an intron in the donor corresponds to the 5' portion of the same intron in the compatible target sequence. The 5' portion of an intron in the donor corresponds to the 3' portion of the same intron in the compatible target sequence. The att site(s) in the donor are compatible for recombination with the att site(s) in the corresponding target sequence. In addition, the orientation of the att sites with respect to the truncated genes is the same in the donor and target sequences.

Donor sequences may be introduced by *Agrobacterium* T-DNA delivery, for which the constructs below are useful. Alternatively, biolistic bombardment (as described in Section VI.B below) or other physical delivery systems may be employed, for which other versions of donor constructs on high copy plasmids, such as pUC18 or pBluescript, for example, are easily derived from the binary plasmids described herein.

The production of a targeted insertion events via either single site or double site recombination between donor sequences and compatible target sequences results in the reconstitution of functional luciferase and NPTII expression cassettes.

Example 76

Construction of a Donor Sequence Containing an attL Site

This donor is constructed by three-way ligation. Fragment 1 is a pNOV2114 vector plus a Nos terminator, which is excised from VSInt-h/218 by digestion with PspOMI and SacI, and purification of the 6063 bp fragment. Fragment 2 is a 3203 bp fragment of pNOV2720 excised with PspOMI and MfeI and containing an Smas promoter and a 5'NPTII gene.

Figure 11:
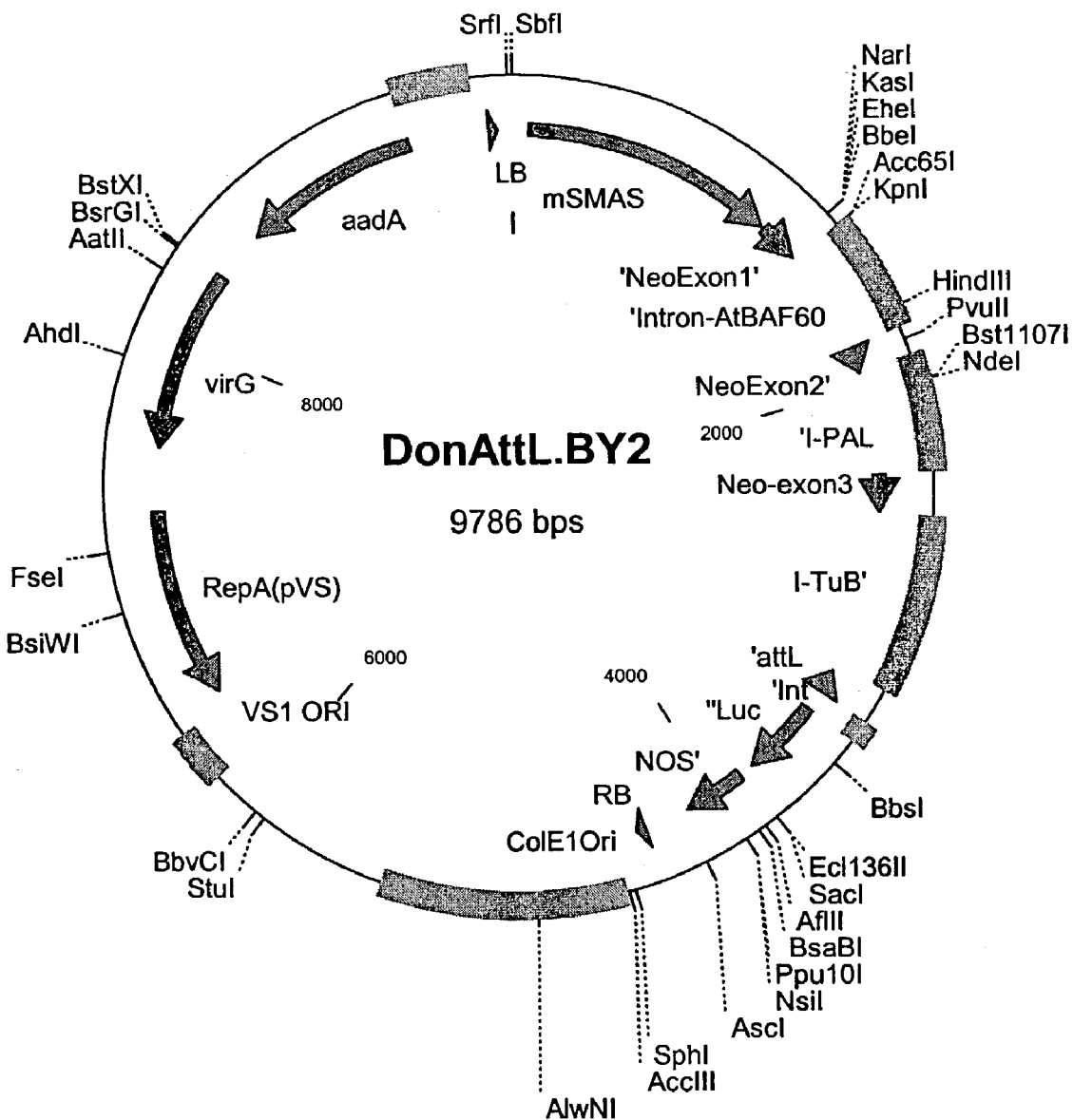
FIG. 11 represents the structure of DonAttL.BY2, an exemplary plasmid harbored in *Agrobacterium* that contains a dicot donor sequence with a single attL site.

Fragment 3 is produced as follows: Plasmid VLucIntronAttL, described in Example 72, is digested with SacI and XhoI, and the 491 bp fragment containing 3'IntronLuc (without terminator) is gel purified. Bluescript vector pBSKS⁻ is digested with XhoI and SacI, treated with alkaline phosphatase, and the vector is gel-purified. These two fragments are ligated together and transformed into *E. coli*. Clones are analyzed by digestion of miniprep DNA with SacI/XhoI, and those that exhibit the desired 491 bp insert are named pBS 3'LucIntron. In preparation for the insertion of an attL, pBS 3'LucIntron is digested with XhoI, treated with alkaline phosphatase, and gel-purified. TOPOAttL (Example 12) is digested with XhoI, and the 113 bp attL fragment is gel-purified in 2% agarose. The attL site is ligated with pBS 3'LucIntron, forming pBS 3'LucIntronAttL. A clone with attL in reversed orientation is identified by digestion with PsiI and confirmed by DNA sequencing. pBS 3'LucIntronAttLrev is digested with Asp718I and ligated with a site change oligonucleotide, 5'-GTA CGG CAA TTG CC-3' (SEQ ID NO:149), to produce an MfeI site, forming pBS 3'LucInAttLMfe. This plasmid is digested with MfeI and SacI, and the 618 bp insert fragment is gel-purified to produce Fragment 3. Fragments 1, 2, and 3 are ligated together to form DonAttL.BY2 (FIG. 11).

Example 77

Construction of DonAttB1.BY2

This donor sequence is constructed through a four-way ligation. Fragment 1 is derived from binary vector pNOV2114 by digestion with Asp718I and PspOMI, treatment with alkaline phosphatase, and gel-purification of the resulting 5667 bp fragment. Fragment 2 is excised from vattPIntron 3'LucNos (vAttP) (Example 14) by digestion with Asp718I/XhoI and gel-purification of the 773 bp fragment containing Intron 3'LucNos. Fragment 3 is formed by annealing an oligonucleotide pair, 5'-TCG AGA GCC TGC TTT TTT GTA CAA ACT TGT CCC C-3' (SEQ ID NO:150) and 5'-AAT TGG GGA CAA GTT TGT ACA AAA AAG CAG GCT C-3' (SEQ ID NO:151), which represents the attB1 site flanked by XhoI and MfeI cohesive ends. Fragment 4 is the Smas promoter/5'NPTII fragment obtained by digestion of pNOV2720 with PspOMI and MfeI and gel purification of the 3203 bp fragment. Four-way ligation and transformation affords colonies that are analyzed by digestion of minipreps with XhoI/XbaI. Selected clones produce the correct fragment pattern (4058, 1744, 1176, 1142, 598, 445, 312, and 93 bp). These clones are analyzed through DNA sequencing and exhibit the predicted structure at all junctions and across the attB1 site.

Example 78

Construction of DonAttB1AttB2.BY2

This donor is constructed in two steps. For the first, DonAttB1.BY2 (Example 77) is digested with MfeI and Asp718I, and the 807 bp fragment containing AttB1LucNos is gel-purified to form Insert #1. pNOV2114 is digested with EcoRI and Asp718I and the 5751 bp vector is gel-purified and ligated to Insert #1 to produce 2114AttB1.3'LucNos. Digestion of miniprep DNA from eight candidate clones with XhoI/XbaI showed that all had the predicted pattern of fragments: 3838, 1744, 445, 297, 95, and 93 bp. From this product, DonAttB1AttB2.BY2 is produced by a 3-way ligation. 2114AttB1.3'LucNos is digested with PspOMI and SbfI to produce the vector for the second step. For Insert A, pNOV2720 is digested with MfeI and PspOMI and the 3203 bp fragment containing Smas Promoter/5'NPTII is gel-purified. Insert B is an annealed oligonucleotide pair (5'-AAT TGA CCC AGC TTT CTT GTA CAA AGT GGT CCC CTG CA-3' (SEQ ID NO:152) and 5'-GGG GAC CAC TTT GTA CAA GAA AGC TGG GTC-3' (SEQ ID NO:153)) representing the attB2 site flanked by MfeI and SbfI cohesive ends. Transformation of the ligation mixture affords 110 colonies. XhoI/XbaI digestion of minipreps from 10 clones identified 2 with correct pattern of fragments: 3838, 2901, 1142, 598, 445, 312, 297, 93, and 90 bp. DNA sequence analysis confirmed the predicted structure at all junctions and across the AttB1 and AttB2 sites.

Example 79

Construction of a pUC-based Dicot Donor Plasmid with Inverted attL Sites

The first cloning step involves a four-way ligation with the following fragments: vector pNEB193 digested with BamHI and XbaI, the 3194 bp XhoI-MfeI fragment from construct DonAttB1AttB2.BY2, the 128 bp XhoI-BglII attL fragment from LPdbAttL (Example 56) and the 120 bp MfeI-AvrII attL fragment from PMIAttLi (Example 63). The resulting plasmid is called pAdF74. In the second step the 878 bp XhoI fragment of DonAttB1AttB2.BY2 (Example 78), carrying the 3'end of the luciferase gene linked to the 3' nos terminator, is ligated into the unique XhoI site of pAdF74. The desired orientation of the 878 bp XhoI insert in the vector is determined using standard restriction digests to yield construct pAdF75. This pUC-based donor construct contains two inverted attL sites and contains the gene fragments necessary to reconstruct functional luciferase and NPTII genes following two L/R recombination events into BY2 target lines containing pAdF60 (FIG. 12).

Example 80

Figure 13:
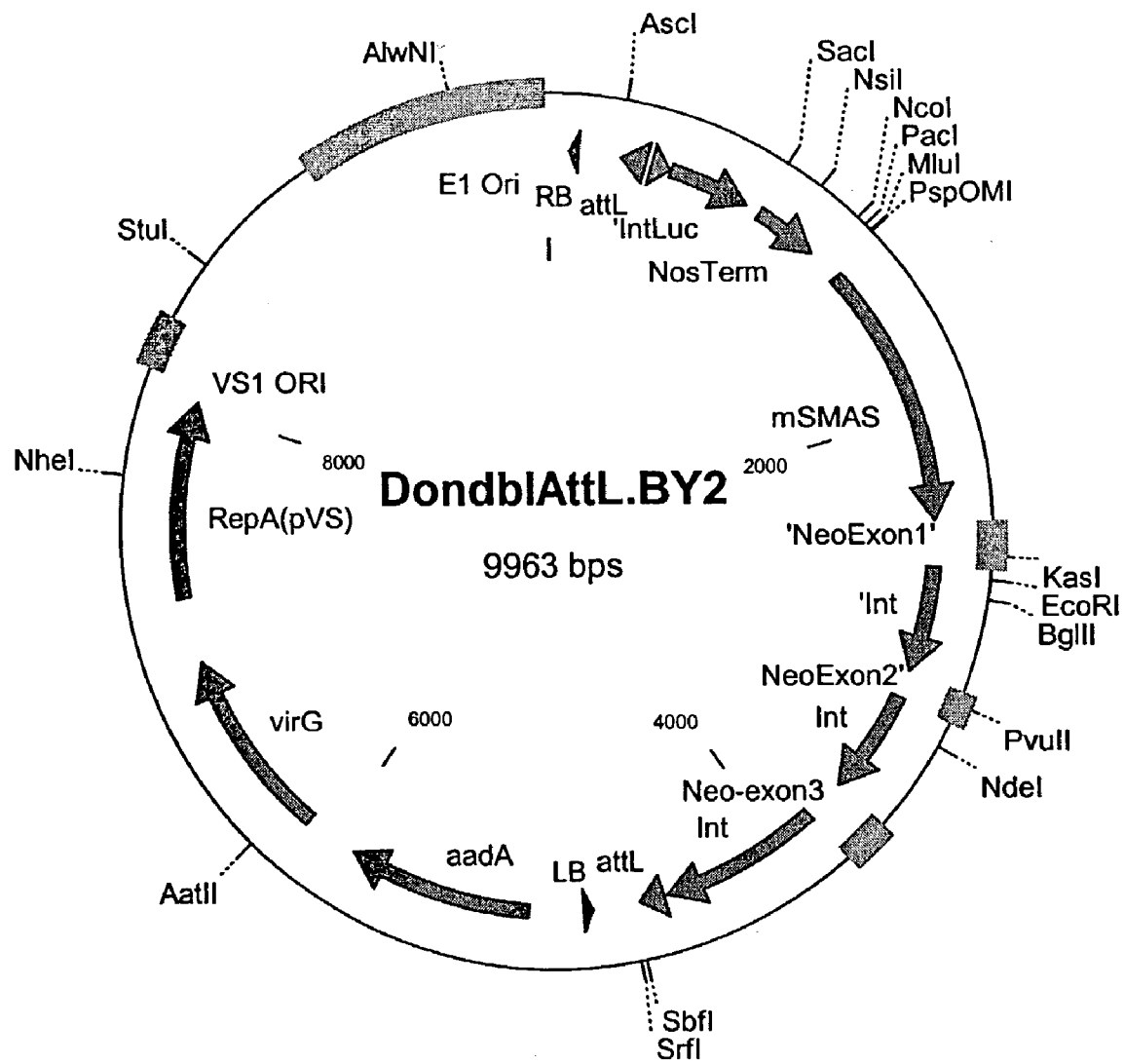
FIG. 13 represents the structure of DondblAttL.BY2, an exemplary plasmid harbored in *Agrobacterium* that contains a dicot donor sequence with two attL sites in inverted orientation.

Cloning Donor Construct DondbAttL.BY2 into Binary Vector pNOV2114 for Delivery as an *Agrobacterium* T-DNA pAdF75, containing DondbAttL.BY2 is digested with AscI and SbfI and the insert 4352 bp fragment is gel-purified. Binary vector pNOV2114 is digested with AscI and SbfI in the presence of alkaline phosphatase and the vector fragment of 5611 bp is gel-purified. Ligation of the donor fragment with the binary vector affords hundreds of transformants. Analysis of five by digestion of minipreps with MfeI/SbfI reveals that all 5 of (2114)DondblAttL.BY2 (FIG. 13) are correct, with fragments of 5604, 4214, and 145 bp (attL-fragment).

3. Production of a Tobacco Target Cell Line

Example 81

Transformation of a Target Sequence into Tobacco Suspension Cells

Figure 10:
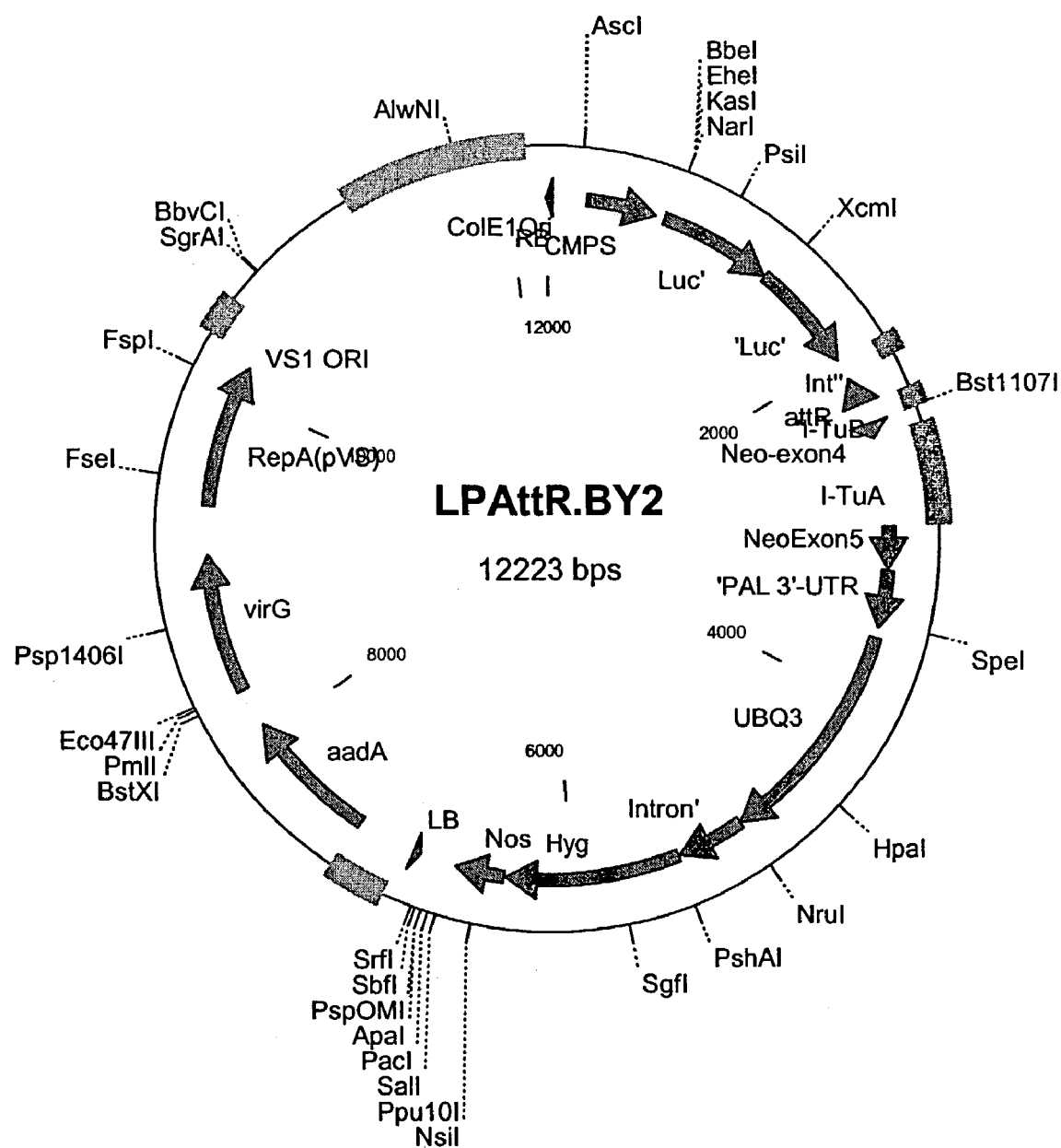
FIG. 10 represents the structure of LPAttR.BY2, an exemplary plasmid harbored in *Agrobacterium* that contains a dicot target sequence with a single attR site.

The *Agrobacterium* LBA4404 strain carrying LPAttR.BY2 (FIG. 10) is inoculated into YP broth with spectinomycin (100 mg/l) and allowed to grow at 25° C. until late logarithmic stage (typically 24 hours). Bacteria are centrifuged and resuspended at $OD_{660}$=0.5 in BY2 liquid medium. Transformation of tobacco BY2 cells is carried out essentially as described in Example 45, except that typically 120 μl of *Agrobacterium* is used per petri dish, and co-cultivations are usually conducted for about 3 days. At the end of that time, plant cells are suspended and pipetted from the petri dish to a 15 ml centrifuge tube, rinsing the petri dish once with sterile BY2 medium and adding the rinse to the tube. Plant cells are centrifuged at 2000 rpm for 2 minutes, and the supernatant is decanted. The BY2 cells are suspended in 3-5 ml and spread on BY2 agar with 15 mg/l hygromycin, 200 mg/liter ticarcillin (BY2Hyg15Tic200) (about 0.5-1 ml packed cells per plate). Plates are incubated in darkness at 28° C., and, after about 2-3 weeks, calli are selected as target sequence clones. Selected clones containing LPAttR.BY2 (FIG. 10) are cultured at 22° C. in ambient light and transferred to fresh plates of BY2Hyg15Tic200 at 2-3 week intervals.

4. Targeted Integration of a Donor Sequence into a Tobacco Target Cell Line

Example 82

Co-Cultivation of a Tobacco Target Cell Line Containing an attR Site with *Agrobacterium* Containing a Donor Construct with an attL Site A target plant cell line containing LPAttR.BY2 (FIG. 10) is grown as a suspension culture, washed to remove antibiotics, and grown overnight in BY2 medium without selection immediately prior to co-cultivation. The target line is subjected to three treatments as follows: (1) 100 μl LBA4404 (DonAttL.BY2)+60 μl LBA4404 (RKInt-hHF)+20 μl LBA4404 (pAdF62A); (2) 180 μl LBA4404 (pNOV273 1) (positive control); and (3) no *Agrobacterium* (untreated control). The LBA4404 cultures are adjusted to $OD_{660}$=0.5 and the indicated volume of the *Agrobacterium* strain is added to 1.8 ml of liquid BY2 medium in a deep petri dish. pAdF62A is a binary vector with an Xis expression cassette, as described in Example 8. pNOV2731 is a positive control kanamycin resistance expression cassette.

Three deep petri dishes (one for each treatment) are prepared, and the following is added to each dish: 7 ml of plant cell suspension containing about 1.5 ml packed cells and 2 ml BY2 medium containing the indicated volumes of *Agrobacterium* culture(s). Bacteria and plant cells are mixed vigorously and stored at ambient temperature (about 22° C.) in darkness for about 3 days. Cells are centrifuged, resuspended, and pipetted onto selective agar. Each co-cultivation is divided between two selection plates of fresh BY2 medium with 100 mg/l kanamycin plus 200 mg/l ticarcillin. Excess moisture is allowed to evaporate in the laminar flow hood, and plates are incubated in darkness at 28° C.

After about 2-3 weeks, colonies are seen on the Treatment 1 and 2 plates, while Treatment 3 plates show no growth. Clones are selected from Treatment 1 plates and transferred to fresh selective BY2 medium. DNA is extracted from rapidly growing clones using the Qiagen Dneasy kit. DNA is analyzed by PCR using primer pairs that are specific for the target sequence (to test the quality of the DNA prep) as well as each of the new recombinant genes, NPTII and luciferase (spanning the joints at the att sites). Primers for the target sequence are InTuAfw (5'-GTA ATT AAG CTT TTC CAC CTC TCT TGT T-3' (SEQ ID NO:154)) and InTuArv (5'-GAT CCT GCA GCA AG GAA AAA TAT TTC AAT AC-3' (SEQ ID NO:155)). Primers for the NPTII junction are Neo3132f (5'-GGC GGT AGT GTA TTA GTG TC-3' (SEQ ID NO:156)) and Neo3637r (5'-GAT GCT CTT CGT CCA GAT CA-3' (SEQ ID NO:157)). Primers for the luciferase junction are Luc1876f (5'-GGA AGC GAC CAA CGC CTT GA-3'(SEQ ID NO:158)) and Luc2387r (5'-TGC GAC ACC TGC GTC GAA GA-3' (SEQ ID NO:159)).

A selected LPAttrR.BY2 transformant gives PCR products with both the Luc and NPTII primer pairs that are the correct size for a targeted event: 581 bp with NPTII primers and 420 bp with Luc primers. The DNA fragments are subjected to sequencing to determine their structure. The sequences confirm that this clone is a result of Int-catalyzed reaction between the attL site in the donor DNA and the attR site in the target. Because a single-site donor T-DNA, such as DonAttL.BY2, is a linear structure, its recombination with LPAttR.BY2 inserted in the plant genome produces a break in the chromosome, corresponding to the free left and right border ends of the donor T-DNA. The plant cell can repair this break by non-homologous end-joining (Gorbunova and Levy (1999) Trends in Plant Science, 4: 263-269) of the left border and the right border. These T-DNA borders are amplified with PCR primers that are situated near each border and pointed "outward," i.e., through the border sequence, to amplify the ends of the T-DNA and any sequence between them. Primers Luc1876f (SEQ ID NO:158) and Neo3637r (SEQ ID NO:157) amplify a fragment of about 550 bp, and its sequence reveals that the donor DNA extends beyond the end of the Luc gene to a position 8 bp before the right border nick site and above the Smas promoter precisely to the nick site in the left border of the T-DNA. A 98 bp filler DNA is situated between the two. Filler consists of 51 bp derived from the Smas promoter portion of the donor sequence, flanked by 16- and 31-bp blocks of unknown sequence. It is concluded that the selected transformant contains a perfect single-site targeted event as catalyzed by Int-h with Xis and IHF.

Example 83

Co-Cultivation of a Tobacco Target Cell Line Containing Inverted attR Sites with *Agrobacterium* Containing a Donor Construct with Inverted attL Sites A target plant line containing pAdF60 (i.e., LPdblAttR.BY2) (FIG. 12) is cultured as a suspension in selective medium. Before co-cultivation, the cells are washed repeatedly with BY2 medium by centrifugation and resuspension to remove all traces of antibiotics. *Agrobacterium* strains containing donor constructs and Int, IHF, and Xis expression cassettes as well as an LBA4404(pNOV2731) positive control strain are grown in YP broth with appropriate antibiotics. The target line is subjected to three treatments as follows: (1) 100 μl DondblAttL.BY2, 100 μl RKInt-h/

218HF (Int-h/218+IHF), and 60 µl Xis; (2) 120 µl pNOV2731 (positive control); and (3) no *Agrobacterium* (untreated control). The LBA4404 culture is adjusted to $OD_{660}=0.5$ and the indicated volume of the *Agrobacterium* strain is added to 1.8 ml of liquid BY2 medium in a deep petri dish.

Three deep petri dishes (one for each treatment) are prepared, and the following is added to each dish: 7 ml of plant cell suspension containing about 1.5 ml packed cells and 2 ml BY2 medium containing the indicated volumes of *Agrobacterium* culture(s). Bacteria and plant cells are mixed vigorously and stored in a 22° C. incubator in darkness for about 3 days. Cells are centrifuged, resuspended, and pipetted onto selective agar. Each co-cultivation is divided between two selection plates of fresh BY2 medium with 100 mg/l kanamycin plus 200 mg/l ticarcillin. Excess moisture is allowed to evaporate in the laminar flow hood, and plates are incubated in darkness at 28° C.

Four weeks after plating on BY2Kan100Tic200, small white spherical clones appear and are transferred to fresh selective medium. Clones are selected and analyzed. PCR analysis shows that a selected clone exhibits both Luc and NPTII amplification products that are the correct size for a transformant targeted on both sides. DNA sequence analysis of the PCR products demonstrates that this transformant is a product of two Int-catalyzed site-specific recombinations.

B. Donor Sequence and Int Delivered Using Microprojectile Bombardment

1. Construction of Target Sequences

Example 84

Construction of a Binary Dicot Vector Containing a Target Sequence with Inverted attL Sites The first step involves the subcloning of the 4196 bp SfoI-Acc65I fragment of construct LPAttP1P2.BY2 into vector pUC18 digested with SfoI and Acc65I to form plasmid pAdF56. This 4196 bp fragment of the target sequence construct LPAttP1P2.BY2 contains an attP1 site and an attP2 site in an inverted orientation: the attP1 site is located downstream of the CMPS promoter:luciferase 5' end gene fragment, within an intron, and in the same orientation as the luciferase coding region (i.e., a forward direction); the attP2 site is located upstream of the 3' end of the neomycin phosphotransferase (NPTII) gene fragment, within an intron, and in reverse orientation with respect to the NPTII coding region.

In the second step, the attP1 site of pAdF56 is replaced by an attL site as follows: a PCR fragment carrying an attL site flanked on its 5' end by an NheI site and on its 3' end by an XhoI site is amplified from construct DonAttL.BY2 (Example 76) using PCR primers NheAttLFOR (5'-GGG CTA GCT GAA GCC TGC TTT TTT ATA CTA-3') (SEQ ID NO:160) and XhoAttLREV (5'-CCC TCG AGA AAT CAA ATA ATG ATT TTA TTT TG-3') (SEQ ID NO:161). The attL PCR fragment is cut with NheI and XhoI, cloned into vector pAdF56, and then digested with NheI and XhoI to form pAdF57A.

In a third step, the attP2 site of pAdF57A is replaced by an attL site as follows: an attL site flanked on its 5' end by an AscI site and on its 3' end by an AvrII site is amplified from DonAttL.BY2 (Example 76) using PCR primers AscAttLFOR (5'-GGG GCG CGC CTG AAG CCT GCT TTT TTA TAC TA-3') (SEQ ID NO:162) and AvrAttLREV (5'-CCC CTA GGA AAT CAA ATA ATG ATT TTA TTT TG-3') (SEQ ID NO:163). The attL PCR product is re-cut with AscI and AvrII and cloned into vector construct pAdF57A digested with AscI and AvrII, forming pAdF57.

Figure 14:
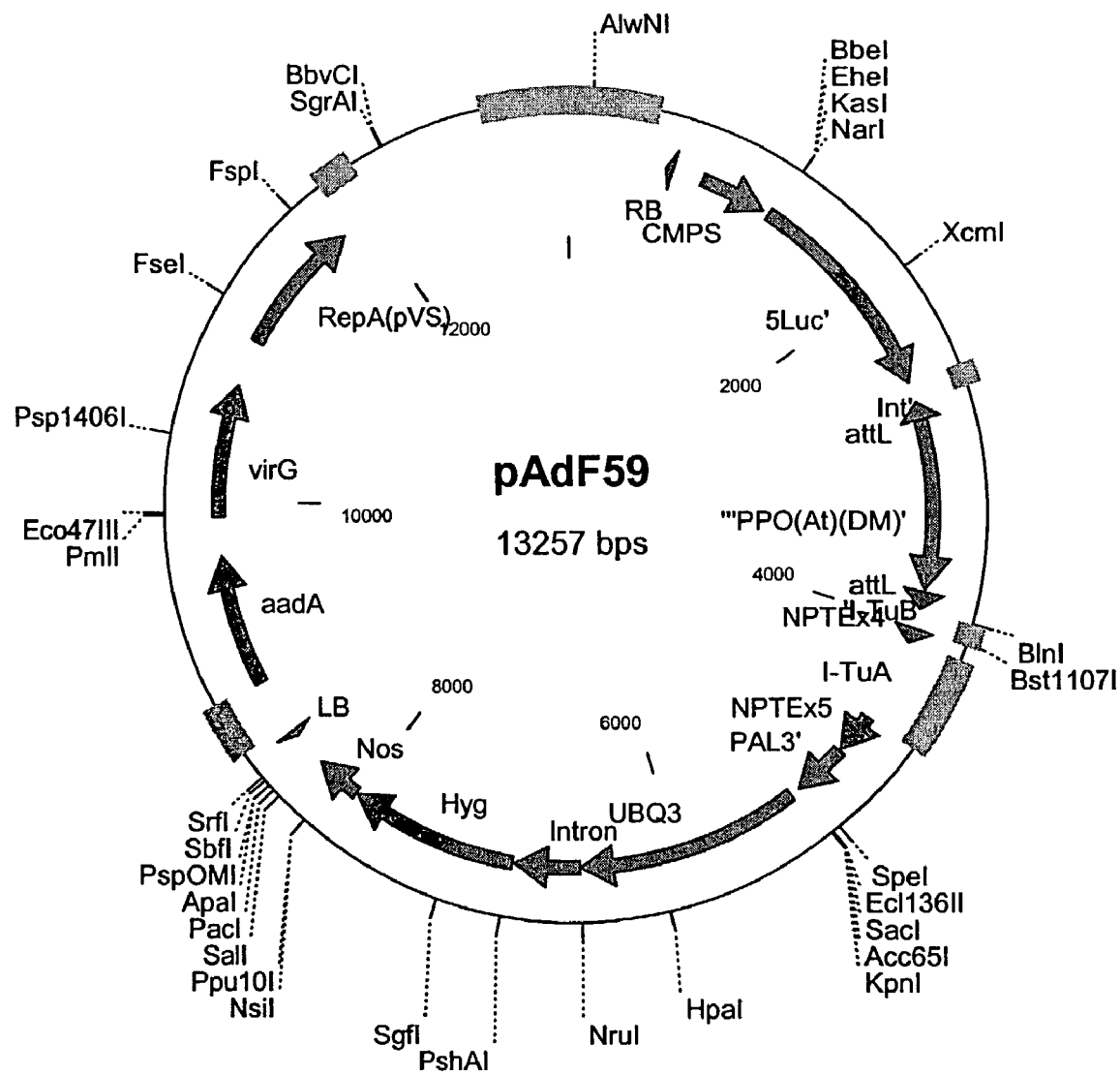
FIG. 14 represents the structure of pAdF59, an exemplary plasmid harbored in *Agrobacterium* that contains a dicot target sequence with two attL sites in inverted orientation.

In the last cloning step, the 3953 bp SfoI-Acc65I fragment of pAdF57 is ligated to the 9326 bp SfoI-Acc65I vector portion of construct LPAttP1P2.BY2 to form binary vector pAdF59 (FIG. 14).

2. Production of a Tobacco Target Cell Line

Example 85

Generation of Transgenic Tobacco BY2 Target Lines

Binary vector pAdF59 (FIG. 14) is electroporated into *Agrobacterium* strain LBA4404. The resulting strain, LBA4404(pAdF59), is co-cultivated with tobacco BY2 suspension culture cells as described above in Example 71B. Independent transformed cell lines carrying the lowest number of T-DNA insertions are identified using Taqman technology. Suspension cell cultures from the latter are initiated by re-suspending calli in liquid BY2 medium supplemented with hygromycin (15 mg/l) and ticarcillin (400 mg/l).

3. Construction of Donor Sequences

Example 86

Construction of a pUC-based Dicot Donor Plasmid with Inverted attR Sites

The first cloning step involves a four-way ligation with the following fragments: (1) vector pNEB193 digested with BamHI and XbaI, (2) the 3194 bp XhoI-MfeI fragment from construct DonAttB1AttB2.BY2, (3) the 186 bp XhoI-BglII attR fragment from LPdbAttR (Example 56), and (4) the 188 bp MfeI-AvrII attR fragment from pBS.DonAttR. (pBS.DonAttR is a derivative of DonAttR.BY2, in which the 4182 bp XhoI fragment is subcloned into the XhoI site of vector pBlueScript KS(–); the product of this non-directional ligation, which includes the NPTII and luciferase genes in opposite orientation to the vector ampicillin resistance gene, is called pBS.DonAttR). The resulting plasmid is called pAdF71.

Figure 15:
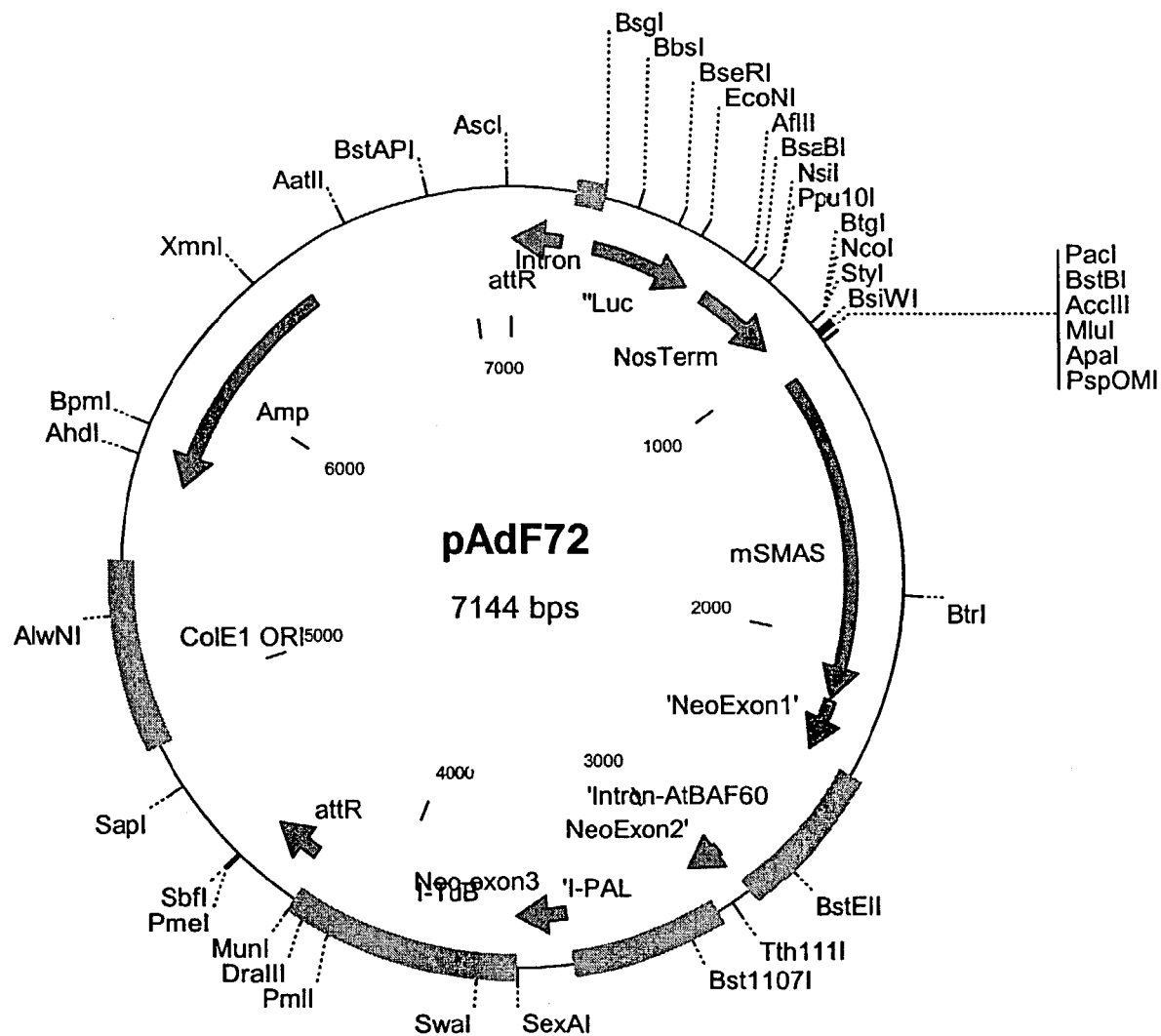
FIG. 15 represents the structure of pAdF72, an exemplary plasmid for biolistic delivery that contains a dicot donor sequence with two attR sites in inverted orientation.

In the second step, the 878 bp XhoI fragment of DonAttB1AttB2.BY2, carrying the 3'end of the luciferase gene linked to the 3' nos terminator, is ligated into the unique XhoI site of pAdF71. The desired orientation of the 878 bp XhoI insert in the vector is determined using standard restriction digests to yield construct pAdF72 (FIG. 15). This pUC-based donor construct contains two inverted attR sites and also contains the gene fragments necessary to reconstruct functional luciferase and NPTII genes following two L/R recombination events into BY2 target lines containing pAdF59.

4. Targeted Integration of a Donor Sequence into a Tobacco Target Cell Line

Example 87

Targeted Integration of a Donor Sequence into Tobacco Chromatin Using Biolistics Suspension cell cultures of a target line containing pAdF59 (carrying inverted attL sites) are grown and cells are prepared for bombardment as described in Example 69. The donor DNA, pAdF72 (FIG. 15), is co-precipitated onto gold particles (0.833 µg/shot) with Int-h/218 and integration host factor (pBSInt-h/218HF) (0.833 µg/shot) and the excisionase (pAdF61) (0.166 µg/shot). Each target plate is shot once at 1100 psi. The plates are then incubated at 28° C. in the dark for 72 hours on high osmotic medium (BY2 with 12% sucrose). The filters topped with the cells are then transferred to selection plates containing BY2 medium supplemented with kanamycin (50 mg/l) and ticarcillin (400 mg/l). 24 hours later, the cells are gently scraped off the filter and spread onto the selective agar using 2 ml of liquid BY2 supplemented with kanamycin (50 mg/l). Two to three weeks later, small calli growing on the selection plates are transferred to fresh plates where they are grown until enough tissue is available for luciferase assays and PCR analysis.

Example 88

Identification of Targeted Events After Bombardment of Donor DNA into a Target Cell Line Four independent kanamycin resistant calli are found to include a functional luciferase gene, as shown in Table 11 below, when ~20 mg of callus is used in a luciferase assay, as described above in Section I.A.3.

TABLE 11

| Target Sequence | Event | RLU |
|---|---|---|
| pAdF59 #5 | 59/5-1 | 40,000,000 |
| pAdF59 #5 | 59/5-3 | 40,000,000 |
| pAdF59 #24 | 59/24-1 | 4,000,000 |
| pAdF59 #24 | 59/24-6 | 850 |

Genomic DNA is extracted from the four kanamycin resistant calli described above using Qiagen DNeasy Plant Mini Kit, and PCR analysis is carried out using PCR primers, as described below. An attP site is predicted to be formed within the target sequence at each L/R recombination site, one located in the NPTII gene, and the other in the luciferase gene. PCR amplification of a DNA fragment covering the kanamycin junction site is done using Qiagen HotStartTaq DNA Polymerase and PCR primers InTuBFw (5'-CAG GTA TAT ATA TGA ATC GAT TTC TCC CTT-3' (SEQ ID NO:184)) and InTuBRv (5'-TCG TCC AGA TCA TCC TGT AAT ACA GAA ATG TT-3' (SEQ ID NO:185)). A PCR product of the predicted size (~1078 bp) is obtained with DNA extracted from events 59/5-1 and 59/24-1. These PCR products are sequenced and match the predicted DNA sequence resulting from targeted integration of the donor DNA into the target sequence through L/R recombination.

A second set of PCR amplification is done using Roche Expand Long Template PCR System and PCR primers 3'Luc448f (5'-GAA GCG AAG GTT GTG GAT CT-3' (SEQ ID NO:164)) and InTuBRv (SEQ ID NO:185)). A PCR product of the predicted size (~5038 bp) is obtained with DNA from events 59/5-1 and 59/24-6. The sequence of the ends of the PCR product from event 59/5-1, covering the two L/R recombination sites (i.e., attP sites), matches the predicted sequence.

Example 89

Viral Amplification of Donor DNA to Improve Targeting Efficiency

The frequency of targeted insertion events using any of the donor/target combinations described herein can be increased by increasing the concentration of donor DNA in the plant cell. The replication system of a geminivirus, such as, for example, beet curly top virus (BCTV) for dicot plants, is useful for this purpose. (See, generally, Stanley et al. (1986) EMBO J. 5(8): 1761-1767.) The biolistic delivery system is described here, but this approach is equally applicable to an *Agrobacterium* delivery system (Stenger et al. (1991) Proc. Natl. Acad. Sci. USA 88: 8029-8033). When a DNA sequence of interest (such as a donor sequence, for example) in an *Agrobacterium* T-DNA is flanked by copies of the viral ori (see below), rolling circle replication leads to the formation of a replicating form carrying the DNA of interest. This may occur either before or after T-DNA integration into the plant genome.

For biolistic delivery, the approach involves incorporating into the donor DNA plasmid a copy of the nucleotide sequence that is a recognition sequence for replication and transcription of the viral genome, the viral ori. This recognition sequence is a palindromic sequence containing a centrally positioned nucleotide sequence that is common to geminiviruses. For BCTV, the recognition sequence (with palindrome in bold) is: 5'-GGG GCC ATC CGG TAA TAT TAA TGC GGA TGG CCC C-3' (SEQ ID NO:165). On BCTV, this sequence is situated in the intergenic region between the open reading frames (ORFs) of the viral plus strand and the ORFs of the minus strand (Timmermans et al. (1994) Annu. Rev. Plant Physiol. Plant Mol. Biol. 45: 79-112).

In preparation for further construction steps, a subclone of BCT viral DNA is constructed in which the coat protein ORF is deleted and replaced by XhoI and EcoRV recognition sites. The American Type Culture Collection (10801 University Blvd. Manassas, Va. 20110-2209) is the source of plasmid pCFH (ATCC Catalog No. PVMC-6, Beet severe curly top virus strain CFH), which contains the CFH strain of beet curly top virus double-stranded DNA linearized at an EcoRI site and inserted into the EcoRI site of the pUC8 vector. The coat protein gene is deleted from the viral DNA by PCR amplification (10 cycles) with Expand High Fidelity PCR System (Roche) using the following primer pair: BCTV-CP-V-Xho-RV (5'-GGC CTC GAG GAT ATC TTG GCA ATT GTA GAT GCT ATT T-3') (SEQ ID NO:166) and BCTV-CP-C-Xho-RV (5'-GGC CTC GAG ATA TCA CAA CGA ACA CTT CCT ATG A-3') (SEQ ID NO:167). The ~4.8 kb PCR fragments are digested with XhoI and self-ligated. A perfect clone is identified by DNA sequencing and called CFH-ΔCP. This plasmid is digested with EcoRI and EcoRV, and the two insert fragments of 1799 bp and 398 bp are gel purified. Three-way ligation of these two inserts with the pUC18 vector, digested with HindIII, rendered blunt by Klenow polymerase, and treated with alkaline phosphatase, produces pUC18DVR1 and pUC18DVR2, clones with the two possible orientations of the viral replicon. We designate as pUC18DVR2 the clone in which ORFV1 and ORFV2 are near the remaining pUC18 polylinker sites. pUC18DVR2 is identified by SphI digestion, yielding fragments of 4131 bp and 825 bp.

From pUC18DVR2, the BCTV intergenic region is amplified by PCR with flanking AscI (bold) and MluI (bold) cloning sites that are needed for the subsequent cloning step. The primer pair for this purpose is: 5'-GGC GCG CCT CAC ATC AAC ATC TTT AGC T-3' (SEQ ID NO:168) and 5'-GGA CGC GTA TTG AAT CGG GCT CTC TTC A-3' (SEQ ID NO:169). The PCR product is TA-cloned in a TOPO vector, and the 166 bp insert is excised with AscI and MluI. This fragment containing the intergenic region of BCTV is ligated into the biolistic delivery form of the double attR donor (pAdF72) (FIG. 15) after digesting the vector with AscI. The orientation of the viral ori insert (forward or reverse) is determined by digesting the product with AscI/XhoI. A clone with each ori orientation is tested for efficiency in targeted integration. The resulting donor plasmids are named VfDonDbAttR.BY2 and VrDonDbAttR.BY2.

To virally amplify the donor sequence within the plant cell, the donor is co-delivered into the plant cell with the viral genes containing the genetic information required for replication. It is desirable that this "helper" viral DNA not be DVR2, because we have found that even DVR2*, a derivative of DVR2 from which part of V2 is deleted, interferes with the recovery of transformants when co-delivered to BY2 cells with pNOV2720, an NPTII expression cassette, by bombardment. Accordingly, the entire set of viral replication genes (i.e., C1-C4) is supplied in a non-replicating form, i.e., a form in which the palindromic region (replication origin) described above is deleted. Because the DNA flanking this ori also serves as a "double promoter" for both plus and minus strand transcription in the intact virus, the entire intergenic region of the virus is replaced with an *Arabidopsis* ubiquitin gene promoter/intron construct, oriented to transcribe the minus strand replication genes. Besides omitting the intergenic region, the "helper" construct also omits all three genes that correspond to the + or V strand of BCTV: V2, the coat protein gene; V3, whose elimination increases the amount of double-stranded DNA vs. single-stranded (virion) DNA (Hormuzdi, S. G. & Bisaro, D. M., Virology 193: 900-909 (1993)); and V1, which enables movement of virus through the plant.

The helper plasmid is constructed by 3-way ligation as follows: pUC18DVR2 is digested with SphI and AscI with alkaline phosphatase, and the 4068 bp vector with partial insert is gel purified. To form the insert, pUC18DVR2 is digested with HinfI and a 596 bp fragment is gel purified. The ends are filled in with Klenow, and the fragment is purified and re-digested with SphI. The 173 bp product is gel-purified and serves as Insert 1 for the three-way ligation. Insert 2, the *Arabidopsis* ubiquitin promoter, is derived from Ubq3Hyg, an expression cassette for hygromycin resistance. The ubq3 promoter together with its leader and intron is tailored for insertion into the helper construct by attaching a SnaBI (bold) linker to the downstream end (replacing a BamHI site with site change oligo 5'-GAT CGG TAC GTA CC-3' (SEQ ID NO:170)) and an AscI (bold) linker to the upstream end (replacing an EcoRI site with the site-change oligo 5'-AAT TGG CGC GCC-3' (SEQ ID NO:171)). The ubq3 promoter fragment is excised by digestion with AscI/SnaBI and serves as Insert 2. The new replication gene helper plasmid, Ubq3Rep, is assembled by 3-way ligation of the vector fragment with Insert1 and Insert2. The structure of Ubq3Rep is confirmed by digestion and DNA sequencing.

VdonDblAttR.BY2 and Ubq3Rep are used as a donor DNA system (replacing pAdF72) in the targeted integration that is carried out as described in Example 87.

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

The foregoing describes the invention with reference to various embodiments and examples. No particular embodiment, example, or element of a particular embodiment or example is to be construed as a critical, required, or essential element or feature of any or all of the claims. As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter. Further, no element described herein is required for the practice of the invention unless expressly described as "essential" or "critical."

It will be appreciated that various modifications and substitutions can be made to the disclosed embodiments without departing from the scope of the invention as set forth in the claims below. The specification, including the drawings and examples, is to be regarded in an illustrative manner, rather than a restrictive one, and all such modifications and substitutions are intended to be included within the scope of the invention. Accordingly, the scope of the invention should be determined by the appended claims and their legal equivalents, rather then by the examples given above. For example, the steps recited in any of the method or process claims may be executed in any feasible order and are not limited to an order presented in any of claims.

What is claimed is:

1. A method for obtaining site-specific recombination of DNA within a plant cell, comprising:
   introducing into a plant cell a target sequence comprising a first Int recognition site capable of being recognized by a Lambda bacteriophage integrase or integrase complex;
   introducing into said plant cell a donor sequence comprising a second Int recognition site capable of being recognized by a Lambda bacteriophage integrase or integrase complex; and
   introducing into said plant cell a Lambda bacteriophage integrase or integrase complex, such that site-specific recombination of said donor sequence is obtained.

2. The method of claim 1, wherein said plant cell is a monocotyledonous plant cell.

3. The method of claim 1, wherein said plant cell is a dicotyledonous plant cell.

4. The method of claim 1, wherein said plant cell is one of a wheat cell, a maize cell, a rice cell, a barley cell, a soybean cell, a cotton plant cell, a tomato cell, and a tobacco cell.

5. The method of claim 1, wherein said target sequence is introduced into said plant cell by one of *Agrobacterium*-mediated transformation, microprojectile bombardment, electroporation, PEG-mediated transformation, and microinjection.

6. The method of claim 1, wherein said target sequence is stably integrated into a genome of said plant cell.

7. The method of claim 6, wherein said plant cell is a target line cell comprising a single copy of said target sequence.

8. The method of claim 1, wherein said first Int recognition site is a modified Lambda bacteriophage integrase recognition site.

9. The method of claim 1, wherein said first Int recognition site comprises attL (SEQ ID NO:174).

10. The method of claim 1, wherein said target sequence comprises at least one of a sequence of interest, a molecular marker, a selectable marker, a visible marker, a negative selectable marker, a promoter, an expression cassette, an intron, and a portion of any of these.

11. The method of claim 10, wherein said target sequence comprises at least one of a PPO gene, a LUC gene, an NPTII gene, a GUS gene, a PMI gene, a HPT gene, and a portion of any of these.

12. The method of claim 1, wherein said target sequence further comprises a third Int recognition site capable of being recognition by a Lambda bacteriophage integrase or integrase complex.

13. The method of claim 12, wherein said first Int recognition site and said third Int recognition site are identical.

14. The method of claim 12, wherein said first Int recognition site and said third Int recognition site are non-identical.

15. The method of claim 12, wherein said first Int recognition site and said third Int recognition site are incapable of recombining with each other.

16. The method of claim 12, wherein at least one of said first Int recognition site and said third Int recognition site is a modified Lambda bacteriophage integrase recognition site.

17. The method of claim 12, wherein said first Int recognition site and said third Int recognition site are in direct orientation with respect to each other.

18. The method of claim 12, wherein said first Int recognition site and said third Int recognition site are in an inverted orientation with respect to each other.

19. The method of claim 12, wherein said first Int recognition site and said third Int recognition site are positioned within said target sequence such that said first Int recognition site and said third Int recognition site are adjacent to one another.

20. The method of claim 12, wherein said first Int recognition site and said third Int recognition site are positioned within said target sequence such that a first nucleotide sequence is located between said first Int recognition site and said third Int recognition site.

21. The method of claim 20, wherein said first nucleotide sequence comprises at least one of a sequence of interest, a molecular marker, a selectable marker, a visible marker, a negative selectable marker, a promoter, an expression cassette, an intron, and a portion of any of these.

22. The method of claim 21, wherein said first nucleotide sequence comprises at least one of a PPO gene, a LUC gene, an NPTII gene, a GUS gene, a PMI gene, a HPT gene, and a portion of any of these.

23. The method of claim 12, wherein each of said first Int recognition site comprises attL (SEQ ID NO:174) and said third Int recognition site comprises attL1 (SEQ ID NO:180).

24. The method of claim 1, wherein said donor sequence is introduced into said plant cell by one of *Agrobacterium*-mediated transformation, microprojectile bombardment, electroporation, PEG-mediated transformation, and microinjection.

25. The method of claim 1, wherein said donor sequence is introduced into said plant cell on a viral replicon.

26. The method of claim 25, wherein said viral replicon is capable of autonomous replication within said plant cell.

27. The method of claim 25, wherein said viral replicon is derived from a geminivirus.

28. The method of claim 27, wherein said geminivirus is one of a maize streak virus, a wheat dwarf virus, a tobacco golden mosaic virus, and a beet curly top virus.

29. The method of claim 25, wherein said viral replicon is introduced into said plant cell by one of *Agrobacterium*-mediated transformation, microprojectile bombardment, electroporation, PEG-mediated transformation, and microinjection.

30. The method of claim 1, wherein said second Int recognition site is a modified Lambda bacteriophage integrase recognition site.

31. The method of claim 1, wherein said second Int recognition site comprises attB (SEQ ID NO:175).

32. The method of claim 1, wherein said donor sequence comprises at least one of a sequence of interest, a molecular marker, a selectable marker, a visible marker, a negative selectable marker, a promoter, an expression cassette, an intron, and a portion of any of these.

33. The method of claim 32, wherein said donor sequence comprises at least one of a PPO gene, a LUC gene, an NPTII gene, a GUS gene, a PMI gene, a HPT gene, and a portion of any of these.

34. The method of claim 12, wherein said donor sequence further comprises a fourth Int recognition site capable of being recognized by a Lambda bacteriophage integrase or integrase complex.

35. The method of claim 34, wherein said second Int recognition site and said fourth Int recognition site are identical.

36. The method of claim 35, wherein said second Int recognition site and said fourth Int recognition site are in inverted orientation with respect to each other.

37. The method of claim 34, wherein said second Int recognition site and said fourth Int recognition site are non-identical.

38. The method of claim 37, wherein said second Int recognition site and said fourth Int recognition site are in direct orientation with respect to each other.

39. The method of claim 37, wherein said second Int recognition site and said fourth Int recognition site are in inverted orientation with respect to each other.

40. The method of claim 34, wherein said second Int recognition site and said fourth Int recognition site are incapable of recombining with each other.

41. The method of claim 34, wherein at least one of said second Int recognition site and said fourth Int recognition site is a modified Lambda bacteriophage integrase recognition site.

42. The method of claim 34, wherein said second Int recognition site and said fourth Int recognition site are positioned within said donor sequence such that said second Int recognition site and said fourth Int recognition site are adjacent to one another.

43. The method of claim 34, wherein said second Int recognition site and said fourth Int recognition site are positioned within said donor sequence such that a pre-selected nucleotide sequence is located between said second Int recognition site and said fourth Int recognition site.

44. The method of claim 43, wherein said pre-selected nucleotide sequence comprises at least one of a sequence of interest, a molecular marker, a selectable marker, a visible marker, a negative selectable marker, a promoter, an expression cassette, an intron, and a portion of any of these.

45. The method of claim 44, wherein said pre-selected nucleotide sequence comprises at least one of a PPO gene, a LUC gene, an NPTII gene, a GUS gene, a PMI gene, a HPT gene, and a portion of any of these.

46. The method of claim 34, wherein said second Int recognition site is capable of recombining with said first Int recognition site and said fourth Int recognition site is capable of recombining with said third Int recognition site.

47. The method of claim 46, wherein each of said second Int recognition site and said fourth Int recognition site comprises attR1 (SEQ ID NO:181).

48. The method of claim 47, wherein each of said first Int recognition site comprises (SEQ ID NO:174) and said third Int recognition site comprises attL1 (SEQ ID NO:181).

49. The method of claim 1, wherein said integrase or integrase complex comprises one of a wild-type Lambda bacteriophage integrase and a modified Lambda bacteriophage integrase.

50. The method of claim 49, wherein said modified Lambda integrase comprises one of Int-h and Int-h/218.

51. The method of claim 50, wherein said integrase or integrase complex further comprises an integration host factor.

52. The method of claim 51, wherein said integrase or integrase complex further comprises an excisionase.

53. The method of claim 1, wherein said integrase or integrase complex is introduced into said plant cell as one or more nucleotide sequences comprising a coding region for each constituent protein of said integrase or integrase complex.

54. The method of claim 53, wherein said one or more nucleotide sequences comprises SEQ ID NO:21.

55. The method of claim 54, wherein SEQ ID NO:21 is modified such that base pair 520 is changed from a "G" to an "A."

56. The method of claim 55, wherein SEQ ID NO:21 is further modified such that base pair 652 is changed from a "G" to an "A."

57. The method of claim 53, wherein said coding region for each constituent protein is operably linked to a plant expressible promoter.

58. The method of claim 57, wherein said plant expressible promoter is one of a constitutive promoter, an inducible promoter, a tissue-specific promoter, a tissue-preferred promoter, a developmentally-regulated promoter, a cell-specific promoter, and an organellar-specific promoter.

59. The method of claim 53, wherein said integrase or integrase complex is stably integrated into a genome of said plant cell.

60. The method of claim 53, wherein said integrase or integrase complex is transiently expressed within said plant cell.

61. The method of claim 60, wherein said integrase or integrase complex is introduced into said plant cell on a viral replicon.

62. The method of claim 61, wherein said viral replicon is capable of autonomous replication within said plant cell.

63. The method of claim 61, wherein said viral replicon is derived from a geminivirus.

64. The method of claim 63, wherein said geminivirus is one of a maize streak virus, a wheat dwarf virus, a tobacco golden mosaic virus, and a beet curly top virus.

65. The method of claim 61, wherein said viral replicon is introduced into said plant cell by one of *Agrobacterium*-mediated transformation, microprojectile bombardment, electroporation, PEG-mediated transformation, and microinjection.

66. The method of claim 60, wherein said integrase or integrase complex is introduced into said plant cell as one or more RNA molecules.

67. The method of claim 53, wherein said coding region for each constituent protein is optimized for expression in said plant cell.

68. The method of claim 1, wherein said integrase or integrase complex is introduced into said plant cell as one or more proteins.

69. The method of claim 68, wherein said one or more proteins is introduced into said plant cell by one of electroporation and microinjection.

70. The method of claim 68, wherein said one or more proteins is introduced into said plant cell through *Agrobacterium* comprising a VirE or a VirF fusion protein.

71. The method of claim 1, wherein introducing said donor sequence and introducing said integrase or integrase complex are performed simultaneously.

72. The method of claim 1, wherein said target sequence is introduced into said plant cell by a first method, said donor sequence is introduced by a second method, and said integrase or integrase complex is introduced by a third method.

73. The method of claim 72, wherein each of said first method, said second method, and said third method is independently selected from the group consisting of *Agrobacterium*-mediated transformation, microprojectile bombardment, electroporation, PEG-mediated transformation, microinjection, and sexual reproduction, and wherein at least one of said first method, said second method, and said third method is other than sexual reproduction.

74. The method of claim 73, wherein said donor sequence and said integrase or integrase complex are introduced into said plant cell simultaneously.

75. The method of claim 73, wherein said target sequence is introduced into said plant cell prior to an introduction of said donor sequence and said integrase or integrase complex.

76. The method of claim 73, wherein said integrase or integrase complex is introduced into said plant cell after said target sequence and said donor sequence have been introduced into said plant cell.

77. The method of claim 73, wherein said donor sequence is stably integrated into a genome of a second plant cell prior to being introduced into said plant cell.

78. The method of claim 34, wherein said target sequence comprises an incomplete nucleotide sequence and said donor sequence comprises a completion sequence, such that recombination between said target sequence and said donor sequence produces a complete nucleotide sequence.

79. The method of claim 78, wherein said incomplete nucleotide sequence comprises at least one of a sequence of interest, a gene, an intron, a promoter, an expression cassette, a selectable marker, a visible marker, and a negative selectable marker.

80. The method of claim 1, wherein said donor sequence comprises a third Int recognition site that does not recombine with said first Int recognition site of said target sequence and is capable of being used in a subsequent recombination of DNA within said plant cell.

81. The method of claim 80, wherein said first Int recognition site, attL (SEQ ID NO:174), said second Int recognition site comprises attR (SEQ ID NO:175), and said third Int recognition site comprises attL1 (SEQ ID NO:180).

82. The method of claim 34, wherein said donor sequence comprises a fifth Int recognition site that does not recombine with either of said first Int recognition site or said third Int recognition site of said target sequence and is capable of being used in a subsequent recombination of DNA within said plant cell.

83. The method of claim 82, wherein said first Int recognition site, comprises attL (SEQ ID NO:174), said second Int recognition site comprises attR (SEQ ID NO:175), said third Int recognition site attL1 (SEQ ID NO:180), said fourth Int recognition site comprises attR1 (SEQ ID NO:181), and said fifth Int recognition site comprises attP2 (SEQ ID NO:179).

84. The method of claim 1, further comprising: identifying a recombination product obtained through sequence exchange between said target sequence and said donor sequence.

85. The method of claim 84, wherein said recombination product comprises at least one newly created Int recognition site, and wherein said newly created Int recognition site is flanked on a first side by sequence obtained from said target sequence and flanked on a second side by sequence obtained from said donor sequence.

86. The method of claim 34, further comprising: identifying a recombination product obtained through sequence exchange between said target sequence and said donor sequence.

87. The method of claim 86, wherein said recombination product comprises at least one newly created Int recognition site, and wherein said newly created Int recognition site is flanked on a first side by sequence obtained from said target sequence and flanked on a second side by sequence obtained from said donor sequence.

88. A method for manipulating a target sequence within a plant cell, comprising:
introducing into a plant cell a target sequence comprising
(a) a first Int recognition site capable of being recognized by a Lambda bacteriophage integrase or integrase complex and a second Int recognition site capable of being recognized by a Lambda bacteriophage integrase or integrase complex that are capable of recombining with each other and (b) a first nucleotide sequence that is situated between said first Int recognition site and said second Int recognition site;
introducing into said plant cell a Lambda bacteriophage integrase or integrase complex; and
identifying a recombination product comprising an altered target sequence.

89. The method of claim 88, wherein said first Int recognition site and said second Int recognition site are in direct orientation, and said altered target sequence does not comprise said first nucleotide sequence.

90. The method of claim 88, wherein said first Int recognition site and said second Int recognition site are in inverted orientation, and said altered target sequence comprises said first nucleotide sequence in an inverted orientation relative to an original orientation of said first nucleotide sequence.

91. The method of claim 88, wherein each of said first Int recognition site comprises attB (SEQ ID NO:172) and said second Int recognition site comprises attP (SEQ ID NO:173).

92. The method of claim 88, wherein said first nucleotide sequence comprises at least one of a sequence of interest, a molecular marker, a selectable marker, a visible marker, a negative selectable marker, a promoter, an expression cassette, an intron, and a portion of any of these.

93. The method of claim 88, wherein said target sequence further comprises a second nucleotide sequence that is not positioned between said first Int recognition site and said second Int recognition site.

94. The method of claim 93, wherein said second nucleotide sequence comprises at least one of a sequence of interest, a molecular marker, a selectable marker, a visible marker, a negative selectable marker, a promoter, an expression cassette, an intron, and a portion of any of these.

95. The method of claim 93, wherein said altered target sequence comprises said first nucleotide sequence in an inverted orientation relative to an original orientation of said first nucleotide sequence and said second nucleotide sequence in an original orientation.

96. The method of claim 88, wherein said integrase or integrase complex comprises one of a wild-type Lambda bacteriophage integrase and a modified Lambda bacteriophage integrase.

97. The method of claim 96, wherein said modified Lambda integrase comprises one of Int-h and Int-h/218.

98. The method of claim 97, wherein said integrase or integrase complex further comprises an integration host factor.

99. The method of claim 98, wherein said integrase or integrase complex further comprises an excisionase.

100. A method for obtaining site-specific recombination of DNA within a plant cell, comprising:
introducing into a genome of a plant cell a target sequence comprising a first Int recognition site that comprises attL (SEQ ID NO:174);
introducing into said plant cell a donor sequence comprising a second Int recognition site that comprises attR (SEQ ID NO:175);
introducing into said plant cell a Lambda bacteriophage integrase or integrase complex; and
identifying a recombination product within said genome of said plant cell obtained through sequence exchange between said target sequence and said donor sequence.

101. The method of claim 100, wherein said integrase or integrase complex comprises one of a wild-type Lambda bacteriophage integrase and a modified Lambda bacteriophage integrase.

102. The method of claim 101, wherein said modified Lambda integrase comprises one of Int-h and Int-h/218.

103. The method of claim 102, wherein said integrase or integrase complex further comprises an integration host factor.

104. The method of claim 103, wherein said integrase or integrase complex further comprises an excisionase.

105. A method for obtaining site-specific recombination of DNA within a plant cell, comprising:
introducing into a genome of a plant cell a target sequence comprising attL (SEQ ID NO:174) as a first Int recognition site and comprising attL1 (SEQ ID NO:180) as a third Int recognition site;
introducing into said plant cell a donor sequence comprising attR (SEQ ID NO:175) as a second Int recognition site and comprising attR1 (SEQ ID NO:181) as a fourth recognition site;
introducing into said plant cell a Lambda bacteriophage integrase or integrase complex; and
identifying a recombination product within said genome of said plant cell obtained through sequence exchange between said target sequence and said donor sequence.

106. The method of claim 105, wherein said integrase or integrase complex comprises one of a wild-type Lambda bacteriophage integrase and a modified Lambda bacteriophage integrase.

107. The method of claim 106, wherein said modified Lambda integrase comprises one of Int-h and Int-h/218.

108. The method of claim 107, wherein said integrase or integrase complex further comprises an integration host factor.

109. The method of claim 108, wherein said integrase or integrase complex further comprises an excisionase.

110. The method of claim 1, further comprising identifying a transgenic plant cell comprising a recombination product within a genome of said transgenic plant cell obtained through sequence exchange between said target sequence and said donor sequence.

111. A transgenic plant cell obtained by the method of claim 110, said transgenic plant cell comprising at least one Int recognition site.

112. The transgenic plant cell of claim 111, wherein said Int recognition site comprises attB (SEQ ID NO:172).

113. A transgenic plant comprising the transgenic plant cell of claim 111.

114. A transgenic plant comprising the transgenic plant cell of claim 112.

115. The method of claim 34, further comprising identifying a transgenic plant cell comprising a recombination product within a genome of said transgenic plant cell obtained through sequence exchange between said target sequence and said donor sequence.

116. A transgenic plant cell obtained by the method of claim 115, said transgenic plant cell comprising at least one Int recognition site.

117. The transgenic plant cell of claim 116, wherein said Int recognition site comprises attP (SEQ ID NO:173).

118. A transgenic plant comprising the transgenic plant cell of claim 116.

119. A transgenic plant comprising the transgenic plant cell of claim 117.

* * * * *

UNITED STATES PATENT AND TRADEMARK OFFICE
CERTIFICATE OF CORRECTION

PATENT NO. : 7,351,877 B2  Page 1 of 1
APPLICATION NO. : 10/403232
DATED : April 1, 2008
INVENTOR(S) : Suttie et al.

It is certified that error appears in the above-identified patent and that said Letters Patent is hereby corrected as shown below:

At column 163, line 48, in claim 12, delete "recognition" and insert therefor --recognized--

At column 164, line 47, in claim 31, delete "attB" and insert therefor --attR--

At column 165, line 44, in claim 48, delete "(SEQ ID NO:174)" and insert therefor --(SEQ ID NO:74)--

At column 165, line 44, in claim 48, insert --attL-- before "(SEQ ID NO:74)"

At column 165, line 45, in claim 48, delete "(SEQ ID NO:181)" and insert therefor --(SEQ ID NO:180)--

At column 167, line 38, in claim 83, delete "site," and insert therefor --site--

Signed and Sealed this

Twenty-fourth Day of June, 2008

JON W. DUDAS
*Director of the United States Patent and Trademark Office*